(12) United States Patent
Do et al.

(10) Patent No.: US 12,031,975 B2
(45) Date of Patent: Jul. 9, 2024

(54) METHODS OF ASSESSING OR MONITORING A RESPONSE TO A CELL THERAPY

(71) Applicant: Juno Therapeutics, Inc., Seattle, WA (US)

(72) Inventors: Trevor Do, Seattle, WA (US); Howard Stern, Seattle, WA (US); Christina Swanson, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 165 days.

(21) Appl. No.: 16/760,381

(22) PCT Filed: Oct. 31, 2018

(86) PCT No.: PCT/US2018/058596
§ 371 (c)(1),
(2) Date: Apr. 29, 2020

(87) PCT Pub. No.: WO2019/089858
PCT Pub. Date: May 9, 2019

(65) Prior Publication Data
US 2021/0132042 A1 May 6, 2021

Related U.S. Application Data

(60) Provisional application No. 62/685,250, filed on Jun. 14, 2018, provisional application No. 62/673,825, filed on May 18, 2018, provisional application No. 62/596,733, filed on Dec. 8, 2017, provisional application No. 62/580,430, filed on Nov. 1, 2017.

(51) Int. Cl.
*G01N 33/50* (2006.01)
*A61K 35/17* (2015.01)
*C07K 14/705* (2006.01)

(52) U.S. Cl.
CPC ......... *G01N 33/5017* (2013.01); *A61K 35/17* (2013.01); *C07K 14/705* (2013.01); *G01N 33/5091* (2013.01); *G01N 2333/70514* (2013.01); *G01N 2800/52* (2013.01)

(58) Field of Classification Search
CPC ........... G01N 33/5017; G01N 33/5091; A61K 35/17; C07K 14/705
See application file for complete search history.

(56) References Cited

U.S. PATENT DOCUMENTS

| | | | |
|---|---|---|---|
| 4,452,773 A | 6/1984 | Molday | |
| 4,690,915 A | 9/1987 | Rosenberg | |
| 4,795,698 A | 1/1989 | Owen | |
| 5,200,084 A | 4/1993 | Liberti | |
| 5,219,740 A | 6/1993 | Miller | |
| 5,424,297 A | 6/1995 | Rubio et al. | |
| 5,504,090 A | 4/1996 | Neely | |
| 5,545,627 A | 8/1996 | Jacobson et al. | |
| 5,565,566 A | 10/1996 | Olsson et al. | |
| 5,635,517 A | 6/1997 | Muller et al. | |
| 5,670,501 A | 9/1997 | Peck et al. | |
| 5,712,291 A | 1/1998 | D'Amato | |
| 5,786,360 A | 7/1998 | Neely | |
| 5,798,368 A | 8/1998 | Muller et al. | |
| 5,861,405 A | 1/1999 | Jacobson et al. | |
| 5,981,524 A | 11/1999 | Peck et al. | |
| 6,040,177 A | 3/2000 | Riddell | |
| 6,066,642 A | 5/2000 | Jacobson et al. | |
| 6,111,090 A | 8/2000 | Gorman et al. | |
| 6,117,998 A | 9/2000 | Neely | |
| 6,207,453 B1 | 3/2001 | Maass | |
| 6,232,297 B1 | 5/2001 | Linden et al. | |
| 6,281,230 B1 | 8/2001 | Muller et al. | |
| 6,313,131 B1 | 11/2001 | Lawyer | |

(Continued)

FOREIGN PATENT DOCUMENTS

| | | |
|---|---|---|
| EP | 0090505 | 8/1990 |
| EP | 0452342 | 10/1991 |

(Continued)

OTHER PUBLICATIONS

US 8,252,592 B2, 08/2012, Sadelain (withdrawn)
Nedergaard et al. "Low density of CD3+, CD4+ and CD8+ cells is associated with increased risk of relapse in squamous cell cervical cancer", Br J Cancer. Oct. 22, 2007;97(8):1135-8. (Year: 2007).*
Feng et al. "Utilizing quantitative immunohistochemistry for relationship analysis of tumor microenvironment of head and neck cancer patients", Journal for Immunotherapy of Cancer 2.Suppl 3 London: BMJ Publishing Group LTD. (Nov. 2014) (Year: 2014).*

(Continued)

*Primary Examiner* — Amy E Juedes
*Assistant Examiner* — Peter Johansen
(74) *Attorney, Agent, or Firm* — MORRISON & FOERSTER LLP

(57) ABSTRACT

Provided are methods and articles of manufacture for use with cell therapy for the treatment of diseases or conditions, e.g., cancer, including for predicting likelihood of the subject responding to a therapy, such as a cell therapy, e.g., a chimeric antigen receptor (CAR) T cell therapy. In some aspects, the predicting is based on detecting certain biomarkers of immune cells associated with and/or that correlate with response following administration of the therapy. The methods generally involve detecting a marker by assaying a biological sample from a subject that is a candidate for treatment, optionally with a cell therapy, to determine if the subject is likely to respond to the therapy. The present disclosure also provides methods for treating a subject having a disease or condition, in some cases involving administration of the cell therapy, based on assessment the biomarker. Also provided herein are reagents and kits for performing the methods.

33 Claims, 16 Drawing Sheets
Specification includes a Sequence Listing.

(56) References Cited

U.S. PATENT DOCUMENTS

| | | |
|---|---|---|
| 6,316,471 B1 | 11/2001 | Muller et al. |
| 6,322,771 B1 | 11/2001 | Linden et al. |
| 6,326,390 B1 | 12/2001 | Leung et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,410,319 B1 | 6/2002 | Raubitschek |
| 6,451,995 B1 | 9/2002 | Cheung |
| 6,458,810 B1 | 10/2002 | Muller et al. |
| 6,476,052 B1 | 11/2002 | Muller et al. |
| 7,025,962 B1 | 4/2006 | Gorman et al. |
| 7,070,995 B2 | 7/2006 | Jensen |
| 7,091,353 B2 | 8/2006 | Robarge et al. |
| 7,132,255 B2 | 11/2006 | Blumberg |
| 7,141,575 B2 | 11/2006 | Gillespie et al. |
| 7,219,016 B2 | 5/2007 | Rimm et al. |
| 7,244,759 B2 | 7/2007 | Muller et al. |
| 7,265,209 B2 | 9/2007 | Jensen |
| 7,320,991 B2 | 1/2008 | Figg et al. |
| 7,354,762 B2 | 4/2008 | Jensen |
| 7,405,219 B2 | 7/2008 | Gillespie et al. |
| 7,446,179 B2 | 11/2008 | Jensen |
| 7,446,190 B2 | 11/2008 | Sadelain |
| 7,446,191 B2 | 11/2008 | Jensen |
| 7,618,632 B2 | 11/2009 | Collins et al. |
| 7,812,135 B2 | 10/2010 | Smith et al. |
| 7,943,743 B2 | 5/2011 | Korman et al. |
| 8,008,449 B2 | 8/2011 | Korman et al. |
| 8,008,450 B2 | 8/2011 | Williams et al. |
| 8,080,554 B2 | 12/2011 | Sitkovsky et al. |
| 8,124,084 B2 | 2/2012 | Lefrancois et al. |
| 8,153,765 B2 | 4/2012 | Park et al. |
| 8,324,353 B2 | 12/2012 | Jensen |
| 8,339,645 B2 | 12/2012 | Nakawaki et al. |
| 8,354,509 B2 | 1/2013 | Carven et al. |
| 8,388,967 B2 | 3/2013 | Smith et al. |
| 8,389,282 B2 | 3/2013 | Sadelain |
| 8,497,118 B2 | 7/2013 | Jensen |
| 8,586,023 B2 | 11/2013 | Shiku et al. |
| 8,591,886 B2 | 11/2013 | Ponath et al. |
| 8,603,477 B2 | 12/2013 | Afar et al. |
| 8,609,089 B2 | 12/2013 | Langermann et al. |
| 8,716,301 B2 | 5/2014 | Sitkovsky et al. |
| 8,716,315 B2 | 5/2014 | Figg et al. |
| 8,802,374 B2 | 8/2014 | Jensen |
| 8,822,647 B2 | 9/2014 | Jensen |
| 8,883,500 B2 | 11/2014 | Sitkovsky et al. |
| 8,911,993 B2 | 12/2014 | June |
| 8,987,279 B2 | 3/2015 | Bamford et al. |
| 11,413,310 B2 | 8/2022 | Albertson et al. |
| 11,564,946 B2 | 1/2023 | Albertson et al. |
| 2002/0045643 A1 | 4/2002 | Muller et al. |
| 2002/0131960 A1 | 9/2002 | Sadelain |
| 2003/0045552 A1 | 3/2003 | Robarge et al. |
| 2003/0170238 A1 | 9/2003 | Gruenberg |
| 2004/0047858 A1 | 3/2004 | Blumberg et al. |
| 2007/0116690 A1 | 5/2007 | Yang et al. |
| 2007/0154958 A1 | 7/2007 | Hamann et al. |
| 2009/0082299 A1 | 3/2009 | Felber et al. |
| 2009/0215053 A1* | 8/2009 | Galon .............. G01N 33/57492 435/6.16 |
| 2010/0028330 A1 | 2/2010 | Collins et al. |
| 2010/0136549 A1 | 6/2010 | Christiansen et al. |
| 2010/0247521 A1 | 9/2010 | Jones et al. |
| 2010/0260748 A1 | 10/2010 | Elkins et al. |
| 2011/0003380 A1 | 1/2011 | Miltenyi |
| 2011/0081311 A1 | 4/2011 | Pavlakis et al. |
| 2011/0111435 A1 | 5/2011 | Dobson et al. |
| 2012/0039906 A1 | 2/2012 | Olive |
| 2012/0114649 A1 | 5/2012 | Langermann et al. |
| 2012/0141413 A1 | 6/2012 | Pavlakis et al. |
| 2012/0177598 A1 | 7/2012 | Lefrancois et al. |
| 2012/0189622 A1 | 7/2012 | Tesar et al. |
| 2013/0149337 A1 | 6/2013 | Cooper |
| 2013/0156774 A1 | 6/2013 | Kuchroo et al. |
| 2013/0287748 A1 | 10/2013 | June |
| 2014/0056922 A1 | 2/2014 | Sitkovsky et al. |
| 2014/0271618 A1 | 9/2014 | Markel et al. |
| 2014/0271635 A1 | 9/2014 | Brogdon |
| 2014/0314795 A1 | 10/2014 | Riddell et al. |
| 2014/0377240 A1 | 12/2014 | Sitkovsky et al. |
| 2015/0210769 A1 | 7/2015 | Freeman et al. |
| 2015/0218274 A1 | 8/2015 | Sabatos-Peyton et al. |
| 2015/0259420 A1 | 9/2015 | Triebel et al. |
| 2015/0283178 A1 | 10/2015 | June et al. |
| 2015/0346210 A1 | 12/2015 | Nitta et al. |
| 2016/0046724 A1 | 2/2016 | Brogdon et al. |
| 2016/0122782 A1 | 5/2016 | Crisman et al. |
| 2016/0152723 A1 | 6/2016 | Chen et al. |
| 2016/0184330 A1 | 6/2016 | Sordillo et al. |
| 2016/0206656 A1 | 7/2016 | Gilbert |
| 2016/0313300 A1 | 10/2016 | Trotter et al. |
| 2016/0362472 A1 | 12/2016 | Bitter et al. |
| 2017/0051035 A1 | 2/2017 | Payne et al. |
| 2017/0306416 A1* | 10/2017 | Bedoya ................ G01N 33/574 |
| 2020/0016199 A1 | 1/2020 | Turtle et al. |
| 2020/0147136 A1 | 5/2020 | Albertson et al. |
| 2020/0191774 A1 | 6/2020 | Christin et al. |
| 2020/0352998 A1 | 11/2020 | Albertson et al. |
| 2022/0031746 A1 | 2/2022 | Gillenwater et al. |
| 2023/0149458 A1 | 5/2023 | Albertson et al. |
| 2023/0172988 A1 | 6/2023 | Albertson et al. |

FOREIGN PATENT DOCUMENTS

| | | |
|---|---|---|
| EP | 2537416 | 12/2012 |
| EP | 1 866 339 | 5/2013 |
| EP | 1 947 183 | 7/2013 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1998/003502 | 1/1998 |
| WO | WO 1998/054170 | 12/1998 |
| WO | WO 1999/018129 | 4/1999 |
| WO | WO 1999/020758 | 4/1999 |
| WO | WO 1999/040196 | 8/1999 |
| WO | WO 1999/052552 | 10/1999 |
| WO | WO 1999/060120 | 11/1999 |
| WO | WO 2000/014257 | 3/2000 |
| WO | WO 2001/003720 | 1/2001 |
| WO | WO 2002/055083 | 7/2002 |
| WO | WO 2002/059106 | 8/2002 |
| WO | WO 2002/068414 | 9/2002 |
| WO | WO 2003/020763 | 3/2003 |
| WO | WO 2004/033685 | 4/2004 |
| WO | WO 2005/007190 | 1/2005 |
| WO | WO 2005/055808 | 6/2005 |
| WO | WO 2005/115451 | 12/2005 |
| WO | WO 2006/000830 | 1/2006 |
| WO | WO 2006/083289 | 8/2006 |
| WO | WO 2006/099875 | 9/2006 |
| WO | WO 2006/121168 | 11/2006 |
| WO | WO 2007/005874 | 1/2007 |
| WO | WO 2007/133822 | 11/2007 |
| WO | WO 2008/147482 | 12/2008 |
| WO | WO 2008/154252 | 12/2008 |
| WO | WO 2009/072003 | 6/2009 |
| WO | WO 2009/080829 | 7/2009 |
| WO | WO 2009/114335 | 9/2009 |
| WO | WO 2010/003118 | 1/2010 |
| WO | WO 2010/019570 | 2/2010 |
| WO | WO 2010/027827 | 3/2010 |
| WO | WO 2010/033140 | 3/2010 |
| WO | WO 2010/052013 | 5/2010 |
| WO | WO 2010/077634 | 7/2010 |
| WO | WO 2010/125571 | 11/2010 |
| WO | WO-2011011453 A2 * | 1/2011 ........... C12Q 1/6886 |
| WO | WO 2011/028683 | 3/2011 |
| WO | WO 2011/044186 | 4/2011 |
| WO | WO 2011/051726 | 5/2011 |
| WO | WO 2011/056983 | 5/2011 |
| WO | WO 2011/066342 | 6/2011 |

(56) References Cited

FOREIGN PATENT DOCUMENTS

| | | |
|---|---|---|
| WO | WO 2011/090754 | 7/2011 |
| WO | WO 2012/062904 | 5/2012 |
| WO | WO 2012/092612 | 7/2012 |
| WO | WO 2012/129514 | 9/2012 |
| WO | WO 2013/006490 | 1/2013 |
| WO | WO 2013/039954 | 3/2013 |
| WO | WO 2013/054331 | 4/2013 |
| WO | WO 2013/071154 | 5/2013 |
| WO | WO 2013/082366 | 6/2013 |
| WO | WO 2013/123061 | 8/2013 |
| WO | WO 2013/126726 | 8/2013 |
| WO | WO 2013/166321 | 11/2013 |
| WO | WO 2014/011984 | 1/2014 |
| WO | WO 2014/022332 | 2/2014 |
| WO | WO 2014/031687 | 2/2014 |
| WO | WO 2014/055668 | 4/2014 |
| WO | WO 2014/059251 | 4/2014 |
| WO | WO 2014/153270 | 9/2014 |
| WO | WO 2014/210064 | 12/2014 |
| WO | WO 2015/079417 | 6/2015 |
| WO | WO 2015/157384 | 10/2015 |
| WO | WO 2015/164675 | 10/2015 |
| WO | WO 2016/019300 | 2/2016 |
| WO | WO 2016/028896 | 2/2016 |
| WO | WO 2016/033570 | 3/2016 |
| WO | WO 2016/057705 | 4/2016 |
| WO | WO 2016/064929 | 4/2016 |
| WO | WO 2016/090312 | 6/2016 |
| WO | WO 2016/090320 | 6/2016 |
| WO | WO 2016/090327 | 6/2016 |
| WO | WO 2016/090329 | 6/2016 |
| WO | WO 2016/164731 | 10/2016 |
| WO | WO 2016/172606 | 10/2016 |
| WO | WO 2016/191755 | 12/2016 |
| WO | WO 2016/191756 | 12/2016 |
| WO | WO 2017/015427 | 1/2017 |
| WO | WO 2017/019848 | 2/2017 |
| WO | WO 2017/040930 | 3/2017 |
| WO | WO 2017/049166 | 3/2017 |
| WO | WO 2017/058850 | 4/2017 |
| WO | WO 2017/096331 | 6/2017 |
| WO | WO 2017/214207 | 12/2017 |
| WO | WO 2018/157171 | 8/2018 |
| WO | WO 2018/223101 | 12/2018 |
| WO | WO 2019/089848 | 5/2019 |
| WO | WO 2020/113188 | 6/2020 |

OTHER PUBLICATIONS

Turtle et al. "CD19 CAR-T cells of defined CD4+:CD8+ composition in adult B cell ALL patients", J Clin Invest. Jun. 1, 2016;126(6):2123-38 (Year: 2016).*

Ansell et al. "Cd4+ T-cell immune response to large B-cell non-Hodgkin's lymphoma predicts patient outcome", J Clin Oncol. Feb. 1, 2001;19(3):720-6. (Year: 2001).*

Li, S., "Engineering Chimeric Antigen Receptor (CAR)-modified T cells for Enhanced Cancer Immunotherapy" ProQuest Dissertations and Theses ProQuest Dissertations Publishing. (2017) (Year: 2017).*

Hung et al. "The Central Role of CD41 T Cells in the Antitumor Immune Response", J Exp Med. Dec. 21, 1998; 188(12): 2357-2368 (Year: 1998).*

Fidler, IJ. "Biological heterogeneity of cancer", Human Vaccines & Immunotherapeutics 8:8, 1141-1142 (Year: 2012).*

The Merck Manuals Online Medical Library, [online]. Whitehouse Station, NJ: Merck Research Laboratories, 2006-2007. [retrieved on Oct. 19, 2020].<URL: https://www.merckmanuals.com/professional/hematology-and-oncology/overview-of-cancer/cellular-and-molecular-basis-of-cancer> (Year: 2020).*

Abramson et al, "High durable CR rates in relapsed/refractory (R/R) aggressive B-NHL treated with the CD19-directed CAR T cell product JCAR017 (Transcend NHL 001): Defined composition allows for dose-finding and definition of pivotal cohort," Blood (2017) 130 (suppl. 1):581.

Abramson et al, "High durable CR rates in R/R aggressive B-NHL treated with JCAR017 (lisocabtagene maraleuce; liso-cel) (Transcend NHL 001): Defined composition CD19-directed CAR T cel product allows for dose-finding and definition of pivotal cohort," oral presentation at ASH 2017 Dec. 9-12, 2017.

Allard et al., "Targeting CD73 enhances the antitumor activity of anti-PD-1 and anti-CTLA-4 mAbs," Clin Cancer Res (2013) 19(20):5626-5635.

Al-Lazikani et al., "Standard conformations for the canonical structures of immunoglobulins," J Mol Biol (1997) 273(4):927-948.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Barrett et al., "Chimeric antigen receptor therapy for cancer," Annu Rev Med. (2014); 65: 333-347.

Beavis et al., "Blockade of A2A receptors potently suppresses the metastasis of CD73+ tumors," PNAS usa (2013) 110:14711-14716.

Benson et al., "CS1-Directed monoclonal antibody therapy for multiple myeloma," J Clin Oncol (2012) 30(16):2012-2015.

Berger et al., "Phase I safety and pharmacokinetic study of CT-011, a humanized antibody interacting with PD-1, in patients with advanced hematologic malignancies," Clin Cancer Res (2008) 14(10):3044-3051.

Bertilaccio, "Low-dose lenalidomide improves CAR-based immunotherapy in CLL by reverting T-cell defects in vivo," Blood (2013) 122:4171.

Bhaumik et al., "U Discovery 5-Plex IF procedure: A fully automated immunofluorescence multiplex solution," (2016).

Blank et al., "Contribution of the PD-L1/PD-1 pathway to T-cell exhaustion: an update on implications for chronic infections and tumor evasion," Cancer Immunol Immunother (2007) 56(5):739-745.

Blom et al., "Systems pathology by multiplexed immunohistochemistry and whole-slide digital image analysis," Sci Rep (2017) 7(1):15580.

Boris-Lawrie et al., "Recent advances in retrovirus vector technology," Cur. Opin. Genet. Develop. (1993) 3:102-109.

Brahmer et al., "Safety and Activity of Anti-PD-L1 Antibody in Patients with Advanced Cancer," N Engl J Med (2012) 366:2455-2465.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177):177ra38.

Brummelkamp et al., "A system for stable expression of short interfering RNAs in mammalian cells," Science (2002) 296(5567):550-553.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Carroll et al., "Targeting the molecular basis for tumour hypoxia," Expert Rev Mol Med (2005) 7(6):1-16.

Cavalieri et al., "Human T lymphocytes transduced by lentiviral vectors in the absence of TCR activation maintain an intact immune competence," Blood (2003) 102(2): 497-505.

Cheadle et al., "Chimeric antigen receptors for T-cell based therapy," Methods Mol Biol. (2012) 907: 645-66.

Cheson et al., "Recommendations for initial evaluation, staging, and response assessment of hodgkin and non-hodgkin lymphoma: The lugano classification," J Clin Oncol (2014) 32(27):3059-3067.

Chervin et al., "Engineering higher affinity T cell receptors using a T cell display system," J Immunol Methods. (2008) 339(2): 175-84.

Chicaybam et al., "An efficient low cost method for gene transfer to T lymphocytes," PLoS One (2013) 8(3): e60298.

(56) References Cited

OTHER PUBLICATIONS

Cho et al., "Human mammalian cell sorting using a highly integrated micro-fabricated fluorescence-activated cell sorter (microFACS)," Lab Chip (2010) 10: 1567-1573.

Chothia et al.,. "The outline structure of the T-cell alpha beta receptor," EMBO J. (1988) 7(12):3745-55.

Chu et al., "CS1-specific chimeric antigen receptor (CAR)-engineered natural killer cells enhance in vitro and in vivo antitumor activity against human multiple myeloma," Leukemia (2014) 28(4):917-927.

Clackson et al., "Making antibody fragments using phage display libraries," Nature (1991) 252(6336):624-628.

Collins et al., "Chemical approaches to targeted protein degradation through modulation of the ubiquitin-proteasome pathway," Biochem J (2017) 474(7):1127-1147.

Cooper et al., "T-cell clones can be rendered specific for CD19: toward the selective augmentation of the graft-versus-B-lineage leukemia effect," Blood. (2003) 101:1637-1644.

Coustan-Smith et al., "Immunological detection of minimal residual disease in children with acute lymphoblastic leukaemia," Lancet (1998) 351:550-554.

Cronstein et al., Adenosine Modulates the Generation of Superoxide Anion by Stimulated Human Neutrophils via Interaction with a Specific Cell Surface Receptor*a*, Ann. N. Y. Acad Sci (1985) 451(1):291-301.

Crump et al., "Outcomes in refractory diffuse large B-cell lymphoma: results from the international Scholar-1 study," Blood (2017) 130(16):1800-8.

Davila et al., "CD19 CAR-targeted T cells induce long-term remission and B Cell Aplasia in an immunocompetent mouse model of B cell acute lymphoblastic leukemia," PLoS One (2013) 8(4):e61338.

De Felipe et al., "Targeting of proteins derived from self-processing polyproteins containing multiple signal sequences," Trafic (2004) 5(8):616-626.

De Felipe, "Skipping the co-expression problem: the new 2A "Chysel" technology," Genetics Vaccines and Therapy (2004) 2:13.

Dixon et al., "Recent developments in multiplexing techniques for immunohistochemistry," Expert Rev Mol Diagn (2015) 15(9):1171-86.

Eisenhauer et al., "New response evaluation criteria in solid tumors: Revised Recist guilines (version 1.1)," Eur J Cancer (2009) 45(2):228-47.

Fecteau et al. "Lenalidomide inhibits the proliferation of CLL cells via a cereblon/p21(WAF1/Cip1)-dependent mechanism independent of functional p53," Blood (2014) 124(10):1637-1644.

Fedorov et al., "PD-1- and CTLA-4-Based Inhibitory Chimeric Antigen Receptors (iCARs) Divert Off-Target Immunotherapy Responses," Sci Transl Medicine (2013) 5(215):215ra172.

Finger et al., "The human PD-1 gene: complete cDNA, genomic organization, and developmentally regulated expression in B cell progenitors," Gene (1997) 197(102):177-187.

Foon et al., "Immunologic classification of leukemia and lymphoma," Blood (1986) 68(1):1-31.

Garfall et al., "Immunotherapy with chimeric antigen receptors for multiple myeloma," Discov Med. (2014) 17(91): 37-46.

Gattinoni, "Moving T memory stem cells to the clinic," Blood (2013) 121(4):567-8.

Gauthier, "Factors associated with duration of response after CD19-specific CAR-T cell therapy for refractory/relapsed B-cell non-Hodgkin lymphoma," J Clin Oncol (2018) 36 (15 suppl.):7567. Abstract.

Gauthier, "Factors associated with duration of response after CD19-specific CAR-T cell therapy for refractory/relapsed B-cell non-Hodgkin lymphoma," J Clin Oncol (2018) 36 (15 suppl.):7567. Presentation.

Gildener-Leapman et al., "Promising systemic immunotherapies in head and neck squamous cell carcinoma," Oral Oncol (2013) 49(12):1089-1096.

Godin et al., "Microfluidics and photonics for Bio-System-on-a-Chip: a review of advancements in technology towards a microfluidic flow cytometry chip," J Biophoton. (2008) 1(5): 355-376.

Hallek et al., "Guidelines for the diagnosis and treatment of chronic lymphocytic leukemia: a report from the International Workshop on Chronic Lymphocytic Leukemia updating the National Cancer Institute-Working Group 1996 guidelines," Blood (2008) 111(12):5446-5456.

Hausler et al., "Anti-CD39 and anti-CD73 antibodies A1 and 7G2 improve targeted therapy in ovarian cancer by blocking adenosine-dependent immune evasion," Am J Transl Res (2014) 6(2):129-139.

Hay et al., "Factors impacting disease-free survival in adult B cell B-ALL patients achieving MRD-negative CR after CD19 CAR-T cells," J Clin Oncol 36 (15 suppl.):7005. Abstract.

Hay et al., "Factors impacting disease-free survival in adult B cell B-ALL patients achieving MRD-negative CR after CD19 CAR-T cells," J Clin Oncol 36 (15 suppl.):7005. Presentation.

Heipel et al., "Pharmacokinetic, pharmacodynamic and blood analytes associated with clinical response and safety in relapsed/refractry aggressive B-NHL patients treated with JCAR017," Blood (2017) 130 (suppl. 1):2835.

Heipel et al., et al., "Pharmacokinetic, pharmacodynamic and blood analytes associated with clinical response and safety in relapsed/refractry aggressive B-NHL patients treated with JCAR017 (lisocabtagene maraleucel; liso-cel)," poster presented at ASH 2017 Dec. 9-12, 2017.

Hermans et al., "The Vital assay: a versatile fluorometric technique for assessing CTL- and NKT-mediated cytotoxicity against multiple targets in vitro and in vivo," J Immunol Methods (2004) 285(1):25-40.

Hershfield, "PEG-ADA: an alternative to haploidentical bone marrow transplantation and an adjunct to gene therapy for adenosine deaminase deficiency," Hum Mutat (1995) 5(2):107-112.

Holler et al., "In vitro evolution of a T cell receptor with high affinity for peptide/MHC," Proc Natl Acad Sci U S A. (2000) 97(10): 5387-5392.

Holler et al., "TCRs with high affinity for foreign pMHC show self-reactivity," Nat Immunol. Jan. 2003;4(1):55-62.

Honegger et al., "Yet another numbering scheme for immunoglobulin variable domains: an automatic modeling and analysis tool," J Mol Biol (2001) 309(3):657-670.

Huang et al., "DNA transposons for modification of human primary T lymphocytes," Methods Mol Biol (2009) 506: 115-126.

Hudecek et al., "Receptor affinity and extracellular domain modifications affect tumor recognition by ROR1-specific chimeric antigen receptor T cells," Clin Cancer Res (2013) 19(12):3153-3164.

Ito et al., "Identification of a Primary Target of Thalidomide Teratogenicity," Science (2010) 327(5971):1345-1350.

Janeway et al., Immunobiology: The Immune System in Health and Disease, 3rd ED., Current Biology Publications (1997), p. 4:33.

Jin et al., "CD73 on tumor cells impairs antitumor T-cell responses: a novel mechanism of tumor-induced immune suppression," Cancer Res (2010) 70(6):2245-2255.

Johnson et al., "Imaging for staging and response assessment in lymphoma," Radiology 2:323-338.

Johnston, et al., "Biolistic transformation: microbes to mice," Nature (1990) 346: 776-777.

Jores et al., "Resolution of hypervariable regions in T-cell receptor beta chains by a modified Wu-Kabat index of amino acid diversity.," PNAS (1990) 87(23):9138-9142.

Juno Therapeutics, "Multiplex Q-IF Analysis," 8th Annual Meeting Boston Area Imaging and Image Anaylsis Interest Group. May 18, 2018.

Klebanoff et al., "Sorting through subsets: which T-cell populations mediate highly effective adoptive immunotherapy?," J Immunother. (2012) 35(9): 651-660.

Kochenderfer et al., "Treating B-cell cancer with T cells expressing anti-CD19 chimeric antigen receptors," Nature Reviews Clinical Oncology (2013) 10:267-276.

Kochenderfer et al., "Construction and preclinical evaluation of an anti-CD19 chimeric antigen receptor," J. Immunotherapy (2009) 32(7): 689-702.

(56) References Cited

OTHER PUBLICATIONS

Koste et al., "T-cell receptor transfer into human T cells with ecotropic retroviral vectors," Gene Therapy (2014) 21: 533-538.
KOTB, "Bacterial pyrogenic exotoxins as superantigens," Clin Microbiol Rev. (1995) 8(3):411-426.
Kuramitsu et al., "Lenalidomide enhances the function of chimeric antigen receptor T cells against the epidermal growth factor receptor variant III by enhancing immune synapses," Cancer Gene Therapy (2015) 22:487-495.
Kurucz et al., "A bacterially expressed single-chain Fv construct from the 2B4 T-cell receptor," Proc Natl Acad Sci U S A. (1993) 90(9): 3830-3834.
Larson et al., "Defined cell composition and precise control over JCAR017 dose enables identification of relationships between chimeric antigen receptor T cell product attributes, pharmacokinetics, and clinical endpoints in NHL," Cancer Res (2018) 78(13 suppl.):abstract nr 960.
Larson, "Precise control over lisocabtagene maraleucel (liso-cel) dose enables identification of relationships between chimeric antigen receptor T cell product attributes, PK, and clinical endpoints in NHL," Oral presentation at AACR 2018 Apr. 14-18, 2018.
Lefranc et al., "IMGT unique numbering for immunoglobulin and T cell receptor variable domains and Ig superfamily V-like domains," Dev Comp Immunol (2003) 27(1):55-77.
Leone et al., "A2aR antagonists: Next generation checkpoint blockade for cancer immunotherapy," Journal (2015) 13:265-272.
Li et al., "Directed evolution of human T-cell receptors with picomolar affinities by phage display", Nat Biotechnol. (2005) 23(3): 349-354.
Lim et al., "Anti-CD20 monoclonal antibodies: historical and future perspectives," Haematologica (2010) 95(1):135-143.
Ling et al., "B-cell and plasma cell antigens: new and previously defined clusters," Leucocyte typing III. (1987) 302-355.
Lipson et al., "Durable cancer regression off-treatment and effective reinduction therapy with an anti-PD-1 antibody," Clin Cancer Res (2013) 19:462-468.
Liu et al., "Inclusion of Strep-tag II in design of antigen receptors for T-cell immunotherapy," Nature Biotechnology (2016) 34(4):430-434.
Lopez-Girona et al., "Cereblon is a direct protein target for immunomodulatory and antiproliferative activities of lenalidomide and pomalidomide," Leukemia (2012) 26:2326-2335.
Maloney et al., "Preliminary safety profile of the CD19-directed defined composition CAR T cell product JCAR017 in relapsed/refractory aggressive B-NHL patients: Potential for outpatient administration," Blood (2017) 131 (suppl. 1):1552.
Maloney et a., "Safety profile of the CD19-directed defined composition CAR T cell product JCAR017 (lisocabtagene maraleucel; liso-cel) in relapsed/refractory aggressive B-NHL patients: Potential for outpatient administration," poster presented at ASH 2017 Dec. 9-12, 2017.
Manuri et al., "piggyBac transposon/transposase system to generate CD19-specific T cells for the treatment of B-lineage malignancies," Hum Gene Ther (2010) 21(4): 427-437.
Martin et al., "Modeling antibody hypervariable loops: a combined algorithm," PNAS (1989) 86(23):9268-9272.
Menzies et al., "New combinations and immunotherapies for melanoma: latest evidence and clinical utility," Ther Adv Med Oncol (2013) 5:278-285.
Miller et al., "Improved retroviral vectors for gene transfer and expression," BioTechniques (1989) 7:980-990.
Miller et al., "Retrovirus packaging cells," Human Gene Therapy (1990) 1:5-14.
Millrine et al., "A Brighter Side to Thalidomide: Its Potential Use in Immunological Disorders," Trends Mol Med (2017) 23(4):348-364.
Miyagishi et al., "U6 promoter-driven siRNAs with four uridine 3' overhangs efficiently suppress targeted gene expression in mammalian cells," Nat Biotechnol (2002) 19:497-500.
Monney et al., "Th1-specific cell surface protein Tim-3 regulates macrophage activation and severity of an autoimmune disease," Nature (2002) 415:536-541.
NCT02631044: Study Evaluating the Safety and Pharmacokinetics of JCAR017 in B-cell Non-Hodgkin Lymphoma (Transcend-NHL-001).
Ngiow et al., "Anti-TIM3 Antibody Promotes T Cell IFN-γ-Mediated Antitumor Immunity and Suppresses Established Tumors," Cancer Res (2011) 71(10):3540-3551.
Ohta et al., "A2A adenosine receptor protects tumors from antitumor T cells," Proc Natl Acad Sci U S A (2006) 103:13132-13137.
Oshima, K. et al., "[Immunomodulatory drugs (IMiDs)]" Nihon Rinsho., 72(6):1130-5 (2014).
Otahal et al., "Lenalidomide enhances antitumor functions of chimeric antigen receptor modified T cells," Oncoimmunology (2016) 5(4):e1115940.
Ott et al., "CTLA-4 and PD-1/PD-L1 Blockade: New Immunotherapeutic Modalities with Durable Clinical Benefit in Melanoma Patients," Clin Cancer Res (2013) 19:5300-9.
Pardoll, "The blockade of immune checkpoints in cancer immunotherapy," Nature Reviews Cancer (2012) 12:252-264.
Park et al., "Treating cancer with genetically engineered T cells," Trends Biotechnol (2011) 29(11):550-557.
Parra et al., "Validation of multiplex immunofluorescence panels using multispectral microscopy for immune-profiling of formalin-fixed and paraffin-embedded human tumor tissues," Sci Rep (2017) 7(1):13380.
Pinna et al., "Novel investigational adenosine A2A receptor antagonists for Parkinson's disease," Expert Opin Investig Drugs (2009) 18:1619-1631.
Portolano et al., "Lack of promiscuity in autoantigen-specific H and L chain combinations as revealed by human H and L chain "roulette"," J Immunol (1993) 150(3):880-887.
Radvanyi et al., "Antagonist Antibodies to PD-1 and B7-H1 (PD-L1) in the Treatment of Advanced Human Cancer-Letter," Clin Cancer Res (2013) 19:5541.
Ramsborg et al., "JCAR017 is a defined composition CAR T cell product with product and process controls that deliver precise doses of CD4 and CD8 CAR T cell to patients with NHL," Blood (2017) 130(suppl. 1):4471.
Ramsborg et al., "JCAR017 (licocabtagene maraleucel; liso-cel) is a defined composition CAR T cell product with product and process controls that deliver precise doses of CD4 and CD8 CAR T cell to patients with NHL," poster presentation at ASH 2017 Dec. 9-12, 2017.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3:319-338.
Robert et al., "What is the role of cytotoxic T lymphocyte-associated antigen 4 blockade in patients with metastatic melanoma?" Oncologist (2009) 14:848-861.
Roberts et al., "Inhibition by adenosine of reactive oxygen metabolite production by human polymorphonuclear leucocytes," Biochem J (1985) 227:669.
Rosenberg, "Cell transfer immunotherapy for metastatic solid cancer—what clinicians need to know," Nat Rev Clin Oncol (2011) 8(10):577-585.
Sadelain et al., "The basic principles of chimeric antigen receptor (CAR) design," Cancer Discov (2013) 3(4):388-398.
Scarpa et al., "Characterization of recombinant helper retroviruses from moloney-based vectors in ecotropic and amphotropic packaging cell lines," Virology (1991) 180(2):849-852.
Schlueter et al., "Specificity and Binding Properties of a Single-chain T Cell Receptor," J Mol Biol (1996) 859-869.
Schrier et al., "The effects of adenosine agonists on human neutrophil function," J Immunol (1986) 137:3284.
Schuler et al., SYFPEITHI, Database for Searching and T-Cell Epitope Prediction. in Immunoinformatics Methods in Molecular Biology, (2007) 409(1): 75-93.
Sharma et al., "Efficient sleeping beauty DNA transposition from DNA minicircles," Molec Ther Nucl Acids (2013) 2, e74.

(56) References Cited

OTHER PUBLICATIONS

Shinohara et al., "Structure and Chromosomal Localization of the Human PD-1 Gene (PDCD1)," Genomics (1995) 23:704-706.

Siddiqi et al., "Patient characteristics and pre-infusion biomarkers of inflammation correlate with clinical outcomes after treatment with the defined composition, CD19-targeted CAR T cell product, JCAR017," Blood (2017) 130(suppl. 1):193.

Siddiqi et al., "Patient characteristics and pre-infusion biomarkers of inflammation correlate with clinical outcomes after treatment with the defined composition, CD19-targeted CAR T cell product, JCAR017 (lisocabtagene maraleucel; liso-cel)," oral presentation at ASH 2017 Dec. 9-12, 2017.

Singh et al., "ProPred: prediction of HLA-DR binding sites," Bioinformatics. (2001) 17(12): 1236-1237.

Sitkovsky et al., "Hostile, hypoxia-A2-adenosinergic tumor biology as the next barrier to overcome for tumor immunologists," Cancer Immunol Res (2014) 2(7):598-605.

Sommermeyer et al., "Fully human CD19-specific chimeric antigen receptors for T-cell therapy," Leukemia (2017) 31(10):2191-9.

Soo Hoo et al., "Characterization of a single-chain T-cell receptor expressed in *Escherichia coli*," Proc Natl Acad Sci U S A. (1992) 89(10): 4759-4763.

Sutherland "Identifying Biomarkers Associated With Clinical Outcomes of Lisocabtagene Maraleucel (Liso-Cel) in NHL: An Integrated Approach," oral presentation presented at EHA 2018 on Jun. 14, 2018.

Swanson et al., "Predicting Clinical Response and Safety of JCAR017 in B-NHL Patients: Potential Importance of Tumor Microenvironment Biomarkers and CAR T-Cell Tumor Infiltration," Blood (2017) 130 (suppl. 1):194.

Swanson et al., "Predicting clinical response and safety of JCAR017 (lisocabtagene maraleucel; liso-cel) in B-NHL patients: Potential importance of tumor microenvironment biomarkers and CAR T cell tumor infiltration," oral presentation presented at ASH 2017 on Dec. 9, 2017.

Swerdlow et al., "The 2016 revision of the World Health Organization classification of lymphoid neoplasms," Blood (2016) 127(20):2375-90.

Tai et al., "Antibody-Based Therapies in Multiple Myeloma," Bone Marrow Research (2010) vol. 2011. Article ID 924058.

Terakura et al., "Generation of CD19-chimeric antigen receptor modified CD8+ T cells derived from virus-specific central memory T cells," Blood (2012) 1:72-82.

Themeli et al., "Generation of tumor-targeted human T lymphocytes from induced pluripotent stem cells for cancer therapy," Nat Biotechnol. (2013) 31(10): 928-933.

Tsujikawa et al., "Quantitative multiplex immunohistochemistry reveals myeloid-inflamed tumor-immune complexity associated with poor prognosis," Cell Rep (2017) 19(1):203-17.

Tsukahara et al., "CD19 target-engineered T-cells accumulate at tumor lesions in human B-cell lymphoma xenograft mouse models," Biochem Biophys Res Commun (2013) 438(1): 84-89.

Turtle et al., "Engineered T cells for anti-cancer therapy," Curr. Opin. Immunol. (2012) 24(5): 633-39.

Van den Neste et al., "Outcome of patients with relapsed diffuse large B-cell lymphoma who fail second-line salvage regimens in the International Coral study," Bone Marrow Transplant (2016) 51(1):51-7.

Van Tendeloo et al., "High-level transgene expression in primary human T lymphocytes and adult bone marrow CD34+ cells via electroporation-mediated gene delivery," Gene Therapy (2000) 7(16): 1431-1437.

Ventana Medical Systems, "Ventana Discovery Ultra Accelerate your research," 2010.

Verhoeyen et al., "Lentiviral vector gene transfer into human T cells," Methods Mol Biol. (2009) 506: 97-114.

Wada et al., "Sequencing CTLA-4 blockade with cell-based immunotherapy for prostate cancer," J Transl Med (2013) 11:89.

Wang et al., "Phenotypic and functional attributes of lentivirus-modified CD19-specific human CD8+ central memory T cells manufactured at clinical scale," J Immunother. (2012) 35(9):689-701.

Weber et al., "Review: anti-CTLA-4 antibody ipilimumab: case studies of clinical response and immune-related adverse events," Oncologist (2007) 12(7):864-872.

Wu et al., "Adoptive T-cell therapy using autologous tumor-infiltrating lymphocytes for metastatic melanoma: current status and future outlook," Cancer (2012) 18(2): 160-175.

Wulfing et al., "Correctly folded T-cell receptor fragments in the periplasm of *Escherichia coli*. Influence of folding catalysts," J Mol Biol. (1994) 242(5): 655-669.

Zhang et al., "CD73: A Novel Target for Cancer Immunotherapy," Cancer Res (2010) 70(16):6407-6411.

Zheng et al., "*Drosophila* Ten-m and Filamin Affect Motor Neuron Growth Cone Guidance," PLoS One (2011) 6(6):e21146.

Avdic et al., "Human Cytomegalovirus-Encoded Human Interleukin-10 (IL-10) Homolog Amplifies Its Immunomodulatory Potential by Upregulating Human IL-10 in Monocytes," J Virol. (2016) 90(8): 3819-3827.

Bishnoi et al. "Serum interleukin (IL)-15 as a biomarker of Alzheimer's disease." *PLoS One* 10.2 (2015): e0117282 (14 pages).

Brudno et al., "Toxicities of chimeric antigen receptor T cells: recognition and management," Blood (2016) 127(26):3321-3330.

Butler et al., "Human cell-based artificial antigen-presenting cells for cancer immunotherapy," Immunol Rev. (2014) 257(1):191-209.

Christiansen et al., "Elevate serum levels of soluble ICAM-1 in non-Hodgkins lymphomas correlate with tumour burden, disease activity and other prognostic markers," Br J Haematology (1996) pp. 639-646.

Clinical Trial Study Record No. NCT02445248, "Study of Efficacy and Safety of CTL019 in Adult DLBCL Patients," (Juliet), May 15, 2015 (9 pages).

Clinical Trial Study Record No. NCT02435849, "Study of Efficacy and Safety of CTL019 in Pediatric ALL Patients," (Eliana), May 6, 2015 (11 pages).

Davila et al., "Efficacy and toxicity management of 19-28z CAR T cell therapy in B cell acute lymphoblastic leukemia," Science Translational Medicine (2014) 6(224):224ra25 (10 pages).

Franke et al., "Antibodies against CD20 or B-cell receptor induce similar transcription patterns in human lymphoma cell lines," PLoS One.(2011) 6(2): e16596 (11 pages).

Imai et al. "Chimeric receptors with 4-1BB signaling capacity provoke potent cytotoxicity against acute lymphoblastic leukemia." *Leukemia* 18.4 (2004): 676-684.

Kahl et al., "Advances and issues in mantle cell lymphoma research: report of the 2014 mantle cell lymphoma consortium workshop," Leukemia & Lymphoma (2015) 56(9):2505-2511.

Kandalaft et al., "A phase I clinical trial of adoptive transfer of folate receptor-alpha redirected autologous T cells for recurrent ovarian cancer," J Transl Med (2012) 10:157 (10 pages).

Klaver et al., "Adoptive T-cell therapy: A need for standard immune monitoring," Immunotherapy (2015) 7(5):513-533.

Kochenderfer et al, "A phase I clinical trial of treatment of B-cell malignancies with autologous anti-CD19-CAR-Transduced T Cells," Blood (2010) 116(21):1179-1180 Abstract 2865.

Kochenderfer et al., "B-cell depletion and remissions of malignancy along with cytokine-associated toxicity in a clinical trial of anti-CD19 chimeric-antigen-receptor-transduced T cells," Blood (2012) 119(12):2709-2720.

Lee et al., "T cells expressing CD19 chimeric antigen receptors for acute lymphoblastic leukaemia in children and yound adults: a phase 1 dose escalation trial," The Lancet (Feb. 2015) 385(9967): 517-528.

Locke et al., "Phase 1 Clinical Results of the ZUMA-1 (KTE-C19-101) Study: a Phase 1-2 Multi-Center Study Evaluating the Safety and Efficacy of Anti-CD19 CAR T Cells (KTE-C19) in Subjects with Refractory Aggressive Non-Hodgkin Lymphoma (NHL)," Blood (Dec. 2015) 126:3991 (6 pages).

(56) References Cited

OTHER PUBLICATIONS

Logan et al., "Minimal residual disease quantification using consensus primers and high-throughput IGH sequencing predicts post-transplant relapse in chronic lymphocytic leukemia," Leukemia (2013) 27(8): 1659-1665.
Maude et al., "Chimeric antigen receptor T cells for sustained remissions in leukemia," N Eng J Med (2014) 371(16):1507-1517.
Meisenberg et al., "Reduced charges and costs associated with outpatient autologous stem cell transplantation," Bone Marrow Transplant. (1998) 21(9):927-32.
Morozova et al., Prospectives of T-cells genetic programming in adoptive immunotherapy of malignancies, 2016, No. 3 (25), p. 23-28.
Myers et al., "Perspectives on outpatient administration of CAR-T cell therapy in aggressive B-cell lymphoma and acute lymphoblastic leukemia," J Immunother Cancer. (2021) 9(4):e002056 (10 pages).
Park et al. "Phase I trial of autologous CD19-targeted CAR-modified T cells as consolidation after purine analog-based first-line therapy in patients with previously untreated CLL," Blood (Nov. 2013) 122(21):874 (5 pages).
Porter et al. "Chimeric antigen receptor T cells persist and induce sustained remissions in relapsed refractory chronic lymphocytic leukemia." *Science translational medicine* 7.303 (2015): 303ra139-303ra139 (13 pages).
Porter et al., "Chimeric antigen receptor-modified T cells in chronic lymphoid leukemia," N Engl J Med. Aug. 25, 2011;365(8):725-33.
Pott et al., "MRD detection in B-cell non-hodgkin lymphomas using Ig gene rearrangements and chromosomal translocations as targets for real-time quantitative PCR," Methods Mol Biol (2013) 971:175-200.
Ritchie et al., "Persistence and efficacy of second generation CAR T cell against the LeY antigen in acute myeloid leukemia," Mol Ther (2013) 21(11):2122-2129.
Slovin et al., "Adoptive Transfer of Autologous T Cells Targeted to Prostate Specific Membrane Antigen (PSMA) for the Treatment of Castrate Metastatic Prostate Cancer (CMPC) DOD," Grant Log# PC081632, https://cdmrp.army.mil/pubs/video/pc/pdf/slovin_poster.pdf, 2013, poster presentation.
Stiff et al., "Autologous hematopoietic stem cell transplants that utilize total body irradiation can safely be carried out entirely on an outpatient basis," Bone Marrow Transplant. (2006) 38(11):757-64.
Sommermeyer et al., "Chimeric antigen receptor-modified T cells derived from defined CD8+ and Cd4+ subsets confer superior antitumor reactivity in vivo," Leukemia (Feb. 2016) 30(2): 492-500.
Teachey et al., "Biomarkers Accurately Predict Cytokine Release Syndrome (CRS) after Chimeric Antigen Receptor (CAR) T Cell Therapy for Acute Lymphoblastic Leukemia (ALL)," Blood (2015) 126(23):1334 (2 pages).
Teachey et al., "Identification of predictive biomarkers for cytokine release syndrome after chimeric antigen receptor T-cell therapy for acute lymphoblastic leukemia," Cancer Discovery (2016) 6(6):664-679.
Turtle et al., "CD19 CAR-T cells of defined CD4+:CD8+ composition in adult B cell ALL patients," J Clin Invest (2016) 126(6):2123-38.
Turtle et al., "CD19 CAR-T Cells Are Highly Effective in Ibrutinib-Refractory Chronic Lymphocytic Leukemia," Blood (Jan. 2016) 128(22): 56 (2 pages).
Turtle et al. "Anti-CD19 chimeric antigen receptor-modified T Cell therapy for B cell non-Hodgkin lymphoma and chronic lymphocytic leukemia: fludarabine and cyclophosphamide lymphodepletion improves in vivo expansion and persistence of CAR-T cells and clinical outcomes." *Blood* 126.23 (2015): 184 (6 pages).
Turtle et al. "Biomarkers of cytokine release syndrome and neurotoxicity after CD19 CAR-T cells and mitigation of toxicity by cell dose." *Blood* 128.22 (2016): 1852 (2 pages).
Turtle et al., "Durable molecular remissions in chronic lymphocytic leukemia treated with CD19-specific chimeric antigen receptor-modified T cells after failure of ibrutinib," J Clin Oncol (2017) 35(26):3010-20.
Turtle et al., "Immunotherapy of non-Hodgkin's lymphoma with a defined ratio of CD8+ and CD4+ CD19-specific chimeric antigen receptor-modified T cells," Sci Transl Med (2016) 8(355):355ra116 (13 pages).
Turtle et al., "Rate of durable complete response in ALL, NHL, and CLL after immunotherapy with optimized lymphodepletion and defined composition CD19 CAR-T cells," 2016 ASCO meeting abstract 102, J. Clin. Oncol. (May 2016) 34(15):Suppl. Abstr 102 (4 pages).
Bergamaschi et al., "Circulating IL-15 exists as heterodimeric complex with soluble IL-15R$\alpha$ in a human and mouse serum," Blood. 2012; 120(1): e1-e8 (Year: 2012).
Chen et al., "Anti-CD19 Chimeric Antigen Receptor T Cells Improve Responses to Chemotherapy-Refractory Mantle Cell Lymphoma: A Case Report." Blood (2016) 128(22):5393 (3 pages).
Geyer et al., Updated results: phase I trial of autologous CD19-targeted CAR T cells in patients with residual CLL following initial purine analog-based therapy, J. Clin. Oncology 34(Suppl 15); 7526; doi: 10.1200/JCO.2016.34.15_suppl.7526; available online May 20, 2016.
Kimbrel et al., "Next-generation stem cells—ushering in a new era of cell-based therapies," Nature Reviews Drug Discovery (2020) 19:463-479.
Lee et al., T cells expressing CD19 chimeric antigen receptors for acute lymphoblastic leukaemia in children and young adults: a phase 1 dose-escalation trial, The Lancet, vol. 385, No. 9967, pp. 517-528.
Makita et al., "Clinical development of anti-CD19 chimeric antigen receptor T-cell therapy for B-cell non-Hodgkin lymphoma," Cancer Science (2017) 108(6):1109-1118.
Maus et al., Chimeric Antigen Receptor T-Cell Therapy for the Community Oncologist, The Oncologist 21: 608-617, 2016.
Santomasso et al., "The other side of CAR T-cell therapy: cytokine release syndrome, neurologic toxicity, and financial burden," Am Soc Clin Oneal Educ Book, 2019; 39: 433-444.
Siddiqi et al., "Rapid MRD-Negative Responses in Patients with Relapsed/Refractory CLL Treated with Liso-Cel, a CD19-Directed CAR T-Cell Product: Preliminary Results from Transcend CLL 004, a Phase 1/2 Study Including Patients with High-Risk Disease Previously Treated with Ibrutinib," Blood, Nov. 29, 2018, vol. 132, No. Supplement 1, 300 (9 pages).
Fraietta et al., "Ibrutinib enhances chimeric antigen receptor T-cell engraftment and efficacy in leukemia," Blood (Mar. 2016) 127(9):1117-1127.
Kochenderfer et al., "Chemotherapy-refractory diffuse large B-cell lymphoma and indolent B-cell malignancies can be effectively treated with autologous T cells expressing an anti-CD19 chimeric antigen receptor," J Clin Oncol (Feb. 2015) 33(6):540-549.
Komarova et al., "Evolution of ibrutinib resistance in chronic lymphocytic leukemia (CLL)," Proc Natl Acad Sci USA (2014) 111(38):13906-13911.
Law et al., "What does it take to bind CAR?," Mol Ther. (2005) 12(4):599-609.
Mount et al., "Cell-based therapy technology classifications and translational challenges," Philos Trans R Soc Lond B Biol Sci. (2015) 370(1680): 20150017 (16 pages).
Neelapu et al., "Chimeric antigen receptor T-cell therapy-assessment and management of toxicities," Nat Rev Clin Oncol. (2018) 15(1):47-62.
Ruella et al., "The Addition of the BTK Inhibitor Ibrutinib to Anti-CD19 Chimeric Antigen Receptor T Cells (CART19) Improves Responses against Mantle Cell Lymphoma," Clin Cancer Res (Jun. 2016) 22(11):2684-2696.
Tirkes et al., "Response criteria in oncologic imaging: review of traditional and new criteria," Radiographics. (2013) 33(5): 1323-41.
Turtle et al., "Addition of Fludarabine to Cyclophosphamide Lymphodepletion Improves In Vivo Expansion of CD19 Chimeric Antigen Receptor-Modified T Cells and Clinical Outcome in Adults with B Cell Acute Lymphoblastic Leukemia," Blood (2015) 126(23):3773 (6 pages).
Turtle et al., "Therapy of B Cell Malignancies with CD19-Specific Chimeric Antigen Receptor-Modified T Cells of Defined Subset Composition," Blood (2014) 124(21):384 (7 pages).

(56) References Cited

OTHER PUBLICATIONS

U.S. Appl. No. 18/510,460, filed Nov. 15, 2023, by Albertson et al. (Copy not submitted herewith pursuant to the waiver of 37 C.F.R. § 1.98(a)(2)(iii) issued by the Office on Sep. 21, 2004).
Brosseau et al., "The immunomodulatory drug lenalidomide restores a vitamin D sensitive phenotype to the vitamin D resistant breast cancer cell line MDA-MB-231 through inhibition of BCL-2: potential for breast cancer therapeutics," Apoptosis (2012) 17:164-173.
Geyer et al., "Implications of Concurrent Ibrutinib Therapy on CART-Cell Manufacturing and Phenotype and on Clinical Outcomes Following CD19-Targeted CAR T-Cell Administration in Adults with Relapsed/Refractory CLL," Blood 128(22):58; available Dec. 2, 2016, 5 pages.
Human Body Weight, Wikipedia, en.wikipedia.org/wiki/Human_body_weight; last visited Dec. 10, 2021, 17 pages.
Janssen Pharmaceutical K.K., "Submission of application for additional indication of "Imbruvica (R)" for untreated chronic lymphocytic leukemia (including small lymphocytic lymphoma)," [online] Published Nov. 21, 2017, 4 pages. <https://www.janssen.com/japan/press-release/20171121> English translation provided.
Jones et al., "Preliminary Results of a Phase 2, Open-Label Study of Venetoclax (ABT-199/GDC-0199) Monotherapy in Patients with Chronic Lymphocytic Leukemia Relapsed after or Refractory to Ibrutinib or Idelalisib Therapy," Blood 126(23):715; available Dec. 3, 2015, 4 pages.
Jones et al., "Venetoclax activity in CLL patients who have relapsed after or are refractory to ibrutinib or idelalisib," J. Clin. Oncology 34(15 Suppl), doi: 10.1200/JCO.2016.34.15_suppl.7519; available online May 20, 2016, 4 pages.
Tang et al., "Opportunities and Challenges of Chimeric Antigen Receptor Modified T Cell Immunotherapy," PLA Journal of Medicine (2015) 27(1):12-25. English translation provided.
Tao et al., "Interleukin-6 up-regulates the expression of interleukin-15 is associated with MAPKs and PI3-K signaling pathways in the human keratinocyte cell line, HaCaT," Mol Biol Rep. (2012) 39(4):4201-5.
Vairy et al., "CTL019 (tisagenlecleucel): CAR-T therapy for relapsed and refractory B-cell acute lymphoblastic leukemia," Drug Des Devel Ther. (2018) 12:3885-3898.
Sheth et al., "Taming the beast: CRS and ICANS after CAR T-cell therapy for All," Bone Marrow Transplant (Mar. 2021) 56(3):552-566.
Tang et al., "The global landscape of cancer cell therapy," Nat Rev Drug Discov (2018) 17(7):465-466.
Yan et al., "Characteristics and Risk Factors of Cytokine Release Syndrome in Chimeric Antigen Receptor T Cell Treatment," Front Immunol (Feb. 23, 2021) 12:611366, 8 pages.

\* cited by examiner

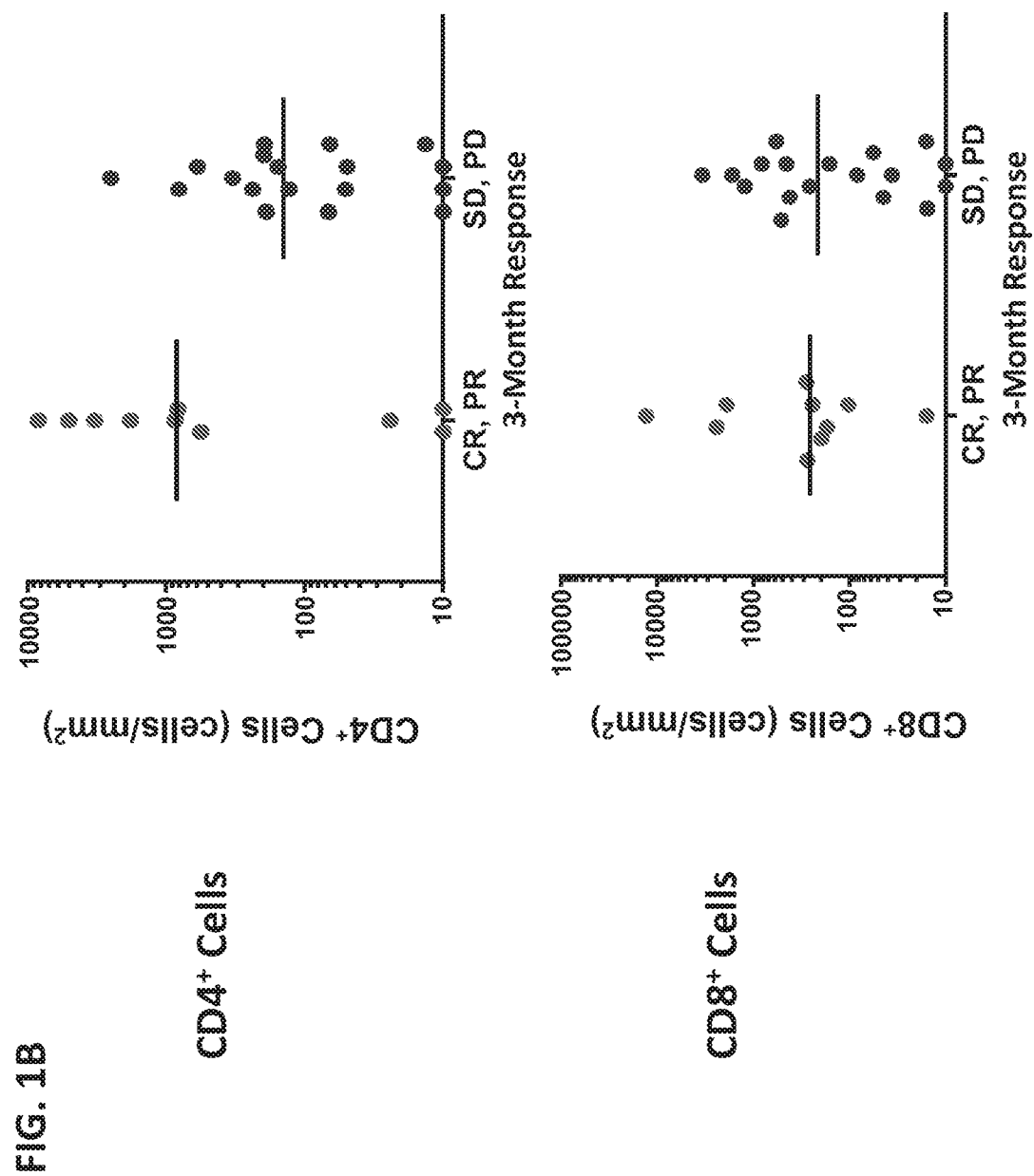

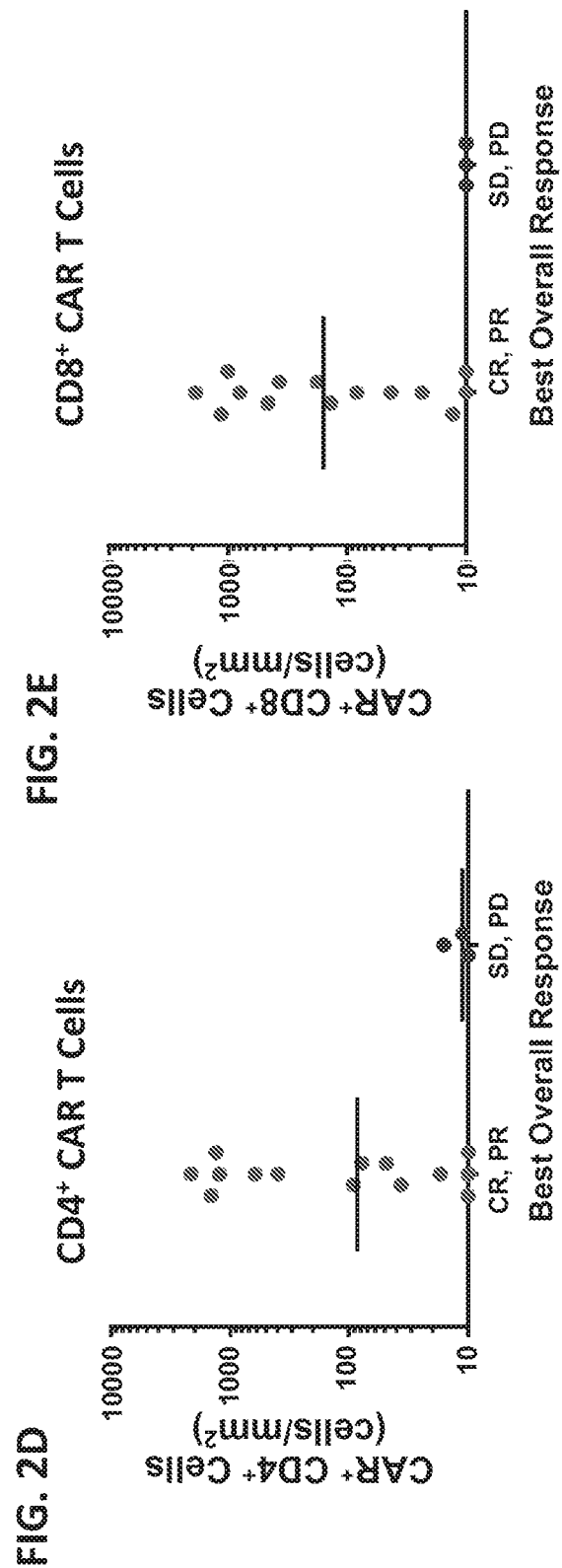

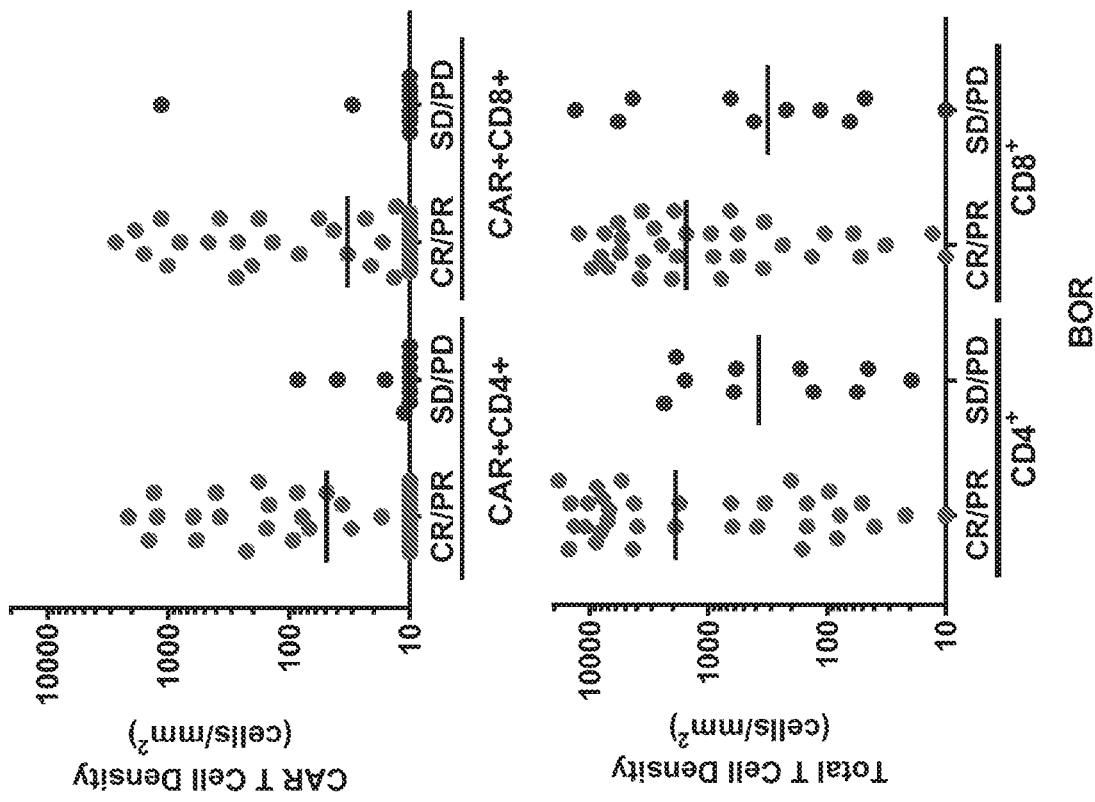

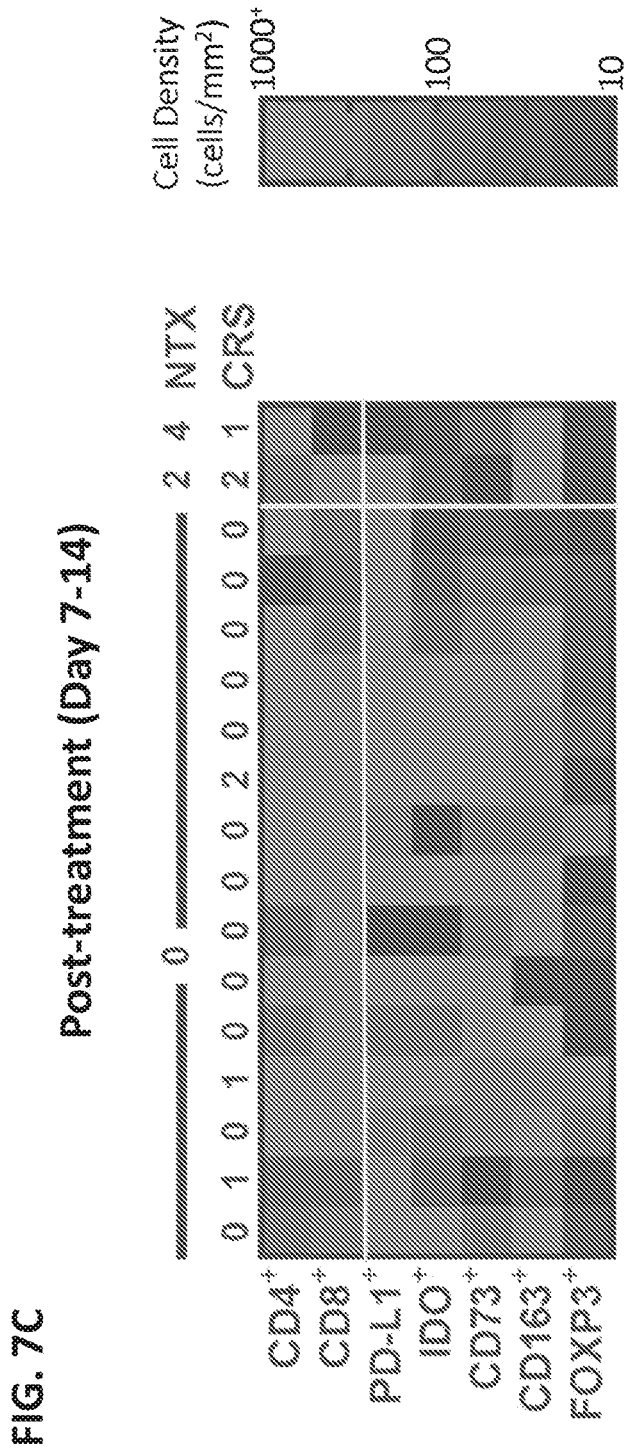

METHODS OF ASSESSING OR MONITORING A RESPONSE TO A CELL THERAPY

CROSS-REFERENCE TO RELATED APPLICATIONS

This application is a National Stage application under 35 U.S.C. § 371 of International Application No. PCT/US2018/058596, filed on Oct. 31, 2018 which claims priority from U.S. provisional patent application 62/580,430, filed Nov. 1, 2017, entitled "METHODS OF ASSESSING OR MONITORING A RESPONSE TO A CELL THERAPY," U.S. provisional patent application 62/596,733, filed Dec. 8, 2017, entitled "METHODS OF ASSESSING OR MONITORING A RESPONSE TO A CELL THERAPY," U.S. provisional patent application 62/673,825, filed May 18, 2018, entitled "METHODS OF ASSESSING OR MONITORING A RESPONSE TO A CELL THERAPY," and U.S. provisional patent application 62/685,250, filed Jun. 14, 2018, entitled "METHODS OF ASSESSING OR MONITORING A RESPONSE TO A CELL THERAPY," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042014400SeqList.txt, created Apr. 22, 2020, which is 36,058 bytes in size. The information in the electronic format of the Sequence Listing is incorporated by reference in its entirety.

FIELD

The present disclosure provides methods and articles of manufacture for use with cell therapy for the treatment of diseases or conditions, e.g., cancer, including for predicting or assessing likelihood of the subject responding to a therapy, such as a cell therapy, e.g., a chimeric antigen receptor (CAR) T cell therapy. In some aspects, the assessing is based on detecting certain biomarkers of immune cells associated with and/or that correlate with response following administration of the therapy. The methods generally involve detecting a marker by assaying a biological sample from a subject that is a candidate for treatment, optionally with a cell therapy, to determine if the subject is likely to respond to the therapy. The present disclosure also provides methods for treating a subject having a disease or condition according to a particular treatment regimen, in some cases involving administration of the cell therapy, based on assessment the biomarker. Also provided herein are reagents and kits for performing the methods.

BACKGROUND

Various methods are available for adoptive cell therapy using engineered cells expressing recombinant receptors, such as chimeric antigen receptor (CARs). Improved methods are needed, for example, to predict and monitor response to administered cells of the therapy. Provided are methods, kits and articles of manufacture that meet such needs.

SUMMARY

Provided are methods of assessing likelihood of a response following administration of a cell therapy, the method including assessing a biological sample for a frequency of CD4+ immune cells, wherein the biological sample is obtained from a subject that is a candidate for receiving a cell therapy for treatment of a disease or condition prior to receiving a cell therapy; and comparing the frequency to a threshold value, thereby determining a likelihood that a subject will achieve a response when treated with the cell therapy. Also provided are methods of selecting a subject for treatment, the method including assessing a biological sample for a frequency of CD4+ immune cells, wherein the biological sample is from a subject that is a candidate for treatment with a cell therapy, said cell therapy optionally containing a dose or composition of genetically engineered cells expressing a recombinant receptor; and the biological sample is obtained from the subject prior to administering the cell therapy; and selecting a subject in which the frequency of CD4+ immune cells in the sample is at or above a threshold value, thereby identifying a subject that likely to achieve a response when treated with the cell therapy.

In some embodiments, the assessing is performed by contacting a biological sample with one or more reagent capable of detecting CD4+ immune cells. In some embodiments, the biological sample is a tumor sample, optionally a tumor biopsy sample. In some embodiments, the immune cells are or contain myeloid cells, T helper cells, monocytes, macrophages, or dendritic cells. In some embodiments, the immune cells are or contain T cells. In some embodiments, the CD4+ immune cells are detected using immunoassay, in situ hybridization, immunohistochemistry, multiplexed immunohistochemistry, or 5-plex immunofluorescent immunohistochemistry.

In some embodiments, the response is a complete response (CR) or partial response (PR). In some embodiments, the response is durable. In some examples, the response is durable for greater than 3 months, 4 months, 5 months, or 6 months.

In some of any such embodiments, the subject is a human.

In some embodiments, the cell therapy contains cells engineered to express a recombinant receptor.

Provided are methods of assessing likelihood of a response following administration of a cell therapy, the method including assessing a biological sample that is a tumor biopsy sample for a frequency of CD4+ immune cells, wherein the biological sample is obtained from a subject that is a candidate for receiving a cell therapy for treatment of a cancer prior to receiving a cell therapy, and the CD4+ immune cells are detected using immunohistochemistry; and comparing the frequency to a threshold value, thereby determining a likelihood that a subject will achieve a response that is a complete response (CR) or a partial response (PR), optionally the response that is durable for greater than 3 months, 4 months, 5 months, or 6 months, when treated with the cell therapy.

Also provided are methods of selecting a subject for treatment including assessing a biological sample that is a tumor biopsy sample for a frequency of CD4+ immune cells, wherein the biological sample is from a subject that is a candidate for treatment with a cell therapy, said cell therapy optionally including a dose or composition of genetically engineered cells expressing a recombinant receptor; the biological sample is obtained from the subject prior to administering the cell therapy; and the CD4+ immune cells are detected using immunohistochemistry; and selecting a subject in which the frequency of CD4+ immune cells in the sample is at or above a threshold value, thereby identifying a subject that likely to achieve a response that is a complete response (CR) or a partial response (PR), optionally the response is durable for greater than 3 months, 4 months, 5 months, or 6 months, when treated with the cell therapy.

In some embodiments, the subject is likely to achieve a response when treated with the cell therapy if the frequency of CD4+ cells is at or above the threshold value; or the subject is not likely to achieve a response when treated with the cell therapy if the frequency of CD4+ cells is below the threshold value. In some embodiments, the threshold level is within 25%, within 20%, within 15%, within 10% or within 5% and/or is within one or two standard deviation(s) below the median or mean frequency of CD4+ immune cells in samples obtained from a group of subjects after the initiation of administration of the cell therapy, wherein each of the subjects of the group went on to achieve a response after administration of the cell therapy. In some embodiments, the threshold level is within 25%, within 20%, within 15%, within 10% or within 5% and/or is within one or two standard deviation(s) below the median or mean frequency of CD4+ immune cells in samples obtained from a group of subjects after the initiation of administration of the cell therapy, wherein each of the subjects of the group went on to achieve a complete response or a partial response after administration of the cell therapy, optionally wherein the response achieved by the group of subjects is durable at 3 months.

In some examples, the threshold value of CD4+ immune cells is determined based on a median value or frequency of CD4+ immune cells observed from a group of subjects that achieved a response after administration of the cell therapy. In some embodiments, the response achieved by the group of subjects is CR or PR. In some embodiments, the response is durable at 3 months. In some of any such embodiments, the threshold level is within 25%, within 20%, within 15%, within 10% or within 5% and/or is within a standard deviation above the median or mean frequency of CD4+ immune cells in samples obtained from a group of subjects after the initiation of administration of the cell therapy, wherein each of the subjects of the group went on to exhibit stable disease (SD) and/or progressive disease (PD). In some embodiments, the threshold value of CD4+ immune cells is or is greater than about 4%, 5%, 6%, 7%, or 8% CD4+ immune cells of the total cells in the biological sample; or the threshold value of CD4+ immune cells is greater than about 100 cells/mm$^2$, 200 cells/mm$^2$, 300 cells/mm$^2$, 400 cells/mm$^2$, 500 cells/mm$^2$, 600 cells/mm$^2$, 700 cells/mm$^2$, 800 cells/mm$^2$, 900 cells/mm$^2$ or 1000 cells/mm$^2$ in the biological sample. In some embodiments, the threshold value of CD4+ immune cells of the total cells is or is greater than about 4%, 5%, 6%, 7%, or 8% CD4+ immune cells in the cellular composition of the biological sample. In some embodiments, the frequency is based on or is a density of the CD4+ immune cells. In some embodiments, the frequency is based on or is a density of the cells measured as CD4+ immune cells/mm$^2$.

In some embodiments, if subject is indicated as likely to achieve a response, selecting the subject for administration of a therapeutic regimen, the therapeutic regimen including administering to the subject the cell therapy, optionally at a non-reduced dose, or the cell therapy, wherein administration of the cell therapy does not include administering, prior to or concurrently with administering the cell therapy, an agent or treatment capable of stimulating, amplifying, potentiating, and/or enhancing an anti-tumor immune response, wherein administration of the agent is to be administered (i) prior to, (ii) within one, two, or three days of, and/or (iii) concurrently with the initiation of administration of the cell therapy to the subject. In some embodiments, if the subject is indicated as not likely to achieve a response, selecting the subject for administration of a therapeutic regimen, the therapeutic regimen including administering to the subject an agent or other treatment capable of stimulating, amplifying, potentiating, and/or enhancing an anti-tumor immune response and the cell therapy, wherein administration of the agent is to be administered (i) prior to, (ii) within one, two, or three days of, and/or (iii) concurrently with the initiation of administration of the cell therapy to the subject, the cell therapy at an increased dose and/or administering an additional dose of the cell therapy; or an alternative therapeutic treatment other than the cell therapy.

In some aspect, the agent or other treatment is or is selected from the group consisting of: an immune-inhibitory molecule, is or contains an immune checkpoint molecule or member of an immune checkpoint pathway and/or is or contains a modulator of an immune checkpoint molecule or pathway. In some examples, the immune checkpoint molecule or pathway is or contains PD-1, PD-L1, PD-L2, CTLA-4, LAG-3, TIM3, VISTA, an adenosine receptor, CD73, CD39, adenosine 2A Receptor (A2AR), or adenosine or a pathway involving any of the foregoing.

In some embodiments, the agent is BY55, MSB0010718C, ipilimumab, Daclizumab, Bevacizumab, Basiliximab, Ipilimumab, Nivolumab, pembrolizumab, MPDL3280A, Pidilizumab, MK-3475, BMS-936559, Atezolizumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MOXR0916, AMP-224, Avelumab, MEDI4736, PDR001, rHIgM12B7, Ulocuplumab, BKT140, Varlilumab, ARGX-110, MGA271, lirilumab, IPH2201, ARGX-115, Emactuzumab, CC-90002 and MNRP1685A or an antibody-binding fragment thereof. In some instances, the immunomodulatory agent is an anti-PD-L1 antibody. In some examples, the anti-PD-L1 antibody is MEDI4736, MDPL3280A, BMS-936559, LY3300054, atezolizumab or avelumab or is an antigen-binding fragment thereof.

In some embodiments, the agent is thalidomide or is a derivative or analogue of thalidomide. In some cases, the agent is lenalidomide or omalidomide, avadomide, a stereoisomer of lenalidomide, pomalidomide, avadomide or a pharmaceutically acceptable salt, solvate, hydrate, co-crystal, clathrate, or polymorph thereof. In some examples, the agent is lenalidomide, a stereoisomer of lenalidomide or a pharmaceutically acceptable salt, solvate, hydrate, co-crystal, clathrate, or polymorph thereof. In some embodiments, the agent is a tryptophan metabolism and/or kynurenine pathway modulator. In some embodiments, the tryptophan metabolism and/or kynurenine pathway modulator, is an inhibitor of one or more enzymes selected from the group consisting of indoleamine-pyrrole 2,3-dioxygenase 1 (IDO1), IDO2, tryptophan 2,3-dioxygenase (TDO) and kynureninase. In some cases, the tryptophan metabolism and/or kynurenine pathway modulator is an inhibitor of indoleamine-pyrrole 2,3-dioxygenase 1 (IDO1). In some examples, the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'- hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F00187, PF-06840003 or pharmaceutically acceptable salt or prodrug thereof or a method thereof.

In some embodiments, the agent is delivered directly into the tumor. In some embodiments, the method further includes administering the therapeutic regimen to the selected subject.

Provided herein are methods of treatment including administering a therapeutic regimen to a subject that is a candidate for receiving a cell therapy for treatment of a disease or condition, wherein the administration is carried out following or based on the results of assessing a biological sample from the subject for frequency of CD4+ immune cells to determine a likelihood that a subject will achieve a response when treated with the cell therapy. In some embodiments, the biological sample is a tumor sample, optionally a tumor biopsy sample.

In some embodiments, the immune cells are or contain myeloid cells, T helper cells, monocytes, macrophages, or dendritic cells. In some cases, the immune cells are or contain T cells. In some embodiments, the CD4+ immune cells are detected using immunoassay, in situ hybridization, immunohistochemistry, multiplexed immunohistochemistry, or 5-plex immunofluorescent immunohistochemistry.

In some embodiments, the response is a complete response (CR) or partial response (PR). In some cases, the response is durable. In some examples, the response is durable for greater than 3 months, 4 months, 5 months, or 6 months. In some of any such embodiments, the subject is a human. In some embodiments, the cell therapy contains cells engineered to express a recombinant receptor.

In some embodiments, the assessing of the frequency of CD4+ cells includes a comparison to a threshold value, wherein the comparison indicates the likelihood that a subject will achieve a response when treated with the cell therapy.

Provided herein are methods of treatment including administering a therapeutic regimen to a subject, that is a candidate for receiving a cell therapy for treatment of a disease or condition but that has not yet been administered the cell therapy, following assessment of a biological sample from the subject for frequency of CD4+ immune cells compared to a threshold value, wherein frequency of CD4+ T cells above the threshold value indicates the subject is likely to achieve a response when administered the cell therapy and a frequency of CD4+ T cells below the threshold value indicates the subject is not likely to achieve a response when administered the cell therapy, wherein if the frequency of CD4+ immune cells is above the threshold level, administering the cell therapy to the subject; or if the frequency of CD4+ immune cells is below the threshold level, administering (i) an agent or other treatment capable of stimulating, amplifying, potentiating, and/or enhancing an anti-tumor immune response and the cell therapy; (ii) the cell therapy at an increased dose and/or administering an additional dose of the cell therapy; or (iii) an alternative therapeutic treatment other than the cell therapy.

Provided are methods of treatment including administering a therapeutic regimen to a subject that is a candidate for receiving a cell therapy for treatment of a cancer, wherein the administration is carried out following or based on the results of assessing a biological sample that is a tumor biopsy sample from the subject for frequency of CD4+ immune cells to determine a likelihood that a subject will achieve a response that is a complete response (CR) or a partial response (PR), optionally the response that is durable for greater than 3 months, 4 months, 5 months, or 6 months, when treated with the cell therapy, wherein the CD4+ immune cells are detected using immunohistochemistry.

In some cases, the subject is likely to achieve a response when treated with the cell therapy if the frequency of CD4+ cells is at or above the threshold value; or the subject is not likely to achieve a response when treated with the cell therapy if the frequency of CD4+ cells is below the threshold value. In some embodiments, the threshold level is within 25%, within 20%, within 15%, within 10% or within 5% and/or is within one or two standard deviation(s) below the median or mean value of CD4+ immune cells in samples obtained from a group of subjects after the initiation of administration of the cell therapy, wherein each of the subjects of the group went on to achieve a response after administration of the cell therapy. In some instances, the threshold value of CD4+ immune cells is determined based on a median value of CD4+ immune cells observed from a group of subjects that achieved a response after administration of the cell therapy. In some embodiments, the response is CR or PR. In some aspects, the response is durable response at 3 months. In some examples, the threshold level is within 25%, within 20%, within 15%, within 10% or within 5% and/or is within a standard deviation above the median or mean frequency of CD4+ immune cells in samples obtained from a group of subjects after the initiation of administration of the cell therapy, wherein each of the subjects of the group went on to exhibit stable disease (SD) and/or progressive disease (PD). In some embodiments, the threshold level is within 25%, within 20%, within 15%, within 10% or within 5% and/or is within one or two standard deviation(s) below the median or mean value of CD4+ immune cells in samples obtained from a group of subjects after the initiation of administration of the cell therapy, wherein each of the subjects of the group went on to achieve a complete response or a partial response after administration of the cell therapy, optionally wherein the response achieved by the group of subjects is durable at 3 months. In some embodiments, the threshold value of CD4+ immune cells is or is greater than about 4%, 5%, 6%, 7%, or 8% CD4+ immune cells of the total cells in the cellular composition of the biological sample. In some embodiments, the frequency is based on or is a density of the CD4+ immune cells. In some cases, the frequency is based on or is a density of the cells measured as CD4+ immune cells/mm$^2$. In some embodiments, the threshold value of CD4+ immune cells is or is greater than about 4%, 5%, 6%, 7%, or 8% CD4+ immune cells of the total cells in the biological sample; or the threshold value of CD4+ immune cells is or is greater than about 100 cells/mm$^2$, 200 cells/mm$^2$, 300 cells/mm$^2$, 400 cells/mm$^2$, 500 cells/mm$^2$, 600 cells/mm$^2$, 700 cells/mm$^2$, 800 cells/mm$^2$, 900 cells/mm$^2$ or 1000 cells/mm$^2$ in the biological sample.

In some embodiments, if the assessing indicates the subject is likely to achieve a response following administration of the cell therapy, the therapeutic regimen includes administering to the subject the cell therapy, optionally at a non-reduced dose; or the cell therapy, wherein administration of the cell therapy does not include administering, prior to or concurrently with administering the cell therapy, an agent or treatment capable of stimulating, amplifying, potentiating, and/or enhancing an anti-tumor immune response. In some embodiments, if the assessing indicates the subject not likely to achieve a response following administration of the cell therapy, the therapeutic regimen includes administering to the subject an agent or other treatment capable of stimulating, amplifying, potentiating, and/or enhancing an anti-tumor immune response and the cell therapy, wherein administration of the agent is to be administered (i) prior to, (ii) within one, two, or three days of, (iii) concurrently with the initiation of administration of the cell therapy to the subject; the cell therapy at an increased dose and/or administering an additional dose of the cell therapy; or an alternative therapeutic treatment other than the cell therapy. In some embodiments, if the frequency of CD4+ T cells is above the threshold value, the cell therapy is administered at a non-reduced dose; or the administration of the cell therapy does not comprise administering, prior to or concurrently with administering the cell therapy, an agent or other treatment capable of stimulating, amplifying, potentiating, and/or enhancing an anti-tumor immune response. In some embodiments, if the frequency of CD4+ T cells is below the threshold value, the agent is to be administered (i) prior to, (ii) within one, two, or three days of, or (iii) concurrently with the initiation of administration of the cell therapy to the subject.

In some embodiments, the agent or other treatment is selected from the group consisting of: an immune-inhibitory molecule, is or contains an immune checkpoint molecule or member of an immune checkpoint pathway and/or is or contains a modulator of an immune checkpoint molecule or pathway. In some cases, the immune checkpoint molecule or pathway is or contains PD-1, PD-L1, PD-L2, CTLA-4, LAG-3, TIM3, VISTA, an adenosine receptor, CD73, CD39, adenosine 2A Receptor (A2AR), or adenosine or a pathway involving any of the foregoing. In some examples, the agent is BY55, MSB0010718C, ipilimumab, Daclizumab, Bevacizumab, Basiliximab, Ipilimumab, Nivolumab, pembrolizumab, MPDL3280A, Pidilizumab, MK-3475, BMS-936559, Atezolizumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MOXR0916, AMP-224, Avelumab, MEDI4736, PDR001, rHIgM12B7, Ulocuplumab, BKT140, Varlilumab, ARGX-110, MGA271, lirilumab, IPH2201, ARGX-115, Emactuzumab, CC-90002 and MNRP1685A or an antibody-binding fragment thereof.

In some embodiments, the immunomodulatory agent is an anti-PD-L1 antibody. In some examples, the anti-PD-L antibody is MEDI14736, MDPL3280A, BMS-936559, LY3300054, atezolizumab or avelumab or is an antigen-binding fragment thereof.

In some embodiments, the agent is thalidomide or is a derivative or analogue of thalidomide. In some cases, the agent is lenalidomide or omalidomide, avadomide, a stereoisomer of lenalidomide, pomalidomide, avadomide or a pharmaceutically acceptable salt, solvate, hydrate, co-crystal, clathrate, or polymorph thereof. In some embodiments, the agent is lenalidomide, a stereoisomer of lenalidomide or a pharmaceutically acceptable salt, solvate, hydrate, co-crystal, clathrate, or polymorph thereof.

In some embodiments, the agent is a tryptophan metabolism and/or kynurenine pathway modulator. In some cases, the tryptophan metabolism and/or kynurenine pathway modulator, is an inhibitor of one or more enzymes selected from the group consisting of indoleamine-pyrrole 2,3-dioxygenase 1 (IDO1), IDO2, tryptophan 2,3-dioxygenase (TDO) and kynureninase. In some aspects, the tryptophan metabolism and/or kynurenine pathway modulator is an inhibitor of indoleamine-pyrrole 2,3-dioxygenase 1 (IDO1). In some examples, the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F00187, PF-06840003 or pharmaceutically acceptable salt or prodrug thereof or a method thereof.

In some embodiments, the agent is delivered directly into the tumor. In some cases, the disease or condition is a cancer. In some examples, the cancer is a myeloma, lymphoma or leukemia. In some of any such embodiments, the disease or condition is a B cell malignancy. In some examples, the B cell malignancy is selected from acute lymphoblastic leukemia (ALL), chronic lymphoblastic leukemia (CLL), acute myelogenous leukemia (AML), chronic myelogenous leukemia (CML), non-Hodgkin lymphoma (NHL), or Diffuse Large B-Cell Lymphoma (DLBCL), or a subtype of any of the foregoing. In some examples, the disease or condition is NHL and the NHL is selected from the group consisting of aggressive NHL, diffuse large B cell lymphoma (DLBCL), NOS (not otherwise specified) (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B). In some embodiments, the disease or condition is or comprises non-Hodgkin lymphoma (NHL).

In some embodiments, the cell therapy is a T cell therapy containing genetically engineered cells expressing a recombinant receptor. In some cases, the recombinant receptor is a T cell receptor or a functional non-T cell receptor. In some embodiments, the recombinant receptor is a chimeric antigen receptor (CAR). In some aspects, the recombinant receptor specifically binds to an antigen associated with a disease or condition and/or expressed in cells associated with the disease or condition.

In some embodiments, the antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. In some examples, the antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen.

In some embodiments, the CAR includes an extracellular antigen-recognition domain that specifically binds to the antigen and an intracellular signaling domain containing an ITAM, wherein optionally, the intracellular signaling domain includes an intracellular domain of a CD3-zeta (CD3ζ) chain; and/or wherein the CAR further includes a costimulatory signaling region, which optionally includes a signaling domain of CD28 or 4-1BB.

In some embodiments, the genetically engineered cells contain T cells or NK cells. In some embodiments, the genetically engineered cells include T cells, and the T cells include CD4+ and/or CD8+ T cells. In some cases, the T cells are primary T cells obtained from a subject. In some embodiments, the cells of the cell therapy are autologous to the subject. In some cases, the cells are allogeneic to the subject. In some embodiments, the cell therapy includes the administration of from or from about $1\times10^5$ to about $1\times10^9$, from or from about $5\times10^5$ to about $5\times10^8$, from or from about $1\times10^6$ to about $1\times10^8$ or from or from about $5\times10^7$ to about $1\times10^8$ total recombinant receptor-expressing cells, total T cells, or total peripheral blood mononuclear cells (PBMCs), each inclusive; or (a) at or about $5\times10^7$; (b) at or about $1\times10^8$; (c) no more than at or about $5\times10^7$; (d) no more than at or about $1\times10^8$; and/or (e) between at or about $5\times10^7$ and at or about $1\times10^8$, each inclusive, total recombinant receptor-expressing cells, total T cells, or total peripheral blood mononuclear cells (PBMCs).

In some of any such embodiments, the cell therapy includes the administration of from or from about $1\times10^5$ to $1\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy includes the administration of no more than $1\times10^8$ total recombinant receptor-expressing cells, total T cells, or total peripheral blood mononuclear cells (PBMCs), no more than $1\times10^7$ total recombinant receptor-expressing cells, total T cells, or total peripheral blood mononuclear cells (PBMCs), no more than $0.5\times10^7$ total recombinant receptor-expressing cells, total T cells, or total peripheral blood mononuclear cells (PBMCs), no more than $1\times10^6$ total recombinant receptor-expressing cells, total T cells, or total peripheral blood mononuclear cells (PBMCs), no more than $0.5\times10^6$ total recombinant receptor-expressing cells, total T cells, or total peripheral blood mononuclear cells (PBMCs).

Provided herein are kits containing a cell therapy and reagents for detecting frequency of CD4+ immune cells in a biological sample obtained from a subject that is a candidate for treatment with the cell therapy, and instructions for comparing the frequency of CD4+ immune cells to a threshold value, thereby identifying a subject that likely to achieve a response when treated with the cell therapy. Also provided are kits containing a cell therapy and instructions for administering a therapeutic regimen including the cell therapy following or based on the results of assessing frequency of CD4+ immune cells in a biological sample obtained from a subject that is a candidate for treatment with the cell therapy. In some embodiments, the biological sample is a tumor biopsy sample.

In some embodiments, the immune cells are or contain myeloid cells, T helper cells, monocytes, macrophages, or dendritic cells. In some aspects, the immune cells are or comprise T cells. In some cases, the CD4+ immune cells are detected using immunoassay, in situ hybridization, immunohistochemistry, multiplexed immunohistochemistry, or 5-plex immunofluorescent immunohistochemistry.

In some embodiments, the response is a complete response (CR) or partial response (PR). In some cases, the response is durable. In some examples, the response is durable for greater than 3 months, 4 months, 5 months, or 6 months. In some embodiments, the subject is a human. In some embodiments, the cell therapy contains cells engineered to express a recombinant receptor.

Provided herein are kits containing a cell therapy and reagents for immunohistochemistry, for detecting frequency of CD4+ immune cells in a biological sample that is a tumor biopsy sample obtained from a subject that is a candidate for treatment with the cell therapy, and instructions for comparing the frequency of CD4+ immune cells to a threshold value, thereby identifying a subject that likely to achieve a response that is a complete response (CR) or a partial response (PR), optionally the response that is durable for greater than 3 months, 4 months, 5 months, or 6 months, when treated with the cell therapy.

Provided herein are kits containing a cell therapy and instructions for administering a therapeutic regimen including the cell therapy following or based on the results of assessing frequency of CD4+ immune cells by immunohistochemistry, in a biological sample that is a tumor biopsy sample obtained from a subject that is a candidate for treatment with the cell therapy, wherein the instructions specify comparing the frequency of CD4+ immune cells to a threshold value, thereby identifying a subject that likely to achieve a response that is a complete response (CR) or a partial response (PR), optionally the response that is durable for greater than 3 months, 4 months, 5 months, or 6 months, when treated with the cell therapy.

In some embodiments, the instructions specify that the frequency of CD4+ immune cells in the sample indicates the subject is or is likely to achieve a response when treated with the cell therapy if the frequency of CD4+ immune cells is at or above a threshold value; or the instructions specify that the frequency of CD4+ immune cells in the sample indicates the subject is or is likely to achieve a response when treated with the cell therapy if the frequency of CD4+ immune cells is below a threshold value. In some embodiments, the threshold level is within 25%, within 20%, within 15%, within 10% or within 5% and/or is within one or two standard deviation(s) below the median or mean value of CD4+ immune cells in samples obtained from a group of subjects after the initiation of administration of the cell therapy, wherein each of the subjects of the group went on to achieve a response after administration of the cell therapy. In some embodiments, the threshold value of CD4+ immune cells is determined based on a median value or frequency of CD4+ immune cells observed from a group of subjects that achieved a response after administration of the cell therapy. In some cases, the response is CR or PR. In some examples, the response is durable response at 3 months. In some embodiments, the threshold level is within 25%, within 20%, within 15%, within 10% or within 5% and/or is within a standard deviation above the median or mean frequency of CD4+ immune cells in samples obtained from a group of subjects after the initiation of administration of the cell therapy, wherein each of the subjects of the group went on to exhibit stable disease (SD) and/or progressive disease (PD). In some embodiments, the threshold value of CD4+ immune cells is or is greater than about 4%, 5%, 6%, 7%, or 8% CD4+ immune cells of the total cells in the cellular composition of the biological sample.

In some embodiments, the frequency is based on or is a density of the CD4+ immune cells. In some embodiments, the frequency is based on or is a density of the cells measured as CD4+ immune cells/mm$^2$. In some embodiments, the instructions specify if the frequency of CD4+ immune cells in the sample indicates the subject is likely to achieve a response, selecting the subject for administration of a therapeutic regimen, the therapeutic regimen including administering to the subject the cell therapy, optionally at a non-reduced dose; or the cell therapy, wherein administration of the cell therapy does not include administering, prior to or concurrently with administering the cell therapy, an agent or treatment capable of stimulating, amplifying, potentiating, and/or enhancing an anti-tumor immune response.

In some embodiments, the instructions specify if the frequency of CD4+ immune cells in the sample indicates the subject is not likely to achieve a response, selecting the subject for administration of a therapeutic regimen, the therapeutic regimen including administering to the subject an agent or other treatment capable of stimulating, amplifying, potentiating, and/or enhancing an anti-tumor immune response and the cell therapy, wherein administration of the agent is to be administered (i) prior to, (ii) within one, two, or three days of, (iii) concurrently with and/or (iv) at first fever following, the initiation of administration of the cell therapy to the subject; the cell therapy at an increased dose and/or administering an additional dose of the cell therapy; or an alternative therapeutic treatment other than the cell therapy.

In some of any such embodiments, the cell therapy is a cell therapy or is a T cell-engaging therapy, optionally wherein the cell therapy contains cells engineered to express a recombinant receptor. In some cases, the cell therapy is an adoptive cell therapy. In some embodiments, the cell therapy is or contains tumor infiltrating lymphocytic (TIL) therapy or contains genetically engineered cells expressing a recombinant receptor that specifically binds to an antigen associated with a disease or condition and/or expressed in cells associated with the disease or condition. In some examples, the genetically engineered cells include T cells or NK cells. In some embodiments, the genetically engineered cells contain T cells, and the T cells include CD4+ and/or CD8+ T cells. In some cases, the T cells are primary T cells obtained from a subject. In some embodiments, the cells of the cell therapy are autologous to the subject. In some cases, the cells are allogeneic to the subject.

In some embodiments, the disease or condition is a cancer. In some examples, the cancer is a myeloma, leukemia or lymphoma. In some cases, the disease or condition is a B cell malignancy. In some embodiments, the B cell malignancy is selected from acute lymphoblastic leukemia (ALL), chronic lymphoblastic leukemia (CLL), acute myelogenous leukemia (AML), chronic myelogenous leukemia (CML), non-Hodgkin lymphoma (NHL), or Diffuse Large B-Cell Lymphoma (DLBCL), or a subtype of any of the foregoing. In some examples, the disease or condition is NHL and the NHL is selected from the group consisting of aggressive NHL, diffuse large B cell lymphoma (DLBCL), NOS (not otherwise specified) (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

In some embodiments, the antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In some embodiments, the antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR VIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen.

In some embodiments, the antigen is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the recombinant receptor is a T cell receptor or a functional non-T cell receptor. In some cases, the recombinant receptor is a chimeric antigen receptor (CAR). In some examples, the CAR includes an extracellular antigen-recognition domain that specifically binds to the antigen and an intracellular signaling domain containing an ITAM, wherein optionally, the intracellular signaling domain includes an intracellular domain of a CD3-zeta (CD3ζ) chain; and/or wherein the CAR further includes a costimulatory signaling region, which optionally includes a signaling domain of CD28 or 4-1BB.

In some embodiments, the kit further contains an agent or treatment capable of stimulating, amplifying, potentiating, and/or enhancing an anti-tumor immune response. In some cases, the agent or other treatment is selected from the group consisting of: an immune-inhibitory molecule, is or contains an immune checkpoint molecule or member of an immune checkpoint pathway and/or is or contains a modulator of an immune checkpoint molecule or pathway. In some embodiments, the immune checkpoint molecule or pathway is or contains PD-1, PD-L1, PD-L2, CTLA-4, LAG-3, TIM3, VISTA, an adenosine receptor, CD73, CD39, adenosine 2A Receptor (A2AR), or adenosine or a pathway involving any of the foregoing. In some examples, the agent is BY55, MSB0010718C, ipilimumab, Daclizumab, Bevacizumab, Basiliximab, Ipilimumab, Nivolumab, pembrolizumab, MPDL3280A, Pidilizumab, MK-3475, BMS-936559, Atezolizumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MOXR0916, AMP-224, Avelumab, MEDI4736, PDR001, rHIgM12B7, Ulocuplumab, BKT140, Varlilumab, ARGX-110, MGA271, lirilumab, IPH2201, ARGX-115, Emactuzumab, CC-90002 and MNRP1685A or an antibody-binding fragment thereof. In some embodiments, the immunomodulatory agent is an anti-PD-L1 antibody. In some cases, the anti-PD-L1 antibody is MEDI4736, MDPL3280A, BMS-936559, LY3300054, atezolizumab or avelumab or is an antigen-binding fragment thereof.

In some embodiments, the agent is thalidomide or is a derivative or analogue of thalidomide. In some examples, the agent is lenalidomide or omalidomide, avadomide, a stereoisomer of lenalidomide, pomalidomide, avadomide or a pharmaceutically acceptable salt, solvate, hydrate, co-crystal, clathrate, or polymorph thereof. In some embodiments, the agent is lenalidomide, a stereoisomer of lenalidomide or a pharmaceutically acceptable salt, solvate, hydrate, co-crystal, clathrate, or polymorph thereof.

In some embodiments, the agent is a tryptophan metabolism and/or kynurenine pathway modulator. In some cases, the tryptophan metabolism and/or kynurenine pathway modulator, is an inhibitor of one or more enzymes selected from the group consisting of indoleamine-pyrrole 2,3-dioxygenase 1 (IDO1), IDO2, tryptophan 2,3-dioxygenase (TDO) and kynureninase. In some examples, the tryptophan metabolism and/or kynurenine pathway modulator is an inhibitor of indoleamine-pyrrole 2,3-dioxygenase 1 (IDO1). In some instances, the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F00187, PF-06840003 or pharmaceutically acceptable salt or prodrug thereof or a method thereof.

In some embodiments, the agent is delivered directly into the tumor.

Provided herein are methods of assessing likelihood of a response to a cell therapy, the method including assessing the ratio of CD8+ cells to CD4+ cells (CD8+:CD4+ ratio) in a sample from a subject having a disease or condition, said subject having previously received administration of a cell therapy containing a dose or composition of genetically engineered cells expressing a recombinant receptor for treating the disease or condition; and comparing the CD8+:CD4+ ratio to a threshold value, thereby determining a likelihood that a subject will achieve a response when treated with the cell therapy. In some embodiments, the subject is likely to achieve a response when treated with the cell therapy if the CD8+:CD4+ ratio is at or above the threshold value; or the subject is not likely to achieve a response when treated with the cell therapy if the CD8+:CD4+ ratio is below the threshold value.

Provided herein are methods of selecting a subject for treatment with an agent, the method including assessing the ratio of CD8+ cells to CD4+ cells (CD8+:CD4+ ratio) in a sample from a subject having a disease or condition, said subject having previously received administration of a cell therapy comprising a dose or composition of genetically engineered cells expressing a recombinant receptor for treating the disease or condition, wherein the subject is selected for administration of the agent if the CD8+:CD4+ ratio is below a threshold level. Also provided herein are methods of selecting a subject for treatment with an agent for potentiating a cell therapy, the method including assessing the ratio of CD8+ T cells to CD4+ T cells (CD8+:CD4+ ratio) in a biological sample from a subject having a disease or condition, said subject having previously received administration of a cell therapy comprising a dose or composition of genetically engineered cells expressing a recombinant receptor for treating the disease or condition; and selecting the subject for administration of the agent if the CD8+:CD4+ ratio is below a threshold level, wherein the agent is an agent capable of stimulating, amplifying, potentiating, and/or enhancing the anti-tumor response of the cell therapy. In some embodiments, the biological sample is a tumor biopsy sample.

Provided here are methods of assessing likelihood of a response to a cell therapy including assessing the ratio of CD8+ cells to CD4+ cells (CD8+:CD4+ ratio) in a sample that is a tumor biopsy sample from a subject having a cancer, said subject having previously received administration of a cell therapy including a dose or composition of genetically engineered cells expressing a recombinant receptor for treating the cancer, and wherein the CD8+:CD4+ ratio is determined based on detection using immunohistochemistry, optionally multiplexed immunohistochemistry; and comparing the CD8+:CD4+ ratio to a threshold value, thereby determining a likelihood that a subject will achieve a response that is a complete response (CR) or a partial response (PR), optionally the response is durable for greater than 3 months, 4 months, 5 months, or 6 months, when treated with the cell therapy. Also provided are methods of selecting a subject for treatment with an agent including assessing the ratio of CD8+ cells to CD4+ cells (CD8+:CD4+ ratio) in a sample that is a tumor biopsy sample from a subject having a cancer, said subject having previously received administration of a cell therapy including a dose or composition of genetically engineered cells expressing a recombinant receptor for treating the cancer, wherein the CD8+:CD4+ ratio is determined based on detection using immunohistochemistry, optionally multiplexed immunohistochemistry and the subject is selected for administration of the agent if the CD8+:CD4+ ratio is below a threshold level.

In some embodiments, the subject is likely to achieve a response when treated with the cell therapy if the CD8+: CD4+ ratio is at or above the threshold value; or the subject is not likely to achieve a response when treated with the cell therapy if the CD8+:CD4+ ratio is below the threshold value. In some embodiments, the subject is likely to achieve a response when treated with the cell therapy if the CD8+: CD4+ ratio is at or above the threshold value; or the subject is not likely to achieve a response when treated with the cell therapy if the CD8+:CD4+ ratio is below the threshold value, optionally wherein the response is a complete response or is a partial response, optionally wherein the response durable for greater than 3 months, 4 months, 5 months or 6 months. In some embodiments, the threshold level is within 25%, within 20%, within 15%, within 10% or within 5% and/or is within one or two standard deviation(s) below the median or mean CD8+:CD4+ ratio in samples obtained from a group of subjects after the initiation of administration of the cell therapy, wherein each of the subjects of the group went on to achieve a response after administration of the cell therapy. In some cases, the threshold value of CD4+ immune cells is determined based on a median CD8+:CD4+ ratio observed from a group of subjects that achieved a response after administration of the cell therapy. In some examples, the response is CR or PR. In some embodiments, the response is durable response at 3 months. In some embodiments, the threshold value is within 25%, within 20%, within 15%, within 10% or within 5% and/or is within one or two standard deviation(s) below the median or mean CD8+:CD4+ ratio in samples obtained from a group of subjects after the initiation of administration of the cell therapy, wherein each of the subjects of the group went on to achieve a complete response (CR) or a partial response (CR) after administration of the cell therapy, optionally wherein the response achieved by the group of subjects is durable at 3 months.

In some embodiments, the threshold level is within 25%, within 20%, within 15%, within 10% or within 5% and/or is within a standard deviation above the median or mean CD8+:CD4+ ratio in samples obtained from a group of subjects after the initiation of administration of the cell therapy, wherein each of the subjects of the group went on to exhibit stable disease (SD) and/or progressive disease (PD).

In some embodiments, the threshold level is a CD8+: CD4+ ratio in a sample from a subject that is at least or at least about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5 or 3.0.

Provided here are methods of assessing likelihood of a response following administration of a cell therapy including assessing a biological sample for a frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells wherein the biological sample is obtained from a subject having a disease or condition, said subject having previously received administration of a cell therapy including a dose or composition of genetically engineered cells expressing a recombinant receptor for treating the disease or condition; and comparing the frequency to a threshold value, thereby determining a likelihood that a subject will achieve a response. Also provided herein are methods of assessing likelihood of a response following administration of a cell therapy, the method including assessing a tumor sample for a frequency of CD8+ T cells and/or recombinant receptor-expressing CD8+ (receptor+/CD8+) cells wherein the tumor sample is obtained from a subject having a cancer, said subject having previously received administration of a cell therapy comprising a dose of genetically engineered cells expressing a recombinant receptor for treating the cancer; and comparing the frequency to a threshold value, thereby determining a likelihood that a subject will achieve a response.

Also provided are methods of selecting a subject for treatment with an agent including assessing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in a sample from a subject having a disease or condition, said subject having previously received administration of a cell therapy including a dose or composition of genetically engineered cells expressing a recombinant receptor for treating the disease or condition, wherein the subject is selected for administration of the agent if frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is above a threshold level. Also provided herein are methods of selecting a subject for treatment with an agent for potentiating a cell therapy, the method including assessing a frequency of CD8+ T cells, and/or recombinant receptor-expressing CD8+ (receptor+/CD8+) T cells in a tumor sample from a subject having a cancer, said subject having previously received administration of a cell therapy comprising a dose of genetically engineered cells expressing a recombinant receptor for treating the cancer; and the subject is selected for administration of the agent if the frequency of CD8+ T cells and/or, recombinant receptor-expressing CD8+ (receptor+/CD8+) T cells a is above a threshold level, wherein the agent is an agent capable of stimulating, amplifying, potentiating, and/or enhancing the anti-tumor response of the cell therapy.

Provided are methods of assessing likelihood of a response following administration of a cell therapy including assessing a biological sample for a frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells, wherein the biological sample that is a tumor biopsy sample is obtained from a subject having a cancer, said subject having previously received administration of a cell therapy including a dose or composition of genetically engineered cells expressing a recombinant receptor for treating the cancer and wherein the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is determined based on detection using immunohistochemistry, optionally multiplexed immunohistochemistry; and comparing the frequency to a threshold value, thereby determining a likelihood that a subject will achieve a response that is a complete response (CR) or a partial response (PR), optionally the response is durable for greater than 3 months, 4 months, 5 months, or 6 months.

Also provided are methods of selecting a subject for treatment with an agent including assessing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in a biological sample that is a tumor biopsy sample from a subject having a cancer, said subject having previously received administration of a cell therapy including a dose or composition of genetically engineered cells expressing a recombinant receptor for treating the cancer, wherein the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is determined based on detection using immunohistochemistry, optionally multiplexed immunohistochemistry and the subject is selected for administration of the agent if frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is above a threshold level.

In some embodiments, the subject is likely to achieve a response when treated with the cell therapy if the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is at or above the threshold value; or the subject is not likely to achieve a response when treated with the cell therapy if the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is below the threshold value.

In some embodiments, the threshold value is within 25%, within 20%, within 15%, within 10% or within 5% and/or is within a standard deviation above the median or mean frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in samples obtained from a group of subjects after the initiation of administration of the cell therapy, wherein each of the subjects of the group went on to exhibit stable disease (SD) and/or progressive disease (PD). In some examples, the threshold level is within 25%, within 20%, within 15%, within 10% or within 5% and/or is within one or two standard deviation(s) below the median or mean frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in samples obtained from a group of subjects after the initiation of administration of the cell therapy, wherein each of the subjects of the group went on to achieve a response after administration of the cell therapy. In some cases, the threshold value of CD8+ cells is determined based on a median frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cell observed from a group of subjects that achieved a response after administration of the cell therapy. In some embodiments, the response is CR or PR. In some embodiments, the response is durable response at 3 months.

In some embodiments, the frequency is based on or is a density of the CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in the sample. In some embodiments, the frequency is based on or is a density of the cells measured as CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells/mm$^2$ in the sample.

Provided herein are methods of assessing likelihood of a response following administration of a cell therapy, the method including assessing a biological sample for a frequency of CD8+ immune cells, wherein the biological sample is obtained from a subject having a disease or condition, said subject having previously received administration of a cell therapy containing a dose or composition of genetically engineered cells expressing a recombinant receptor for treating the disease or condition; and comparing the frequency to a threshold value, thereby determining a likelihood that a subject will achieve a response.

Provided herein are methods of assessing likelihood of a response to a cell therapy including assessing a sample from a subject for the frequency of CD8+ immune cells that express a recombinant receptor among total cells expressing the recombinant receptor, said subject having previously received administration of a cell therapy including a dose of genetically engineered cells expressing the recombinant receptor for treating a disease or condition; and comparing the frequency of recombinant receptor-expressing CD8+ immune cells to a threshold value, thereby determining a likelihood that a subject will achieve a response when treated with the cell therapy.

Provided herein is a method of assessing likelihood of a response following administration of a cell therapy including assessing a biological sample for a frequency of CD8+ immune cells, wherein the biological sample that is a tumor biopsy sample is obtained from a subject having a cancer, said subject having previously received administration of a cell therapy including a dose or composition of genetically engineered cells expressing a recombinant receptor for treating the cancer, wherein the frequency of CD8+ immune cells is determined based on detection using immunohistochemistry; and comparing the frequency to a threshold value, thereby determining a likelihood that a subject will achieve a response that is a complete response (CR) or a partial response (PR), optionally the response is durable for greater than 3 months, 4 months, 5 months, or 6 months.

Provided are methods of assessing likelihood of a response to a cell therapy including assessing a sample that is a tumor biopsy sample from a subject for the frequency of CD8+ immune cells that express a recombinant receptor among total cells expressing the recombinant receptor, said subject having previously received administration of a cell therapy including a dose of genetically engineered cells expressing the recombinant receptor for treating a cancer, wherein the frequency of CD8+ immune cells is determined based on detection using immunohistochemistry; and comparing the frequency of recombinant receptor-expressing CD8+ immune cells to a threshold value, thereby determining a likelihood that a subject will achieve a response a response that is a complete response (CR) or a partial response (PR), optionally the response is durable for greater than 3 months, 4 months, 5 months, or 6 months when treated with the cell therapy. In some embodiment, the subject is likely to achieve a response when treated with the cell therapy if the frequency of CD8+ immune cells is at or above the threshold value; or the subject is not likely to achieve a response when treated with the cell therapy if the frequency of CD8+ immune cells is below the threshold value.

Provided herein are methods of assessing likelihood of a response to a cell therapy including assessing a frequency of CD8+ T cells in one or more sample(s) from a subject having a disease or condition, said subject being a candidate for and having received administration of a cell therapy comprising a dose of genetically engineered cells expressing a recombinant receptor for treating the disease or condition, wherein a first sample is obtained prior to administration of the cell therapy and a second sample is obtained after the initiation of administration of the cell therapy; and comparing the frequency of CD8+ T cells in the second sample compared to the first sample to a threshold value, wherein a degree of increase in the frequency compared to the threshold value is associated with a likelihood that a subject will achieve a response when treated with the cell therapy.

In some embodiments, the threshold value is within 25%, within 20%, within 15%, within 10% or within 5% and/or is within a standard deviation above the median or mean frequency of CD8+ immune cells in samples obtained from a group of subjects after the initiation of administration of the cell therapy, wherein each of the subjects of the group went on to exhibit stable disease (SD) and/or progressive disease (PD). In some embodiments, the threshold level is within 25%, within 20%, within 15%, within 10% or within 5% and/or is within one or two standard deviation(s) below the median or mean frequency of CD8+ immune cells in samples obtained from a group of subjects after the initiation of administration of the cell therapy, wherein each of the subjects of the group went on to achieve a response after administration of the cell therapy. In some examples, the threshold value of CD8+ immune cells is determined based on a median frequency of CD8+ immune cells observed from a group of subjects that achieved a response after administration of the cell therapy. In some cases, the response is CR or PR. In some examples, the response is durable response at 3 months. In some embodiments, the threshold value of CD8+ immune cells is within 25%, within 20%, within 15%, within 10% or within 5% and/or is within one or two standard deviation(s) below the median or mean frequency of CD8+ immune cells in samples obtained from a group of subjects after the initiation of administration of the cell therapy a complete response (CR). In some cases, the threshold value of CD8+ immune cells is within 25%, within 20%, within 15%, within 10% or within 5% and/or is within a standard deviation above the median or mean frequency of CD8+ immune cells in samples obtained from a group of subjects after the initiation of administration of the cell therapy a partial response (PR). In some embodiments, the frequency is based on or is a density of the CD8+ immune cells. In some embodiments, the frequency is based on or is a density of the cells measured as CD8+ immune cells/mm$^2$.

Provided are methods of assessing likelihood of a response to a cell therapy, the method including assessing a sample from a subject for the percentage of CD8+ cells that express a recombinant receptor among total cells expressing the recombinant receptor, said subject having previously received administration of a cell therapy containing a dose of genetically engineered cells expressing the recombinant receptor for treating a disease or condition; and comparing the percentage of recombinant receptor-expressing CD8+ cells to a threshold value, thereby determining a likelihood that a subject will achieve a response when treated with the cell therapy. In some instances, the threshold value is within 25%, within 20%, within 15%, within 10% or within 5% and/or is within a standard deviation above the median or mean percentage of recombinant receptor-expressing CD8+ cells in samples obtained from a group of subjects after the initiation of administration of the cell therapy, wherein each of the subjects of the group went on to exhibit stable disease (SD) and/or progressive disease (PD).

In some embodiments, the method further includes selecting a subject for treatment with an agent if the subject is determined not likely to achieve a response. In some cases, the response is a complete response (CR). In some embodiments, the response is durable. In some examples, the response is durable for greater than 3 months, 4 months, 5 months, or 6 months.

In some embodiments, the sample from the subject is obtained after the initiation of administration of the cell therapy. In some cases, the sample from the subject is obtained within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the cell therapy. In some aspects, the sample from the subject is obtained at a time before a peak or maximum level of the cells of the cell therapy is detectable in the blood of the subject.

Provided herein are methods of assessing likelihood of a response to a cell therapy, the method including assessing the frequency of CD8+ cells in one or more sample(s) from a subject having a disease or condition, said subject being a candidate for administration of a cell therapy containing a dose or composition of genetically engineered cells expressing a recombinant receptor for treating the disease or condition, wherein a first sample is obtained prior to administration of the cell therapy and a second sample is obtained after the initiation of administration of the cell therapy; and comparing the increase in the frequency of CD8+ cells in the second sample compared to the first sample to a threshold value, thereby determining a likelihood that a subject will achieve a response when treated with the cell therapy.

In some embodiments, the subject is likely to achieve a response when treated with the cell therapy if the increase in the frequency of CD8+ cells in the second sample compared to the first sample that is at or above a threshold level; or the subject is not likely to achieve a response when treated with the cell therapy if the increase in the frequency of CD8+ cells in the second sample compared to the first sample that is below the threshold value.

In some embodiments, the method further includes selecting a subject for treatment with an agent if the subject is determined not likely to achieve a response. In some cases, the response is a complete response (CR) or partial response (PR). In some embodiments, the response is durable. In some examples, the response is durable for greater than 3 months, 4 months, 5 months, or 6 months.

Provided are methods of selecting a subject for treatment with an agent, the method including assessing the frequency of CD8+ cells in one or more sample(s) from a subject having a disease or condition, said subject being a candidate for administration of a cell therapy containing a dose or composition of genetically engineered cells expressing a recombinant receptor for treating the disease or condition, wherein a first sample is obtained prior to administration of the cell therapy and a second sample is obtained after the initiation of administration of the cell therapy, wherein the subject is selected for administration of the agent if an increase in the frequency of CD8+ cells in the second sample compared to the first sample is below a threshold level. Also provided are methods of selecting a subject for treatment with an agent for potentiating a cell therapy including assessing a frequency of CD8+ T cells in one or more sample(s) from a subject having a disease or condition, said subject being a candidate for and having received administration of a cell therapy comprising a dose of genetically engineered cells expressing a recombinant receptor for treating the disease or condition, wherein a first sample is obtained prior to administration of the cell therapy and a second sample is obtained after the initiation of administration of the cell therapy; and selecting the subject for administration of an agent if an increase in the frequency of CD8+ T cells in the second sample compared to the first sample is below a threshold level, wherein the agent is an agent capable of stimulating, amplifying, potentiating, and/or enhancing the anti-tumor response of the cell therapy.

In some embodiments, the second sample is obtained within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the cell therapy. In some embodiments, the second sample is obtained at a time before a peak or maximum level of the cells of the cell therapy is detectable in the blood of the subject. In some embodiments, the subject is likely to achieve a response when treated with the cell therapy if the increase in the frequency of CD8+ cells is at or above the threshold value; or the subject is not likely to achieve a response when treated with the cell therapy if the increase in the frequency of CD8+ cells is below the threshold value.

In some embodiments, the threshold level is within 25%, within 20%, within 15%, within 10% or within 5% and/or is within a standard deviation above the median or mean of the increase in the frequency of CD8+ cells in the second sample compared to the first sample obtained from a group of subjects after the initiation of administration of the cell therapy, wherein each of the subjects of the group went on to exhibit stable disease (SD) and/or progressive disease (PD).

In some embodiments, the threshold level is within 25%, within 20%, within 15%, within 10% or within 5% and/or is within one or two standard deviation(s) below the median or mean increase in the frequency of CD8+ cells in samples obtained from a group of subjects after the initiation of administration of the cell therapy, wherein each of the subjects of the group went on to achieve a response after administration of the cell therapy. In some embodiments, the threshold value of CD8+ immune cells is determined based on a median increase in the frequency of CD8+ cells observed from a group of subjects that achieved a response after administration of the cell therapy. In some cases, the response is CR or PR. In some embodiments, the response is durable response at 3 months. In some cases, the threshold level is an increase in the frequency of CD8+ cells in the second sample compared to the first sample from a subject that is at least or at least about +0.1%, +0.25%, +0.5%, +0.75%, +1%, +2%, +3%, +4%, +5%, +6%, +7%, +8%, +9%, +10%, +11%, +12%, +13%, +14%, +15% or +20%. In some embodiments, the frequency is based on or is a density of the CD8+ cells. In some examples, the frequency is based on or is a density of the cells measured as CD8+ cells/mm$^2$. In some embodiments, the assessment of the frequency of CD8+ T cells and/or recombinant receptor-expressing CD8+ (receptor+/CD8+) cells in the sample is determined by immunofluorescence, immunocytochemistry, immunohistochemistry and/or flow cytometry.

In some embodiments, the assessing is performed by contacting a biological sample with one or more reagent capable of detecting CD4+ expression and/or CD8+ expression in cells. In some cases, the method further includes assessing one or more additional parameters in the samples. In some embodiments, the additional parameter is the frequency of cells expressing an additional biomarker. In some embodiments, the method further includes comparing the frequency of cells expressing the additional biomarker to a threshold value, thereby determining a likelihood that a subject will achieve a response when treated with the cell therapy. In some cases, the subject is likely to achieve a response when treated with the cell therapy if the frequency of cells expressing the additional biomarker is at or above the threshold value; or the subject is not likely to achieve a response when treated with the cell therapy if the frequency of cells expressing the additional biomarker is below the threshold value. In some embodiments, the threshold level is within 25%, within 20%, within 15%, within 10% or within 5% and/or is within one or two standard deviation(s) below the median or mean frequency of cells expressing the additional biomarker in samples obtained from a group of subjects after the initiation of administration of the cell therapy, wherein each of the subjects of the group went on to achieve a response after administration of the cell therapy. In some examples, the threshold value of the additional marker is determined based on a median frequency of cells expressing the additional biomarker observed from a group of subjects that achieved a response after administration of the cell therapy.

In some embodiments, the response is CR or PR. In some embodiments, the response is durable response at 3 months. In some cases, the threshold level is within 25%, within 20%, within 15%, within 10% or within 5% and/or is within a standard deviation above the median or mean frequency of frequency of cells expressing the additional biomarker in samples obtained from a group of subjects after the initiation of administration of the cell therapy, wherein each of the subjects of the group went on to exhibit stable disease (SD) and/or progressive disease (PD). In some embodiments, frequency of cells expressing the additional biomarker is assessed in one or more sample(s) from the subject, wherein a first sample is obtained prior to administration of the cell therapy and a second sample is obtained after the initiation of administration of the cell therapy.

In some embodiments, the method further includes comparing the increase in the frequency of cells expressing the additional biomarker in the second sample compared to the first sample to a threshold value, thereby determining a likelihood that a subject will achieve a response when treated with the cell therapy. In some embodiments, the subject is likely to achieve a response when treated with the cell therapy if the increase in the frequency of cells expressing the additional biomarker is at or above the threshold value; or the subject is not likely to achieve a response when treated with the cell therapy if the increase in the frequency of cells expressing the additional biomarker is below the threshold value. In some examples, the threshold level is within 25%, within 20%, within 15%, within 10% or within 5% and/or is within one or two standard deviation(s) below the median or mean increase in frequency of cells expressing the additional biomarker in samples obtained from a group of subjects after the initiation of administration of the cell therapy, wherein each of the subjects of the group went on to achieve a response after administration of the cell therapy. In some cases, the threshold value of CD4+ immune cells is determined based on a median increase in frequency of cells expressing the additional biomarker observed from a group of subjects that achieved a response after administration of the cell therapy.

In some embodiments, the response achieved by the group of subjects is CR or PR. In some embodiments, the response achieved by the group of subjects is durable at 3 months. In some cases, the threshold level is within 25%, within 20%, within 15%, within 10% or within 5% and/or is within a standard deviation above the median or mean increase in frequency of frequency of cells expressing the additional biomarker in samples obtained from a group of subjects after the initiation of administration of the cell therapy, wherein each of the subjects of the group went on to exhibit stable disease (SD) and/or progressive disease (PD). In some embodiments, the frequency is based on or is a density of cells expressing the additional biomarker. In some embodiments, the frequency is based on or is a density of the cells measured as the number of cells expressing the additional biomarker cells/mm$^2$.

In some examples, the additional biomarker is a biomarker associated with immune modulation. In some instances, the additional biomarker is selected from among one or more of CD73, FOXP3, CD163, IDO and PD-L1. In some cases, the additional biomarker is IDO and/or PD-L1.

In some embodiments, the sample is a tumor sample and/or the sample contains or is likely to contain tumor cells. In some examples, the biological sample is a tumor sample, optionally a tumor biopsy sample. In some embodiments, the sample is or contains a lymph node sample, bone marrow sample, blood sample, plasma sample, or serum sample. In some cases, the sample is or contains a lymph node sample. In some embodiments, the method is carried out ex vivo. In some embodiments, the assessment of the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in the sample is determined by immunofluorescence, immunocytochemistry, immunohistochemistry and/or flow cytometry. In some embodiments, the assessment of the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in the sample is determined multiplexed immunohistochemistry, or 5-plex immunofluorescent immunohistochemistry. In some cases, the assessment of the frequency of the additional biomarker in the sample is determined using immunoassay, in situ hybridization, immunohistochemistry, multiplexed immunohistochemistry, or 5-plex immunofluorescent immunohistochemistry and/or flow cytometry. In some examples, the immune cells are or include myeloid cells, T helper cells, monocytes, macrophages, or dendritic cells. In some cases, the immune cells are or include T cells.

In some embodiments, the disease or condition is a tumor. In some cases, the tumor is associated with a cancer. In some embodiments, the disease or condition is or includes a leukemia or a lymphoma. In some examples, the disease or condition is selected from and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL). In some cases, the disease or condition is or includes non-Hodgkin lymphoma (NHL), or a subtype of any of the foregoing. In some instances, the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

In some embodiments, the cell therapy is a T cell therapy containing genetically engineered cells expressing a recombinant receptor. In some cases, the recombinant receptor is a T cell receptor or a functional non-T cell receptor. In some embodiments, the recombinant receptor is a chimeric antigen receptor (CAR). In some embodiments, the recombinant receptor specifically binds to an antigen associated with the disease or condition or expressed in cells of the environment of a lesion associated with the disease or condition.

In some embodiments, the antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens, bacterial antigens, and/or parasitic antigens.

In some embodiments, the antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen. In some examples, the antigen is CD19.

In some embodiments, the CAR includes an extracellular antigen-recognition domain that specifically binds to the antigen and an intracellular signaling region including an ITAM, wherein optionally, the intracellular signaling region includes an intracellular domain of a CD3-zeta (CD3ζ) chain; and/or wherein the CAR further includes a costimulatory signaling region, which optionally includes a signaling domain of CD28 or 4-1BB. In some examples, the CAR further includes a spacer and/or a hinge region.

In some embodiments, the genetically engineered cells include T cells or NK cells. In some cases, the genetically engineered cells include T cells, and the T cells include CD4+ and/or CD8+ T cells. In some cases, the T cells are primary T cells obtained from a subject. In some embodiments, the cells of the cell therapy are autologous to the subject. In some cases, the cells are allogeneic to the subject.

In some embodiments, the cell therapy includes the administration of from or from about $1\times10^5$ to about $1\times10^9$, from or from about $5\times10^5$ to about $5\times10^8$, or from or from about $1\times10^6$ to about $1\times10^8$ total recombinant receptor-expressing cells, total T cells, or total peripheral blood mononuclear cells (PBMCs), each inclusive; or at or about $1\times10^7$; (b) at or about $1.5\times10^8$; (c) no more than at or about $1\times10^7$; (d) no more than at or about $1.5\times10^8$; and/or (e) between at or about $1\times10^7$ and at or about $1.5\times10^8$ total recombinant receptor-expressing cells, total T cells, or total peripheral blood mononuclear cells (PBMCs). In some embodiments, the cell therapy includes the administration of from or from about $1\times10^5$ to about $1\times10^9$, from or from about $5\times10^5$ to about $5\times10^8$, from or from about $1\times10^6$ to about $1\times10^8$ or from or from about $5\times10^7$ to about $1\times10^8$ total recombinant receptor-expressing cells, total T cells, or total peripheral blood mononuclear cells (PBMCs), each inclusive; or (a) at or about $5\times10^7$; (b) at or about $1\times10^8$; (c) no more than at or about $5\times10^7$; (d) no more than at or about $1\times10^8$; and/or (e) between at or about $5\times10^7$ and at or about $1\times10^8$, each inclusive, total recombinant receptor-expressing cells, total T cells, or total peripheral blood mononuclear cells (PBMCs).

In some embodiments, the cell therapy includes the administration of from or from about $1\times10^5$ to $1\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy includes the administration of no more than $1\times10^8$ total recombinant receptor-expressing cells, total T cells, or total peripheral blood mononuclear cells (PBMCs), no more than $1\times10^7$ total recombinant receptor-expressing cells, total T cells, or total peripheral blood mononuclear cells (PBMCs), no more than $0.5\times10^7$ total recombinant receptor-expressing cells, total T cells, or total peripheral blood mononuclear cells (PBMCs), no more than $1\times10^6$ total recombinant receptor-expressing cells, total T cells, or total peripheral blood mononuclear cells (PBMCs), no more than $0.5\times10^6$ total recombinant receptor-expressing cells, total T cells, or total peripheral blood mononuclear cells (PBMCs).

In some embodiments, the dose of genetically engineered cells is administered in a single pharmaceutical composition including the cells or as a plurality of compositions together including the cells. In some embodiments, the engineered cells administered is a split dose, wherein the cells of the dose are administered in a plurality of compositions, collectively including the cells of the dose, over a period of no more than three days.

In some embodiments, the agent is an agent capable of stimulating, amplifying, potentiating, and/or enhancing the anti-tumor response of the cell therapy. In some embodiments, the agent is or contains a dose or composition containing genetically engineered CD4+ and/or CD8+ T cells expressing a recombinant receptor.

In some embodiments, the agent is or contains a cytokine or a chemokine. In some embodiments, the agent is or contains an immune-inhibitory molecule, is or contains an immune checkpoint molecule or member of an immune checkpoint pathway and/or is or contains a modulator of an immune checkpoint molecule or pathway. In some cases, the immune checkpoint molecule or pathway is or contains PD-1, PD-L1, PD-L2, CTLA-4, LAG-3, TIM3, VISTA, an adenosine receptor, CD73, CD39, adenosine 2A Receptor (A2AR), or adenosine or a pathway involving any of the foregoing. In some examples, the agent is BY55, MSB0010718C, ipilimumab, Daclizumab, Bevacizumab, Basiliximab, Ipilimumab, Nivolumab, pembrolizumab, MPDL3280A, Pidilizumab, MK-3475, BMS-936559, Atezolizumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MOXR0916, AMP-224, Avelumab, MEDI4736, PDR001, rHIgM12B7, Ulocuplumab, BKT140, Varlilumab, ARGX-110, MGA271, lirilumab, IPH2201, ARGX-115, Emactuzumab, CC-90002 and MNRP1685A or an antibody-binding fragment thereof.

In some embodiments, the immunomodulatory agent is an anti-PD-L1 antibody. In some examples, the anti-PD-L antibody is MEDI14736, MDPL3280A, BMS-936559, LY3300054, atezolizumab or avelumab or is an antigen-binding fragment thereof.

In some embodiments, the agent is thalidomide or is a derivative or analogue of thalidomide. In some cases, the agent is lenalidomide or omalidomide, avadomide, a stereoisomer of lenalidomide, pomalidomide, avadomide or a pharmaceutically acceptable salt, solvate, hydrate, co-crystal, clathrate, or polymorph thereof. In some cases, the agent is lenalidomide, a stereoisomer of lenalidomide or a pharmaceutically acceptable salt, solvate, hydrate, co-crystal, clathrate, or polymorph thereof. In some aspects, the agent is a tryptophan metabolism and/or kynurenine pathway modulator. In some examples, the tryptophan metabolism and/or kynurenine pathway modulator, is an inhibitor of one or more enzymes selected from the group consisting of indoleamine-pyrrole 2,3-dioxygenase 1 (IDO1), IDO2, tryptophan 2,3-dioxygenase (TDO) and kynureninase. In some cases, the tryptophan metabolism and/or kynurenine pathway modulator is an inhibitor of indoleamine-pyrrole 2,3-dioxygenase 1 (IDO1). In some embodiments, the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat, 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F00187, PF-06840003 or pharmaceutically acceptable salt or prodrug thereof or a method thereof.

In some embodiments, the agent is delivered directly into the tumor.

Provided herein are kits containing a cell therapy and reagents for detecting the ratio of CD8+ cells to CD4+ cells (CD8+:CD4+ ratio) in a sample obtained from a subject having previously received administration of a cell therapy, and instructions for comparing the CD8+:CD4+ ratio to a threshold value, thereby identifying a subject that likely to achieve a response when treated with the cell therapy. Also provided are kits containing a cell therapy and instructions for administering an additional agent following or based on the results of assessing the CD8+:CD4+ ratio in a sample obtained from a sample obtained from a subject having previously received administration of a cell therapy.

Provided are kits containing a cell therapy and reagents for detecting the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in one or more sample(s) obtained from a subject having previously received administration of a cell therapy, and instructions for comparing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells to a threshold value, thereby identifying a subject that likely to achieve a response when treated with the cell therapy.

Also provided are kits containing a cell therapy and instructions for administering an additional agent following or based on the results of assessing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in one or more sample(s) obtained from a sample obtained from a subject having previously received administration of a cell therapy. In some embodiments, a first sample is obtained prior to administration of the cell therapy and a second sample is obtained after the initiation of administration of the cell therapy.

Also provided are kits containing a cell therapy and reagents for detecting the ratio of CD8+ T cells to CD4+ T cells (CD8+:CD4+ ratio) in a sample obtained from a subject having previously received administration of a cell therapy, and instructions for carrying out any of the methods described herein.

Also provided are kits containing a cell therapy and reagents for detecting the ratio of CD8+ T cells to CD4+ T cells (CD8+:CD4+ ratio) in a sample obtained from a subject having previously received administration of a cell therapy, and instructions for carrying out any of the methods described herein.

Also provided are kits containing a cell therapy and reagents for detecting the frequency of CD8+ T cells, or recombinant receptor-expressing CD8+ (receptor+/CD8+) T cells in one or more sample(s) obtained from a subject having previously received administration of a cell therapy, and instructions for carrying out any of the methods described herein.

In some embodiments, the kit further contains reagents for detecting the frequency of cells expressing an additional biomarker. In some examples, the additional biomarker is selected from among one or more of CD73, FOXP3, CD163, IDO and PD-L1. In some cases, the additional biomarker is IDO and/or PD-L1.

In some of any such embodiments, the frequency is based on or is a density of the cells.

Provided herein is an article of manufacture including any of the kits described herein.

BRIEF DESCRIPTION OF THE DRAWINGS

FIG. 1B shows the pre-treatment CD4+ T cell density and CD8+ T cell density in tumor biopsies of subjects that went on to develop a best overall response of CR/PR or SD/PD at three months.

FIG. 2D-2E show the density (cells/mm$^2$) of CD4+CAR+ T cells (FIG. 2D) and CD8+ CAR+ T cells (FIG. 2E) in post-treatment tumor biopsies of subjects that went on to develop a best overall response of CR/PR as compared to SD/PD.

FIGS. 3C and 3D show the density (cells/mm$^2$) of CD4+ and CD8+ CAR+ T cells (FIG. 3C) and CD4+ and CD8+ total T cells (FIG. 3D) in post-treatment (7-14 day) tumor biopsies of subjects that went on to develop a best overall response of CR/PR as compared to SD/PD.

Figure 4:
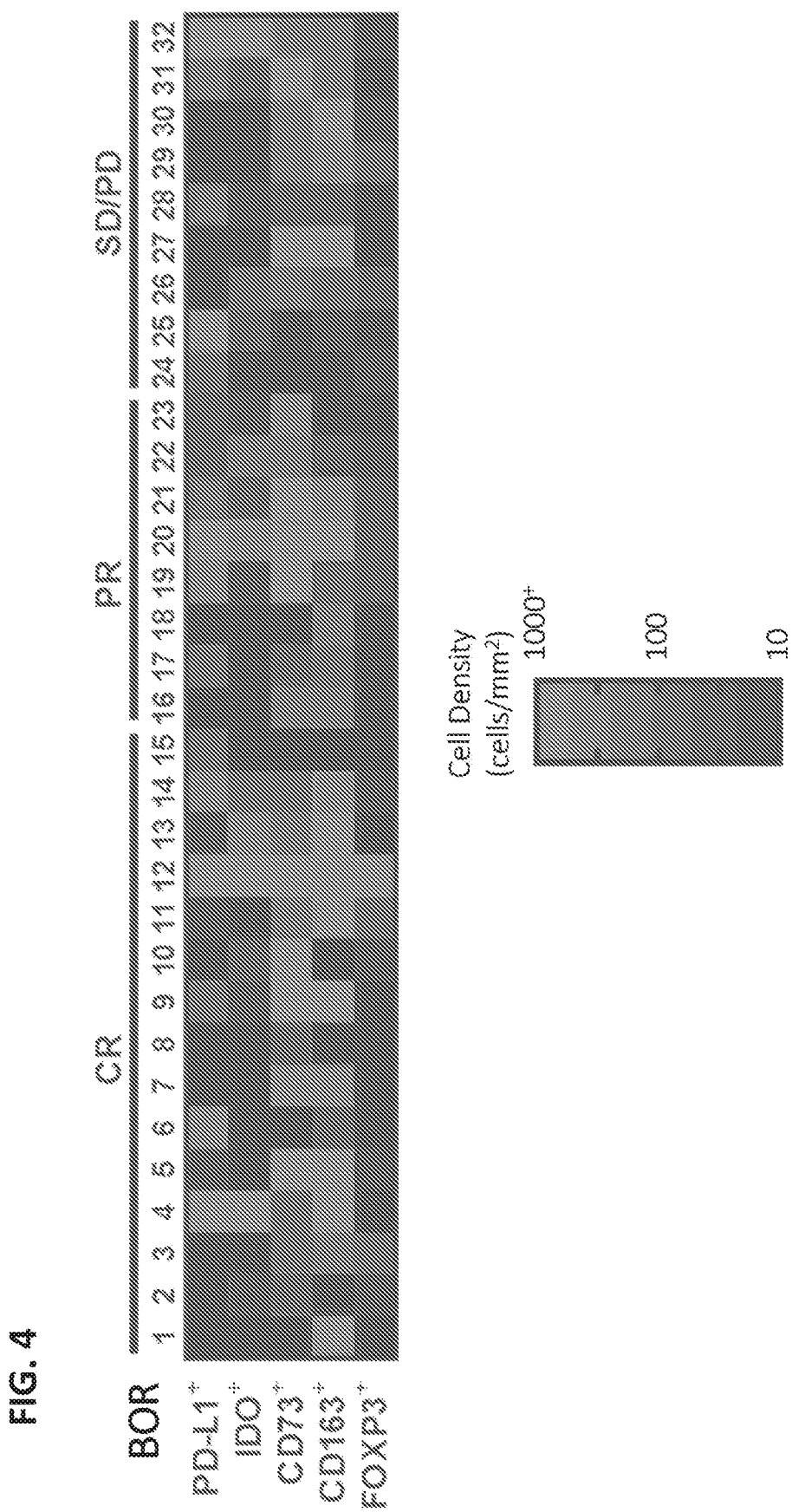

FIG. 4 depicts expression levels of immunosuppressive factors in pre-treatment tumors in subjects who achieved a best overall response of CR, PR, or SD/PD.

Figure 5A:
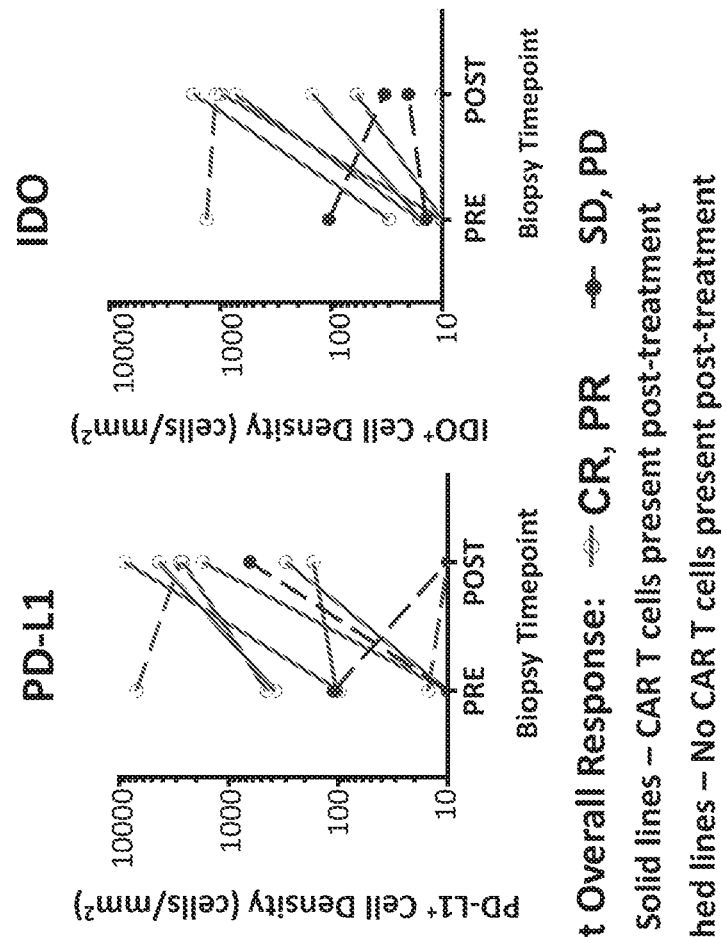

FIG. 5A shows the density of cells expressing immunosuppressive factors PD-L1 and IDO post-treatment compared to pre-treatment in matched biopsy pairs.

Figure 5B:
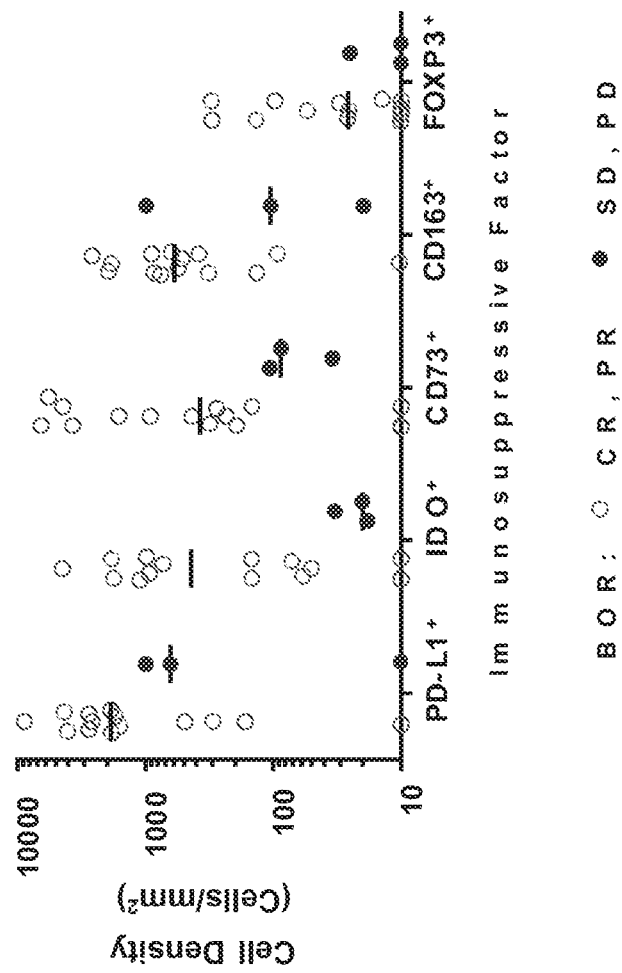

FIG. 5B shows the density of cells expressing immunosuppressive factors PD-L1, IDO, CD73, CD163, and FOXP3, in subjects that achieved CR or PR compared to SD or OD.

Figure 6A:
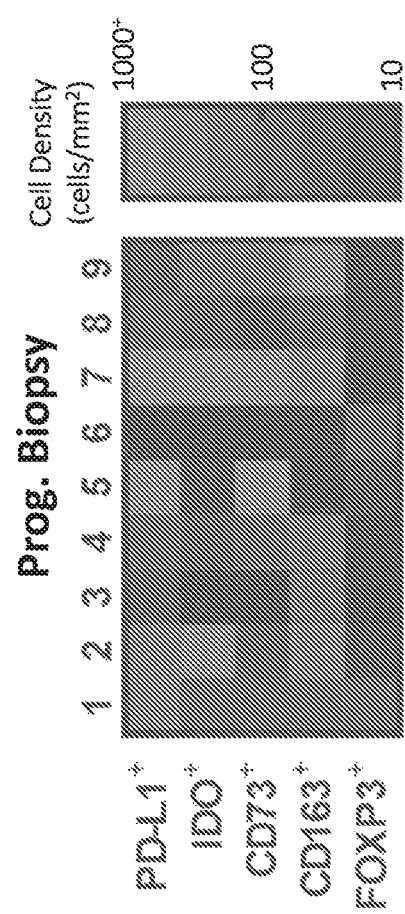
Figure 6B:
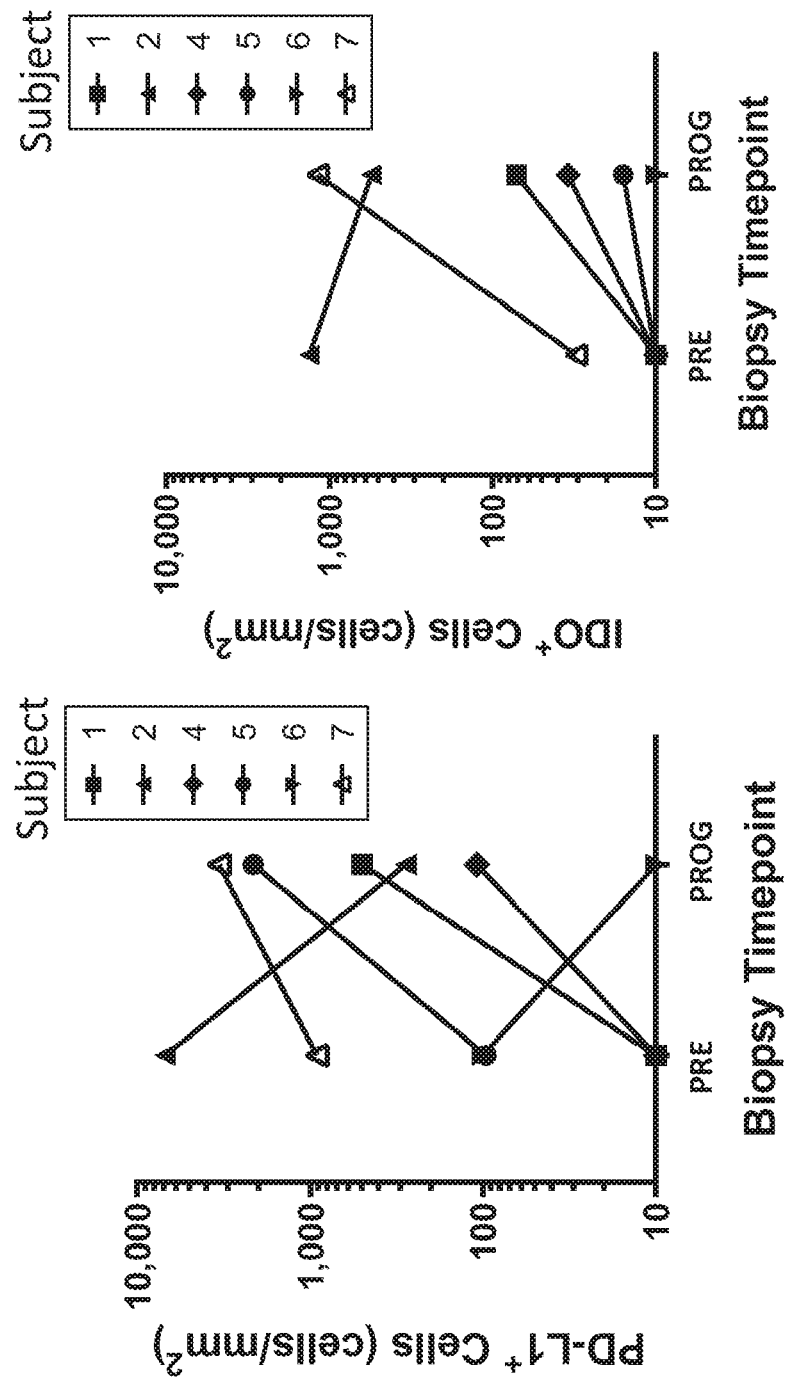
Figure 6C:
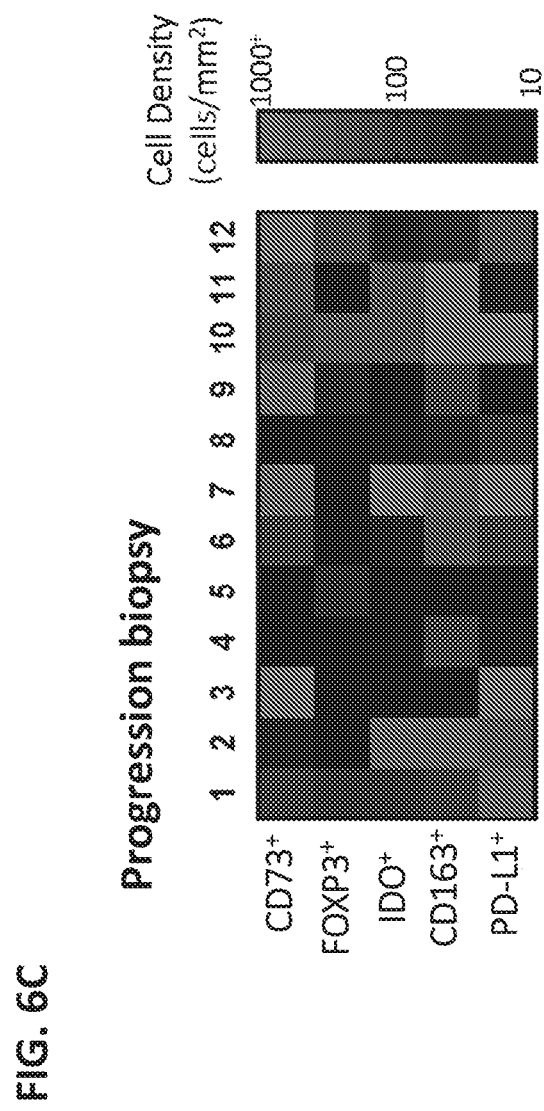

FIG. 6A and FIG. 6C shows expression of immunosuppressive factors PD-L1, IDO, CD73, CD163, and FOXP3 in tumor biopsies at disease progression.

FIG. 6B shows the density of cells expressing immunosuppressive factors PD-L1 and IDO in matched biopsies obtained at pre-treatment (PRE) and disease progression (PROG).

Figure 7A:
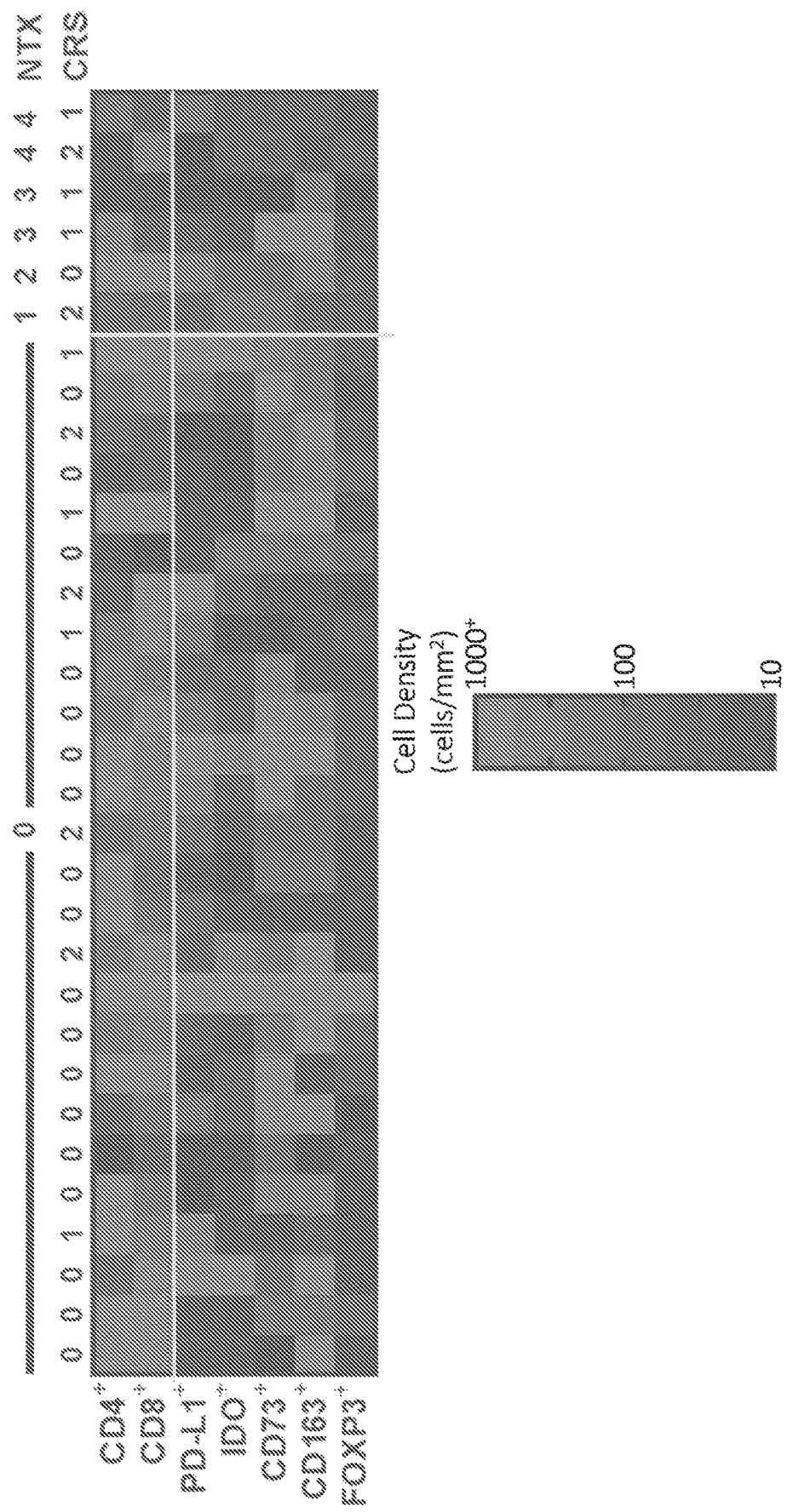

FIG. 7A shows the density of T cells (CD4+ or CD8+) or T cells positive for certain immunosuppressive factor expression in pre-treatment biopsies and safety outcomes (CRS or neurotoxicity) observed.

Figure 7B:
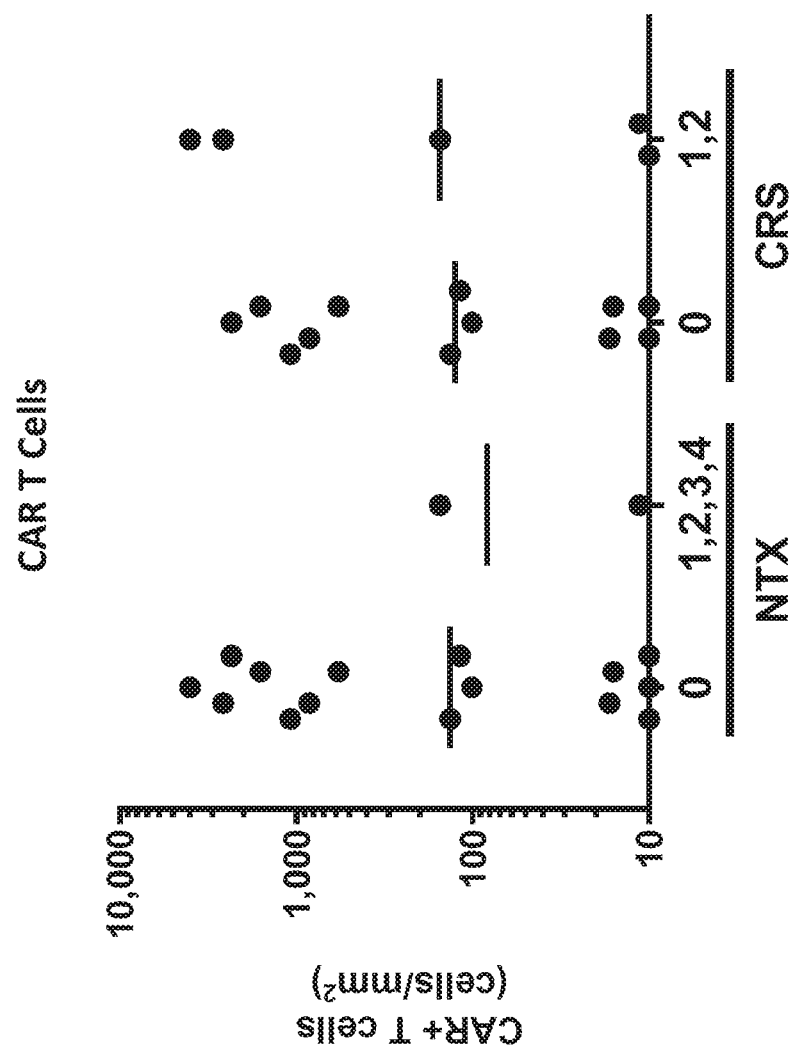

FIG. 7B-7C shows the density of T cells (CD4+ or CD8+) or T cells positive for certain immunosuppressive factor expression in post-treatment biopsies and safety outcomes (CRS or neurotoxicity) observed.

DETAILED DESCRIPTION

Provided herein are methods of determining, assessing, and/or measuring the likelihood of a response following administration of a therapy, e.g., a cell therapy, that include one or more steps for measuring, assessing, determining, and/or quantifying one or more biomarker(s), e.g., tumor microenvironment (TME) biomarkers and/or immune cell biomarkers or number and/or frequency of cells expressing such biomarkers, in a sample obtained from the subject. In some embodiments, the sample is a tumor or a portion thereof, such as a biopsy sample. In some embodiments, the sample, such as a tumor or portion thereof, such as a biopsy sample, is assessed for density of cells of a particular phenotype as described, such as CD4+ or CD8+ cells, or of such cells among recombinant receptor (e.g. CAR) expressing cells. In some embodiments, the measuring, assessing, determining, and/or quantifying one or more cell biomarker is performed prior to administration of a therapy. In some embodiments, the measuring, assessing, determining, and/or quantifying one or more biomarker is performed after initiation of administration of a therapy. In some embodiments, pre- and post-treatment biopsies are obtained from the same subject. In some embodiments, the matched pre- and post-treatment biopsies are compared. In some embodiments, paired samples from a subject can be taken pre-treatment as a baseline for assessing likelihood of response and post-treatment to assess or monitor response. Also provided herein are methods of treatment that include one or more steps of administering to a subject a dose of a therapy, e.g. a cell therapy, for treatment of a disease or condition following and/or based on the results of assessing the biomarker(s) which indicates the likelihood of the subject responding to administration of the therapy, e.g. cell therapy. Also provided herein are methods of treatment that include one or more steps of administering a further or an additional treatment.

In particular embodiments, the biomarker is associated with and/or correlated to likelihood, of a response to administration of and/or associated with the therapy. In some embodiments, the biomarker, e.g., immune cell biomarker, is assessed in a sample obtained from a subject that is a candidate for receiving the therapy prior to or after administration of the therapy, e.g., cell therapy. In some embodiments, the assessment of the biomarker is used to determine the dosage, schedule and/or regimen. In some embodiments, also provided are methods for selecting a subject for treatment. In some embodiments, a subject is selected for treatment with a cell therapy and/or a therapy with additional agent(s) or doses based on the assessment of the biomarker. In some embodiments, a subject is selected for treatment with an agent that can stimulate, amplify, potentiate and/or enhance the anti-tumor response of the cell therapy.

Immunotherapies, such as adoptive cell therapies (including those involving the administration of cells expressing chimeric receptors specific for a disease or disorder of interest, such as chimeric antigen receptors (CARs) and/or other recombinant antigen receptors), can be effective in treating cancer and other diseases and disorders. In certain contexts, available approaches to adoptive cell therapy may not always be entirely satisfactory. In some aspects, the response after administration of the engineered cells is reduced or declines in some subjects.

Predicting the response to the administration of a therapy, e.g., a cell therapy, in individual subjects is useful for evaluating, monitoring, and/or tailoring current or potential therapies for individual subjects, particularly in the context of maximizing benefits and effectiveness of the therapy. In some aspects, the methods provided herein may be used to evaluate, monitor, and/or tailor current or potential therapies for individual subjects, e.g., a cell therapy or CAR-T cell therapy.

In some embodiments, the methods can be used to assess or determine the likelihood that a subject will or is likely to respond to a cell therapy, e.g. CAR-T cell therapy, such as respond by developing a complete response and/or durable response to the cell therapy. In some aspects, the provided embodiments are based on observations that response, such as durable response, e.g. at 3 months, is associated with higher levels of CD4+ cells in pretreatment tumors. In some embodiments, the methods provided herein contain one or more steps of assessing a biomarker, e.g., immune cell biomarker, as provided herein in a sample obtained from the subject, to predict or assess likelihood of a response associated with administration of the therapy in subjects. In certain embodiments, the immune cell biomarker is CD4, and the methods include assessing the presence or absence of CD4+ cells in a sample from the subject. In some embodiments, the sample is a tumor sample, such as a tumor biopsy. In some embodiments, the immune cell biomarker detected from a sample obtained from the subject is useful for predicting likelihood of response associated with administration of the therapy, such as based on comparison to a threshold value of CD4+ cells, e.g. as determined from a control group of subjects. In particular embodiments, the therapy is a cell therapy, such as a CAR-T cell therapy. In some embodiments, by practice of the methods provided herein a subject that is not likely to respond to the therapy may be identified before the therapy is administered, so that the subject may receive an agent or treatment capable of stimulating, amplifying, potentiating, and/or enhancing an anti-tumor immune response, a particular dose of the therapy and/or receive an alternative therapy.

Also provided herein are methods for monitoring a response in a subject subsequent to the subject having received a cell therapy, e.g. CAR-T cell therapy, such as to determine if the therapy is effective in the subject and/or that the subject is likely to develop a complete response to the cell therapy. In some aspects, the provided methods are based on observations that patients having developed a complete response following administration of a cell therapy, e.g. CAR-T cell therapy, had a higher ratio of CD8+ T cells compared to CD4+ T cells, such as CD8+ CAR-T cells to CD4+ CAR-T cells, that had infiltrated the tumor area compared to subjects whose best overall response was stable disease or progressive disease. In some aspects embodiments, methods of monitoring a response or assessing whether a response is likely to be effective following administration of a cell therapy, e.g., CAR-T cells, includes determining the ratio of CD8+ T cells compared to CD4+ T cells in a sample from the subject following administration of the cell therapy. In some embodiments, the sample is a tumor sample, such as a tumor biopsy. In some embodiments, the ratio of CD8+ to CD4+ T cells from a sample obtained from the subject is useful for assessing whether a subject having received the cell therapy is likely to develop a complete response, including a response that is durable, such as based on comparison to a threshold value of the ratio of CD8+ to CD4+ T cells, e.g. as determined from a control group of subjects. In particular embodiments, the therapy is a cell therapy, such as a CAR-T cell therapy. In some embodiments, the methods provided herein may identify that a subject is not likely to respond to the therapy soon after the therapy is administered, so that the therapeutic regimen for the subject may be modified.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. METHODS OF ASSESSING A LIKELIHOOD OF RESPONSE

Provided herein are methods to assess, predict, infer, and/or estimate likelihood of a response to a therapy, such as a cell therapy. In certain embodiments, the biomarker, e.g., immune cell biomarker, is assessed in a sample obtained from a subject that has a disease or condition and/or is suspected of having a disease or condition. In some embodiments, subject has received, will receive, or is a candidate to receive a therapy. In some embodiments, the therapy is an administration of a cell therapy. In particular embodiments, the therapy is an immunotherapy, e.g., cell therapy. In certain embodiments, the cell therapy treats and/or is capable of treating the disease or condition. In some embodiments, the therapy is a cell therapy that contains one or more engineered cells. In some embodiments, the engineered cells express a recombinant receptor. In particular embodiments, the recombinant receptor is a CAR.

In some embodiments, the biomarker is assessed in a sample obtained from the subject. In particular embodiments of the provided methods, the sample is a biological sample, such as a tumor sample, that is taken, collected, and/or obtained from a subject. In particular embodiments, the sample is taken, collected, and/or obtained from a subject who has been, who will be, or is a candidate to be administered a therapy. In particular embodiments, the sample is taken, collected, and/or obtained prior to the initiation of treatment with or administration of the therapy, e.g., the cell therapy. In some embodiments, the sample is taken, collected, and/or obtained after administration of the treatment with the therapy, e.g., the cell therapy. In some embodiments, the sample is a tumor biopsy sample.

In particular embodiments, the biomarker, e.g., immune cell biomarker, is assessed in a subject who has been, who will be, or is a candidate to be administered a therapy. In particular embodiments, the biomarker is assessed prior to the initiation of treatment with or administration of the therapy, e.g., the cell therapy. In some embodiments, the biomarker is assessed within or within about 0, 1, 2, 3, 4, 5, 6, 9, 12, 18 or 24 hours, or 2, 3, 4, 5, 6, 7, 8, 9, 10, 11, 12, 14, 21 or 28 days prior to the initiation of administration of the therapy, e.g., cell therapy.

In particular embodiments, the biomarker is assessed after the initiation of treatment with or administration of the therapy, e.g., the cell therapy. In some embodiments, the biomarker is assessed within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the therapy, e.g., cell therapy.

In some embodiments, the assessing of the sample includes determining a frequency of cells expressing a particular biomarker. In some embodiments, frequency or number of cells can be assessed by determining the density of the cells in a sample from a subject, such as a tumor sample. Determining the density of the cells may be determined by any known method in the art. In some embodiments, density of cells positive for a cell biomarker may be expressed as the number of cells that are counted per one unit of surface area of tissue sample, e.g., as the number of cells, for example, T cells or B cells that are counted per cm$^2$ or mm$^2$ of surface area of tumor tissue sample. The density of cells positive for a cell biomarker may also be expressed as the number of cells per one volume unit of sample, e.g. as the number of cells per cm$^3$ of tumor tissue sample. In some cases, the frequency or density of cells positive for a marker may also consist of the percentage of cells per total cells detected in the sample (set at 100%), or the percentage of cells per total of a type of cells, e.g., a total of cells that express a different particular biomarker. In some embodiments, the frequency of the cells positive for a biomarker is assessed as a percentage of cells that are positive for, negative for and/or have a particular expression level of a particular biomarker, among a total number of cells in the sample, or a total number of cells that express or do not express a different biomarker.

In some embodiments, the biomarker, e.g., immune cell biomarker, is assessed in a sample obtained from a subject that has or is suspected of having a condition or disease. In some embodiments, the subject has or is suspected of having a cancer or proliferative disease. In particular embodiments, the subject has a disease or condition, or is suspected of having a disease or condition, that is associated with an antigen and/or is associated with diseased cells that express the antigen.

In some embodiments, the subject is administered, will be administered, or is a candidate to be administered a therapy, e.g., an immunotherapy and/or a cell therapy. Further provided herein are methods of administering a cell therapy, such as methods of selecting a subject and administering a dose of cell therapy, wherein the subject is selected based on the likelihood of a response in the subject to a therapy. Also provided herein are methods of administering a cell therapy, such as methods of monitoring response in a subject after administration of the cell therapy. In some embodiments, provided are methods for selecting a subject for treatment, treatment with a cell therapy and/or a therapy with additional agent(s) or doses based on the likelihood of a response in the subject to a therapy.

In certain embodiments, the methods include steps to assess, determine, measure, and/or quantify the likelihood that a subject will respond to a cell therapy. In some embodiments, the subject's likelihood of response is assessed, determined, measured and/or quantified by a method of assessing a biomarker, such as described herein. In particular embodiments, if the subject is determined to be likely to respond to the therapy, the subject is administered an initial dose of a cell therapy, such as, in some aspects, is a standard dose of a cell therapy. In certain embodiments, the subject is determined to not be likely to have a response to the administered cell therapy, the subject is administered a modified dose of a cell therapy, for example a dose that is greater than the initial dose, such as, in some aspects, a standard dose of the cell therapy, an additional dose of the cell therapy and/or a modified dose of cell therapy. In particular embodiments, the subject is determined to not be likely to have a response to the administered cell therapy, the subject is also administered an agent or treatment capable of stimulating, amplifying, potentiating, and/or enhancing an anti-tumor immune response, such as any as described herein. In some embodiments, the treatment regimen may be modified based on results from the assessment of the biomarker for likelihood of response. In some embodiments, the response is a complete response (CR) or partial response (PR). In some embodiments, the response is a complete response (CR). In some cases, the response is a CR and the subject is minimal residual disease (MRD) negative. In some examples, the response is a CR but the subject is MRD positive.

Provided are methods of assessing the likelihood of a response and/or method of predicting a response to a treatment, e.g., a cell therapy. Also provided are methods of selecting subjects, e.g., subjects having a disease or condition, for treatment. Methods also are provided for monitoring a subject for response, such as for the likelihood of developing or achieving a complete response and/or durable response to the cell therapy. In some embodiments, the methods involve assessing particular parameters associated with the biomarker in a sample from a subject. In particular embodiments, the sample is taken, collected, and/or obtained from a subject who has been, who will be, or is a candidate to be administered a therapy. In some embodiments, the method for assessing likelihood of a subject responding to a cell therapy includes one or more steps including comparing the assessed presence or level of a biomarker to a threshold value for the biomarker. In some embodiments, the method for assessing likelihood of a subject responding to a therapy includes comparison of a parameter associated with one or more biomarkers, such as a ratio between one or more biomarkers or the frequency or number of cells expressing such biomarkers, and/or a change, e.g., an increase or decrease of a one or more biomarkers or the frequency or number of cells expressing such biomarkers, or an increase or decrease of one or more parameters associated with one or more biomarkers.

In accord with methods, kits and articles of manufacture described herein, the biomarker, e.g., immune cell biomarker, is associated with and/or correlate to likelihood of response to the therapy.

In some embodiments, exemplary biomarkers include markers associated with immune cell subtypes, subpopulations and/or phenotypes, markers associated with disease state or disease burden, such as tumor-associated biomarkers, markers associated with a specific activity, function and/or a specific microenvironment, such as markers associated with immunosuppressive activity or function, or expression of the recombinant receptor. In some aspects, such biomarkers can be assessed in a sample from a subject, such as a sample from a subject who is a candidate for or has been administered a cell therapy, before the initiation of administration of cell therapy (for example, as described herein in Section I.A) and/or after the initiation of administration of cell therapy (for example, as described herein in Section I.B). In some embodiments, the presence, number, frequency and/or density of cells expressing the one or more biomarkers in a sample from the subject can be assessed using any of the methods or assays described herein, for example, in Section I.C.

In some embodiments, the assessed biomarker is a biomarker associated with a subtype and/or phenotype of immune cells. In some embodiments, the assessed biomarker is a biomarker indicative of and/or associated with a particular phenotype or subtype of immune cells. In some embodiments, the biomarker is the presence or absence of one or more specific molecules, including surface molecules and/or molecules that may accumulate or be produced by the cells or a subpopulation of cells within a T cell composition. In some embodiments, the phenotype, as indicated by the presence, absence and/or expression of a biomarker, directly or inversely, indicates or is indicative of a biological activity of the cells or of a population of cells. In some embodiments, the assessed biomarker is a marker expressed on immune cells, such as particular types of immune cells. In particular embodiments, the biomarker is present on, absent on and/or expressed on a type of immune cells, such as T cells. In some aspects, the biomarker is present on, absent on and/or expressed on one or more of the cells administered for cell therapy. In some embodiments, the biomarker is present on, absent on and/or expressed on immune cells from the body of the subject. In some embodiments, the assessed biomarker is a T cell biomarker, e.g., a marker expressed on T cells. In some embodiments, the assessed biomarker is a biomarker indicative of or associated with a subtype, a subpopulation and/or phenotype of a T cell. In certain embodiments, the biomarker is or includes positive or negative expression of CD3, CD4 and/or CD8. Exemplary biomarker, e.g., immune cell biomarkers associated with and/or correlated with a likelihood of response to the therapy that may be detected in a sample collected or obtained from a subject include CD4 and/or CD8. In some embodiments, the biomarker is CD4 and/or CD8, optionally positive expression of CD4 and/or CD8.

In some embodiments, the subjects are administered a cell therapy comprising engineered immune cells, e.g., engineered immune cells, that express a recombinant receptor, such as a chimeric antigen receptor (CAR). In some embodiments, the biomarker assessed in a sample from a subject after administration of the cell therapy, comprises the expression, e.g. surface expression, of a recombinant receptor (e.g., CAR) or a transduction marker or a surrogate marker indicating and/or correlating to expression of a recombinant receptor (e.g., CAR). In some embodiments, the expression of the recombinant receptor, such as the CAR, is assessed with an antibody or fragment thereof that binds to and/or recognizes the recombinant receptor, or a transduction or a surrogate marker. In some embodiments, the recombinant receptor is a CAR, and the agent is an antigen or an epitope thereof that is specific to the CAR, or is an antibody or fragment thereof that binds to and/or recognizes the CAR, or a combination thereof. The agent is an antibody or an active fragment, variant, or portion thereof that binds to the CAR. In certain embodiments, the antibody or the active fragment, variant, or portion thereof that binds to the CAR is an anti-idiotypic (anti-ID) antibody. In some embodiments, the antibody or the active fragment, variant, or portion thereof binds to, such as specifically binds to, the transduction marker or surrogate marker. In some embodiments, the biomarker is a transduction marker or surrogate marker that can be used to detect CAR+ T cells. In some embodiments, the biomarker is a CAR+ T cell marker.

In certain embodiments, the biomarker is or includes positive or negative expression of CD3, CD4, CD8, and/or a recombinant receptor, e.g. a CAR. In certain embodiments, the recombinant receptor is a CAR. In particular embodiments the biomarker comprises CD3+/CAR+, CD4+/CAR+, and/or CD8+/CAR+.

In some embodiments, the assessed biomarker is a biomarker associated with disease state or disease burden. In some embodiments, the assessed biomarker is a biomarker that is present and/or expressed in a disease or condition, e.g., a disease or condition to be treated with the cell therapy, e.g., as described herein, for example, in Section II. In some embodiments, the assessed biomarker is a molecule, an antigen or a marker associated with a cancer, a proliferative disease or a tumor. In some embodiments, the assessed biomarker is a biomarker that is expressed on cancer or tumor cells. In some embodiments, the biomarker is an antigen associated with a B cell malignancy, for example, selected from CD20, CD19, CD22, ROR1, CD45, CD21, CD5, CD33, Igkappa, Iglambda, CD79a, CD79b and/or CD30. In some embodiments, the biomarker is CD19 and/or CD20.

In some embodiments, the biomarker is a marker associated with a specific activity, function and/or a specific microenvironment, such as markers associated with immunosuppressive activity or function. In some embodiments, the biomarker is associated with immunosuppressive function, activity and/or immunosuppressive conditions, e.g., immunosuppressive conditions in the TME. In some embodiments, the biomarker is associated with immunosuppression mediated by tumor cells in the TME. In some embodiments, the biomarker is selected from among PD-1 (CD279), PD-L1 (CD274, B7-H1), PDL2 (CD273, B7-DC), CTLA-4, LAG-3 (CD223), TIM-3,4-1BB (CD137), 4-1BBL (CD137L), GITR (TNFRSF18, AITR), CD40, OX40 (CD134, TNFRSF4), CXCR2, tumor associated antigens (TAA), B7-H3, B7-H4, BTLA, HVEM, GAL9, B7H3, B7H4, VISTA, KIR, 2B4 (belongs to the CD2 family of molecules and is expressed on all NK, γδ, and memory CD8+ (αβ) T cells), CD160 (also referred to as BY55), CGEN-15049, CEACAM (e.g., CEACAM-1, CEACAM-3 and/or CEACAM-5), TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, CD73, FOXP3, CD163, IDO (e.g., IDO1 and/or IDO2) and a transforming growth factor receptor (TGFR; e.g., TGFR beta). In some embodiments, the biomarker is selected from among CD73, FOXP3, CD163, IDO (e.g., IDO1 and/or IDO2), and PD-L1. In some embodiments, the biomarker is IDO (e.g., IDO1 and/or IDO2) or PD-L1.

A. Pre-Administration Assessment

Provided herein are provided herein are methods to assess, predict, infer, and/or estimate likelihood of a response to a therapy, such as a cell therapy. In some embodiments, the subject is administered, will be administered, or is a candidate to be administered a therapy, e.g., an immunotherapy and/or a cell therapy. Further provided herein are methods of administering a cell therapy, such as methods of selecting a subject and administering a dose of cell therapy, wherein the subject is selected based on assessment of a biomarker for likelihood of response. For example, the response is a complete response (CR) or partial response (PR). In some embodiments, the biomarker is an immune cell biomarker, such as a marker of a particular T cell phenotypes. In some aspects, the biomarker assessed is a CD4, and the percentage or frequency of CD4+ cells is determined. In some embodiments, the frequency is assessed as a density of CD4+ cells detected in a tumor biopsy sample. In some aspects, the density of the CD4+ cells is measured as CD4+ immune cells/mm$^2$. In some aspects, the biomarker is assessed in a sample that contains immune cells, myeloid cells, T helper cells, monocytes, macrophages, and/or dendritic cells.

In some embodiments, the methods for predicting or assessing that a subject is likely to respond to a cell therapy prior to treatment with the therapy involve assessing the presence and/or expression of one or more biomarkers, such as the presence, number or frequency of CD4+ immune cells, e.g. CD4+ T cells, in a sample, such as a tumor sample, from a subject that has a disease or condition and/or is a candidate for receiving a cell therapy, e.g. T cell therapy. In particular embodiments, the sample is taken, collected, and/or obtained prior to the initiation of treatment with or administration of the therapy, e.g., the cell therapy. In some embodiments, the subject is a candidate for administration of cell therapy. In some embodiments, the subject is selected based on such assessment. In some embodiments, the subject is selected for treatment with an agent, e.g., an agent for stimulating, amplifying, potentiating, and/or enhancing an anti-tumor immune response, e.g., of the cell therapy. For example, in some embodiments, the subject is selected for treatment with an agent if the presence, expression and/or parameters associated with a biomarker is below a particular threshold and/or likelihood of achieving a particular level of response, e.g., complete response (CR) or partial response (PR) is low.

In some examples, the frequency of CD4+ cells and/or CD8+ cells detected in a sample obtained from the subject is associated with and/or correlated with a likelihood of response to the therapy. Thus, in some aspects, the provided methods relate to identifying subjects, prior to receiving an immunotherapy, such as a cell therapy (e.g. CAR-T cells), who may or is likely to respond to the therapy. In some embodiments, the response is a complete response (CR) or partial response (PR). In some embodiments, the response is a complete response (CR). In some cases, the response is a CR and the subject is minimal residual disease (MRD) negative. In some examples, the response is a CR but the subject is MRD positive. In some further embodiments, the response is durable. For example, in some cases, the response is durable for greater than 2 months, 3 months, 4 months, 5 months, 6 months, 7 months, 8 months, 9 months, 10 months, 11 months, 12 months, 18 months or 24 months or more. In some aspects, the provided methods relate to monitoring subjects, after receiving an immunotherapy, such as a cell therapy (e.g. CAR-T cells), who may be responding or is likely to respond to the therapy. In some aspects, the methods can be used to determine if the treatment regimen for the subject should be modified following the administration of the therapy and/or is a candidate for receiving an agent or treatment capable of stimulating, amplifying, potentiating, and/or enhancing an anti-tumor immune response. In some embodiments, the methods can be used to select a subject for treatment with an additional agent, e.g., an agent or treatment capable of stimulating, amplifying, potentiating, and/or enhancing an anti-tumor immune response, and/or an additional dose of the cell therapy.

In some aspects, the provided embodiments, including methods of assessing likelihood of a response following administration of a cell therapy involve assessing a biological sample that is a tumor biopsy sample for a frequency of CD4+ immune cells, wherein the biological sample is obtained from a subject that is a candidate for receiving a cell therapy for treatment of a cancer prior to receiving a cell therapy, and the CD4+ immune cells are detected using immunohistochemistry; and comparing the frequency to a threshold value, thereby determining a likelihood that a subject will achieve a response is a complete response (CR) or a partial response (PR), optionally the response that is durable for greater than 3 months, 4 months, 5 months, or 6 months, when treated with the cell therapy. In some cases, the response is a CR and the subject is minimal residual disease (MRD) negative. In some examples, the response is a CR but the subject is MRD positive.

In some aspects, the provided embodiments, including methods of assessing likelihood of a response following administration of a cell therapy involve assessing a tumor sample for a frequency of CD8+ T cells and/or recombinant receptor-expressing CD8+ (receptor+/CD8+) cells wherein the tumor sample is obtained from a subject having a cancer, said subject having previously received administration of a cell therapy comprising a dose of genetically engineered cells expressing a recombinant receptor for treating the cancer; and comparing the frequency to a threshold value, thereby determining a likelihood that a subject will achieve a response.

In some aspects, the provided embodiments, including methods of selecting a subject for treatment involve assessing a biological sample that is a tumor biopsy sample for a frequency of CD4+ immune cells, wherein: the biological sample is from a subject that is a candidate for treatment with a cell therapy, said cell therapy optionally comprising a dose or composition of genetically engineered cells expressing a recombinant receptor; the biological sample is obtained from the subject prior to administering the cell therapy; and the CD4+ immune cells are detected using immunohistochemistry; and selecting a subject in which the frequency of CD4+ immune cells in the sample is at or above a threshold value, thereby identifying a subject that likely to achieve a response that is a complete response (CR) or a partial response (PR), optionally the response is durable for greater than 3 months, 4 months, 5 months, or 6 months, when treated with the cell therapy.

In some aspects, the provided embodiments, including methods of selecting a subject for treatment with an agent for potentiating a cell therapy involve assessing the ratio of CD8+ T cells to CD4+ T cells (CD8+:CD4+ ratio) in a biological sample from a subject having a disease or condition, said subject having previously received administration of a cell therapy comprising a dose or composition of genetically engineered cells expressing a recombinant receptor for treating the disease or condition; and selecting the subject for administration of the agent if the CD8+:CD4+ ratio is below a threshold level, wherein the agent is an agent capable of stimulating, amplifying, potentiating, and/or enhancing the anti-tumor response of the cell therapy. In some embodiments, the biological sample is a tumor biopsy sample.

In some aspects, the provided embodiments, including methods of treatment involve administering a therapeutic regimen to a subject that is a candidate for receiving a cell therapy for treatment of a cancer, wherein the administration is carried out following or based on the results of assessing a biological sample that is a tumor biopsy sample from the subject for frequency of CD4+ immune cells to determine a likelihood that a subject will achieve a response is a complete response (CR) or a partial response (PR), optionally the response that is durable for greater than 3 months, 4 months, 5 months, or 6 months, when treated with the cell therapy, wherein the CD4+ immune cells are detected using immunohistochemistry. In some aspects, the provided embodiments, including methods of treatment involve administering a therapeutic regimen to a subject, that is a candidate for receiving a cell therapy for treatment of a disease or condition but that has not yet been administered the cell therapy, following assessment of a biological sample from the subject for frequency of CD4+ immune cells compared to a threshold value, wherein frequency of CD4+ T cells above the threshold value indicates the subject is likely to achieve a response when administered the cell therapy and a frequency of CD4+ T cells below the threshold value indicates the subject is not likely to achieve a response when administered the cell therapy, wherein if the frequency of CD4+ immune cells is above the threshold level, administering the cell therapy to the subject; or if the frequency of CD4+ immune cells is below the threshold level, administering (i) an agent or other treatment capable of stimulating, amplifying, potentiating, and/or enhancing an anti-tumor immune response and the cell therapy; (ii) the cell therapy at an increased dose and/or administering an additional dose of the cell therapy; or (iii) an alternative therapeutic treatment other than the cell therapy.

In some embodiments, the subject is likely to achieve a response when treated with the cell therapy if the frequency of CD4+ cells is at or above the threshold value; or the subject is not likely to achieve a response when treated with the cell therapy if the frequency of CD4+ cells is below the threshold value. In some aspects, frequency is based on or is a density of the CD4+ immune cells. In some embodiments, the frequency is based on or is a density of the cells measured as CD4+ immune cells/mm$^2$.

In some aspects, the thresholds value can be determined based on a median or mean frequency of CD4+ cells in a sample observed in a group of subjects that have been previously administered a cell therapy, and went onto achieve a complete response (CR) or partial response (PR). In some examples, the threshold level is within 25%, within 20%, within 15%, within 10% or within 5% and/or is within one or two standard deviation(s) below the median or mean value of CD4+ immune cells in samples obtained from a group of subjects after the initiation of administration of the cell therapy, wherein each of the subjects of the group went on to achieve a response after administration of the cell therapy. In some embodiments, the threshold value of CD4+ immune cells is determined based on a median value frequency of CD4+ immune cells observed from a group of subjects that achieved a response after administration of the cell therapy. In some embodiments, the response achieved by the group of subjects is CR or PR. In some embodiments, the response is durable at 3 months.

In some aspects, the threshold value can be determined based on a median or mean frequency of CD4+ cells in a sample observed in a group of subjects that have been previously administered a cell therapy, and went onto exhibit stable disease (SD) and/or progressive disease (PD). In some embodiments, the threshold level is within 25%, within 20%, within 15%, within 10% or within 5% and/or is within a standard deviation above the median or mean frequency of CD4+ immune cells in samples obtained from a group of subjects after the initiation of administration of the cell therapy, wherein each of the subjects of the group went on to exhibiting stable disease (SD) and/or progressive disease (PD).

In some embodiments, exemplary threshold value of CD4+ immune cells is or is greater than about 4%, 5%, 6%, 7%, or 8% CD4+ immune cells of the total cells in the biological sample, such as a tumor biopsy. In some embodiments, the threshold value of CD4+ immune cells is or is greater than about 100 cells/mm$^2$, 200 cells/mm$^2$, 300 cells/mm$^2$, 400 cells/mm$^2$, 500 cells/mm$^2$, 600 cells/mm$^2$, 700 cells/mm$^2$, 800 cells/mm$^2$, 900 cells/mm$^2$ or 1000 cells/mm$^2$ in the biological sample, such as a tumor biopsy. In some embodiments, the subject is identified as likely to achieve a response when treated with the cell therapy if the frequency of CD4+ cells is at or above the threshold value of at or greater than about 4%, 5%, 6%, 7%, or 8% CD4+ immune cells of the total cells in the biological sample, such as a tumor biopsy or is at or greater than about 200 cells/mm$^2$, 300 cells/mm$^2$, 400 cells/mm$^2$, 500 cells/mm$^2$, 600 cells/mm$^2$ 700 cells/mm$^2$, 800 cells/mm$^2$, 900 cells/mm$^2$ or 1000 cells/mm$^2$ in the biological sample, such as a tumor biopsy. In some embodiments, the subject is identified as not likely to achieve a response when treated with the cell therapy if the frequency of CD4+ cells is below the forgoing threshold value. In some embodiments, the threshold value is about 5%, 6% or 7%, or within a range defined by any of the foregoing, CD4+ immune cells of the total cells in the biological sample, such as a tumor biopsy. In some embodiments, the threshold value of CD4+ immune cells is about 200 cells/mm$^2$, 300 cells/mm$^2$ or 400 cells/mm$^2$, 500 cells/mm$^2$, 600 cells/mm$^2$, 700 cells/mm$^2$, 800 cells/mm$^2$ or 900 cells/mm$^2$, or within a range defined by any of the foregoing, in the biological sample, such as a tumor biopsy.

In certain embodiments of the methods provided herein, the subject is administered an initial dose of a therapy, such as, in some aspects, is a standard dose of the therapy, e.g., an immunotherapy or a cell therapy. In certain embodiments, the likelihood that the subject will respond to the cell therapy is determined by one or more methods of assessing a biomarker in a sample obtained from the subject. In certain embodiments, the subject is determined to be likely to respond to the cell therapy by performing one or more methods described in Section I, and the subject is administered an initial dose of the cell therapy, such as, in some aspects, is a standard dose of the cell therapy. In particular embodiments, the subject is determined to be likely to respond to the cell therapy by performing one or more methods described in Section I, and the subject is administered an initial dose of the cell therapy, such as, in some aspects, is a standard dose of the cell therapy and not administered any agents or treatment that are capable of stimulating, amplifying, potentiating, and/or enhancing an anti-tumor immune response.

In some aspects, the subject is determined not likely to respond to the cell therapy, and the subject is administered the cell therapy and an agent or other treatment capable of stimulating, amplifying, potentiating, and/or enhancing an anti-tumor immune response and the cell therapy. In some instances, the administration of the agent can be administered prior to, within one, two, or three days of, and/or concurrently with the initiation of administration of the cell therapy to the subject. In some instances, the administration of the agent can be administered after the initiation of administration of the cell therapy to the subject. In some embodiments, the subject is determined not likely to respond to the cell therapy, and the subject is administered an alternative therapeutic treatment other than the cell therapy. In some embodiments, the subject is determined not likely to respond to the cell therapy, and the subject is administered an increased dose of the therapeutic cell composition or an additional dose of the therapeutic cell composition. In some embodiments, the cell therapy is a T cell therapy. In some embodiments, the T cell therapy contains cells that express a recombinant receptor. In some embodiments, the recombinant receptor is a CAR.

In certain embodiments, if it is determined that the subject will likely respond to administration of or associated with the cell therapy as assessed by one or more of the provided methods, such as described in Section I, then the subject is administered an initial dose of the cell therapy, such as, in some aspects, is a standard dose of the cell therapy. In certain embodiments, if it is determined that the subject will likely not respond to administration of or associated with the cell therapy as assessed by one or more of the methods provided herein, such as described in Section I, then the subject is administered an increased dose of the cell therapy or an additional dose of the cell therapy. In some cases, the additional dose is a standard dose of the cell therapy.

In some aspects, the size of the initial dose and/or any additional or subsequent doses, which in some aspects can be the standard dose, is determined by the subject's likelihood of responding to the cell therapy, such as assessed by the methods provided herein. In some embodiments, the size of the first and/or subsequent dose is inversely correlated with the likelihood of response. In some aspects, as in the context of a likelihood of response, the subject is administered a standard number of cells. In other embodiments, as in the context of a lower likelihood of response, the subject is administered a larger number of cells.

In some embodiments, an increased dose is greater than or equal to 190%, 185%, 180%, 175%, 170%, 165%, 160%, 155%, 150%, 145%, 140%, 135%, 130%, 125%, 120%, 115%, 110%, or 105% of the initial dose, such as a standard dose.

In certain embodiments, an increased dose of a therapeutic cell composition contains greater than or equal to 190%, greater than or equal to 180%, greater than or equal to 170%, greater than or equal to 160%, greater than or equal to 150%, greater than or equal to 140%, greater than or equal to 130%, greater than or equal to 120%, or greater than or equal to 110% of the total amount of cells, CAR+ cells, CAR+CD4+ cells, and/or CD8+CAR+ cells of the initial dose, which in some aspects can be a standard dose of the therapeutic cell composition. In some embodiments, an increased dose of a therapeutic cell composition contains greater than or equal to 190%, greater than or equal to 180%, greater than or equal to 170%, greater than or equal to 160%, greater than or equal to 150%, greater than or equal to 140%, greater than or equal to 130%, greater than or equal to 120%, or greater than or equal to 110% of the amount of CAR+ cells of the initial dose, which in some aspects can be a standard dose of the therapeutic cell composition total amount of cells per kg of subject body weight, CAR+ cells per kg of subject body weight, CAR+CD4+ cells per kg of subject body weight, and/or CD8+CAR+ cells per kg of subject body weight.

B. Post-Administration Assessment

In some embodiments, the provided methods involve assessing likelihood of a response to a cell therapy based on particular biomarkers and/or parameters associated with one or more biomarkers in a subject who have previously been administered a cell therapy. In some embodiments, the assessment is performed after initiation of the administration of the cell therapy. In some embodiments, the provided methods involve assessing the likelihood of response based on particular biomarkers and/or parameters associated with one or more biomarkers, shortly after the initiation of administration of the cell therapy, e.g., before assessing the response outcome or before the response outcome is manifested. In some embodiments, the methods involve assessing particular biomarkers in a subject both before and after initiation of administration of the cell therapy.

In some embodiments, also provided are methods of selecting subjects for treatment with an agent, based on the assessment of likelihood of a response to a cell therapy. In some embodiments, the subject is selected for treatment with an agent after the initiation of administration of cell therapy, based on the assessment of the biomarkers and/or parameters associated with biomarkers, and corresponding likelihood of response to cell therapy. In some embodiments, the subject is selected for treatment with an agent that can enhance, boost and/or promotes the efficacy and/or safety of the therapeutic effect of the cell therapy. In some embodiments, if the subject who has been administered the cell therapy is determined to be unlikely to respond to the cell therapy or to have a low likelihood of complete response (CR) and/or partial response (PR), the treatment regimen may be modified based on results from the assessment of the biomarker for likelihood of response.

Provided herein are methods for assessing the likelihood of a response in a subject following administration of a cell therapy by detecting and assessing a biomarker. In some embodiments, the biomarker is a tumor microenvironment (TME) biomarker and/or an immune cell biomarker. In some aspects, the biomarker is indicative of T cell phenotypes, is a biomarker of immunosuppressive pathway, or the biomarker is an antigen, e.g., a tumor antigen. In some embodiments, the biomarker is expressed on immune cells, myeloid cells, T helper cells, monocytes, macrophages, or dendritic cells. In some cases, the biomarker is indicative of the presence or frequency of immune cells, myeloid cells, T helper cells, monocytes, macrophages, or dendritic cells. In some cases, the biomarker is expressed on one or more other cells in the tumor microenvironment (TME), such as tumor cells, endothelial cells, fibroblasts, adipocytes and/or pericytes. In some cases, the biomarker is indicative of the presence or frequency of other cells in the TME, such as tumor cells, endothelial cells, fibroblasts, adipocytes and/or pericytes.

In some embodiments, the biomarker is selected from among a CAR+ T cell marker, CD4, CD8, CD19, CD20, CD73, FOXP3, CD163, IDO (e.g., IDO1 and/or IDO2), or PD-L1. In some particular embodiments, the biomarker is an immune cell biomarker such as CD4 or CD8. In some embodiments, the method of assessing includes determining a ratio of CD4+ and CD8+ cells in the sample. In some embodiments, the biomarker is a marker that is exogenously introduced into the cells, e.g., cells used in cell therapy, to detect particular cells, e.g., cells for administration in the cell therapy. In some embodiments, the biomarker is a marker used to detect introduction of nucleic acids, e.g., by genetic engineering, into cells, e.g., cells for administration in the cell therapy. In some embodiments, the biomarker is a transduction marker and/or surrogate marker. In some embodiments, the cells for administration in the cell therapy are immune cells, e.g., T cells, engineered to express a recombinant receptor, e.g., CAR. In some embodiments, the biomarker is a transduction marker or surrogate marker that can be used to detect CAR+ T cells. In some embodiments, the biomarker is a CAR+ T cell marker.

In some embodiments, the methods for monitoring or determining if a subject is likely to develop a response, such as a complete response and/or durable response, following administration of a cell therapy, e.g. CAR-T cells, involves assessing the frequency of cells expressing a biomarker (e.g. CD4+ cells) or ratio of cells expressing different biomarkers (e.g. CD8+/CD4+), such as described. In certain embodiments, the subject has a disease or condition and has received a cell therapy, e.g. a T cell therapy. In some embodiments, the methods can be used to select or identify subjects in which further treatment options may be desirable, e.g. to improve the likelihood of treatment of the disease or condition.

In some embodiments, the biomarker is a biomarker associated with immune modulation. In some embodiments, the biomarker is associated with immunosuppression or immunosuppressive conditions, e.g., immunosuppressive conditions in the TME. In some embodiments, the biomarker is associated with immunosuppression mediated by tumor cells in the TME. In some embodiments, the biomarker is selected from among CD73, FOXP3, CD163, IDO, and PD-L1.

Exemplary biomarkers for assessment include the level or presence of a CAR+ T cell marker, CD4, CD8, CD19, CD20, CD73, FOXP3, CD163, IDO, or PD-L1, the frequency of cells expressing one or more of a CAR+ T cell marker, CD4, CD8, CD19, CD20, CD73, FOXP3, CD163, IDO, or PD-L1, and/or any parameters associated with one or more of the foregoing biomarkers, such as a relative ratio or a change in level, presence and/or frequency in one or more samples. In some embodiments, the frequency is assessed as a density of cells positive for the biomarker.

In some cases, the biomarker is CD8 and the frequency or density of CD8+ cells in a tumor biopsy is assessed. In some embodiments, the methods include assessing or determining the percentage of CD8+ cells that express a recombinant receptor among total cells expressing the recombinant receptor in the sample obtained from the subject after initiation of the administration of the cell therapy. In some embodiments, the biomarker is CD8 and CD4 and the methods include assessing or determining the ratio of CD8+ T cells to CD4+ T cells in the sample, or the ratio of a CAR+ T cell subset thereof. In some embodiments, the frequency of the CD8+ or CD4+ is based on or is a density of the CD8+ cells or CD4+ cells in a sample. In some embodiments, the frequency is based on or is a density of the cells measured as CD8+ cells/mm$^2$ or CD4+ cells/mm$^2$ in a sample, such as a tumor biopsy sample. In some embodiments, the frequency is based on or is the percentage of CD8+ cells or CD4+ cells among the total cells in the assessed sample, such as a tumor biopsy sample.

In some embodiments, the methods of assessing likelihood of a response to a cell therapy involves assessing the ratio of CD8+ cells to CD4+ cells (CD8+:CD4+ ratio) in a sample from a subject. In some embodiments, the ratio is determined in a sample obtained from the subject after the initiation of cell therapy. In some embodiments, the subject has a disease or condition, and has previously received administration of a cell therapy comprising a dose or composition of genetically engineered cells expressing a recombinant receptor for treating the disease or condition. In some embodiments, the methods involve comparing the CD8+:CD4+ ratio to a threshold value, thereby determining a likelihood that a subject will achieve a response when treated with the cell therapy. In some embodiments, the subject is likely to achieve a response when treated with the cell therapy if the CD8+:CD4+ ratio is at or above the threshold value; or the subject is not likely to achieve a response when treated with the cell therapy if the CD8+:CD4+ ratio is below the threshold value. In some embodiments, if the subject is determined not likely to achieve a response, the subject can be selected for administration of an agent.

In some aspects, the provided embodiments, including methods of assessing likelihood of a response to a cell therapy involves assessing a frequency of CD8+ T cells in one or more sample(s) from a subject having a disease or condition, said subject being a candidate for and having received administration of a cell therapy comprising a dose of genetically engineered cells expressing a recombinant receptor for treating the disease or condition, wherein a first sample is obtained prior to administration of the cell therapy and a second sample is obtained after the initiation of administration of the cell therapy; and comparing the frequency of CD8+ T cells in the second sample compared to the first sample to a threshold value, wherein a degree of increase in the frequency compared to the threshold value is associated with a likelihood that a subject will achieve a response when treated with the cell therapy.

In some aspects, the provided embodiments, including methods of assessing likelihood of a response following administration of a cell therapy involve (a) assessing the ratio of CD8+ cells to CD4+ cells (CD8+:CD4+ ratio) in a sample that is a tumor biopsy sample from a subject having a cancer, said subject having previously received administration of a cell therapy comprising a dose or composition of genetically engineered cells expressing a recombinant receptor for treating the cancer, and wherein the CD8+:CD4+ ratio is determined based on detection using immunohistochemistry; and comparing the CD8+:CD4+ ratio to a threshold value, thereby determining a likelihood that a subject will achieve a response that is a complete response (CR) and/or a partial response (PR), optionally the response is durable for greater than 3 months, 4 months, 5 months, or 6 months, when treated with the cell therapy.

In some aspects, the provided embodiments, including methods of selecting a subject for treatment involve assessing the ratio of CD8+ cells to CD4+ cells (CD8+:CD4+ ratio) in a sample that is a tumor biopsy sample from a subject having a cancer, said subject having previously received administration of a cell therapy comprising a dose or composition of genetically engineered cells expressing a recombinant receptor for treating the cancer, wherein the CD8+:CD4+ ratio is determined based on detection using immunohistochemistry, optionally multiplexed immunohistochemistry and the subject is selected for administration of the agent if the CD8+:CD4+ ratio is below a threshold level.

In some embodiments, the assessment can be performed using a sample from the subject that is obtained after the initiation of administration of the cell therapy. In some embodiments, the sample from the subject is obtained within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the cell therapy. In some embodiments, the sample from the subject is obtained at a time before a peak or maximum level of the cells of the cell therapy is detectable in the blood of the subject. In some embodiments, the assessment can be performed more than once, e.g., at more than one different time points after the initiation of administration of the cell therapy, e.g., for monitoring and/or periodic assessment of the treated subjects.

In some embodiments, the response is a complete response (CR). In some cases, the response is a CR and the subject is minimal residual disease (MRD) negative. In some examples, the response is a CR but the subject is MRD positive. In some embodiments, the response is durable. In some embodiments, the response is durable for greater than 3 months, 4 months, 5 months, or 6 months.

In some embodiments, provided are methods of selecting a subject for treatment with an agent that involves assessing the ratio of CD8+ cells to CD4+ cells (CD8+:CD4+ ratio) in a sample from a subject having a disease or condition, said subject having previously received administration of a cell therapy comprising a dose or composition of genetically engineered cells expressing a recombinant receptor for treating the disease or condition, wherein the subject is selected for administration of the agent if the CD8+:CD4+ ratio is below a threshold level.

In some aspects, in some embodiments, provided are methods of selecting a subject for treatment with an agent for potentiating a cell therapy involving assessing a frequency of CD8+ T cells in one or more sample(s) from a subject having a disease or condition, said subject being a candidate for and having received administration of a cell therapy comprising a dose of genetically engineered cells expressing a recombinant receptor for treating the disease or condition, wherein a first sample is obtained prior to administration of the cell therapy and a second sample is obtained after the initiation of administration of the cell therapy; and selecting the subject for administration of an agent if an increase in the frequency of CD8+ T cells in the second sample compared to the first sample is below a threshold level, wherein the agent is an agent capable of stimulating, amplifying, potentiating, and/or enhancing the anti-tumor response of the cell therapy.

In any of such cases, an exemplary threshold level can be determined based on the CD8+:CD4+ ratio, CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells observed in a subject group that ultimately did not show objective response, e.g., from a subject group wherein each of the subjects went on to exhibit stable disease (SD) and/or progressive disease (PD). In some embodiments, the threshold level is within 25%, within 20%, within 15%, within 10% or within 5% and/or is within a standard deviation above the median or mean CD8+:CD4+ ratio in samples obtained from a group of subjects after the initiation of administration of the cell therapy, wherein each of the subjects of the group went on to exhibit stable disease (SD) and/or progressive disease (PD). In some embodiments, the threshold value is within 25%, within 20%, within 15%, within 10% or within 5% and/or is within a standard deviation above the median or mean frequency of CD8+ immune cells in samples obtained from a group of subjects after the initiation of administration of the cell therapy, wherein each of the subjects of the group went on to exhibit stable disease (SD) and/or progressive disease (PD). In some cases, the threshold value is within 25%, within 20%, within 15%, within 10% or within 5% and/or is within a standard deviation above the median or mean percentage of recombinant receptor-expressing CD8+ cells in samples obtained from a group of subjects after the initiation of administration of the cell therapy, wherein each of the subjects of the group went on to exhibit stable disease (SD) and/or progressive disease (PD). In some cases, the threshold value is within 25%, within 20%, within 15%, within 10% or within 5% and/or is within a standard deviation above the median or mean frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in samples obtained from a group of subjects after the initiation of administration of the cell therapy, wherein each of the subjects of the group went on to exhibit stable disease (SD) and/or progressive disease (PD).

In some aspects, the provided embodiments are based in some aspects on the observation that in a cohort of subjects administered a CAR+ cell therapy, subjects that went on to have a complete response (CR) was observed to have higher ratio of $CD8^+CAR^+$ T cells to $CD4^+CAR^+$ T cells compared to the ratio in subjects with a best overall response of stable disease (SD) and/or progressive disease (PD). In some instances, the provided embodiments are based in some aspects on the observation that in a cohort of subjects administered a CAR+ cell therapy, subjects that went on to have a complete response (CR) was observed to have higher frequency or density of CD8+ cells or CAR-expressing CD8+ T cells compared to the frequency or density of CD8+ cells or CAR-expressing CD8+ T cells in subjects with a best overall response of stable disease (SD) and/or progressive disease (PD).

In any of such cases, an exemplary threshold level can be determined based on the CD8+:CD4+ ratio, frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells, observed in a subject group that ultimately achieved objective response, e.g., from a subject group wherein each of the subjects went on to achieve complete response (CR) and/or partial response (PR). In some embodiments, the threshold level is within 25%, within 20%, within 15%, within 10% or within 5% and/or is within one or two standard deviations below the median or mean CD8+:CD4+ ratio in samples obtained from a group of subjects after the initiation of administration of the cell therapy, wherein each of the subjects of the group went on to exhibit CR and/or PR. In some embodiments, the threshold value is within 25%, within 20%, within 15%, within 10% or within 5% and/or is within one or two standard deviations below the median or mean frequency of CD8+ immune cells in samples obtained from a group of subjects after the initiation of administration of the cell therapy, wherein each of the subjects of the group went on to exhibit CR and/or PR. In some cases, the threshold value is within 25%, within 20%, within 15%, within 10% or within 5% and/or is within one or two standard deviations below the median or mean percentage of recombinant receptor-expressing CD8+ cells in samples obtained from a group of subjects after the initiation of administration of the cell therapy, wherein each of the subjects of the group went on to exhibit CR and/or PR. In some cases, the threshold value is within 25%, within 20%, within 15%, within 10% or within 5% and/or is within one or two standard deviations below the median or mean frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in samples obtained from a group of subjects after the initiation of administration of the cell therapy, wherein each of the subjects of the group went on to exhibit CR and/or PR.

In some aspects, the provided embodiments are based in some aspects on the observation that in a cohort of subjects administered a CAR+ cell therapy, subjects that went on to have a complete response (CR) and/or partial response (PR) was observed to have higher ratio of $CD8^+ CAR^+$ T cells to $CD4^+ CAR^+$ T cells compared to the ratio in subjects with a best overall response of stable disease (SD) and/or progressive disease (PD). In some instances, the provided embodiments are based in some aspects on the observation that in a cohort of subjects administered a CAR+ cell therapy, subjects that went on to have a complete response (CR) and/or partial response (PR) was observed to have higher frequency or density of CD8+ cells or CAR-expressing CD8+ T cells compared to the frequency or density of CD8+ cells or CAR-expressing CD8+ T cells in subjects with a best overall response of stable disease (SD) and/or progressive disease (PD).

In some embodiments, the threshold level is within 25%, within 20%, within 15%, within 10% or within 5% and/or is within one or two standard deviation(s) below the median or mean CD8+:CD4+ ratio in samples obtained from a group of subjects after the initiation of administration of the cell therapy, wherein each of the subjects of the group went on to achieve a response after administration of the cell therapy. In some embodiments, the threshold value of CD4+ immune cells is determined based on a median CD8+:CD4+ ratio observed from a group of subjects that achieved a response after administration of the cell therapy. In some embodiments, the response achieved by the group of subjects is CR and/or PR. In some embodiments, the response is durable at 3 months.

In some embodiments, exemplary threshold level for assessing the likelihood of response and/or selecting a subject for treatment with an agent for a CD8+:CD4+ ratio in a sample from a subject is a ratio of at least or at least about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5 or 3.0.

In some aspects, the provided embodiments, including methods of assessing likelihood of a response following administration of a cell therapy involve assessing a biological sample for a frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells wherein the biological sample, such as a tumor biopsy is obtained from a subject having a disease or condition, said subject having previously received administration of a cell therapy comprising a dose or composition of genetically engineered cells expressing a recombinant receptor for treating the disease or condition; and comparing the frequency to a threshold value, thereby determining a likelihood that a subject will achieve a response.

In some aspects, the provided embodiments, including methods of selecting a subject for treatment with an agent involve assessing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in a sample from a subject having a disease or condition, said subject having previously received administration of a cell therapy comprising a dose or composition of genetically engineered cells expressing a recombinant receptor for treating the disease or condition, wherein the subject is selected for administration of the agent if frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is above a threshold level.

In some aspects, the provided embodiments, including methods of assessing likelihood of a response following administration of a cell therapy involve assessing a biological sample for a frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells, wherein the biological sample, such as a tumor biopsy that is a tumor biopsy sample is obtained from a subject having a cancer, said subject having previously received administration of a cell therapy comprising a dose or composition of genetically engineered cells expressing a recombinant receptor for treating the cancer and wherein the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is determined based on detection using immunohistochemistry, optionally multiplexed immunohistochemistry; and comparing the frequency to a threshold value, thereby determining a likelihood that a subject will achieve a response that is a complete response (CR) and/or a partial response (PR), optionally the response is durable for greater than 3 months, 4 months, 5 months, or 6 months.

In some aspects, the provided embodiments, including methods of selecting a subject for treatment with an agent involve assessing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in a biological sample that is a tumor biopsy sample from a subject having a cancer, said subject having previously received administration of a cell therapy comprising a dose or composition of genetically engineered cells expressing a recombinant receptor for treating the cancer, wherein the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is determined based on detection using immunohistochemistry, optionally multiplexed immunohistochemistry and the subject is selected for administration of the agent if frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is above a threshold level.

In some embodiments, the subject is likely to achieve a response when treated with the cell therapy if the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is at or above the threshold value; or the subject is not likely to achieve a response when treated with the cell therapy if the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is below the threshold value.

In some embodiments, the threshold value is within 25%, within 20%, within 15%, within 10% or within 5% and/or is within a standard deviation above the median or mean frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in samples obtained from a group of subjects after the initiation of administration of the cell therapy, wherein each of the subjects of the group went on to exhibit stable disease (SD) and/or progressive disease (PD).

In some embodiments, the threshold level is within 25%, within 20%, within 15%, within 10% or within 5% and/or is within one or two standard deviation(s) below the median or mean frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in samples obtained from a group of subjects after the initiation of administration of the cell therapy, wherein each of the subjects of the group went on to achieve a response after administration of the cell therapy. In some embodiments, the threshold value of CD8+ cells is determined based on a median frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cell observed from a group of subjects that achieved a response after administration of the cell therapy. In some embodiments, the response achieved by the group of subjects is CR and/or PR. In some embodiments, the response is durable at 3 months.

In some embodiments, the frequency is based on or is a density of the CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells. In some embodiments, the frequency is based on or is a density of the cells measured as CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells/mm$^2$.

In some embodiments, exemplary threshold for CD4+ cell density in a sample obtained from the subject after administration of the cell therapy, is or is greater than about 500 CD4+ cells/mm$^2$, 1000 CD4+ cells/mm$^2$, 2000 CD4+ cells/mm$^2$, 3000 CD4+ cells/mm$^2$, 4000 CD4+ cells/mm$^2$, 5000 CD4+ cells/mm$^2$, 6000 CD4+ cells/mm$^2$, 7000 CD4+ cells/mm$^2$, 8000 CD4+ cells/mm$^2$, 9000 CD4+ cells/mm$^2$ or 10000 CD4+ cells/mm$^2$ in the biological sample, such as a tumor biopsy. In some embodiments, exemplary threshold for total CD4+ cell density in a sample obtained from the subject after administration of the cell therapy, is about 1000 CD4+ cells/mm$^2$, 2000 CD4+ cells/mm$^2$, 3000 CD4+ cells/mm$^2$ or 4000 CD4+ cells/mm$^2$, or within a range defined by any of the foregoing, in the biological sample, such as a tumor biopsy. In some aspects, the subject is likely to achieve a response when treated with the cell therapy if the density of CD4+ cells is at or above the threshold value; or the subject is not likely to achieve a response when treated with the cell therapy if the density of CD4+ cells is below the threshold value, in a sample obtained from the subject after administration of cell therapy.

In some embodiments, exemplary threshold for CD8+ cell density in a sample obtained from the subject after administration of the cell therapy, is or is greater than about 80 CD8+ cells/mm$^2$, 90 CD8+ cells/mm$^2$, 100 CD8+ cells/mm$^2$, 200 CD8+ cells/mm$^2$, 300 CD8+ cells/mm$^2$, 400 CD8+ cells/mm$^2$, 500 CD8+ cells/mm$^2$, 600 CD8+ cells/mm$^2$, 700 CD8+ cells/mm$^2$, 800 CD8+ cells/mm$^2$, 900 CD8+ cells/mm$^2$, 1000 CD8+ cells/mm$^2$, 2000 CD8+ cells/mm$^2$, 3000 CD8+ cells/mm$^2$, 4000 CD8+ cells/mm$^2$, 5000 CD8+ cells/mm$^2$, 6000 CD8+ cells/mm$^2$, 7000 CD8+ cells/mm$^2$, 8000 CD8+ cells/mm$^2$, 9000 CD8+ cells/mm$^2$ or 10000 CD8+ cells/mm$^2$ in the biological sample, such as a tumor biopsy. In some embodiments, exemplary threshold for total CD8+ cell density in a sample obtained from the subject after administration of the cell therapy, is about 80 CD8+ cells/mm$^2$, 90 CD8+ cells/mm$^2$, 100 CD8+ cells/mm$^2$, 200 CD8+ cells/mm$^2$, 300 CD8+ cells/mm$^2$, 400 CD8+ cells/mm$^2$, 500 CD8+ cells/mm$^2$, 600 CD8+ cells/mm$^2$, 700 CD8+ cells/mm$^2$, 800 CD8+ cells/mm$^2$, 900 CD8+ cells/mm$^2$, 1000 CD8+ cells/mm$^2$ or 2000 CD8+ cells/mm$^2$, or within a range defined by any of the foregoing, in the biological sample, such as a tumor biopsy. In some aspects, the subject is likely to achieve a response when treated with the cell therapy if the density of CD8+ cells is at or above the threshold value; or the subject is not likely to achieve a response when treated with the cell therapy if the density of CD8+ cells is below the threshold value, in a sample obtained from the subject after administration of cell therapy.

In some embodiments, exemplary threshold for percentage of T cells that express the recombinant receptor (e.g., CAR), such as the percentage of CAR+ cells, among total T cells in a sample obtained from the subject after administration of the cell therapy, is or is greater than about 2%, 3%, 4%, 5%, 6%, 7% 9%, 10%, 15%, 20% or 25%, of the total T cells in the biological sample, such as a tumor biopsy. In some embodiments, exemplary threshold for the percentage of CAR+ cells among total T cells in a sample obtained from the subject after administration of the cell therapy, is about 3%, 4%, 5%, 6%, 7%, 8%, 9%, 10% or 15%, or within a range defined by any of the foregoing, of the total T cells in the biological sample, such as a tumor biopsy. In some aspects, the subject is likely to achieve a response when treated with the cell therapy if the percentage of CAR+ cells among total T cells is at or above the threshold value; or the subject is not likely to achieve a response when treated with the cell therapy if the percentage of CAR+ cells among total T cells is below the threshold value, in a sample obtained from the subject after administration of cell therapy.

In some embodiments, exemplary threshold for density of T cells that express the recombinant receptor (e.g., CAR), such as CAR+ T cell density in a sample obtained from the subject after administration of the cell therapy, is or is greater than about 20 CAR+ T cells/mm$^2$ 30 CAR+ T cells/mm$^2$, 40 CAR+ T cells/mm$^2$, 50 CAR+ T cells/mm$^2$, 60 CAR+ T cells/mm$^2$, 70 CAR+ T cells/mm$^2$, 80 CAR+ T cells/mm$^2$, 90 CAR+ T cells/mm$^2$, 100 CAR+ T cells/mm$^2$, 200 CAR+ T cells/mm$^2$, 300 CAR+ T cells/mm$^2$, 400 CAR+ T cells/mm$^2$, 500 CAR+ T cells/mm$^2$, 600 CAR+ T cells/mm$^2$, 700 CAR+ T cells/mm$^2$, 800 CAR+ T cells/mm$^2$, 900 CAR+ T cells/mm$^2$, 1000 CAR+ T cells/mm$^2$, 2000 CAR+ T cells/mm$^2$ or 3000 CAR+ T cells/mm$^2$ in the biological sample, such as a tumor biopsy. In some embodiments, exemplary threshold for CAR+ T cell density in a sample obtained from the subject after administration of the cell therapy, is about 70 CAR+ T cells/mm$^2$, 80 CAR+ T cells/mm$^2$, 90 CAR+ T cells/mm$^2$, 100 CAR+ T cells/mm$^2$, 200 CAR+ T cells/mm$^2$, 300 CAR+ T cells/mm$^2$ or 400 CAR+ T cells/mm$^2$, or within a range defined by any of the foregoing, in the biological sample, such as a tumor biopsy. In some aspects, the subject is likely to achieve a response when treated with the cell therapy if the density of CAR+ T cells is at or above the threshold value; or the subject is not likely to achieve a response when treated with the cell therapy if the density of CAR+ T cells is below the threshold value, in a sample obtained from the subject after administration of cell therapy.

In some embodiments, exemplary threshold for density of CD4+ cells that express the recombinant receptor (e.g., CAR), such as CD4+/CAR+ T cell density in a sample obtained from the subject after administration of the cell therapy, is or is greater than about 10 CD4+/CAR+ T cells/mm$^2$, 20 CD4+/CAR+ T cells/mm$^2$, 30 CD4+/CAR+ T cells/mm$^2$, 40 CD4+/CAR+ T cells/mm$^2$, 50 CD4+/CAR+ T cells/mm$^2$, 60 CD4+/CAR+ T cells/mm$^2$, 70 CD4+/CAR+ T cells/mm$^2$, 80 CD4+/CAR+ T cells/mm$^2$, 90 CD4+/CAR+ T cells/mm$^2$, 100 CD4+/CAR+ T cells/mm$^2$, 200 CD4+/CAR+ T cells/mm$^2$, 300 CD4+/CAR+ T cells/mm$^2$, 400 CD4+/CAR+ T cells/mm$^2$, 500 CD4+/CAR+ T cells/mm$^2$, 600 CD4+/CAR+ T cells/mm$^2$, 700 CD4+/CAR+ T cells/mm$^2$, 800 CD4+/CAR+ T cells/mm$^2$, 900 CD4+/CAR+ T cells/mm$^2$, 1000 CD4+/CAR+ T cells/mm$^2$ or 2000 CD4+/CAR+ T cells/mm$^2$ in the biological sample, such as a tumor biopsy. In some embodiments, exemplary threshold for CD4+/CAR+ T cell density in a sample obtained from the subject after administration of the cell therapy, is about 20 CD4+/CAR+ T cells/mm$^2$, 30 CD4+/CAR+ T cells/mm$^2$, 40 CD4+/CAR+ T cells/mm$^2$, 50 CD4+/CAR+ T cells/mm$^2$, 60 CD4+/CAR+ T cells/mm$^2$, 70 CD4+/CAR+ T cells/mm$^2$, 80 CD4+/CAR+ T cells/mm$^2$, 90 CD4+/CAR+ T cells/mm$^2$ or 100 CD4+/CAR+ T cells/mm$^2$, or within a range defined by any of the foregoing, in the biological sample, such as a tumor biopsy. In some aspects, the subject is likely to achieve a response when treated with the cell therapy if the density of CD4+/CAR+ T cells is at or above the threshold value; or the subject is not likely to achieve a response when treated with the cell therapy if the density of CD4+/CAR+ T cells is below the threshold value, in a sample obtained from the subject after administration of cell therapy.

In some embodiments, exemplary threshold for density of CD8+ cells that express the recombinant receptor (e.g., CAR), such as CD8+/CAR+ T cell density in a sample obtained from the subject after administration of the cell therapy, is or is greater than about 10 CD8+/CAR+ T cells/mm$^2$, 20 CD8+/CAR+ T cells/mm$^2$, 30 CD8+/CAR+ T cells/mm$^2$, 40 CD8+/CAR+ T cells/mm$^2$, 50 CD8+/CAR+ T cells/mm$^2$, 60 CD8+/CAR+ T cells/mm$^2$, 70 CD8+/CAR+ T cells/mm$^2$, 80 CD8+/CAR+ T cells/mm$^2$, 90 CD8+/CAR+ T cells/mm$^2$, 100 CD8+/CAR+ T cells/mm$^2$, 200 CD8+/CAR+ T cells/mm$^2$, 300 CD8+/CAR+ T cells/mm$^2$, 400 CD8+/CAR+ T cells/mm$^2$, 500 CD8+/CAR+ T cells/mm$^2$, 600 CD8+/CAR+ T cells/mm$^2$, 700 CD8+/CAR+ T cells/mm$^2$, 800 CD8+/CAR+ T cells/mm$^2$, 900 CD8+/CAR+ T cells/mm$^2$, 1000 CD8+/CAR+ T cells/mm$^2$ or 2000 CD8+/CAR+ T cells/mm$^2$ in the biological sample, such as a tumor biopsy. In some embodiments, exemplary threshold for CD8+/CAR+ T cell density in a sample obtained from the subject after administration of the cell therapy, is about 20 CD8+/CAR+ T cells/mm$^2$, 30 CD8+/CAR+ T cells/mm$^2$, 40 CD8+/CAR+ T cells/mm$^2$, 50 CD8+/CAR+ T cells/mm$^2$, 60

CD8+/CAR+ T cells/mm$^2$, 70 CD8+/CAR+ T cells/mm$^2$, 80 CD8+/CAR+ T cells/mm$^2$, 90 CD8+/CAR+ T cells/mm$^2$, 100 CD8+/CAR+ T cells/mm$^2$ or 200 CD8+/CAR+ T cells/mm$^2$, or within a range defined by any of the foregoing, in the biological sample, such as a tumor biopsy. In some aspects, the subject is likely to achieve a response when treated with the cell therapy if the density of CD8+/CAR+ T cells is at or above the threshold value; or the subject is not likely to achieve a response when treated with the cell therapy if the density of CD8+/CAR+ T cells is below the threshold value, in a sample obtained from the subject after administration of cell therapy.

In some embodiments, exemplary threshold for percentage of CD8+ cells among recombinant receptor (e.g., CAR)-expressing T cells in a sample obtained from the subject after administration of the cell therapy, is or is greater than about 20%, 30%, 40%, 50%, 60% or 70%, 80% or 90%, of the total CAR+ T cells in the biological sample, such as a tumor biopsy. In some embodiments, exemplary threshold for the percentage of CD8+ cells among total CAR+ T cells in a sample obtained from the subject after administration of the cell therapy, is about 30%, 40%, 50%, 60%, 70% or 80%, or within a range defined by any of the foregoing, of the total T cells in the biological sample, such as a tumor biopsy. In some aspects, the subject is likely to achieve a response when treated with the cell therapy if the percentage of CD8+ cells among CAR+ T cells is at or above the threshold value; or the subject is not likely to achieve a response when treated with the cell therapy if the percentage of CD8+ cells among CAR+ T cells is below the threshold value, in a sample obtained from the subject after administration of cell therapy. In some aspects, the response is a complete response (CR).

In some aspects, the provided embodiments, including methods of assessing likelihood of a response following administration of a cell therapy involve assessing a biological sample for a frequency of CD8+ immune cells, wherein the biological sample, such as a tumor biopsy is obtained from a subject having a disease or condition, said subject having previously received administration of a cell therapy comprising a dose or composition of genetically engineered cells expressing a recombinant receptor for treating the disease or condition; and comparing the frequency to a threshold value, thereby determining a likelihood that a subject will achieve a response.

In some aspects, the provided embodiments, including methods of assessing likelihood of a response to a cell therapy involve assessing a sample from a subject for the frequency of CD8+ immune cells that express a recombinant receptor among total cells expressing the recombinant receptor, said subject having previously received administration of a cell therapy comprising a dose of genetically engineered cells expressing the recombinant receptor for treating a disease or condition; and comparing the frequency of recombinant receptor-expressing CD8+ immune cells to a threshold value, thereby determining a likelihood that a subject will achieve a response when treated with the cell therapy.

In some aspects, the provided embodiments, including methods of assessing likelihood of a response following administration of a cell therapy involve assessing a biological sample for a frequency of CD8+ immune cells, wherein the biological sample, such as a tumor biopsy that is a tumor biopsy sample is obtained from a subject having a cancer, said subject having previously received administration of a cell therapy comprising a dose or composition of genetically engineered cells expressing a recombinant receptor for treating the cancer, wherein the frequency of CD8+ immune cells is determined based on detection using immunohistochemistry; and comparing the frequency to a threshold value, thereby determining a likelihood that a subject will achieve a response that is a complete response (CR) and/or a partial response (PR), optionally the response is durable for greater than 3 months, 4 months, 5 months, or 6 months.

In some aspects, the provided embodiments, including methods of assessing likelihood of a response to a cell therapy involve assessing a sample that is a tumor biopsy sample from a subject for the frequency of CD8+ immune cells that express a recombinant receptor among total cells expressing the recombinant receptor, said subject having previously received administration of a cell therapy comprising a dose of genetically engineered cells expressing the recombinant receptor for treating a cancer, wherein the frequency of CD8+ immune cells is determined based on detection using immunohistochemistry; and comparing the frequency of recombinant receptor-expressing CD8+ immune cells to a threshold value, thereby determining a likelihood that a subject will achieve a response a response that is a complete response (CR) and/or a partial response (PR), optionally the response is durable for greater than 3 months, 4 months, 5 months, or 6 months when treated with the cell therapy.

In some embodiments, the subject is likely to achieve a response when treated with the cell therapy if the frequency of CD8+ immune cells is at or above the threshold value; or the subject is not likely to achieve a response when treated with the cell therapy if the frequency of CD8+ immune cells is below the threshold value. In some embodiments, the threshold value is within 25%, within 20%, within 15%, within 10% or within 5% and/or is within a standard deviation above the median or mean frequency of CD8+ immune cells in samples obtained from a group of subjects after the initiation of administration of the cell therapy, wherein each of the subjects of the group went on to exhibit stable disease (SD) and/or progressive disease (PD).

In some embodiments, the threshold level is within 25%, within 20%, within 15%, within 10% or within 5% and/or is within one or two standard deviation(s) below the median or mean frequency of CD8+ immune cells in samples obtained from a group of subjects after the initiation of administration of the cell therapy, wherein each of the subjects of the group went on to achieve a response after administration of the cell therapy. In some embodiments, the threshold value of CD8+ immune cells is determined based on a median frequency of CD8+ immune cells observed from a group of subjects that achieved a response after administration of the cell therapy. In some embodiments, the response achieved by the group of subjects is CR and/or PR. In some embodiments, the response is durable at 3 months. In some embodiments, the threshold value of CD8+ immune cells is within 25%, within 20%, within 15%, within 10% or within 5% and/or is within one or two standard deviation(s) below the median or mean frequency of CD8+ immune cells in samples obtained from a group of subjects after the initiation of administration of the cell therapy a complete response (CR). In some embodiments, the threshold value of CD8+ immune cells is within 25%, within 20%, within 15%, within 10% or within 5% and/or is within a standard deviation below the median or mean frequency of CD8+ immune cells in samples obtained from a group of subjects after the initiation of administration of the cell therapy a partial response (PR).

In some embodiments, the frequency is based on or is a density of the CD8+ immune cells. In some embodiments, the frequency is based on or is a density of the cells measured as CD8+ immune cells/mm$^2$.

In some embodiments, the methods involve assessing a parameter associated with a biomarker, such as a change in the level, expression or frequency of a biomarker between one or more time points, e.g., prior to initiation of cell therapy and after initiation of cell therapy. In some embodiments, the degree or magnitude of the change, e.g., increase or decrease, is assessed to determine the likelihood of response and/or to select subjects for treatment.

In some embodiments, the methods of assessing likelihood of a response to a cell therapy involves assessing the change in the number or percentage of CD8+ cells in one or more sample(s) from a subject. In some embodiments, the change is determined between a first sample obtained prior to administration of the cell therapy and a second sample obtained after the initiation of administration of the cell therapy. In some embodiments, pre- and post-treatment biopsies are obtained from the same subject. In some embodiments, the matched pre- and post-treatment biopsies are compared. In some embodiments, paired samples from a subject can be taken pre-treatment as a baseline for assessing likelihood of response and post-treatment to assess or monitor response.

In some embodiments, the subject has a disease or condition, and has previously received administration of a cell therapy comprising a dose or composition of genetically engineered cells expressing a recombinant receptor for treating the disease or condition. In some embodiments, the methods involve comparing the increase in the number or percentage of CD8+ cells in the second sample compared to the first sample to a threshold value, thereby determining a likelihood that a subject will achieve a response when treated with the cell therapy. In some embodiments, the subject is likely to achieve a response when treated with the cell therapy if the increase in the number or percentage of CD8+ cells in the second sample compared to the first sample that is at or above a threshold level; or the subject is not likely to achieve a response when treated with the cell therapy if the increase in the number or percentage of CD8+ cells in the second sample compared to the first sample that is below the threshold value. In some embodiments, if the subject is determined not likely to achieve a response, the subject can be selected for administration of an agent.

In some embodiments, the response is a complete response (CR) and/or a partial response (PR). In some embodiments, the response is durable. In some embodiments, the response is durable for greater than 3 months, 4 months, 5 months, or 6 months.

In some embodiments, provided are methods of selecting a subject for treatment with an agent that involves assessing the number or percentage of CD8+ cells in one or more sample(s) from a subject having a disease or condition, said subject being a candidate for administration of a cell therapy comprising a dose or composition of genetically engineered cells expressing a recombinant receptor for treating the disease or condition, wherein a first sample is obtained prior to administration of the cell therapy and a second sample is obtained after the initiation of administration of the cell therapy, wherein the subject is selected for administration of the agent if an increase in the number or percentage of CD8+ cells in the second sample compared to the first sample is below a threshold level.

In some embodiments, the methods of assessing likelihood of a response to a cell therapy involves assessing the change in the number or percentage of CD8+ cells in one or more sample(s) from a subject. In some embodiments, the change is determined between a first sample obtained prior to administration of the cell therapy and a second sample obtained after the initiation of administration of the cell therapy.

In some embodiments, the assessment can be performed using a second sample from the subject that is obtained after the initiation of administration of the cell therapy. In some embodiments, the second sample from the subject is obtained within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the cell therapy. In some embodiments, the second sample from the subject is obtained at a time before a peak or maximum level of the cells of the cell therapy is detectable in the blood of the subject. In some embodiments, the assessment can be performed more than once, e.g., at more than one different time points after the initiation of administration of the cell therapy, e.g., for monitoring and/or periodic assessment of the treated subjects.

In any of such cases, an exemplary threshold level can be determined based on the increase in the number or percentage of CD8+ cells in the second sample compared to the first sample observed in a subject group that ultimately did not show objective response, e.g., from a subject group wherein each of the subjects went on to exhibit stable disease (SD) and/or progressive disease (PD). In some embodiments, the threshold level is within 25%, within 20%, within 15%, within 10% or within 5% and/or is within a standard deviation above the median or mean increase in the number or percentage of CD8+ cells in the second sample compared to the first sample obtained from a group of subjects after the initiation of administration of the cell therapy, wherein each of the subjects of the group went on to exhibit stable disease (SD) and/or progressive disease (PD).

In some embodiments, the threshold level for assessing the likelihood of response and/or selecting a subject for treatment with an agent for an increase in the number or percentage of CD8+ cells in the second sample compared to the first sample from a subject is an increase (+) of at least or at least about +0.1%, +0.25%, +0.5%, +0.75%, +1%, +2%, +3%, +4%, +5%, +6%, +7%, +8%, +9%, +10%, +11%, +12%, +13%, +14%, +15% or +20%.

In some aspects, the provided embodiments are based in some aspects on the observation that in a cohort of subjects administered a CAR+ cell therapy, subjects that went on to have a complete response (CR) and/or a partial response (PR) was observed to have a larger increase in CD8$^+$ cells in a tumor sample compared to subjects with a best overall response of stable disease (SD) and/or progressive disease (PD).

In some embodiments, any of the methods provided herein further comprises assessing one or more additional parameters in the samples. In some embodiments, the additional parameter is the number or percentage of cells expressing an additional biomarker. In some embodiments, the additional biomarker is a biomarker associated with immune modulation. In some embodiments, the additional biomarker is selected from among one or more of CD73, FOXP3, CD163, IDO and PD-L1. In some embodiments, a subject can be selected for administration of an agent, if the patient is observed to exhibit a change in the levels expressing IDO and/or PD-L1 between the first sample and the second sample.

In certain embodiments of the methods provided herein, the subject has been administered an initial dose of a cell therapy, such as, in some aspects, is a standard dose of the cell therapy. In some embodiments, the subject is determined to be likely to respond to the cell therapy as described above (e.g., likely to achieve a CR or a PR), and the subject does not receive additional therapy. In some embodiments, the subject is determined to be not likely to respond to the cell therapy, as described above (e.g., likely to achieve a PD or SD), the subject is selected or identified for administered agents or treatments that are capable of stimulating, amplifying, potentiating, and/or enhancing an anti-tumor immune response. In some embodiments, such agents are any agents described herein, e.g., in Section IV. In some embodiments, the agent can be administered after the assessment, e.g., after the initiation of cell therapy. In some embodiments, the assessment and/or administration of the agent can be performed more than once e.g., for monitoring and/or periodic assessment of the treated subjects.

C. Methods and Reagents for Assessing Biomarkers

In certain embodiments, the sample that is assessed is a biological sample. In certain embodiments, the sample is a tissue sample. In particular embodiments, the sample is or includes a tissue affected, or suspected of being affected, by a disease or condition. In some embodiments, the sample is or includes a tissue affected, or suspected of being affected by a cancer or a proliferative disease. In some embodiments, the sample is a tumor sample and/or the sample comprises or is likely to comprise tumor cells. In some embodiments, the sample is a tumor biopsy.

In certain embodiments, the sample is collected from a tissue having or suspected of having a tumor. In particular embodiments, the sample is or includes a tumor and/or a tumor microenvironment. In particular embodiments, the tumor is precancerous or cancerous, or is suspected of being cancerous or precancerous. In certain embodiments, the tumor is a primary tumor, i.e., the tumor is found at the anatomical site where the lesion initially developed or appeared. In some embodiments, the tumor is a secondary tumor, e.g., a cancerous tumor that originated from a cell within a primary tumor located within a different site in the body. In some embodiments, the sample contains one or more cells that are cancer cells and/or tumor cells.

In particular embodiments, the sample is collected from a lesion and/or a tumor that is associated with or caused by, or is suspected of being associated with or caused by, a non-hematologic cancer, e.g., a solid tumor. In some embodiments, the tumor is associated with or caused by, or is suspected of being associated with or caused by, a bladder, a lung, a brain, a melanoma (e.g. small-cell lung, melanoma), a breast, a cervical, an ovarian, a colorectal, a pancreatic, an endometrial, an esophageal, a kidney, a liver, a prostate, a skin, a thyroid, or a uterine cancer. In some embodiments, the lesion is associated with or caused by a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma. In certain embodiments, the sample contains one or more cancer cells. In some embodiments, the sample contains one or more cells that are suspected of being cancerous.

In some embodiments, the sample is collected from a lesion or tumor that is associated with or caused by a B cell malignancy or hematological malignancy. In some embodiments, the lesion or tumor is associated with a myeloma, e.g., a multiple myeloma (MM), a lymphoma or a leukemia, lymphoblastic leukemia (ALL), non-Hodgkin's lymphoma (NHL), chronic lymphocytic leukemia (CLL), a diffuse large B-cell lymphoma (DLBCL), and/or acute myeloid leukemia (AML).

In some embodiments, the sample is a tissue sample, e.g., a tissue biopsy. In particular embodiments, the sample is obtained, collected, or taken from connective tissue, muscle tissue, nervous tissue, or epithelial tissue. In certain embodiments, the lesion is present on the heart, vasculature, salivary glands, esophagus, stomach, liver, gallbladder, pancreas, intestines, colon, rectum, hypothalamus, pituitary gland, pineal gland, thyroid, parathyroid, adrenal gland, kidney, ureter, bladder, urethra, lymphatic system, lymph nodes, skin, muscle, brain, spinal cord, nerves, ovaries, uterus, testes, prostate, pharynx, larynx, trachea, bronchi, lungs, diaphragm, bone, cartilage, ligaments, or tendons. In particular embodiments, the sample is obtained, collected, or taken from the lymph node or the bone marrow.

In particular embodiments, the sample contains immune cells. In particular embodiments, the sample contains the therapy, e.g., the immunotherapy and/or the cell therapy. In particular embodiments, the sample contains cells, e.g., engineered cells, of a cell therapy. In particular embodiments, the therapy is a T cell therapy and the sample contains engineered T cells and/or any T cells of the therapy. In particular embodiments, the sample contains engineered cells that express a recombinant receptor, e.g., a CAR. In some embodiments, the sample contains cells expressing a CAR. In certain embodiments, the sample contains cells from the therapy or components of a therapy described herein.

In certain embodiments, the sample is obtained, collected, or taken from the subject at one or more time points prior to or after treatment with the therapy, e.g., an immunotherapy and/or a cell therapy. In particular embodiments, the sample is obtained, collected, and/or taken from the subject prior to a treatment with a cell therapy. In particular embodiments, the cell therapy is a T cell therapy. In certain embodiments, the T cell therapy contains one or more engineered cells. In particular embodiments, the therapeutic T cell therapy contains cells that express a recombinant receptor, e.g., a CAR. In some embodiments, the sample from the subject contains engineered cells, cells expressing a recombinant receptor, or cells expressing a CAR. In some embodiments, the sample from the subject contains cells expressing an antigen that can be detected, or cells expressing a CAR containing an antigen that can be detected.

In particular embodiments, the sample is or contains lymph node tissue. In some embodiments, the sample is or contains a peripheral lymph node tissue. In some embodiments, the lymph node sample contains, or is suspected of containing, at least one diseased cell or cancer cell. In particular embodiments, the diseased cell or cancer cell is a B cell.

In particular embodiments, the sample is or contains bone marrow. In some embodiments, the sample is or contains bone marrow aspirates. In some embodiments, the bone marrow sample contains, or is suspected of containing, at least one diseased cell or cancer cell. In particular embodiments, the diseased cell or cancer cell is a B cell.

In some embodiments, the sample is a blood sample. In certain embodiments, the sample is a serum sample. In some embodiments, the sample is a peripheral blood sample. In some embodiments, the blood sample contains, or is suspected of containing, at least one diseased cell or cancer cell. In particular embodiments, the diseased cell or cancer cell is a B cell.

In some embodiments, the sample contains immune cells. In particular embodiments, the sample contains immune cells expressing a biomarker provided herein. In some embodiments, the T cells express markers of immunosuppressive pathways. In some embodiments, the sample contains CD4+ or CD8+ immune cells. For example, in some instances, the sample contains myeloid cells, T helper cells, monocytes, macrophages, and/or dendritic cells.

In some embodiments, one or more sample(s) are obtained from a subject who has been, who will be, or is a candidate to be administered a therapy, e.g., a cell therapy. In some embodiments, a sample is obtained from the subject prior to initiation of administration of the cell therapy. In some embodiments, a sample is obtained from the subject after initiation of administration of the cell therapy. In some embodiments, a sample is obtained from the subject prior to and after the initiation of administration of the cell therapy. In particular embodiments, the sample is obtained prior to the initiation of treatment with or administration of the therapy, e.g., the cell therapy. In some embodiments, the sample is obtained within or within about 0, 1, 2, 3, 4, 5, 6, 9, 12, 18 or 24 hours, or 2, 3, 4, 5, 6, 7, 8, 9, 10, 11, 12, 14, 21 or 28 days prior to the initiation of administration of the therapy, e.g., cell therapy. In particular embodiments, the sample is obtained after the initiation of treatment with or administration of the therapy, e.g., the cell therapy. In some embodiments, the sample is obtained within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the therapy, e.g., cell therapy. In some embodiments, the same biomarker is assessed and/or compared in the one or more samples. In some embodiments, one or more different biomarkers and/or parameters associated with the one or more biomarkers is assessed and/or compared in the one or more samples.

In some embodiments, the biomarker is indicative of a cell phenotype, e.g., an immune cell phenotype. In some embodiments, the biomarker is indicative of a lineage, differentiation state and/or activity of an immune cell. In some embodiments, the biomarker is associated with activity, phenotypes, proliferation and/or function of the cells used for therapy. In some embodiments, the biomarker is a marker expressed on the surface of an immune cell, e.g., a lymphoid cell and/or a myeloid cell. In some embodiments, the biomarker is selected from among CD4 and CD8. In some embodiments, the biomarker is CD4. In some embodiments, the biomarker is CD8.

In some embodiments, the biomarker is a biomarker expressed on one or more other cells in the tumor microenvironment (TME), such as tumor cells, endothelial cells, fibroblasts, adipocytes and/or pericytes. In some embodiments, the biomarker is expressed on tumor cells. In some embodiments, the biomarker is an antigen, e.g. a tumor antigen. In some embodiments, the biomarker is an antigen specifically targeted by the cell therapy, e.g., an antigen that is recognized by or binds a recombinant receptor expressed on the cells administered for cell therapy. In some embodiments, the biomarker is selected from among CD19 and CD20.

In some embodiments, the biomarker is indicative of tumor burden in a sample. In some embodiments, the biomarker is indicative of immunosuppressive pathway or activity in the sample. In some embodiments, the biomarkers assessed are used to evaluate immunosuppressive pathways by detecting expression of PD-L1, IDO (e.g. IDO1), CD73, CD163, and FOXP3.

In some embodiments, two or more biomarkers are assessed in a sample. For example the two or more biomarkers are part of a panel of biomarkers is assessed in a sample. In some further embodiments, one or more panels of biomarkers, each containing more than one biomarker, is assessed in a sample. An exemplary panel of biomarkers may include PD-L1, IDO, CD73, CD163, and FOXP3. In some particular embodiments, an exemplary panel of biomarkers includes CD4, CD19, CD20, CD8 and a biomarker for detecting CAR-expressing cells (e.g. a cell surface surrogate marker for CAR-expressing cells).

In some embodiments, positive or negative expression of a biomarker is determined by incubating cells with one or more antibodies or other binding agent that specifically bind to one or more biomarkers expressed or expressed (marker$^+$) at a relatively higher level (marker$^{high}$) In particular embodiments, the positive or negative expression is determined by immunohistochemistry, immunofluorescence, flow cytometry, or any other suitable method for detecting specific biomarkers.

In some embodiments, one or more parameters associated with one or more biomarkers can be used in assessment. In some embodiments, the parameter includes a change and/or an alteration, e.g., an increase, an elevation, a decrease or a reduction, in levels, values or measurements of a biomarker compared to the levels, values or measurements of the same biomarker in a different time point of assessment, a different condition, a reference point and/or a different subject is determined or assessed. For example, in some embodiments, an increase or decrease in particular biomarkers, e.g., number or frequency of CD4+ cell and/or CD8+ cells in a sample, compared to the same biomarker in a different condition, e.g., before or after administration of the cell therapy, can be determined. In some embodiments, the change, e.g., an increase or decrease is greater than or greater than about 0.1%, 0.25%, 0.5%, 0.75%, 1%, 2%, 3%, 4%, 5%, 6%, 7%, 8%, 9%, 10%, 11%, 12%, 13%, 14%, 15% or 20%. In some embodiments, the change, e.g., an increase or decrease is greater than or greater than about 1.2-fold, 1.5-fold, 2-fold, 3-fold, 4-fold, 5-fold, 10-fold or more. In some embodiments, the levels, values or measurements of two or more biomarkers are determined, and relative levels and/or ratios are determined. In some embodiments, the determined levels, values or measurements of biomarkers are compared to the levels, values or measurements from a control sample or an untreated sample. In some embodiments, the determined levels, values or measurements of biomarkers are compared to the levels from a sample from the same subject but at a different time point. The values obtained in the quantification of individual biomarker can be combined for the purpose of disease assessment, e.g., by forming an arithmetical or logical operation on the levels, values or measurements of biomarkers by using multiparametric analysis. In some embodiments, a ratio of two or more specific biomarkers can be calculated.

In some embodiments, any of the described biomarkers and/or parameters associated with biomarkers can be used among other parameters or biomarkers to assess or characterize the activity, phenotypes, proliferation and/or function of the T cells used for therapy, before, during or after engineering, correlate with treatment outcomes or toxicity outcomes, to identify or select patients for treatment, and/or to determine dosing or other treatment regimes.

Also provided are articles of manufacture containing a reagent capable of detecting or that is specific for a biomarker. In some embodiments, instructions are provided for assessing a biological sample for the biomarker from a subject that is a candidate for treatment, optionally with a cell therapy, said cell therapy optionally including a dose or composition of genetically engineered cells expressing a recombinant receptor. Also provided are instructions for using the reagents to detect the biomarker and assess the one or more biomarker in a sample obtained from a subject that is a candidate for treatment, optionally with a cell therapy.

In some embodiments, methods or assays to detect or determine the level, presence, concentration, activity and/or effect of the biomarker includes any of the known methods for detecting levels of metabolites, proteins, nucleic acids or other biomolecules in a biological sample. For example, the methods for detection include immunohistochemistry, enzyme-linked immunosorbent assay (ELISA), enzyme immunoassay (EIA), immunofluorescence, polymerase chain reaction (PCR), reverse transcriptase PCR (RT-PCR), in situ PCR, quantitative PCR, flow cytometry, fluorescence-activated cell sorting (FACS), enzymatic activity assays, gas chromatography/mass spectroscopy (GC/MS), high performance liquid chromatography (HPLC), liquid chromatography-dual mass spectrometry (LC-MS/MS), liquid chromatography-electrospray ionization-tandem mass spectrometry (LC-ESI-MS), nuclear magnetic resonance (NMR), in situ hybridization, Western blot, Northern blot, Southern blot, in vivo imaging, microarrays, transcriptome sequencing, and/or any high throughput methods. In some embodiments, the one or more biomarkers is assessed using an in vitro ELISA, a colorimetric test, an immunoassay, in situ hybridization, immunohistochemistry, multiplexed immunohistochemistry, immunofluorescence, multiplexed immunofluorescence or 5-plex fluorescent immunohistochemistry.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273,927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Pluckthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

Table 1A, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1A

Boundaries of CDRs according to various numbering schemes.

| CDR | Kabat | Chothia | AbM | Contact |
|---|---|---|---|---|
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89--L97 | L89--L97 | L89--L96 |
| CDR-H1 (Kabat Numbering[1]) | H31--H35B | H26--H32.34 | H26--H35B | H30--H35B |
| CDR-H1 (Chothia Numbering[2]) | H31--H35 | H26--H32 | H26--H35 | H30--H35 |

TABLE 1A-continued

Boundaries of CDRs according to various numbering schemes.

| CDR | Kabat | Chothia | AbM | Contact |
|---|---|---|---|---|
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes, or other known schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes, or other known schemes. In some embodiments, specific CDR sequences are specified. Exemplary CDR sequences of provided antibodies are described using various numbering schemes, although it is understood that a provided antibody can include CDRs as described according to any of the other aforementioned numbering schemes or other numbering schemes known to a skilled artisan.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the antibodies included in the provided CARs are antibody fragments. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; heavy chain variable ($V_H$) regions, single-chain antibody molecules such as scFvs and single-domain antibodies comprising only the $V_H$ region; and multispecific antibodies formed from antibody fragments. In some embodiments, the antigen-binding domain in the provided CARs is or comprises an antibody fragment comprising a variable heavy chain ($V_H$) and a variable light chain ($V_L$) region. In particular embodiments, the antibodies are single-chain antibody fragments comprising a heavy chain variable ($V_H$) region and/or a light chain variable ($V_L$) region, such as scFvs.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

Also provided are antibody immunoconjugates comprising an antibody against one or more of the biomarkers described herein, e.g., immune cell biomarker, attached to a label, which can generate a detectable signal, indirectly or directly. These antibody immunoconjugates can be used for research or diagnostic applications. The label is preferably capable of producing, either directly or indirectly, a detectable signal. For example, the label may be radio-opaque or a radioisotope, such as $^3H$, $^4C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example $^{99}Tc$ or $^{123}I$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

In some embodiments, the antibody immunoconjugate is detectable indirectly. For example, a secondary antibody that is specific for the antibody against the marker expressed on a population of myeloid cells immunoconjugate and contains a detectable label can be used to detect the antibody immunoconjugate.

In some embodiments, antibodies capable of detecting or that is specific the inflammatory markers provided herein may be identified, screened for, or characterized for their physical/chemical properties and/or biological activities by various known assays. In one aspect, the antibody is tested for its antigen binding activity, e.g., by known methods such as an immunoassay, ELISA, Western blotting, and/or flow cytometric assays, including cell-based binding assays.

1. Histochemistry, Immunohistochemistry or Immunofluorescence

In some embodiments, the level, presence, amount or concentration, of the biomarker or biomarkers is assayed using histochemistry (HC), immunohistochemistry (IHC) or immunofluorescence (IF). In some aspects, HC, IHC or IF staining methods can be carried out to detect one or more biomarkers based on enzymatic reactions using a reagent or reagents that binds the biomarker, such as an antibody (e.g. monoclonal or polyclonal antibodies). In some cases, the IHC is multiplex IHC in which 2, 3, 4, 5, 6, 7, 8, 9, or 10 or more biomarkers are assessed. In some cases, the IF is multiplex IF in which 2, 3, 4, 5, 6, 7, 8, 9, or 10 or more biomarkers are assessed. In some examples, the biomarkers assessed include PD-L1, IDO, CD73, CD163, FOXP3, CD4, CD19, CD20, CD8 and/or a marker for detecting CAR-expressing cells. In some particular embodiments, panels of biomarkers are assessed. For example, a first panel is used to assess biomarkers indicative of immunosuppressive pathways by detecting the level, presence, amount, or concentration of PD-L1, IDO, CD73, CD163, and FOXP3 expressing cells and a second panel of biomarkers is used and includes CD4, CD19, CD20, CD8 and a marker indicative of the presence of CAR T cells.

In some embodiments, the HC, IHC or IF assays for use in the methods herein include those that use a reagent that is a binding partner to detect various biomarkers of interest. The reagent can be labeled or unlabeled. Typically, the assaying includes a detection system that makes the presence of the markers visible, to either the human eye or a digital system, such as an automated scanning system, for qualitative or quantitative analyses. In a direct IHC or IF assay, binding is determined directly upon binding of the binding partner (e.g. first antibody) to the tissue or biomarker due to the use of a labeled reagent. In an indirect IHC or IF assay, a secondary antibody or second binding partner is necessary to detect the binding of the first binding partner, as it is not labeled.

In such methods, generally a slide-mounted tissue sample (e.g. a formalin-fixed paraffin-embedded (FFPE) tissue section) is stained with a labeled reagent. In some particular examples, the tissue sample is a tumor biopsy sample. In some embodiments, the reagent is conjugated to small molecules, e.g., biotin, that are detected via a labeled binding partner or antibody. In some examples, the reagent is conjugated to or linked to a detectable moiety, e.g., a fluorescent (fluorophore) or chemiluminescent (chromophore) compound or a fluorescent, chemiluminescent or a bioluminescent protein or an enzyme. Exemplary detectable moieties can include fluorescein isothiocyanate (FITC), phycoerythrin, peridinin, chlorophyll protein or luciferin. In some embodiments, the reagent is conjugated to or linked to a fluorophore. Exemplary fluorophores hydroxycoumarin, Cascade Blue, Dylight 405, Pacific Orange, Alexa Fluor 430, Fluorescein, Oregon Green, Alexa Fluor 488, BODIPY 493, 2.7-Diochlorofluorescien, ATTO 488, Chromeo 488, Dylight 488, HiLyte 488, Alexa Fluor 555, ATTO 550, BODIPY TMR-X, CF 555, Chromeo 546, Cy3, TMR, TRITC, Dy547, Dy548, Dy549, HiLyte 555, Dylight 550, BODIPY 564, Alexa Fluor 568, Alexa Fluor 594, Rhodamine, Rhodamine 6G, Texas Red, Red610, Alexa Fluor 610, Alexa Fluor 633, Dylight 633, Alexa Fluor 647, APC, ATTO 655, CF633, CF640R, Chromeo642, Cy5, Dylight 650, Alexa Fluor 680, Alexa Fluor 700, Cy 5.5, ICG, Alexa Fluor 750, Dylight 755, Cy7, Cy7.5, Alexa Fluor 790, Dylight 800, Qdot® 525, Qdot® 565, Qdot® 605, Qdot® 655, Qdot® 705, Qdot® 800, coumarin, DCC and FAM (Carboxyfluorescein).

In other examples, the reagents are conjugated to detectable proteins which permit direct detection, such as, for example, conjugated to a fluorescent protein, bioluminescent protein or enzyme. Exemplary enzymatic staining methods for detecting a protein of interest include enzymatic interactions that can be visualized using different enzymes such as peroxidase, alkaline phosphatase, or different chromogens. Further, examples of enzyme labels include horseradish peroxidase, alkaline phosphatase, glucose oxidase, and β-galactosidase. Colorimetric substrates for horseradish peroxidase include ABTS (2,2'-azino-1-bis(3-ethylbenzothiazoline-6-sulphonic acid)), OPD (o-phenylenediamine dihydrochloride), TMB (tetramethylbenzidine), 4CN (4-chloro-1-napthol), DAB (3,3'-diaminobenzidine), and AEC (3-amino-9-ethylcarbazole). Colorimetric substrates for alkaline phosphatase include BCIP (5-bromo-4-chloro-3-indolyl-phosphate), and NBT (nitro-blue tetrazolium chloride)—often used together. Colorimetric substrates for glucose oxidase include NBT. Colorimetric substrates for β-galactosidase include X-Gal (5-bromo-4-chloro-3-indolyl-β-D-galactopyranoside) alone or in combination may be used. In other examples, the reagent is conjugated to peptides or proteins that can be detected via a labeled binding partner or antibody. In some particular embodiments, the methods include contacting the section with a biomarker specific reagent, contacting the section with a labeled antibody (conjugated to an enzyme label) and contacting the section with a colorimetric substrate of the enzyme label.

In some embodiments, the biomarker is detected using a reagent that can be detected by labeled secondary reagents, such as labeled antibodies that recognize the biomarker. In some aspects, the reagent is a binding reagent that specifically binds the biomarker, e.g., immune cell biomarker. In some cases, the binding reagent is an antibody or antigen-binding fragment thereof, an aptamer or a nucleic acid probe. The antibodies that bind the biomarker can be labeled for detection or can be detected with a secondary antibody that binds the first antibody.

In some embodiments, the signal of the reagent is amplified by a tyramide signal (e.g. using probe-conjugated tyramide molecules). For example, tyramides can be conjugated to a detectable label, such as biotin or fluorescent labels. Furthermore, in some embodiments, the tyramides are substrates for horseradish peroxidase, such as described in Dixon et al., Expert Rev Mol Diagn (2015) 15(9): 1171-1186.

The methods can further involve using a reagent to visualize cellular structures such as cytoplasm, nuclei, or cell membranes, thereby generating a structure-stained image. For example, stains including hematoxylin, eosin, periodic acid-Schiff's stain, Mason's Trichrome, Gomori Trichrome, silver salts, Wright's, Giemsa, 4',6-diamidino-2-phenylindole (DAPI), and others can be used to visualize such cellular structures. Using these visualizations, the images can then be used to identify cells or tissues.

In some embodiments, the HC, IHC or HF may be performed to be used to detect one or more biomarkers, e.g. multiplex IHC or multiplex IF. For example, the method comprises performing serial immunohistochemistry (IHC) or immunofluorescence (IF) on one sample (e.g., one section). After a first staining cycle, a second staining cycle that involves contacting the section with another biomarker specific reagent, a labeled antibody with an enzyme label, and a colorimetric substrate of the enzyme label and generating a digital image of the section is performed. Furthermore, additional staining cycles may be performed to detect additional biomarkers. In further examples, a second staining cycle, third staining cycle, fourth staining cycle, fifth staining cycle, sixth staining cycle, and seventh staining cycle are completed. See e.g., Parra et al., Sci Rep. (2017) 7(1):13380; Tsujikawa et al., Cell Rep, (2017) 19(1): 203-217; Blom et al., Sci Rep. (2017) 7(1): 15580.

In some embodiments, a deactivation step may be performed between any staining cycles or between the detection of one biomarker and a different biomarker. In some cases, the deactivation step is used to denature the primary and secondary antibody conjugate. In some aspects, the deactivation may be performed by exposure to various chemical agents (e.g., an inhibitor), by exposing to a buffer or solution of a particular pH, or by altering the temperature of the sample. For example, between any staining cycles, a heating step may be performed. In some particular embodiments, the deactivation step involves heating the section or sample to at least 90° C. See e.g., published U.S. patent Appl. No. US20170160171, US20150346210, US20070154958).

In some examples, the methods for assessing biomarkers is performed using commercially available regents or using reagents compatible with commercially available systems for multiplex IHC or multiplex IF. In some embodiments, the commercially available systems include reagents for assessing biomarkers. See e.g., Bio-Plex (Bio-Rad Laboratories, Inc.), Meso Scale Discovery multiplex assay kits, Multi-Analyte Profiling (MAP) (Myriad RBM), DISCOVERY 5-plex system (Ventana Medical Systems, Inc.) or Opal Multiplex Immunohistochemistry (PerkinElmer).

In some embodiments, the resulting stained samples are visualized by any optical or non-optical imaging device to detect the stain or biomarker label. For example, visualization of the detectable signal may be performed using bright field. fluorescent, upright or inverted optical microscopes, scanning confocal microscopes, cameras, scanning or tunneling electron microscopes, scanning probe microscopes and imaging infrared detectors. In some cases, the method further includes acquiring an image, such as a digital image of the sample (e.g. the section). In some examples, the image can be captured digitally. The digital image can be generated using devices including the use of a microscope equipped with a camera that can capture a digital image of the cells within the context of the tissue and with digital storage capabilities (within the camera or in another device) that can save the image.

The obtained images can then be used for quantitatively or semi-quantitatively determining the level, presence, amount or concentration of the biomarker in the sample. Various automated sample processing, scanning, analysis, and/or quantification systems are suitable for use with immunohistochemistry methods for assessing biomarkers described herein. Such systems can include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.). In some embodiments, the system for analyzing the samples is integrated into the system used for performing the assay for assessing the biomarker. See e.g., the DISCOVERY 5-plex system (Ventana Medical Systems, Inc.). In particular, detection can be made manually or by image processing techniques involving computer processors and software. Using such software, for example, the images can be configured, calibrated, standardized and/or validated based on factors including, for example, stain quality or stain intensity, using procedures known to one of skill in the art (see e.g. published U.S. patent Appl. No. US20100136549).

The image can be quantitatively or semi-quantitatively analyzed and scored based on staining intensity of the sample. Quantitative or semi-quantitative histochemistry, immunohistochemistry or immunofluorescence refers to method of scanning and scoring samples that have undergone histochemistry, immunohistochemistry or immunofluorescence, to identify and quantitate the presence, level, amount or concentration of a specified biomarker. Quantitative or semi-quantitative methods can employ imaging software to detect staining densities or amount of staining or methods of detecting staining by the human eye, where a trained operator ranks results numerically. For example, images can be quantitatively analyzed using a pixel count algorithms and other methods that measure or quantitate or semi-quantitate the degree of staining; see e.g. U.S. Pat. No. 7,219,016; published U.S. Pat. Appl. Nos. US20100136549 and 20110111435.

In some embodiments, the number of biomarker positive cells is assessed and quantified. In addition, the total area or the total number of cells in the assessed area is quantified. The various quantifications can be used to determine a percentage or ratio of cells that are positive for one or more biomarkers in sampled area or volume or a unit area or volume.

The various quantifications can be used to determine the number of cells that are positive for one or more biomarkers in sampled area or volume or a unit area or volume. In some examples, the number of biomarker positive cells is divided by the total number of cells assessed, e.g., the total number of cells in the sample area or volume or a unit area or volume, to determine a percentage or ratio of biomarker positive cells. In some examples, the number of biomarker positive cells is divided by the total number of particular subpopulation or subtypes or cells, e.g., the total number of cells that express a different biomarker in the sample area or volume or a unit area or volume, to determine a percentage or ratio of biomarker positive cells. In some examples, the percentage of CD4+ or CD8+ cells among total number of cells in the sampled area or volume is determined. In some examples, the percentage CD4+ or CD8+ cells among the total number of cells that express the recombinant receptor (e.g., CAR), such as the percentage of CD4+/CAR+ cells or CD8+/CAR+ cells among the total CAR+ cells in the sampled area or volume is determined. In some embodiments, a sample can have at least or about at least or about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 40%, 45%, 50%, 55%, 60%, 65%, 70%, 75%, 80%, 85%, 90%, 95% or more biomarker positive cells as compared to the total number of cells in the assessed area or volume or a unit area or volume.

In some cases, a density of biomarker positive cells for a given area is determined. For example, the biomarker positive cells detected in the sample can be quantified as the number of biomarker positive cells of the area imaged or assessed or a unit area, e.g., the number of biomarker positive cells per $mm^2$ or $cm^2$ of the assessed biological sample, such as a tumor biopsy sample. In some examples, the total number of CD4+ or CD8+ cells, the total number of CAR+ cells, or the total number of CD4+/CAR+ cells or CD8+/CAR+ cells is determined in a sampled area or volume or a unit area or volume, such as $mm^2$ or $cm^2$ of the assessed biological sample, such as a tumor biopsy sample. For example, in some embodiments, the density of CD4+ or CD8+ cells is determined as the number of CD4+ or CD8+ cells/$mm^2$ of a sample, optionally a tumor biopsy sample. In some embodiments, the density of CAR+, CD4+/CAR+ or CD8+/CAR+ cells is determined as the number of CAR+, CD4+/CAR+ or CD8+/CAR+ cells/$mm^2$ of a sample, optionally a tumor biopsy sample. In some examples, the total number of PD-L1+ cells or IDO+ cells is determined in a sampled area or volume or a unit area or volume, such as $mm^2$ or $cm^2$ of the assessed biological sample, such as a tumor biopsy sample.

In some embodiments, the sample is assessed and analyzed for two or more biomarkers. For example, more than one image of biomarker-positive cells or, more than one section may be obtained from the same sample. Each image may be obtained by assessing a biomarker or a panel of biomarkers. In some embodiments, one image is obtained for a first panel of biomarkers, and a second image is obtained for a second panel of biomarkers. The images from the first and second panel of biomarkers may be analyzed to obtain quantitative data regarding the sample. Furthermore, additional images may be obtained for an additional number of biomarkers or panels of biomarkers. The images from various staining cycles can be merged. In some cases, the methods involve processing or merging the first, second, third, fourth, fifth, sixth, seventh, eighth, ninth, tenth, eleventh, twelfth, or more digital images into a composite image. In some cases, the various images are from one sample that is obtained from one subject. In some cases, the quantitative data obtained from the images may be combined and analyzed.

In some embodiments, a panel of biomarker specific reagents is used to label the sample in succession. The panel can include two, three, four, five, six, seven, eight, nine, or ten biomarker specific reagents. Additional panels may be used to assess a section obtained from the same sample or subject. In some particular embodiments, the first panel is used to assess biomarkers indicative of immunosuppressive pathways by detecting the level, presence, amount, or concentration of PD-L1, IDO, CD73, CD163, and FOXP3 expressing cells and the second panel of biomarkers assessed includes CD4, CD19, CD20, CD8 and a marker indicative of the presence of CAR T cells. In some embodiments, the images from the more than one panel of biomarkers can be merged and analyzed.

II. METHOD OF TREATMENT

In some embodiments, the therapy is an administration of a cell therapy. In particular embodiments, the therapy is an immunotherapy. In certain embodiments, the cell therapy treats and/or is capable of treating the disease or condition. In some embodiments, the therapy is a cell therapy that contains one or more engineered cells. In some embodiments, the engineered cells express a recombinant receptor. In particular embodiments, the recombinant receptor is a CAR.

In some embodiments, the disease or condition, e.g., a cancer or proliferative disorder, is associated with αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens, bacterial antigens, and/or parasitic antigens. In certain embodiments, the subject has a disease or condition, or is suspected of having a disease or condition, that is associated with CD19 and/or is associated with diseased cells that express CD19.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM). In some embodiments, disease or condition is a B cell malignancy selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the disease or condition is a B cell malignancy. In some embodiments, the B cell malignancy is a leukemia or a lymphoma. In some aspects, the disease or condition is acute lymphoblastic leukemia (ALL), adult ALL, chronic lymphoblastic leukemia (CLL), non-Hodgkin lymphoma (NHL), or Diffuse Large B-Cell Lymphoma (DLBCL). In some cases, the disease or condition is an NHL, such as or including an NHL that is an aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B). In some aspects, the recombinant receptor, such as a CAR, specifically binds to an antigen associated with the disease or condition or expressed in cells of the environment of a lesion associated with the B cell malignancy. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30, or combinations thereof.

In some embodiments, the disease or condition is a myeloma, such as a multiple myeloma. In some aspects, the recombinant receptor, such as a CAR, specifically binds to an antigen associated with the disease or condition or expressed in cells of the environment of a lesion associated with the multiple myeloma. Antigens targeted by the receptors in some embodiments include antigens associated with multiple myeloma. In some aspects, the antigen, e.g., the second or additional antigen, such as the disease-specific antigen and/or related antigen, is expressed on multiple myeloma, such as B cell maturation antigen (BCMA), G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI and/or FcRH5. Other exemplary multiple myeloma antigens include CD56, TIM-3, CD33, CD123, CD44, CD20, CD40, CD74, CD200, EGFR, β2-Microglobulin, HM1.24, IGF-1R, IL-6R, TRAIL-R1, and the activin receptor type IIA (ActRIIA). See Benson and Byrd, J. Clin. Oncol. (2012) 30(16): 2013-15; Tao and Anderson, Bone Marrow Research (2011): 924058; Chu et al., Leukemia (2013) 28(4):917-27; Garfall et al., Discov Med. (2014) 17(91):37-46. In some embodiments, the antigens include those present on lymphoid tumors, myeloma, AIDS-associated lymphoma, and/or post-transplant lymphoproliferations, such as CD38. Antibodies or antigen-binding fragments directed against such antigens are known and include, for example, those described in U.S. Pat. Nos. 8,153,765; 8,603,477, 8,008,450; U.S. Pub. No. US20120189622 or US20100260748; and/or International PCT Publication Nos. WO2006099875, WO2009080829 or WO2012092612 or WO2014210064. In some embodiments, such antibodies or antigen-binding fragments thereof (e.g. scFv) are contained in multispecific antibodies, multispecific chimeric receptors, such as multispecific CARs, and/or multispecific cells.

In some embodiments, the antigen is a pathogen-specific or pathogen-expressed antigen. In some embodiments, the antigen is a viral antigen (such as a viral antigen from HIV, HCV, HBV, etc.), bacterial antigens, and/or parasitic antigens.

The disease or condition that is treated in some aspects can be any in which expression of an antigen is associated with, specific to, and/or expressed on a cell or tissue of a disease, disorder or condition and/or involved in the etiology of a disease, condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the immunomodulatory polypeptide and/or recombinant receptor, e.g., the chimeric antigen receptor or TCR, specifically binds to an antigen associated with the disease or condition. In some embodiments, the subject has a disease, disorder or condition, optionally a cancer, a tumor, an autoimmune disease, disorder or condition, or an infectious disease.

A. Administration

In some embodiments, the methods include administration of the engineered cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell-based therapy is or comprises administration of cells, such as T cells, that target a molecule expressed on the surface of a lesion, such as a tumor or a cancer. In some embodiments, the immune cells express a T cell receptor (TCR) or other antigen-binding receptor. In some embodiments, the immune cells express a recombinant receptor, such as a transgenic TCR or a chimeric antigen receptor (CAR). In some embodiments, the cells are autologous to the subject. In some embodiments, the cells are allogeneic to the subject.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) *Nat Rev Clin Oncol.* 8(10):577-85). See, e.g., Themeli et al., (2013) *Nat Biotechnol.* 31(10): 928-933; Tsukahara et al., (2013) *Biochem Biophys Res Commun* 438(1): 84-9; Davila et al., (2013) *PLoS ONE* 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells. In some embodiments, administration of the cell dose or any additional therapies, e.g., the lymphodepleting therapy, intervention therapy and/or combination therapy, is carried out via outpatient delivery.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$, such as between or between about 200 mg/m$^2$ and 400 mg/m$^2$ or 250 mg/m$^2$ and 350 mg/m$^2$, inclusive. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 mg/m$^2$ of cyclophosphamide, daily for 3 days, prior to initiation of the cell therapy.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m$^2$, 15 mg/m$^2$ and 50 mg/m$^2$, 20 mg/m$^2$ and 40 mg/m$^2$, or 24 mg/m$^2$ and 35 mg/m$^2$, inclusive. In some instances, the subject is administered about 30 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 mg/m$^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the first or subsequent dose.

In some embodiments, the provided methods include one or more steps of administering to a subject cells of the output cell composition, such as a composition of cells described in Section V. In certain embodiments, the cells of the output cell composition include engineered CD4+ T cells and engineered CD8+ T cells. In some embodiments, the engineered CD4+ and CD8+ T cells express a T cell receptor (TCR) or other antigen-binding receptor. In some embodiments, the immune cells express a recombinant receptor, such as a transgenic TCR or a chimeric antigen receptor (CAR). In some embodiments, the cells of the output cell composition are autologous to the subject. In some embodiments, the cells are allogeneic to the subject.

In certain embodiments, the CD4+ T cells and CD8+ T cells of the output cell composition are administered to the subject in the same composition, dose, or mixture. Thus, in some embodiments, the recombinant receptor expressing CD4+ T cells and recombinant receptor expressing CD8+ T cells, e.g., CAR+CD4+ and CAR+CD8+ are administered to the subject in the same composition, dose, or mixture.

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the standard dose of cells comprises between at or about 2×10$^5$ of the cells/kg and at or about 2×10$^6$ of the cells/kg, such as between at or about 4×10$^5$ of the cells/kg and at or about 1×10$^6$ of the cells/kg or between at or about 6×10$^5$ of the cells/kg and at or about 8×10$^5$ of the cells/kg. In some embodiments, the standard dose of cells comprises no more than 2×10$^5$ of the cells (e.g. antigen-expressing, such as CAR-expressing cells) per kilogram body weight of the subject (cells/kg), such as no more than at or about 3×10$^5$ cells/kg, no more than at or about 4×10$^5$ cells/kg, no more than at or about 5×10$^5$ cells/kg, no more than at or about 6×10$^5$ cells/kg, no more than at or about 7×10$^5$ cells/kg, no more than at or about 8×10$^5$ cells/kg, no more than at or about 9×10$^5$ cells/kg, no more than at or about 1×10$^6$ cells/kg, or no more than at or about 2×10$^6$ cells/kg. In some embodiments, the standard dose of cells comprises at least or at least about or at or about 2×10$^5$ of the cells (e.g. antigen-expressing, such as CAR-expressing cells) per kilogram body weight of the subject (cells/kg), such as at least or at least about or at or about 3×10$^5$ cells/kg, at least or at least about or at or about 4×10$^5$ cells/kg, at least or at least about or at or about 5×10$^5$ cells/kg, at least or at least about or at or about 6×10$^5$ cells/kg, at least or at least about or at or about 7×10$^5$ cells/kg, at least or at least about or at or about 8×10$^5$ cells/kg, at least or at least about or at or about 9×10$^5$ cells/kg, at least or at least about or at or about 1×10$^6$ cells/kg, or at least or at least about or at or about 2×10$^6$ cells/kg.

In certain embodiments, the cells are administered to the subject at a standard dose. In particular embodiments, the standard dose is or contains a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, the dose of cells is a flat dose of cells or fixed dose of cells such that the dose of cells is not tied to or based on the body surface area or weight of a subject.

In some embodiments, for example, where the subject is a human, the standard dose includes fewer than about $5 \times 10^8$ total recombinant receptor (e.g., CAR)-expressing cells, T cells, or peripheral blood mononuclear cells (PBMCs), e.g., in the range of about $1 \times 10^6$ to $5 \times 10^8$ such cells, such as $2 \times 10^6$, $5 \times 10^6$, $1 \times 10^7$, $5 \times 10^7$, $1 \times 10^8$ or $5 \times 10^8$ total such cells, or the range between any two of the foregoing values.

In some aspects, the pharmaceutical compositions and formulations are provided as unit dose form compositions including the number of cells for administration in a given dose or fraction thereof. In some embodiments, the provided methods produce cells in a predictable timeline to dosing as compared to other methods of incubating (e.g., stimulating) cells. In some cases, the dose of cells for administration is determined based on the number of naïve-like cells in the input cell composition. In some embodiments, the unit dose is a standard dose.

In some aspects, the size of a dose, e.g., standard dose is determined by the burden of the disease or condition in the subject. For example, in some aspects, the number of cells administered in the dose is determined based on the tumor burden that is present in the subject immediately prior to administration of the initiation of the dose of cells. In some embodiments, the size of the first and/or subsequent standard dose is inversely correlated with disease burden. In some aspects, as in the context of a large disease burden, the subject is administered a low number of cells. In other embodiments, as in the context of a lower disease burden, the subject is administered a larger number of cells.

In some embodiments, the dose of genetically engineered cells comprises from or from about $1 \times 10^5$ to $5 \times 10^8$ total CAR-expressing T cells, $1 \times 10^5$ to $2.5 \times 10^8$ total CAR-expressing T cells, $1 \times 10^5$ to $1 \times 10^8$ total CAR-expressing T cells, $1 \times 10^5$ to $5 \times 10^7$ total CAR-expressing T cells, $1 \times 10^5$ to $2.5 \times 10^7$ total CAR-expressing T cells, $1 \times 10^5$ to $1 \times 10^7$ total CAR-expressing T cells, $1 \times 10^5$ to $5 \times 10^6$ total CAR-expressing T cells, $1 \times 10^5$ to $2.5 \times 10^6$ total CAR-expressing T cells, $1 \times 10^5$ to $1 \times 10^6$ total CAR-expressing T cells, $1 \times 10^6$ to $5 \times 10^8$ total CAR-expressing T cells, $1 \times 10^6$ to $2.5 \times 10^8$ total CAR-expressing T cells, $1 \times 10^6$ to $1 \times 10^8$ total CAR-expressing T cells, $1 \times 10^6$ to $5 \times 10^7$ total CAR-expressing T cells, $1 \times 10^6$ to $2.5 \times 10^7$ total CAR-expressing T cells, $1 \times 10^6$ to $1 \times 10^7$ total CAR-expressing T cells, $1 \times 10^6$ to $5 \times 10^6$ total CAR-expressing T cells, $1 \times 10^6$ to $2.5 \times 10^6$ total CAR-expressing T cells, $2.5 \times 10^6$ to $5 \times 10^8$ total CAR-expressing T cells, $2.5 \times 10^6$ to $2.5 \times 10^8$ total CAR-expressing T cells, $2.5 \times 10^6$ to $1 \times 10^8$ total CAR-expressing T cells, $2.5 \times 10^6$ to $5 \times 10^7$ total CAR-expressing T cells, $2.5 \times 10^6$ to $2.5 \times 10^7$ total CAR-expressing T cells, $2.5 \times 10^6$ to $1 \times 10^7$ total CAR-expressing T cells, $2.5 \times 10^6$ to $5 \times 10^6$ total CAR-expressing T cells, $5 \times 10^6$ to $5 \times 10^8$ total CAR-expressing T cells, $5 \times 10^6$ to $2.5 \times 10^8$ total CAR-expressing T cells, $5 \times 10^6$ to $1 \times 10^8$ total CAR-expressing T cells, $5 \times 10^6$ to $5 \times 10^7$ total CAR-expressing T cells, $5 \times 10^6$ to $2.5 \times 10^7$ total CAR-expressing T cells, $5 \times 10^6$ to $1 \times 10^7$ total CAR-expressing T cells, $1 \times 10^7$ to $5 \times 10^8$ total CAR-expressing T cells, $1 \times 10^7$ to $2.5 \times 10^8$ total CAR-expressing T cells, $1 \times 10^7$ to $1 \times 10^8$ total CAR-expressing T cells, $1 \times 10^7$ to $5 \times 10^7$ total CAR-expressing T cells, $1 \times 10^7$ to $2.5 \times 10^7$ total CAR-expressing T cells, $2.5 \times 10^7$ to $5 \times 10^8$ total CAR-expressing T cells, $2.5 \times 10^7$ to $2.5 \times 10^8$ total CAR-expressing T cells, $2.5 \times 10^7$ to $1 \times 10^8$ total CAR-expressing T cells, $2.5 \times 10^7$ to $5 \times 10^7$ total CAR-expressing T cells, $5 \times 10^7$ to $5 \times 10^8$ total CAR-expressing T cells, $5 \times 10^7$ to $2.5 \times 10^8$ total CAR-expressing T cells, $5 \times 10^7$ to $1 \times 10^8$ total CAR-expressing T cells, $1 \times 10^8$ to $5 \times 10^8$ total CAR-expressing T cells, $1 \times 10^8$ to $2.5 \times 10^8$ total CAR-expressing T cells, or $2.5 \times 10^8$ total CAR-expressing T cells.

In some embodiments, the dose of genetically engineered cells comprises at least or at least about $1 \times 10^5$ CAR-expressing cells, at least or at least about $2.5 \times 10^5$ CAR-expressing cells, at least or at least about $5 \times 10^5$ CAR-expressing cells, at least or at least about $1 \times 10^6$ CAR-expressing cells, at least or at least about $2.5 \times 10^6$ CAR-expressing cells, at least or at least about $5 \times 10^6$ CAR-expressing cells, at least or at least about $1 \times 10^7$ CAR-expressing cells, at least or at least about $2.5 \times 10^7$ CAR-expressing cells, at least or at least about $5 \times 10^7$ CAR-expressing cells, at least or at least about $1 \times 10^8$ CAR-expressing cells, at least or at least about $2.5 \times 10^8$ CAR-expressing cells, or at least or at least about $5 \times 10^8$ CAR-expressing cells.

In some embodiments, the cell therapy comprises administration of a dose comprising a number of cell from or from about $1 \times 10^5$ to $5 \times 10^8$ total recombinant receptor-expressing cells, total T cells, or total peripheral blood mononuclear cells (PBMCs), from or from about $5 \times 10^5$ to $1 \times 10^7$ total recombinant receptor-expressing cells, total T cells, or total peripheral blood mononuclear cells (PBMCs) or from or from about $1 \times 10^6$ to $1 \times 10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1 \times 10^5$ total recombinant receptor-expressing cells, total T cells, or total peripheral blood mononuclear cells (PBMCs), such at least or at least $1 \times 10^6$, at least or at least about $1 \times 10^7$, at least or at least about $1 \times 10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1 \times 10^5$ to $5 \times 10^8$ CD3+ or CD8+ total T cells or CD3+ or CD8+ recombinant receptor-expressing cells, from or from about $5 \times 10^5$ to $1 \times 10^7$ CD3+ or CD8+ total T cells or CD3+ or CD8+ recombinant receptor-expressing cells, or from or from about $1 \times 10^6$ to $1 \times 10^7$ CD3+ or CD8+ total T cells or CD3+ or CD8+ recombinant receptor-expressing cells, each inclusive. In some embodiments, the cell therapy comprises administration of a dose comprising a number of cell from or from about $1 \times 10^5$ to $5 \times 10^8$ total CD3+/CAR+ or CD8+/CAR+ cells, from or from about $5 \times 10^5$ to $1 \times 10^7$ total CD3+/CAR+ or CD8+/CAR+ cells, or from or from about $1 \times 10^6$ to $1 \times 10^7$ total CD3+/CAR+ or CD8+/CAR+ cells, each inclusive. In some embodiments, the cell therapy comprises the administration of from or from about $1 \times 10^5$ to about $1 \times 10^9$, from or from about $5 \times 10^5$ to about $5 \times 10^8$, from or from about $1 \times 10^6$ to about $1 \times 10^8$, from or from about $5\times10^7$ to about $1\times10^8$ total recombinant receptor-expressing cells, total T cells, or total peripheral blood mononuclear cells (PBMCs), each inclusive; or (a) at or about $5\times10^7$; (b) at or about $1\times10^8$; (c) no more than at or about $5\times10^7$; (d) no more than at or about $1\times10^8$; and/or (e) between at or about $5\times10^7$ and at or about $1\times10^8$, each inclusive, total recombinant receptor-expressing cells, total T cells, or total peripheral blood mononuclear cells (PBMCs).

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1\times10^6$ and $5\times10^8$ total recombinant receptor (e.g., CAR)-expressing CD8+ cells, e.g., in the range of about $5\times10^6$ to $1\times10^8$ such cells, such cells $1\times10^7$, $2.5\times10^7$, $5\times10^7$, $7.5\times10^7$, $1\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing CD8+ T cells, $1\times10^7$ to $2.5\times10^7$ total recombinant receptor-expressing CD8+ T cells, from or from about $1\times10^7$ to $0.75\times10^8$ total recombinant receptor-expressing CD8+ T cells, each inclusive. In some embodiments, the dose of cells comprises the administration of or about $1\times10^7$, $2.5\times10^7$, $5\times10^7$ $7.5\times10^7$, $1\times10^8$, or $5\times10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as over no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose.

Thus, the dose of cells may be administered as a split dose, e.g., a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include $CD8^+$ and $CD4^+$ T cells, respectively, and/or CD8+- and CD4+-enriched populations, respectively, e.g., CD4+ and/or CD8+ T cells each individually including cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ cells expressing a recombinant receptor to CD8+ cells expressing a recombinant receptor and/or of CD4+ cells to CD8+ cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+CD4+:CAR+ CD8+ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or anti-tumor activity of the T cell therapy.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of $CD4^+$ to $CD8^+$ cells) is between at or about 1:5 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, the methods also include administering one or more additional doses of cells expressing a chimeric antigen receptor (CAR) and/or lymphodepleting therapy, and/or one or more steps of the methods are repeated. In some embodiments, the one or more additional dose is the same as the initial dose. In some embodiments, the one or more additional dose is different from the initial dose, e.g., higher, such as 2-fold, 3-fold, 4-fold, 5-fold, 6-fold, 7-fold, 8-fold, 9-fold or 10-fold or more higher than the initial dose, or lower, such as e.g., such as 2-fold, 3-fold, 4-fold, 5-fold, 6-fold, 7-fold, 8-fold, 9-fold or 10-fold or more lower than the initial dose. In some embodiments, administration of one or more additional doses is determined based on response of the subject to the initial treatment or any prior treatment, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the size of the standard dose is determined by the activity of the cells of the cell therapy, e.g., as determined by measuring one or more parameters of the cell therapy. In some aspects, the number of cells administered in the dose is determined based on the activity of the cells of the cell therapy. In some embodiments, the size of the first and/or subsequent dose is inversely correlated with the amount or level of activity in the cells.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

The cells can be administered by any suitable means. The cells are administered in a dosing regimen to achieve a therapeutic effect, such as a reduction in tumor burden. Dosing and administration may depend in part on the schedule of administration of the immunomodulatory compound, which can be administered prior to, subsequent to and/or simultaneously with initiation of administration of the T cell therapy. Various dosing schedules of the T cell therapy include but are not limited to single or multiple administrations over various time-points, bolus administration, and pulse infusion. In certain embodiments, the engineered T cells express a recombinant receptor. In certain embodiments, the engineered T cells express a CAR.

In particular embodiments, the ratio of the CD4+ T cells to CD8+ T cells that are administered to the subject in the same composition, dose, or mixture is between 5:1 to 0.2:1, between 4:1 to 0.25:1, between 3:1 to 0.33:1, between 2:1 to 0.5:1, between 1.5:1 to 0.66:1, or between 1.25:1 to 0.8:1. In some embodiments, the ratio of CD4+ T cells to CD8+ T cells administered to the subject in the same composition, dose, or mixture is or is about 2.0:1, 1.9:1, 1.8:1, 1.7:1, 1.6:1, 1.5:1, 1.4:1, 1.3:1, 1.2:1, 1.1:1, 1.0:1, 0.9:1, 0.8:1, 0.7:1, 0.6:1, or 0.5:1.

In particular embodiments, the ratio of recombinant receptor expressing CD4+ T cells to recombinant receptor expressing CD8+ T cells that are administered to the subject in the same composition, dose, or mixture is between 5:1 to 0.2:1, between 4:1 to 0.25:1, between 3:1 to 0.33:1, between 2:1 to 0.5:1, between 1.5:1 to 0.66:1, or between 1.25:1 to 0.8:1. In certain embodiments, the ratio of recombinant receptor expressing CD4+ T cells to recombinant receptor expressing CD8+ T cells that are administered to the subject in the same composition, dose, or mixture is or is about 2.0:1, 1.9:1, 1.8:1, 1.7:1, 1.6:1, 1.5:1, 1.4:1, 1.3:1, 1.2:1, 1.1:1, 1.0:1, 0.9:1, 0.8:1, 0.7:1, 0.6:1, or 0.5:1. In particular embodiments, ratio of the administered recombinant receptor expressing CD4+ T cells to recombinant receptor expressing CD8+ T cells is or is about 1:1. In some embodiments, the recombinant receptor is a TCR or a CAR. In particular embodiments, the recombinant receptor is a CAR.

In some embodiments, the ratio of engineered CD4+ T cells to engineered CD8+ T cells of the dose, composition, or mixture that is administered to the subject is within a certain tolerated difference or range of error of such a defined, desired, or fixed ratio. In some embodiments, the tolerated difference is within of or of about 1%, 2%, 3%, 4%, 5%, 10%, 15%, 20%, 25%, 30%, 35%, 40%, 45%, or 50%, of the target, defined, preferred, and/or fixed ratio.

In some embodiments, a composition of cells produced by the methods provided herein, e.g., an output composition, having a ratio of engineered CD4+ T cells to engineered CD8+ T cells of between 2:1 and 0.5:1 is administered to a subject in a single composition, dose, or mixture. In certain embodiments, the composition contains a ratio of engineered CD4+ T cells to engineered CD8+ T cells of or of about 1:1. In some embodiments, a cell composition produced from an input cell composition, has a ratio of engineered CD4+ T cells to engineered CD8+ T cells of between 2:1 and 0.5:1 and is administered to a subject in a single composition, dose, or mixture. In particular embodiments, the cell composition produced from an input cell composition has a ratio of engineered CD4+ T cells to engineered CD8+ T cells of 1:1 with a tolerated difference of 50%, 25%, 10%, or less.

B. Response Assessment

In some embodiments, the subject's response to the administration of the therapy is assessed and correlated with the assessment of the biomarker. In some aspects, the administration in accord with the provided methods generally reduces or prevents the expansion or burden of the disease or condition in the subject. For example, where the disease or condition is a tumor, the methods generally reduce tumor size, bulk, metastasis, percentage of blasts in the bone marrow or molecularly detectable cancer, and/or improve prognosis or survival or other symptom associated with tumor burden. Also provided are methods of assessing a subject's response to the administration of the therapy.

In some respects, progression-free survival (PFS) is described as the length of time during and after the treatment of a disease, such as cancer, that a subject lives with the disease but it does not get worse. In some aspects, objective response (OR) is described as a measurable response. In some aspects, objective response rate (ORR) is described as the proportion of patients who achieved complete response (CR) or partial response (PR). In some further embodiments, the response is durable. For example, in some cases, the response is durable for greater than 2 months, 3 months, 4 months, 5 months, or 6 months. In some aspects, overall survival (OS) is described as the length of time from either the date of diagnosis or the start of treatment for a disease, such as cancer, that subjects diagnosed with the disease are still alive. In some aspects, event-free survival (EFS) is described as the length of time after treatment for a cancer ends that the subject remains free of certain complications or events that the treatment was intended to prevent or delay. These events may include the return of the cancer or the onset of certain symptoms, such as bone pain from cancer that has spread to the bone, or death.

In some embodiments, the method reduces the burden of the disease or condition, e.g., number of tumor cells, size of tumor, duration of patient survival or event-free survival, to a greater degree and/or for a greater period of time as compared to the reduction that would be observed with a comparable method using an alternative dosing regimen, such as one in which the subject receives one or more alternative therapeutic agents and/or one in which the subject does not receive a dose of cells and/or a lymphodepleting agent in accord with the provided methods. In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified.

In some embodiments, the event-free survival rate or overall survival rate of the subject is improved by the methods, as compared with other methods, for example, methods in which the subject receives one or more alternative therapeutic agents and/or one in which the subject does not receive a dose of cells and/or a lymphodepleting agent in accord with the provided methods. For example, in some embodiments, event-free survival rate or probability for subjects treated by the methods at 6 months following the dose is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods, for example, methods in which the subject receives one or more alternative therapeutic agents and/or one in which the subject does not receive a dose of cells and/or a lymphodepleting agent in accord with the provided methods. For example, in some embodiments, the probability of relapse at 6 months following the first dose is less than about 80%, less than about 70%, less than about 60%, less than about 50%, less than about 40%, less than about 30%, less than about 20%, or less than about 10%.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood or bone marrow in the context of certain hematological malignancies. Disease burden can include, in some embodiments, the mass of a tumor, the number or extent of metastases and/or the percentage of blast cells present in the bone marrow.

In some aspects, response assessment utilizes any of clinical, hematologic, and/or molecular methods.

1. IWCLL Response Criteria

In some aspects, response rates in subjects, such as subjects with CLL, are based on the International Workshop on Chronic Lymphocytic Leukemia (IWCLL) response criteria (Hallek, et al., Blood 2008, Jun. 15; 111(12): 5446-5456; also called IWCLL 2008). In some aspects, these criteria are described as follows: complete remission (CR), which in some aspects requires the absence of peripheral blood clonal lymphocytes by immunophenotyping, absence of lymphadenopathy, absence of hepatomegaly or splenomegaly, absence of constitutional symptoms and satisfactory blood counts; complete remission with incomplete marrow recovery (CRi), which in some aspects is described as CR above, but without normal blood counts; partial remission (PR), which in some aspects is described as ≥50% fall in lymphocyte count, ≥50% reduction in lymphadenopathy or ≥50% reduction in liver or spleen, together with improvement in peripheral blood counts; progressive disease (PD), which in some aspects is described as ≥50% rise in lymphocyte count to >5×10$^9$/L, ≥50% increase in lymphadenopathy, ≥50% increase in liver or spleen size, Richter's transformation, or new cytopenias due to CLL; and stable disease, which in some aspects is described as not meeting criteria for CR, CRi, PR or PD.

In some embodiments, the subjects exhibits a CR or OR if, within 1 month of the administration of the dose of cells, lymph nodes in the subject are less than at or about 20 mm in size, less than at or about 10 mm in size or less than at or about 10 mm in size.

2. Disease in Bone Marrow or Blood

In some embodiments, a subject has leukemia. The extent of disease burden can be determined by assessment of residual leukemia in blood or bone marrow.

In some embodiments, a subject exhibits morphologic disease if there are greater than or equal to 5% blasts in the bone marrow, for example, as detected by light microscopy, such as greater than or equal to 10% blasts in the bone marrow, greater than or equal to 20% blasts in the bone marrow, greater than or equal to 30% blasts in the bone marrow, greater than or equal to 40% blasts in the bone marrow or greater than or equal to 50% blasts in the bone marrow. In some embodiments, a subject exhibits complete or clinical remission if there are less than 5% blasts in the bone marrow.

In some embodiments, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia cell in 10,000 normal cells or 1 leukemia cell in 100,000 normal cells. In some embodiments, a subject exhibits MRD that is molecularly detectable if at least or greater than 1 leukemia cell in 10,000 cells detected or 1 leukemia cell in 100,000 cells is detected, such as by PCR or flow cytometry. In some embodiments, the disease burden of a subject is molecularly undetectable or MRD⁻, such that, in some cases, no leukemia cells are able to be detected in the subject using PCR or flow cytometry techniques.

In some embodiments, an index clone of the leukemia, e.g. CLL, is not detected in the bone marrow of the subject (or in the bone marrow of greater than 50%, 60%, 70%, 80%, 90% or more of the subjects treated according to the methods. In some embodiments, an index clone of the leukemia, e.g. CLL, is assessed by IGH deep sequencing. In some embodiments, the index clone is not detected at a time that is at or about or at least at or about 1, 2, 3, 4, 5, 6, 12, 18 or 24 months following the administration of the cells.

a. Determination of MRD by Flow Cytometry

In some aspects MRD is detected by flow cytometry. Flow cytometry can be used to monitor bone marrow and peripheral blood samples for cancer cells. In particular aspects, flow cytometry is used to detect or monitor the presence of cancer cells in bone marrow. In some aspects, multiparameter immunological detection by flow cytometry is used to detect cancer cells (see for example, Coustan-Smith et al., (1998) *Lancet* 351:550-554). In some aspects, multiparameter immunological detection by mass cytometry is used to detect cancer cells. In some examples, 1, 2, 3, 4, 5, 6, 7, 8, 9, 10, 11, 12, 13, 14, 15, 20, 25, 30, 35, 40, 45 or 50 parameters can be used to detect cancer cells. The antigens used for detection are selected based on the cancer being detected (Foon and Todd (1986) *Blood* 68:1-31).

In some examples, bone marrow is harvested by bone marrow aspirates or bone marrow biopsies, and lymphocytes are isolated for analysis. Monoclonal and/or polyclonal antibodies conjugated to a fluorochrome (e.g., fluorescein isothiocyanate (FITC), phycoerythrin, peridinin chlorophyll protein, or biotin) can be used to detect epitopes, such as terminal deoxynucleotidyl transferase (TdT), CD3, CD10, CD11c, CD13, CD14, CD33, CD19, CD20, CD21, CD22, CD23, CD34, CD45, CD56, CD79b, IgM, and/or KORSA3544, on isolated lymphocytes. Labeled cells can then be detected using flow cytometry, such as multiparameter flow cytometry, or mass cytometry, to detect multiple epitopes.

Lymphoid cells can be identified and gated based on a light-scatter dot plot and then secondarily gated to identify cell populations expressing the immunophenotypic features of interest. Exemplary epitopes are set forth in Table 1B below. Other immunologic classification of leukemias and lymphomas are provided by Foon and Todd (Blood (1986) 68(1): 1-31). In some aspects, flow cytometric assessment of MRD can be achieved by quantifying live lymphocytes bearing one or more CLL immunophenotypes (e.g., low forward/side scatter; $CD3^{neg}$; $CD5^+$; $CD14^{neg}$; $CD19^+$; $CD23^+$; $CD45^+$; $CD56^{neg}$)

TABLE 1B

Exemplary Immunophenotype and Cytogentics Characteristics

| Disease | Immunophenotype | Cytogenetics |
|---|---|---|
| Chronic Lymphocytic Leukemia (CLL) | Pan-B+; CD5+; CD23+; CD79b/CD22 weak; FMC7−; sig weak | Trisomy12<br>del(13)(q14.3)<br>del 11q22-q23<br>del 17p13 (p53)<br>t(11; 14)(q13; q32) BCL1/IgH rearrangement<br>t(14; 19)(q32; q13)<br>IgH deletion (14q32)<br>del(6q)<br>+8q24<br>+3<br>+18<br>del 6q21 |
| Small lymphocytic lymphoma (SLL) | Pan-B+; CD5+; CD23+; CD10−; sIgM+ faint | del(6)(q21-23) |
| Lymphoplasmacytic lymphoma | Pan-B+; CD5−; CD10−; cyIgM+ | t(9; 14)(p13; q32) PAX5/IgH |
| Follicle centre cell lymphoma | Pan-B+; CD10+/−; CD5−; sIg+ | t(14; 18)(q32; q21)/BCL2 Rearr |
| Diffuse large cell lymphoma | CD19+; CD22+; CD10−/+; SIg+ | t(14; 18) and p53 mutations<br>t(3; V)(q27; V)/BCL6 Rearr<br>variants c-MYC Rearr |
| Burkitt's lymphoma | Pan-B+; TdT−; CD10+; CD5−; sIgM+ | t(8; 14)(q24; q32) or variants/c-MYC R earr |
| Burkitt-like lymphoma | Pan-B+; TdT−; CD10−/+ CD5−; sIg+ | t(8; 14) or variants<br>t(8; 14)+ t(14; 18) |
| Mantle cell lymphoma | Pan-B+; CD5+; CD23−; CD10−/+; sIgM+ bright | t(11; 14)(q13; q32)/BCL1 Rearr |

TABLE 1B-continued

Exemplary Immnunophenotype and Cytogentics Characteristics

| Disease | Immunophenotype | Cytogenetics |
|---|---|---|
| Marginal zone B-cell lymphoma (MZBCL) | pan-B+; CD5−/+; CD10−; CD23−; CD11c+/−; cyIg+ (40% of the cells), sIgM+ bright; sIgD− | t(11; 18)(q21; q21)/PI2/MLT fusion: Extra-nodal low-grade MALT lymphoma; indolent disease<br>t(1; 14)(p21; q32): Extra-nodal MALT lymphoma<br>del(7)(q22-31): Splenic MZBCL/+3q: Nodal, extra-nodal and splenic MZBCL |

+: positive in >90% of the cases
+/−: positive in more than 50% of the cases
−/+: positive in less than 50% of cases
−: positive in <10% of the cases
Pan-B markers: e.g., CD19, CD20, CD79a
sIG: surface immunoglobulins
cyIg: cytoplasmic immunoglobulins b. IGH Deep Sequencing In some aspects, deep sequencing of the immunoglobulin heavy chain (IGH) locus of harvested B cells can be used to detect minimal residual disease (MRD). Clonal presence of a particular IgG rearrangement can provide a marker to detect the presence of B cell malignancies, such as CLL or NHL and/or residual presence of malignant cells thereof. In some aspects cells such as a population containing or suspected of containing B cells are harvested and isolated from blood. In some aspects, cells are harvested and isolated from bone marrow, e.g., from bone marrow aspirates or bone marrow biopsies and/or from other biological samples. In some aspects, polymerase chain reaction (PCR) amplification of the complementarity determining region 3 (CDR3) is achieved using primers to highly conserved sequences within the V and J regions of the gene locus, which may be used to identify clonal populations of cells for purposes of assessing minimal residual disease. Other methods for detecting clonal populations, such as single cell sequencing approaches, including those providing information regarding number of cells of a particular lineage and/or expressing a particular variable chain such as variable heavy chain or binding site thereof, such as a clonal population, may be used. In some aspects, the IGH DNA is amplified using a degenerate primers or primers recognizing regions of variable chains shared among different cell clones, such as those recognizing consensus V and degenerate consensus J region of the IGH sequence. An exemplary sequence of the V region is ACACGGCCTCGTGTATTACTGT (SEQ ID NO: 24). An exemplary degenerate consensus sequence of the J region is ACCTGAGGAGACGGTGACC (SEQ ID NO: 25).

The PCR product or sequencing result in some aspects is specific to the rearranged allele and serves as a clonal marker for MRD detection. Following PCR amplification of the CDR3 region, PCR products can be sequenced to yield patient-specific oligonucleotides constructed as probes for allele-specific PCR for sensitive detection of MRD following treatment of B-cell malignancies with CAR-T cell therapy, e.g. CD19 CAR-T cell therapy. In examples where a PCR product is not generated using the consensus primers, V region family-specific primers for the framework region 1 can be used instead.

In some aspects, persistence of PCR-detectable tumor cells such as cells of the B cell malignancy such as the NHL or CLL, such as detectable IGH sequences corresponding to the malignant or clonal IGH sequences, after treatment is associated with increased risk of relapse. In some aspects, patients who are negative for malignant IGH sequences following treatment (in some aspects, even in the context of other criteria indicating progressive disease or only a partial response, such as persistence of enlarged lymph nodes or other criteria that may in some contexts be associated with disease or lack of complete response) may be deemed to have increased likelihood of PFS or to enter into CR or durable CR or prolonged survival, compared to patients with persistent malignant IGH sequences. In some embodiments, such prognostic and staging determinations are particularly relevant for treatments in which clearance of malignant cells is observed within a short period of time following administration of the therapy, e.g., in comparison to resolution of other clinical symptoms such as lymph node size or other staging criteria. For example, in some such aspects, absence of detectable IGH or minimal residual disease in a sample such as the bone marrow may be a preferred readout for response or likelihood of response or durability thereof, as compared to other available staging or prognostic approaches. In some aspects, results from MRD, e.g., IGH deep sequencing information, may inform further intervention or lack thereof. For example, the methods and other provided embodiments in some contexts provide that a subject deemed negative for malignant IGH may in some aspects be not further treated or not be further administered a dose of the therapy provided, or that the subject be administered a lower or reduced dose. Conversely, it may be provided or specified that a subject exhibiting MRD via IGH deep sequencing be further treated, e.g., with the therapy initially administered at a similar or higher dose or with a further treatment.

3. Lugano Criteria

In some respects, response is assessed using the Lugano criteria (Cheson et al., JCO Sep. 20, 2014 vol. 32 no. 27 3059-3067; Johnson et al., (2015) Imaging for staging and response assessment in lymphoma. Radiology 2:323-338). Lugano criteria include evaluation by imaging, tumor bulk measurements, and assessments of spleen, liver, and bone marrow involvement.

In some aspects, response assessed using the Lugano criteria involves the use of positron emission tomography (PET)-computed tomography (CT) and/or CT as appropriate for imaging evaluation. PET-CT evaluations may further comprise the use of fluorodeoxyglucose (FDG), to assess FDG uptake, in FDG-avid lymphomas. FDG-avid lymphomas include Hodgkin lymphoma (HL) and certain non-Hodgkin lymphomas (NHL), including diffuse large B cellular lymphoma (DLBCL), marginal zone NHL with an aggressive transformation, and FDG-avid nodal lymphomas (essentially all histologic types except: chronic lymphocytic leukemia (CLL), small lymphocytic lymphoma, lymphoplasmacytic lymphoma/Waldenström macroglobulinaemia, and mycosis fungoides). In some cases, for non-FDG-avid histologies, CT is the preferred imaging method. In some aspects, the post-treatment scans are taken as long as possible after administration of treatment. In some aspects the post-treatment scans are taken a minimum of 3 weeks after therapy, such as 3 weeks, 4 weeks, 5 weeks, 6 weeks, 7 weeks, 8 weeks, 9 weeks, 10 weeks, 11 weeks, 12, weeks or more after administration of treatment.

In some aspects, where PET-CT will be used to assess response in FDG-avid histologies, a 5-point scale, such as the Deauville five-point scale (Deauville 5ps), may be used for evaluation or staging. The Deauville score is based on visual interpretation of fluorodeoxyglucose (FDG) uptake, visualized by PET/CT scans, of each lesion, compared to two reference organs, the mediastinum (i.e., blood pool) and the liver. One assessment (initial staging) is made prior to treatment and a second round of FDG PET/CT scans is used to evaluate residual masses (in comparison to the FDG update in the reference organs) during and/or after treatment. The scale ranges from 1 to 5, where 1 is best and 5 is the worst. Each FDG-avid (or previously FDG-avid) lesion is rated independently. In some respects, the 5-point scale comprises the following criteria: 1, no uptake above background; 2, uptake≤mediastinum; 3, uptake>mediastinum but≤liver; 4, uptake moderately>liver; 5, uptake markedly higher than liver (e.g., maximum standard uptake value ($SUV_{MAX}$>2× liver; 5a) and/or new lesion (on response evaluation) that is possibly related to lymphoma (5b); X, new areas of uptake unlikely to be related to lymphoma.

A Deauville score of 1 or 2 is considered to represent complete metabolic response (CMR) at interim and end of treatment. A Deauville score of 3 also represents CMR, but interpretation of score 3 depends on the timing of the assessment, the clinical context and the treatment. A Deauville score of 4 or 5 at interim is considered to represent partial metabolic response. However, a Deauville score of 4 or 5 at the end of treatment represents residual metabolic disease, if the uptake has reduced from baseline; no metabolic response (NMR) if there is no change in uptake from baseline; and progressive metabolic disease (PMD) if there in an increase in uptake from baseline and/or there are new lesions. At interim and end of treatment, NMR or PMD indicates treatment failure.

In some aspects, a complete response at the end of treatment, as described using the Lugano criteria, involves a complete metabolic response and a complete radiologic response at various measureable sites. In some aspects, these sites include lymph nodes and extralymphatic sites, wherein a CR is described as a score of 1, 2, or 3 with or without a residual mass on the 5-point scale, when PET-CT is used. In some aspects, in Waldeyer's ring or extranodal sites with high physiologic uptake or with activation within spleen or marrow (e.g., with chemotherapy or myeloid colony-stimulating factors), uptake may be greater than normal mediastinum and/or liver. In this circumstance, complete metabolic response may be inferred if uptake at sites of initial involvement is no greater than surrounding normal tissue even if the tissue has high physiologic uptake. In some aspects, response is assessed in the lymph nodes using CT, wherein a CR is described as no extralymphatic sites of disease and target nodes/nodal masses must regress to ≤1.5 cm in longest transverse diameter of a lesion (LDi). Further sites of assessment include the bone marrow wherein PET-CT-based assessment should indicate a lack of evidence of FDG-avid disease in marrow and a CT-based assessment should indicate a normal morphology, which if indeterminate should be IHC negative. Further sites may include assessment of organ enlargement, which should regress to normal. In some aspects, non-measured lesions and new lesions are assessed, which in the case of CR should be absent. (Cheson et al., JCO Sep. 20, 2014 vol. 32 no. 27 3059-3067; Johnson et al., (2015) Imaging for staging and response assessment in lymphoma. Radiology 2:323-338).

4. Response Evaluation Criteria in Solid Tumors (RECIST) Criteria

In some aspects, Response Evaluation Criteria in Solid Tumors (RECIST) criteria are used to determine objective tumor response; in some aspects, in solid tumors. (Eisenhauer et al., European Journal of Cancer 45 (2009) 228-247.) In some aspects, the RECIST criteria are used to determine objective tumor response for target lesions. In some respects, a complete response as determined using RECIST criteria is described as the disappearance of all target lesions and any pathological lymph nodes (whether target or non-target) must have reduction in short axis to <10 mm. In other aspects, a partial response as determined using RECIST criteria is described as at least a 30% decrease in the sum of diameters of target lesions, taking as reference the baseline sum diameters. In other aspects, progressive disease (PD) is described as at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm (in some aspects the appearance of one or more new lesions is also considered progression). In other aspects, stable disease (SD) is described as neither sufficient shrinkage to qualify for PR nor sufficient increase to qualify for PD, taking as reference the smallest sum diameters while on study.

III. CELL THERAPY AND ENGINEERING CELLS

In some embodiments, the cells for use in or administered in connection with the provided methods contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or CD8+ or CD4+ cells are enriched or selected. Among the compositions are pharmaceutical compositions and formulations for administration, such as for adoptive cell therapy. Also provided are therapeutic methods for administering the cells and compositions to subjects, e.g., patients, in accord with the provided methods, and/or with the provided articles of manufacture or compositions.

In some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

A. Chimeric Antigen Receptors (CARs)

In some embodiments of the provided methods and uses, chimeric receptors, such as a chimeric antigen receptors, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

Exemplary antigen receptors, including CARs, and methods for engineering and introducing such receptors into cells, include those described, for example, in international patent application publication numbers WO2000/14257, WO2013/126726, WO2012/129514, WO2014/031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the antigen targeted by the receptor is a tumor antigen or cancer marker. In some embodiments, the antigen or ligand the antigen is or includes $\alpha v \beta 6$ integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22R$\alpha$), IL-13 receptor alpha 2 (IL-13R$\alpha$2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens, bacterial antigens, and/or parasitic antigens.

Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the antigen or antigen binding domain is CD19. In some embodiments, the scFv contains a VH and a VL derived from an antibody or an antibody fragment specific to CD19. In some embodiments, the antibody or antibody fragment that binds CD19 is a mouse derived antibody such as FMC63 and SJ25C1. In some embodiments, the antibody or antibody fragment is a human antibody, e.g., as described in U.S. Patent Publication No. US 2016/0152723.

In some embodiments, the scFv is derived from FMC63. FMC63 generally refers to a mouse monoclonal IgG1 antibody raised against Nalm-1 and -16 cells expressing CD19 of human origin (Ling, N. R., et al. (1987). *Leucocyte typing III*. 302). The FMC63 antibody comprises CDRH1 and H2 set forth in SEQ ID NOS: 38, 39 respectively, and CDRH3 set forth in SEQ ID NOS: 40 or 54 and CDRL1 set forth in SEQ ID NOS: 35 and CDR L2 36 or 55 and CDR L3 sequences 37 or 34. The FMC63 antibody comprises the heavy chain variable region ($V_H$) comprising the amino acid sequence of SEQ ID NO: 41 and the light chain variable region ($V_L$) comprising the amino acid sequence of SEQ ID NO: 42. In some embodiments, the svFv comprises a variable light chain containing the CDRL1 sequence of SEQ ID NO:35, a CDRL2 sequence of SEQ ID NO:36, and a CDRL3 sequence of SEQ ID NO:37 and/or a variable heavy chain containing a CDRH1 sequence of SEQ ID NO:38, a CDRH2 sequence of SEQ ID NO:39, and a CDRH3 sequence of SEQ ID NO:40. In some embodiments, the scFv comprises a variable heavy chain region set forth in SEQ ID NO:41 and a variable light chain region set forth in SEQ ID NO:42. In some embodiments, the variable heavy and variable light chain are connected by a linker. In some embodiments, the linker is set forth in SEQ ID NO:56. In some embodiments, the scFv comprises, in order, a $V_H$, a linker, and a $V_L$. In some embodiments, the scFv comprises, in order, a $V_L$, a linker, and a $V_H$. In some embodiments, the svFc is encoded by a sequence of nucleotides set forth in SEQ ID NO:57 or a sequence that exhibits at least 85%, 86%, 87%, 88%, 89%, 90%, 91%, 92%, 93%, 94%, 95%, 96%, 97%, 98%, or 99% sequence identity to SEQ ID NO:57. In some embodiments, the scFv comprises the sequence of amino acids set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III*. 302). The SJ25C1 antibody comprises CDRH1, H2 and H3 set forth in SEQ ID NOS: 47-49, respectively, and CDRL1, L2 and L3 sequences set forth in SEQ ID NOS: 44-46, respectively. The SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51. In some embodiments, the svFv comprises a variable light chain containing the CDRL1 sequence of SEQ ID NO:44, a CDRL2 sequence of SEQ ID NO: 45, and a CDRL3 sequence of SEQ ID NO:46 and/or a variable heavy chain containing a CDRH1 sequence of SEQ ID NO:47, a CDRH2 sequence of SEQ ID NO:48, and a CDRH3 sequence of SEQ ID NO:49. In some embodiments, the scFv comprises a variable heavy chain region set forth in SEQ ID NO:50 and a variable light chain region set forth in SEQ ID NO:51. In some embodiments, the variable heavy and variable light chain are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some embodiments, the antigen is BCMA. In some embodiments, the scFv contains a VH and a VL derived from an antibody or an antibody fragment specific to BCMA. In some embodiments, the antibody or antibody fragment that binds BCMA is or contains a VH and a VL from an antibody or antibody fragment set forth in International Patent Applications, Publication Number WO 2016/090327 and WO 2016/090320.

In some embodiments, the antigen is GPRC5D. In some embodiments, the scFv contains a VH and a VL derived from an antibody or an antibody fragment specific to GPRC5D. In some embodiments, the antibody or antibody fragment that binds GPRC5D is or contains a VH and a VL from an antibody or antibody fragment set forth in International Patent Applications, Publication Number WO 2016/090329 and WO 2016/090312.

In some embodiments, the antigen is CD20. In some embodiments, the scFv contains a VH and a VL derived from an antibody or an antibody fragment specific to CD20. In some embodiments, the antibody or antibody fragment that binds CD20 is an antibody that is or is derived from Rituximab, such as is Rituximab scFv.

In some embodiments, the antigen is CD22. In some embodiments, the scFv contains a VH and a VL derived from an antibody or an antibody fragment specific to CD22. In some embodiments, the antibody or antibody fragment that binds CD22 is an antibody that is or is derived from m971, such as is m971 scFv.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers include, but are not limited to, those described in Hudecek et al. (2013) *Clin. Cancer Res.*, 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5. In some embodiments, the spacer has the sequence set forth in SEQ ID NOS: 27-33. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 27-33, 58, 59.

In some embodiments, the antigen receptor comprises an intracellular domain linked directly or indirectly to the extracellular domain. In some embodiments, the chimeric antigen receptor includes a transmembrane domain linking the extracellular domain and the intracellular signaling domain. In some embodiments, the intracellular signaling domain comprises an ITAM. For example, in some aspects, the antigen recognition domain (e.g. extracellular domain) generally is linked to one or more intracellular signaling components, such as signaling components that mimic activation through an antigen receptor complex, such as a TCR complex, in the case of a CAR, and/or signal via another cell surface receptor. In some embodiments, the chimeric receptor comprises a transmembrane domain linked or fused between the extracellular domain (e.g. scFv) and intracellular signaling domain. Thus, in some embodiments, the antigen-binding component (e.g., antibody) is linked to one or more transmembrane and intracellular signaling domains.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28.

In some embodiments, the extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

The receptor, e.g., the CAR, generally includes at least one intracellular signaling component or components. In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

In some embodiments, the chimeric antigen receptor contains an intracellular domain of a T cell costimulatory molecule. In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the two receptors induce, respectively, an activating and an inhibitory signal to the cell, such that ligation of one of the receptor to its antigen activates the cell or induces a response, but ligation of the second inhibitory receptor to its antigen induces a signal that suppresses or dampens that response. Examples are combinations of activating CARs and inhibitory CARs (iCARs). Such a strategy may be used, for example, to reduce the likelihood of off-target effects in the context in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the antigen receptor further includes a marker and/or cells expressing the CAR or other antigen receptor further includes a surrogate marker, such as a cell surface marker, which may be used to confirm transduction or engineering of the cell to express the receptor. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, a E2A or a F2A. Extrinsic marker genes may in some cases be utilized in connection with engineered cell to permit detection or selection of cells and, in some cases, also to promote cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing.

Exemplary surrogate markers can include truncated cell surface polypeptides, such as a truncated human epidermal growth factor receptor 2 (tHER2), a truncated epidermal growth factor receptor (EGFRt, exemplary EGFRt sequence set forth in SEQ ID NO: 7 or 16) or a prostate-specific membrane antigen (PSMA) or modified form thereof. EGFRt may contain an epitope recognized by the antibody cetuximab (Erbitux®) or other therapeutic anti-EGFR antibody or binding molecule, which can be used to identify or select cells that have been engineered with the EGFRt construct and a recombinant receptor, such as a chimeric antigen receptor (CAR), and/or to eliminate or separate cells expressing the receptor. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, or epidermal growth factor receptor (e.g., tEGFR).

In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. An exemplary T2A linker sequence comprises the sequence of amino acids set forth in SEQ ID NO: 6 or 17 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17.

In some embodiments, the marker is or comprises a fluorescent protein, such as green fluorescent protein (GFP), enhanced green fluorescent protein (EGFP), such as superfold GFP, red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the nucleic acid encoding the marker is operably linked to a polynucleotide encoding for a linker sequence, such as a cleavable linker sequence, e.g., a T2A. For example, a marker, and optionally a linker sequence, can be any as disclosed in PCT Pub. No. WO2014031687.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6 or 17, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 7 or 16, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known. Examples of 2A sequences that can be used in the methods and nucleic acids disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Publication No. 20070116690.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

B. TCRs

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or $C_\beta$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPred1 (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPred1 (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al. PNAS (USA) 89, 4759 (1992); Wulfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)5-P- wherein P is proline, G is glycine and S is serine (SEQ ID NO:22). In some embodiments, the linker has the sequence GSADDAKKDAAKKDGKS (SEQ ID NO:23)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

C. Chimeric Auto-Antibody Receptor (CAAR)

In some embodiments, the recombinant receptor is a chimeric autoantibody receptor (CAAR). In some embodiments, the CAAR is specific for an autoantibody. In some embodiments, a cell expressing the CAAR, such as a T cell engineered to express a CAAR, can be used to specifically bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling region comprises a secondary or costimulatory signaling region (secondary intracellular signaling regions).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

D. Genetically Engineered Cells and Methods of Producing Cells

In some embodiments, the provided methods involve administering to a subject having a disease or condition cells expressing a recombinant antigen receptor. Various methods for the introduction of genetically engineered components, e.g., recombinant receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

E. Vectors and Methods for Genetic Engineering

In some embodiments, cells, e.g. T cells, are engineered by introduction, such as by transduction, of one or more polynucleotides (e.g., nucleic acid molecules) encoding recombinant receptors. In some aspects, a vector, such as an expression vector, e.g. a viral vector, is introduced into cells for genetically engineering cells to express the receptors. In some aspects, the recombinant receptor is or contains a chimeric antigen receptor (CAR). In some aspects, the recombinant receptor is or contains a T cell receptor (TCR), e.g., a transgenic TCR.

In some cases, the nucleic acid sequence encoding the recombinant receptor, e.g., chimeric antigen receptor (CAR) contains a signal sequence that encodes a signal peptide. Non-limiting exemplary examples of signal peptides include, for example, the GMCSFR alpha chain signal peptide set forth in SEQ ID NO: 61 and encoded by the nucleotide sequence set forth in SEQ ID NO: 60, the CD8 alpha signal peptide set forth in SEQ ID NO: 26, the CD33 signal peptide set forth in SEQ ID NO:62.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the anti-CD3/anti-CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

F. Cells and Preparation of Cells for Genetic Engineering

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L$-$CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are $CD45RO^-$, $CD45RA^+$, $CD62L^+$, $CD4^+$ T cells. In some embodiments, central memory CD4+ cells are $CD62L^+$ and $CD45RO^+$. In some embodiments, effector $CD4^+$ cells are $CD62L^-$ and $CD45RO^-$.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to $-80°$ C. at a rate of $1°$ per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti-CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al.(2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

IV. AGENTS OR TREATMENTS FOR ENHANCING CELL THERAPY

In some embodiments, the provided methods and articles of manufacture can be used in connection with, or involve or include, one or more agents or treatments for stimulating, amplifying, potentiating, and/or enhancing an anti-tumor immune response, e.g., of the cell therapy. In some examples, the agent or other treatment capable of stimulating, amplifying, potentiating, and/or enhancing an anti-tumor immune response is administered prior to and/or concurrently with administration of a therapeutic cell composition comprising the genetically engineered cells. For example, in some aspects, the agent or other treatment is an immunomodulatory compound. In some cases, administration of the agent or treatment for stimulating, amplifying, potentiating, and/or enhancing an anti-tumor immune response is based on assessment of the biomarker (e.g., immune cell biomarker) in a sample obtained from the subject.

The provided methods, compositions, combinations, kits and uses may involve administration of an immunomodulatory compound that can be administered prior to, subsequently to, during, simultaneously or near simultaneously, sequentially and/or intermittently with administration of the T cell therapy, e.g., administration of T cells expressing a chimeric antigen receptor (CAR).

In some embodiments, the methods involve selection of subjects for treatment with an agent, and/or administration of an agent after assessment of the biomarker. In some embodiments, the agent is an additional therapeutic agent. In some embodiments, the agent is administered as part of a combination treatment or combination therapy. In some embodiments, the one or more additional therapeutic intervention includes, for example, an antibody, an engineered cell, a receptor and/or an agent, such as a cell expressing a recombinant receptor, and/or cytotoxic or therapeutic agent, e.g., a chemotherapeutic agent. In some embodiments, the agent includes an immunomodulatory agent, immune checkpoint inhibitor, adenosine pathway or adenosine receptor antagonist or agonist and kinase inhibitors. In some embodiments, the agent can modulate the activity, persistence and/or efficacy of the cell therapy, e.g., cells engineered to express recombinant receptors.

In some embodiments, the agent can enhance, boost and/or promotes the efficacy and/or safety of the therapeutic effect of the cell therapy. In some embodiments, the agent enhances or improves the efficacy, survival or persistence of the administered cells, e.g., cells expressing the binding molecule or a recombinant receptor. In some embodiments, administration of the agent can boost, augment, or increase the expansion of genetically engineered cells administered to a subject. In some embodiments, the agent is selected from among a protein phosphatase inhibitor, a kinase inhibitor, a cytokine, an immunomodulator, or an agent that decreases the level or activity of a regulatory T (Treg) cell. In some embodiments, the agent enhances safety, by virtue of reducing or ameliorating adverse effects of the administered the cell therapy. In some embodiments, the agent can treat the same disease, condition or a comorbidity. In some embodiments, the agent can ameliorate, reduce or eliminate one or more toxicities, adverse effects or side effects that are associated with administration of the cell therapy, e.g., CAR-expressing cells.

In some embodiments, the agent includes chemotherapy, radiation therapy, surgery, transplantation, adoptive cell therapy, antibodies, cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, immune checkpoint inhibitors, antibiotics, angiogenesis inhibitors, metabolic modulators or other therapeutic agents or any combination thereof. In some embodiments, the agent is a protein, a peptide, a nucleic acid, a small molecule agent, a cell, a toxin, a lipid, a carbohydrate or combinations thereof, or any other type of therapeutic agent, e.g. radiation. In some embodiments, the agent includes surgery, chemotherapy, radiation therapy, transplantation, administration of cells expressing a recombinant receptor, e.g., CAR, kinase inhibitor, immune checkpoint inhibitor, mTOR pathway inhibitor, immunosuppressive agents, immunomodulators, antibodies, immunoablative agents, antibodies and/or antigen binding fragments thereof, antibody conjugates, other antibody therapies, cytotoxins, steroids, cytokines, peptide vaccines, hormone therapy, antimetabolites, metabolic modulators, drugs that inhibit either the calcium dependent phosphatase calcineurin or the p70S6 kinase FK506) or inhibit the p70S6 kinase, alkylating agents, anthracyclines, *vinca* alkaloids, proteosome inhibitors, GITR agonists, protein tyrosine phosphatase inhibitors, protein kinase inhibitors, an oncolytic virus, and/or other types of immunotherapy. In some embodiments, the agent or treatment is bone marrow transplantation, T cell ablative therapy using chemotherapy agents such as, fludarabine, external-beam radiation therapy (XRT), cyclophosphamide, and/or antibody therapy.

In some embodiments, the engineered cells, are administered in combination with other engineered cells, e.g., other CAR-expressing cells. In some embodiments, the agent is a kinase inhibitor, e.g., an inhibitor of Bruton's tyrosine kinase (Btk), e.g., ibrutinib. In some embodiments, the agent is an adenosine pathway or adenosine receptor antagonist or agonist. In some embodiments, the agent is an immunomodulator such as thalidomide or a thalidomide derivative (e.g., lenalidomide). In some embodiments, the agent is a cytotoxic or chemotherapy agent, a biologic therapy (e.g., antibody, e.g., monoclonal antibody, or cellular therapy), or an inhibitor (e.g., kinase inhibitor).

In some embodiments, a chemotherapeutic agent (sometimes referred to as a cytotoxic agent) is administered to the subject to disrupt a lesion. In certain embodiments, the lesion is tumor. In particular embodiments, the lesion is cancerous. In particular embodiments, the chemotherapeutic agent is any agent known to those of skill in the art to be effective for the treatment, prevention or amelioration of hyperproliferative disorders such as cancer. Chemotherapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices and nucleotide sequences encoding biologically active proteins, polypeptides or peptides), antibodies, synthetic or natural inorganic molecules, mimetic agents, and synthetic or natural organic molecules. In particular embodiments, chemotherapeutic drugs include alkylating agents, anthracyclines, cytoskeletal disruptors (taxanes), epothilones, histone deacetylase inhibitors, topoisomerase inhibitors, topoisomerase II inhibitors, kinase inhibitors, nucleotide analogs and precursor analogs, peptide antibiotics, platinum-based agents, and *vinca* alkaloids and derivatives.

In certain embodiments, a lesion is disrupted by administering a chemotherapeutic agent to modulate genetically engineered cells in vivo. Chemotherapeutic agents may include, but are not limited to, abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In some embodiments, exemplary chemotherapeutic agents include an anthracycline (e.g., doxorubicin, such as liposomal doxorubicin); a *vinca* alkaloid (e.g., vinblastine, vincristine, vindesine, vinorelbine); an alkylating agent (e.g., cyclophosphamide, decarbazine, melphalan, ifosf- amide, temozolomide); an immune cell antibody (e.g., alemtuzamab, gemtuzumab, rituximab, tositumomab); an antimetabolite (including, e.g., folic acid antagonists, pyrimidine analogs, purine analogs and adenosine deaminase inhibitors such as fludarabine); a TNFR glucocorticoid induced TNFR related protein (GITR) agonist; a proteasome inhibitor (e.g., aclacinomycin A, gliotoxin or bortezomib); an immunomodulatory such as thalidomide or a thalidomide derivative (e.g., lenalidomide).

In some embodiments, the agent is cell therapy, e.g., adoptive cell therapy. In some embodiments, the agent includes administration of engineered cells, e.g., additional CAR-expressing cell. In some embodiments, the agent is an additional dose and/or a modified dose of the administered cell therapy. In some embodiments, the agent is or comprises a dose or composition comprising genetically engineered CD8+ T cells expressing a recombinant receptor. In some embodiments, the agent is or comprises a modified dose or composition of the T cells, comprising a different ratio of CD4+:CD8+ T cells compared to the initial dose of the cell therapy.

In some embodiments, the additional engineered cell is a CAR-expressing cell that expresses the same or different recombinant receptor as the engineered cells. In some embodiments, the recombinant receptor, e.g., CAR, expressed on the additional engineered cell, recognizes a different antigen and/or epitope. In some embodiments, the recombinant receptor, e.g., CAR, expressed on the additional engineered cell, recognizes a different epitope of the same antigen as the first engineered cell. In some embodiments, the recombinant receptor, e.g., CAR, expressed on the additional engineered cell, recognizes a different antigen, e.g., a different tumor antigen or combination of antigens. For example, in some embodiments, the recombinant receptor, e.g., CAR, expressed on the additional engineered cell, targets cancer cells that express early lineage markers, e.g., cancer stem cells, while other CAR-expressing cells target cancer cells that express later lineage markers. In such embodiments, the additional engineered cell is administered prior to, concurrently with, or after administration (e.g., infusion) of the CAR-expressing cells described herein. In some embodiments, the additional engineered cell expresses allogeneic CAR.

In some embodiments, the configurations of one or more of the CAR molecules comprise a primary intracellular signaling domain and two or more, e.g., 2, 3, 4, or 5 or more, costimulatory signaling domains. In some embodiments, the one or more of the CAR molecules may have the same or a different primary intracellular signaling domain, the same or different costimulatory signaling domains, or the same number or a different number of costimulatory signaling domains. In some embodiments, the one or more of the CAR molecules can be configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

In some embodiments, the agent is any of the multispecific binding molecules and/or cells engineered to express one or more of the binding molecules described herein and/or cells engineered to express additional binding molecules, e.g., recombinant receptors, e.g., CAR, that target a different antigen. In some embodiments, the agent is a cell engineered to express a recombinant receptor, e.g., CAR, targeting a different epitope and/or antigen, e.g., a different antigen associated with a disease or condition. In some embodiments, the agent is a cell engineered to express a recombinant receptor, e.g., CAR, targeting a second or additional antigen expressed in multiple myeloma, e.g., CD38, CD138, CS-1, BAFF-R, TACI and/or FcRH5.

In some embodiments, the agent is an immunomodulatory agent. In some embodiments, the combination therapy includes an immunomodulatory agent that can stimulate, amplify and/or otherwise enhance an anti-tumor immune response, e.g. anti-tumor immune response from the administered engineered cells, such as by inhibiting immunosuppressive signaling or enhancing immunostimulant signaling. In some embodiments, the immunomodulatory agent is a peptide, protein or is a small molecule. In some embodiments, the protein can be a fusion protein or a recombinant protein. In some embodiments, the immunomodulatory agent binds to an immunologic target, such as a cell surface receptor expressed on immune cells, such a T cells, B cells or antigen-presenting cells. For example, in some embodiments, the immunomodulatory agent is an antibody or antigen-binding antibody fragment, a fusion protein, a small molecule or a polypeptide. In some embodiments, the cell therapy are administered in combination with an agent that is an antibody or an antigen-binding fragment thereof, such as a monoclonal antibody.

In some embodiments, the immunomodulatory agent blocks, inhibits or counteracts a component of the immune checkpoint pathway. The immune system has multiple inhibitory pathways that are involved in maintaining self-tolerance and for modulating immune responses. Tumors can use certain immune-checkpoint pathways as a major mechanism of immune resistance, particularly against T cells that are specific for tumor antigens (Pardoll (2012) Nature Reviews Cancer 12:252-264), e.g., engineered cells such as CAR-expressing cells. Because many such immune checkpoints are initiated by ligand-receptor interactions, they can be readily blocked by antibodies against the ligands and/or their receptors.

Therefore, therapy with antagonistic molecules blocking an immune checkpoint pathway, such as small molecules, nucleic acid inhibitors (e.g., RNAi) or antibody molecules, are becoming promising avenues of immunotherapy for cancer and other diseases. In contrast to the majority of anti-cancer agents, checkpoint inhibitors do not necessarily target tumor cells directly, but rather target lymphocyte receptors or their ligands in order to enhance the endogenous antitumor activity of the immune system.

As used herein, the term "immune checkpoint inhibitor" refers to molecules that totally or partially reduce, inhibit, interfere with or modulate one or more checkpoint proteins. Checkpoint proteins regulate T-cell activation or function. These proteins are responsible for co-stimulatory or inhibitory interactions of T-cell responses. Immune checkpoint proteins regulate and maintain self-tolerance and the duration and amplitude of physiological immune responses. In some embodiments, the subject can be administered an agent that can enhance or boost the immune response, e.g., immune response effected by the administered cell therapy, recombinant receptors, cells and/or compositions provided herein, against a disease or condition, e.g., a cancer, such as any described herein.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors, ligands and/or receptor-ligand interaction. In some embodiments, modulation, enhancement and/or stimulation of particular receptors can overcome immune checkpoint pathway components. Illustrative immune checkpoint molecules that may be targeted for blocking, inhibition, modulation, enhancement and/or stimulation include, but are not limited to, PD-1 (CD279), PD-L1 (CD274, B7-H1), PDL2 (CD273, B7-DC), CTLA-4, LAG-3 (CD223), TIM-3,4-1BB (CD137), 4-1BBL (CD137L), GITR (TNFRSF18, AITR), CD40, OX40 (CD134, TNFRSF4), CXCR2, tumor associated antigens (TAA), B7-H3, B7-H4, BTLA, HVEM, GAL9, B7H3, B7H4, VISTA, KIR, 2B4 (belongs to the CD2 family of molecules and is expressed on all NK, γδ, and memory CD8+ (αβ) T cells), CD160 (also referred to as BY55), CGEN-15049, CEACAM (e.g., CEACAM-1, CEACAM-3 and/or CEACAM-5), TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and a transforming growth factor receptor (TGFR; e.g., TGFR beta). Immune checkpoint inhibitors include antibodies, or antigen binding fragments thereof, or other binding proteins, that bind to and block or inhibit and/or enhance or stimulate the activity of one or more of any of the said molecules.

Exemplary immune checkpoint inhibitors include Tremelimumab (CTLA-4 blocking antibody, also known as ticilimumab, CP-675,206), anti-OX40, PD-L1 monoclonal antibody (Anti-B7-H1; MEDI4736), MK-3475 (PD-1 blocker), nivolumab (anti-PD-1 antibody), CT-011 (anti-PD-1 antibody), BY55 monoclonal antibody, AMP224 (anti-PD-L1 antibody), BMS-936559 (anti-PD-L1 antibody), MPLDL3280A (anti-PD-L1 antibody), MSB0010718C (anti-PD-L1 antibody) and ipilimumab (anti-CTLA-4 antibody, also known as Yervoy®, MDX-010 and MDX-101). Exemplary of immunomodulatory antibodies include, but are not limited to, Daclizumab (Zenapax), Bevacizumab (Avastin®), Basiliximab, Ipilimumab, Nivolumab, pembrolizumab, MPDL3280A, Pidilizumab (CT-011), MK-3475, BMS-936559, MPDL3280A (Atezolizumab), tremelimumab, IMP321, BMS-986016, LAG525, urelumab, PF-05082566, TRX518, MK-4166, dacetuzumab (SGN-40), lucatumumab (HCD122), SEA-CD40, CP-870, CP-893, MEDI6469, MEDI6383, MOXR0916, AMP-224, MSB0010718C (Avelumab), MEDI4736, PDR001, rHIgM12B7, Ulocuplumab, BKT140, Varlilumab (CDX-1127), ARGX-110, MGA271, lirilumab (BMS-986015, IPH2101), IPH2201, ARGX-115, Emactuzumab, CC-90002 and MNRP1685A or an antibody-binding fragment thereof. Other exemplary immunomodulators include, e.g., afutuzumab (available from Roche); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon .gamma., CAS 951209-71-5, available from IRX Therapeutics).

Programmed cell death 1 (PD-1) is an immune checkpoint protein that is expressed in B cells, NK cells, and T cells (Shinohara et al., 1995, Genomics 23:704-6; Blank et al., 2007, Cancer Immunol Immunother 56:739-45; Finger et al., 1997, Gene 197:177-87; Pardoll (2012) Nature Reviews Cancer 12:252-264). The major role of PD-1 is to limit the activity of T cells in peripheral tissues during inflammation in response to infection, as well as to limit autoimmunity. PD-1 expression is induced in activated T cells and binding of PD-1 to one of its endogenous ligands acts to inhibit T-cell activation by inhibiting stimulatory kinases. PD-1 also acts to inhibit the TCR "stop signal". PD-1 is highly expressed on Treg cells and may increase their proliferation in the presence of ligand (Pardoll (2012) Nature Reviews Cancer 12:252-264). Anti-PD 1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Exemplary anti-PD-1 antibodies include nivolumab (Opdivo by BMS), pembrolizumab (Keytruda by Merck), pidilizumab (CT-011 by Cure Tech), lambrolizumab (MK-3475 by Merck), and AMP-224 (Merck), nivolumab (also referred to as Opdivo, BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are described in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are described in WO2009/101611. Pembrolizumab (formerly known as lambrolizumab, and also referred to as Keytruda, MK03475; Merck) is a humanized IgG4 monoclonal antibody that binds to PD-1. Pembrolizumab and other humanized anti-PD-1 antibodies are described in U.S. Pat. No. 8,354,509 and WO2009/114335. Other anti-PD-1 antibodies include AMP 514 (Amplimmune), among others, e.g., anti-PD-1 antibodies described in U.S. Pat. No. 8,609,089, US 2010028330, US 20120114649 and/or US 20150210769. AMP-224 (B7-DCIg; Amplimmune; e.g., described in WO2010/027827 and WO2011/066342), is a PD-L2 Fc fusion soluble receptor that blocks the interaction between PD-1 and B7-H1.

PD-L1 (also known as CD274 and B7-H1) and PD-L2 (also known as CD273 and B7-DC) are ligands for PD-1, found on activated T cells, B cells, myeloid cells, macrophages, and some types of tumor cells. Anti-tumor therapies have focused on anti-PD-L1 antibodies. The complex of PD-1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., 2012, N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51). Exemplary anti-PD-L1 antibodies include MDX-1105 (Medarex), MEDI4736 (Medimmune) MPDL3280A (Genentech), BMS-935559 (Bristol-Myers Squibb) and MSB0010718C. MEDI4736 (Medimmune) is a human monoclonal antibody that binds to PD-L1, and inhibits interaction of the ligand with PD-1. MDPL3280A (Genentech/Roche) is a human Fc optimized IgG1 monoclonal antibody that binds to PD-L. MDPL3280A and other human monoclonal antibodies to PD-L1 are described in U.S. Pat. No. 7,943,743 and U.S. Publication No. 20120039906. Other anti-PD-L1 binding agents include YW243.55.S70 (see WO2010/077634) and MDX-1105 (also referred to as BMS-936559, and, e.g., anti-PD-L1 binding agents described in WO2007/005874).

Cytotoxic T-lymphocyte-associated antigen (CTLA-4), also known as CD152, is a co-inhibitory molecule that functions to regulate T-cell activation. CTLA-4 is a member of the immunoglobulin superfamily that is expressed exclusively on T-cells. CTLA-4 acts to inhibit T-cell activation and is reported to inhibit helper T-cell activity and enhance regulatory T-cell immunosuppressive activity. Although the precise mechanism of action of CTLA-4 remains under investigation, it has been suggested that it inhibits T cell activation by outcompeting CD28 in binding to CD80 and CD86, as well as actively delivering inhibitor signals to the T cell (Pardoll (2012) Nature Reviews Cancer 12:252-264). Anti-CTLA-4 antibodies have been used in clinical trials for the treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTLA-4 is the kinetics of anti-tumor effect, with a lag period of up to 6 months after initial treatment required for physiologic response. In some cases, tumors may actually increase in size after treatment initiation, before a reduction is seen (Pardoll (2012) Nature Reviews Cancer 12:252-264). Exemplary anti-CTLA-4 antibodies include ipilimumab (Bristol-Myers Squibb) and tremelimumab (Pfizer). Ipilimumab has recently received FDA approval for treatment of metastatic melanoma (Wada et al., 2013, J Transl Med 11:89).

Lymphocyte activation gene-3 (LAG-3), also known as CD223, is another immune checkpoint protein. LAG-3 has been associated with the inhibition of lymphocyte activity and in some cases the induction of lymphocyte anergy. LAG-3 is expressed on various cells in the immune system including B cells, NK cells, and dendritic cells. LAG-3 is a natural ligand for the MHC class II receptor, which is substantially expressed on melanoma-infiltrating T cells including those endowed with potent immune-suppressive activity. Exemplary anti-LAG-3 antibodies include BMS-986016 (Bristol-Myers Squib), which is a monoclonal antibody that targets LAG-3. IMP701 (Immutep) is an antagonist LAG-3 antibody and IMP731 (Immutep and GlaxoSmithKline) is a depleting LAG-3 antibody. Other LAG-3 inhibitors include IMP321 (Immutep), which is a recombinant fusion protein of a soluble portion of LAG-3 and Ig that binds to MHC class II molecules and activates antigen presenting cells (APC). Other antibodies are described, e.g., in WO2010/019570 and US 2015/0259420

T-cell immunoglobulin domain and mucin domain-3 (TIM-3), initially identified on activated Th1 cells, has been shown to be a negative regulator of the immune response. Blockade of TIM-3 promotes T-cell mediated anti-tumor immunity and has anti-tumor activity in a range of mouse tumor models. Combinations of TIM-3 blockade with other immunotherapeutic agents such as TSR-042, anti-CD137 antibodies and others, can be additive or synergistic in increasing anti-tumor effects. TIM-3 expression has been associated with a number of different tumor types including melanoma, NSCLC and renal cancer, and additionally, expression of intratumoral TIM-3 has been shown to correlate with poor prognosis across a range of tumor types including NSCLC, cervical, and gastric cancers. Blockade of TIM-3 is also of interest in promoting increased immunity to a number of chronic viral diseases. TIM-3 has also been shown to interact with a number of ligands including galectin-9, phosphatidylserine and HMGB1, although which of these, if any, are relevant in regulation of anti-tumor responses is not clear at present. In some embodiments, antibodies, antibody fragments, small molecules, or peptide inhibitors that target TIM-3 can bind to the IgV domain of TIM-3 to inhibit interaction with its ligands. Exemplary antibodies and peptides that inhibit TIM-3 are described in US 2015/0218274, WO2013/006490 and US 2010/0247521. Other anti-TIM-3 antibodies include humanized versions of RMT3-23 (Ngiow et al., 2011, Cancer Res, 71:3540-3551), and clone 8B.2C12 (Monney et al., 2002, Nature, 415:536-541). Bi-specific antibodies that inhibit TIM-3 and PD-1 are described in US 2013/0156774.

In some embodiments, the agent is a CEACAM inhibitor (e.g., CEACAM-1, CEACAM-3, and/or CEACAM-5 inhibitor). In some embodiments, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In some embodiments, the anti-CEACAM antibody binds to CEACAM-5 as described in, e.g., Zheng et al. PLoS One. (2011) 6(6): e21146), or crossreacts with CEACAM-1 and CEACAM-5 as described in, e.g., WO 2013/054331 and US 2014/0271618.

4-1BB, also known as CD137, is transmembrane glycoprotein belonging to the TNFR superfamily. 4-1BB receptors are present on activated T cells and B cells and monocytes. An exemplary anti-4-1BB antibody is urelumab (BMS-663513), which has potential immunostimulatory and antineoplastic activities.

Tumor necrosis factor receptor superfamily, member 4 (TNFRSF4), also known as OX40 and CD134, is another member of the TNFR superfamily. OX40 is not constitutively expressed on resting naïve T cells and acts as a secondary co-stimulatory immune checkpoint molecule. Exemplary anti-OX40 antibodies are MEDI6469 and MOXR0916 (RG7888, Genentech).

In some embodiments, the agent includes a molecule that decreases the regulatory T cell (Treg) population. Methods that decrease the number of (e.g., deplete) Treg cells are known in the art and include, e.g., CD25 depletion, cyclophosphamide administration, and modulating Glucocorticoid-induced TNFR family related gene (GITR) function. GITR is a member of the TNFR superfamily that is upregulated on activated T cells, which enhances the immune system. Reducing the number of Treg cells in a subject prior to apheresis or prior to administration of engineered cells, e.g., CAR-expressing cells, can reduce the number of unwanted immune cells (e.g., Tregs) in the tumor microenvironment and reduces the subject's risk of relapse. In some embodiments, the agent includes a molecule targeting GITR and/or modulating GITR functions, such as a GITR agonist and/or a GITR antibody that depletes regulatory T cells (Tregs). In some embodiments, the agent includes cyclophosphamide. In some embodiments, the GITR binding molecule and/or molecule modulating GITR function (e.g., GITR agonist and/or Treg depleting GITR antibodies) is administered prior to the engineered cells, e.g., CAR-expressing cells. For example, in some embodiments, the GITR agonist can be administered prior to apheresis of the cells. In some embodiments, cyclophosphamide is administered to the subject prior to administration (e.g., infusion or re-infusion) of the engineered cells, e.g., CAR-expressing cells or prior to apheresis of the cells. In some embodiments, cyclophosphamide and an anti-GITR antibody are administered to the subject prior to administration (e.g., infusion or re-infusion) of the engineered cells, e.g., CAR-expressing cells or prior to apheresis of the cells.

In some embodiments, the agent is a GITR agonist. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No. 090505B 1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B1, U.S. Pat. Nos. 7,812,135, 8,388,967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726. An exemplary anti-GITR antibody is TRX518.

In some embodiments, the agent enhances tumor infiltration or transmigration of the administered cells, e.g., CAR-expressing cells. For example, in some embodiments, the agent stimulates CD40, such as CD40L, e.g., recombinant human CD40L. Cluster of differentiation 40 (CD40) is also a member of the TNFR superfamily. CD40 is a costimulatory protein found on antigen-presenting cells and mediates a broad variety of immune and inflammatory responses. CD40 is also expressed on some malignancies, where it promotes proliferation. Exemplary anti-CD40 antibodies are dacetuzumab (SGN-40), lucatumumab (Novartis, antagonist), SEA-CD40 (Seattle Genetics), and CP-870,893. In some embodiments, the agent that enhances tumor infiltration includes tyrosine kinase inhibitor sunitnib, heparanase, and/or chemokine receptors such as CCR2, CCR4, and CCR7.

In some embodiments, the lesion is disrupted by administering an immunomodulatory agent that is a structural or functional analog or derivative of thalidomide and/or an inhibitor of E3 ubiquitin ligase. In some embodiments, the immunomodulatory agent binds to cereblon (CRBN). In some embodiments, the immunomodulatory agent binds to the CRBN E3 ubiquitin-ligase complex. In some embodiments, the immunomodulatory agent binds to CRBN and the CRBN E3 ubiquitin-ligase complex. In some embodiments, the immunomodulatory agent up-regulates the protein or gene expression of CRBN. In some aspects, CRBN is the substrate adaptor for the $CRL4^{CRBN}$ E3 ubiquitin ligase, and modulates the specificity of the enzyme. In some embodiments, binding to CRB or the CRBN E3 ubiquitin ligase complex inhibits E3 ubiquitin ligase activity. In some embodiments, the immunomodulatory agent induces the ubiquitination of KZF1 (Ikaros) and IKZF3 (Aiolos) and/or induces degradation of IKZF1 (Ikaros) and IKZF3 (Aiolos). In some embodiments, the immunomodulatory agent induces the ubiquitination of casein kinase A (CK1α) by the $CRL4^{CRBN}$ E3 ubiquitin ligase. In some embodiments, the ubiquitination of CK1α results in CK1α degradation.

In some embodiments, the immunomodulatory agent is an inhibitor of the Ikaros (IKZF1) transcription factor. In some embodiments, the immunomodulatory agent enhances ubiquitination of Ikaros. In some embodiments, the immunomodulatory agent enhances the degradation of Ikaros. In some embodiments, the immunomodulatory agent down-regulates the protein or gene expression of Ikaros. In some embodiments, administration of the immunomodulatory agent causes a decrease in Ikaros protein levels.

In some embodiments, the immunomodulatory agent is an inhibitor of the Aiolos (IKZF3) transcription factor. In some embodiments, the immunomodulatory agent enhances ubiquitination of Aiolos. In some embodiments, the immunomodulatory agent enhances the degradation of Aiolos. In some embodiments, the immunomodulatory agent downregulates the protein or gene expression of Aiolos. In some embodiments, administration of the immunomodulatory agent causes a decrease in Aiolos protein levels.

In some embodiments, the immunomodulatory agent is an inhibitor of both the Ikaros (IKZF1) and Aiolos (IKZF3) transcription factors. In some embodiments, the immunomodulatory agent enhances ubiquitination of both Ikaros and Aiolos. In some embodiments, the immunomodulatory agent enhances the degradation of both Ikaros and Aiolos. In some embodiments, the immunomodulatory agent enhances ubiquitination and degradation of both Ikaros and Aiolos. In some embodiments, administration of the immunomodulatory agent causes both Aiolos protein levels. and Ikaros protein levels to decrease.

In some embodiments, the immunomodulatory agent is a selective cytokine inhibitory drug (SelCID). In some embodiments, the immunomodulatory agent inhibits the activity of phosphodiesterase-4 (PDE4). In some embodiments, the immunomodulatory agent suppresses the enzymatic activity of the CDC125 phosphatases. In some embodiments, the immunomodulatory agent alters the intracellular trafficking of CDC125 phosphatases.

In some embodiments, the immunomodulatory agent is thalidomide (2-(2,6-dioxopiperidin-3-yl)-1H-isoindole-1,3 (2H)-dione) or an analog or derivative of thalidomide. In certain embodiments, a thalidomide derivative includes structural variants of thalidomide that have a similar biological activity. Exemplary thalidomide derivatives include, but are not limited to lenalidomide (REVLIMMUNOMODULATORY COMPOUND™; Celgene Corporation), pomalidomide (also known as ACTIMMUNOMODULATORY COMPOUND™ or POMALYST™ (Celgene Corporation)), CC-1088, CDC-501, and CDC-801, and the compounds disclosed in U.S. Pat. Nos. 5,712,291; 7,320, 991; and 8,716,315; U.S. Appl. No. 2016/0313300; and PCT Pub. Nos. WO 2002/068414 and WO 2008/154252.

In some embodiments, the immunomodulatory agent is 1-oxo- and 1,3 dioxo-2-(2,6-dioxopiperldin-3-yl) isoindolines substituted with amino in the benzo ring as described in U.S. Pat. No. 5,635,517 which is incorporated herein by reference.

In some embodiments, the immunomodulatory agent is a compound of the following formula:

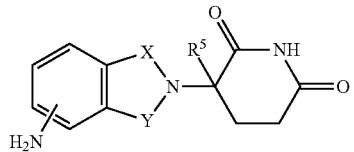

wherein one of X and Y is —C(O)— and the other of X and Y is —C(O)— or —CH$_2$—, and R$^5$ is hydrogen or lower alkyl, or a pharmaceutically acceptable salt thereof. In some embodiments, X is —C(O)— and Y is —CH$_2$—. In some embodiments, both X and Y are —C(O)—. In some embodiments, R$^5$ is hydrogen. In other embodiments, R$^5$ is methyl.

In some embodiments, the immunomodulatory compound is a compound that belongs to a class of substituted 2-(2,6-dioxopiperidin-3-yl)phthalimmunomodulatory compounds and substituted 2-(2,6-dioxopiperldin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference.

In some embodiments, the immunomodulatory agent is a compound of the following formula:

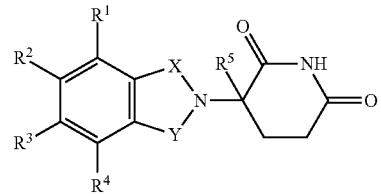

wherein
one of X and Y is —C(O)— and the other of X and Y is —C(O)— or —CH$_2$—;

(1) each of R$^1$, R$^2$, R$^3$, and R$^4$ are independently halo, alkyl of 1 to 4 carbon atoms, or alkoxy or 1 to 4 carbon atoms, or (2) one of R$^1$, R$^3$, R$^4$, and R$^5$ is —NHR$^a$ and the remaining of R$^1$, R$^2$, R$^3$, and R$^4$ is are hydrogen, wherein R$^a$ is hydrogen or alkyl of 1 to 8 carbon atoms;

R$^5$ is hydrogen or alkyl of 1 to 8 carbon atoms, benzyl, or halo;

provided that R$^5$ is other than hydrogen if X and Y are —C(O)— and (i) each of R$^1$, R$^2$, R$^3$, and R$^4$ is fluoro; or (ii) one of R$^1$, R$^2$, R$^3$, and R$^4$ is amino; or a pharmaceutically acceptable salt thereof.

In some embodiments, the immunomodulatory agent is a compound that belongs to a class of isoindole-immunomodulatory compounds disclosed in U.S. Pat. No. 7,091, 353, U.S. Patent Publication No. 2003/0045552, and International Application No. PCT/USOI/50401 (International Publication No. WO02/059106), each of which are incorporated herein by reference. For example, in some embodiments, the immunomodulatory agent is [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2, 3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2, 6-dioxo(3-piperidyl))-1,3-dioxoisoindolin-4-yl) methyl}cyclopropyl-carboxamide; 2-chloro-N-{(2-(2,6-dioxo(3-piperidyl))-1,3-dioxoisoindolin-4-yl) methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl) methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl) methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1, 3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]

methyl}(octylamino)carboxamide; or N-{[2-(2,6-dioxo(3-piperidyl))-1,3-dioxoisoindolin-4-yl]methyl}(benzylamino)carboxamide.

In some embodiments, the immunomodulatory agent is a compound that belongs to a class of isoindole-immunomodulatory compounds disclosed in U.S. Patent Application Publication Nos. 2002/0045643, International Publication No. WO 98/54170, and U.S. Pat. No. 6,395,754, each of which is incorporated herein by reference. In some embodiments, the immunomodulatory agent is a tetra substituted 2-(2,6-dioxopiperdin-3-yl)-1-oxoisoindolines described in U.S. Pat. No. 5,798,368, which is incorporated herein by reference. In some embodiments, the immunomodulatory agent is 1-oxo and 1,3-dioxo-2-(2,6-dioxopiperidin-3-yl) isoindolines disclosed in U.S. Pat. No. 6,403,613, which is incorporated herein by reference. In some embodiments the immunomodulatory agent is a 1-oxo or 1,3-dioxoisoindoline substituted in the 4- or 5-position of the indoline ring as described in U.S. Pat. Nos. 6,380,239 and 7,244,759, both of which are incorporated herein by reference.

In some embodiments, the immunomodulatory agent is 2-(4-amino-1-oxo-1,3-dihydro-isoindol-2-yl)-4-carbamoyl-butyric acid or 4-(4-amino-1-oxo-1,3-dihydro-isoindol-2-yl)-4-carbamoyl-butyric acid. In some embodiments, the immunomodulatory compound is 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, or 2-{4-[(furan-2-yl-methyl)-amino]-1,3-dioxo-1,3-dihydro-isoindol-2-yl}-pentanedioic acid.

In some embodiments, the immunomodulatory agent is a isoindoline-1-one or isoindoline-1,3-dione substituted in the 2-position with 2,6-dioxo-3-hydroxypiperidin-5-yl as described in U.S. Pat. No. 6,458,810, which is incorporated herein by reference. In some embodiments, the immunomodulatory compound is 3-(5-amino-2-methyl-4-oxo-4H-quinazolin-3-yl)-piperidine-2,6-dione, or an enantiomer or a mixture of enantiomers thereof; or a pharmaceutically acceptable salt, solvate, hydrate, co-crystal, clathrate, or polymorph thereof. In some embodiments, the immunomodulatory compound is 3-[4-(4-morpholin-4-ylmethyl-benzyloxy)-1-oxo-1,3-dihydro-isoindol-2-yl]-piperidine-2,6-dione.

In some embodiments, the immunomodulatory agent is as described in Oshima, K. et al., *Nihon Rinsho.*, 72(6):1130-5 (2014); Millrine, D. et al., *Trends Mol Med.*, 23(4):348-364 (2017); and Collins, et al., *Biochem J.*, 474(7):1127-1147 (2017).

In some embodiments, the immunomodulatory agent is lenalidomide, pomalidomide, avadomide, a stereoisomer of lenalidomide, pomalidomide, avadomide or a pharmaceutically acceptable salt, solvate, hydrate, co-crystal, clathrate, or polymorph thereof. In some embodiments, the immunomodulatory compound is lenalidomide, a stereoisomer of lenalidomide or a pharmaceutically acceptable salt, solvate, hydrate, co-crystal, clathrate, or polymorph thereof. In some embodiments, the immunomodulatory compound is lenalidomide, or ((RS)-3-(4-Amino-1-oxo-1,3-dihydro-2H-isoindol-2-yl)piperidine-2,6-dione).

In certain embodiments, the lesion is disrupted by administering the thalidomide derivative lenalidomide, ((RS)-3-(4-Amino-1-oxo-1,3-dihydro-2H-isoindol-2-yl)piperidine-2,6-dione) to the subject. Lenalidomide is FDA approved for the treatment of multiple myeloma, myelodysplastic syndrome associated with deletion 5q, and most recently in relapsed/refractory mantle-cell lymphoma (MCL). Lenalidomide generally is a synthetic derivative of thalidomide, and is currently understood to have multiple immunomodulatory effects, including enforcement of immune synapse formation between T cell and antigen presenting cells (APCs). For example, in some cases, lenalidomide modulates T cell responses and results in increased interleukin (IL)-2 production in $CD4^+$ and $CD8^+$ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al., Oncoimmunology (2016) 5(4):e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues. Lenalidomide also can enhance T-cell proliferation and interferon-γ production in response to activation of T cells via CD3 ligation or dendritic cell-mediated activation. In addition, lenalidomide is thought to decrease proliferation of pro-inflammatory cytokines including TNF-a, IL-1, IL-6, and IL-12 and enhance antibody-dependent cellular cytotoxicity (ADCC) via increased NK cell activation. Lenalidomide can also induce malignant B cells to express higher levels of immunostimulatory molecules such as CD80, CD86, HLA-DR, CD95, and CD40 (Fecteau et al., Blood (2014) 124(10):1637-1644). Cereblon, an E3 ubiquitin ligase, was identified as the primary target for thalidomide-induced teratogenesis (Ito et al., T., (2010) Science 327: 1345-1350). Lenalidomide also targets cereblon and it has been shown that this leads to the reduction of c-Myc and IRF4 expression while also increasing expression of p21 that leads to G1 cell-cycle arrest (Lopez-Girona et al., (2012) Leukemia 26: 2326-2335).

In some embodiments, the agent includes thalidomide drugs or analogs thereof and/or derivatives thereof, such as lenalidomide, pomalidomide or apremilast. See, e.g., Bertilaccio et al., Blood (2013) 122:4171, Otahal et al., Oncoimmunology (2016) 5(4):e1115940; Fecteau et al., Blood (2014) 124(10):1637-1644 and Kuramitsu et al., Cancer Gene Therapy (2015) 22:487-495). Lenalidomide ((RS)-3-(4-Amino-1-oxo-1,3-dihydro-2H-isoindol-2-yl)piperidine-2,6-dione; also known as Revlimid) is a synthetic derivative of thalidomide, and has multiple immunomodulatory effects, including enforcement of immune synapse formation between T cell and antigen presenting cells (APCs). For example, in some cases, lenalidomide modulates T cell responses and results in increased interleukin (IL)-2 production in CD4+ and CD8+ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al., Oncoimmunology (2016) 5(4):e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues. Lenalidomide also can enhance T-cell proliferation and interferon-γ production in response to activation of T cells via CD3 ligation or dendritic cell-mediated activation. Lenalidomide can also induce malignant B cells to express higher levels of immunostimulatory molecules such as CD80, CD86, HLA-DR, CD95, and CD40 (Fecteau et al., Blood (2014) 124(10):1637-1644).

In some embodiments, the agent is a B-cell inhibitor. In some embodiments, the agent is one or more B-cell inhibitors selected from among inhibitors of CD10, CD19, CD20, CD22, CD34, CD123, CD79a, CD79b, CD179b, FLT-3, or ROR1, or a combination thereof. In some embodiments, the B-cell inhibitor is an antibody (e.g., a mono- or bispecific antibody) or an antigen binding fragment thereof. In some embodiments, the agent is an engineered cell expressing recombinant receptors that target B-cell targets, e.g., CD10, CD19, CD20, CD22, CD34, CD123, CD79a, CD79b, CD179b, FLT-3, or ROR1.

In some embodiments, the agent is a CD20 inhibitor, e.g., an anti-CD20 antibody (e.g., an anti-CD20 mono- or bi-specific antibody) or a fragment thereof. Exemplary anti-CD20 antibodies include but are not limited to rituximab, ofatumumab, ocrelizumab (also known as GA101 or RO5072759), veltuzumab, obinutuzumab, TRU-015 (Trubion Pharmaceuticals), ocaratuzumab (also known as AME-133v or ocaratuzumab), and Pro131921 (Genentech). See, e.g., Lim et al. Haematologica. (2010) 95(1):135-43. In some embodiments, the anti-CD20 antibody comprises rituximab. Rituximab is a chimeric mouse/human monoclonal antibody IgG1 kappa that binds to CD20 and causes cytolysis of a CD20 expressing cell. In some embodiments, the agent includes rituximab. In some embodiments, the CD20 inhibitor is a small molecule.

In some embodiments, the agent is a CD22 inhibitor, e.g., an anti-CD22 antibody (e.g., an anti-CD22 mono- or bi-specific antibody) or a fragment thereof. Exemplary anti-CD22 antibodies include epratuzumab and RFB4. In some embodiments, the CD22 inhibitor is a small molecule. In some embodiments, the antibody is a monospecific antibody, optionally conjugated to a second agent such as a chemotherapeutic agent. For instance, in some embodiments, the antibody is an anti-CD22 monoclonal antibody-MMAE conjugate (e.g., DCDT2980S). In some embodiments, the antibody is an scFv of an anti-CD22 antibody, e.g., an scFv of antibody RFB4. In some embodiments, the scFv is fused to all of or a fragment of *Pseudomonas* exotoxin-A (e.g., BL22). In some embodiments, the scFv is fused to all of or a fragment of (e.g., a 38 kDa fragment of) *Pseudomonas* exotoxin-A (e.g., moxetumomab pasudotox). In some embodiments, the anti-CD22 antibody is an anti-CD19/CD22 bispecific antibody, optionally conjugated to a toxin. For instance, in some embodiments, the anti-CD22 antibody comprises an anti-CD19/CD22 bispecific portion, (e.g., two scFv ligands, recognizing human CD19 and CD22) optionally linked to all of or a portion of diphtheria toxin (DT), e.g., first 389 amino acids of diphtheria toxin (DT), DT 390, e.g., a ligand-directed toxin such as DT2219ARL). In some embodiments, the bispecific portion (e.g., anti-CD 19/anti-CD22) is linked to a toxin such as deglycosylated ricin A chain (e.g., Combotox).

In some embodiments, the immunomodulatory agent is a cytokine. In some embodiments, the immunomodulatory agent is a cytokine or is an agent that induces increased expression of a cytokine in the tumor microenvironment. Cytokines have important functions related to T cell expansion, differentiation, survival, and homeostasis. Cytokines that can be administered to the subject receiving the cell therapy include one or more of IL-2, IL-4, IL-7, IL-9, IL-15, IL-18, and IL-21. In some embodiments, the cytokine administered is IL-7, IL-15, or IL-21, or a combination thereof. In some embodiments, administration of the cytokine to the subject that has sub-optimal response to the administration of the engineered cells, e.g., CAR-expressing cells improves efficacy and/or anti-tumor activity of the administered cells, e.g., CAR-expressing cells.

By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. For example, the immunomodulatory agent is a cytokine and the cytokine is IL-4, TNF-α, GM-CSF or IL-2.

In some embodiments, the agent includes an interleukin-15 (IL-15) polypeptide, an interleukin-15 receptor alpha (IL-15Rα) polypeptide, or combination thereof, e.g., hetIL-15 (Admune Therapeutics, LLC). hetIL-15 is a heterodimeric non-covalent complex of IL-15 and IL-15Rα. hetIL-15 is described in, e.g., U.S. Pat. No. 8,124,084, U.S. 2012/0177598, U.S. 2009/0082299, U.S. 2012/0141413, and U.S. 2011/0081311. In some embodiments, the immunomodulatory agent can contain one or more cytokines. For example, the interleukin can include leukocyte interleukin injection (Multikine), which is a combination of natural cytokines. In some embodiments, the immunomodulatory agent is a Toll-like receptor (TLR) agonist, an adjuvant or a cytokine.

In some embodiments, the agent is an agent that ameliorates or neutralizes one or more toxicities or side effects associated with the cell therapy. In some embodiments, the agent is selected from among a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitors of TNFα include, but are not limited to, xanthine derivatives (e.g. pentoxifylline) and bupropion. An example of an IL-6 inhibitor is an anti-IL-6 antibody molecule such as tocilizumab, sarilumab, elsilimomab, CNTO 328, ALD518/BMS-945429, CNTO 136, CPSI-2364, CDP6038, VX30, ARGX-109, FE301, and FM101. In some embodiments, the anti-IL-6 antibody molecule is tocilizumab. In some embodiments, the agent is an IL-1R inhibitor, such as anakinra.

In some embodiments, the agent is a modulator of adenosine levels and/or an adenosine pathway component. Adenosine can function as an immunomodulatory agent in the body. For example, adenosine and some adenosine analogs that non-selectively activate adenosine receptor subtypes decrease neutrophil production of inflammatory oxidative products (Cronstein et al., Ann. N.Y. Acad. Sci. 451:291, 1985; Roberts et al., Biochem. J., 227:669, 1985; Schrier et al., J. Immunol. 137:3284, 1986; Cronstein et al., Clinical Immunol. Immunopath. 42:76, 1987). In some cases, concentration of extracellular adenosine or adenosine analogs can increase in specific environments, e.g., tumor microenvironment (TME). In some cases, adenosine or adenosine analog signaling depends on hypoxia or factors involved in hypoxia or its regulation, e.g., hypoxia inducible factor (HIF). In some embodiments, increase in adenosine signaling can increase in intracellular cAMP and cAMP-dependent protein kinase that results in inhibition of proinflammatory cytokine production, and can lead to the synthesis of immunosuppressive molecules and development of Tregs (Sitkovsky et al., Cancer Immunol Res (2014) 2(7):598-605). In some embodiments, the agent can reduce or reverse immunosuppressive effects of adenosine, adenosine analogs and/or adenosine signaling. In some embodiments, the agent can reduce or reverse hypoxia-driven A2-adenosinergic T cell immunosuppression. In some embodiments, the agent is selected from among antagonists of adenosine receptors, extracellular adenosine-degrading agents, inhibitors of adenosine generation by CD39/CD73 ectoenzymes, and inhibitors of hypoxia-HIF-1α signaling. In some embodiments, the agent is an adenosine receptor antagonist or agonist.

Inhibition or reduction of extracellular adenosine or the adenosine receptor by virtue of an inhibitor of extracellular adenosine (such as an agent that prevents the formation of, degrades, renders inactive, and/or decreases extracellular adenosine), and/or an adenosine receptor inhibitor (such as an adenosine receptor antagonist) can enhance immune response, such as a macrophage, neutrophil, granulocyte, dendritic cell, T- and/or B cell-mediated response. In addition, inhibitors of the Gs protein mediated cAMP dependent intracellular pathway and inhibitors of the adenosine receptor-triggered Gi protein mediated intracellular pathways, can also increase acute and chronic inflammation.

In some embodiments, the agent is an adenosine receptor antagonist or agonist, e.g., an antagonist or agonist of one or more of the adenosine receptors A2a, A2b, A1, and A3. A1 and A3 inhibit, and A2a and A2b stimulate, respectively, adenylate cyclase activity. Certain adenosine receptors, such as A2a, A2b, and A3, can suppress or reduce the immune response during inflammation. Thus, antagonizing immunosuppressive adenosine receptors can augment, boost or enhance immune response, e.g., immune response from administered cells, e.g., CAR-expressing T cells. In some embodiments, the agent inhibits the production of extracellular adenosine and adenosine-triggered signaling through adenosine receptors. For example, enhancement of an immune response, local tissue inflammation, and targeted tissue destruction can be enhanced by inhibiting or reducing the adenosine-producing local tissue hypoxia; by degrading (or rendering inactive) accumulated extracellular adenosine; by preventing or decreasing expression of adenosine receptors on immune cells; and/or by inhibiting/antagonizing signaling by adenosine ligands through adenosine receptors.

An antagonist is any substance that tends to nullify the action of another, as an agent that binds to a cell receptor without eliciting a biological response. In some embodiments, the antagonist is a chemical compound that is an antagonist for an adenosine receptor, such as the A2a, A2b, or A3 receptor. In some embodiments, the antagonist is a peptide, or a pepidomimetic, that binds the adenosine receptor but does not trigger a Gi protein dependent intracellular pathway. Exemplary antagonists are described in U.S. Pat. Nos. 5,565,566; 5,545, 627, 5,981,524; 5,861,405; 6,066, 642; 6,326,390; 5,670,501; 6,117,998; 6,232,297; 5,786, 360; 5,424,297; 6,313,131, 5,504,090; and 6,322,771.

In some embodiments, the agent is an A2 receptor (A2R) antagonist, such as an A2a antagonist. Exemplary A2R antagonists include KW6002 (istradefyline), SCH58261, caffeine, paraxanthine, 3,7-dimethyl-1-propargylxanthine (DMPX), 8-(m-chlorostyryl) caffeine (CSC), MSX-2, MSX-3, MSX-4, CGS-15943, ZM-241385, SCH-442416, preladenant, vipadenant (BII014), V2006, ST-1535, SYN-115, PSB-1115, ZM241365, FSPTP, and an inhibitory nucleic acid targeting A2R expression, e.g., siRNA or shRNA, or any antibodies or antigen-binding fragment thereof that targets an A2R. In some embodiments, the agent is an A2R antagonist described in, e.g., Ohta et al., Proc Natl Acad Sci USA (2006) 103:13132-13137; Jin et al., Cancer Res. (2010) 70(6):2245-2255; Leone et al., Computational and Structural Biotechnology Journal (2015) 13:265-272; Beavis et al., Proc Natl Acad Sci USA (2013) 110:14711-14716; and Pinna, A., Expert Opin Investig Drugs (2009) 18:1619-1631; Sitkovsky et al., Cancer Immunol Res (2014) 2(7):598-605; U.S. Pat. Nos. 8,080,554; 8,716,301; US 20140056922; WO2008/147482; U.S. Pat. No. 8,883,500; US 20140377240; WO02/055083; U.S. Pat. Nos. 7,141,575; 7,405,219; 8,883,500; 8,450,329 and 8,987,279).

In some embodiments, the antagonist is an antisense molecule, inhibitory nucleic acid molecule (e.g., small inhibitory RNA (siRNA)) or catalytic nucleic acid molecule (e.g. a ribozyme) that specifically binds mRNA encoding an adenosine receptor. In some embodiments, the antisense molecule, inhibitory nucleic acid molecule or catalytic nucleic acid molecule binds nucleic acids encoding A2a, A2b, or A3. In some embodiments, an antisense molecule, inhibitory nucleic acid molecule or catalytic nucleic acid targets biochemical pathways downstream of the adenosine receptor. For example, the antisense molecule or catalytic nucleic acid can inhibit an enzyme involved in the Gs protein- or Gi protein-dependent intracellular pathway. In some embodiments, the agent includes dominant negative mutant form of an adenosine receptor, such as A2a, A2b, or A3.

In some embodiments, the agent that inhibits extracellular adenosine includes agents that render extracellular adenosine non-functional (or decrease such function), such as a substance that modifies the structure of adenosine to inhibit the ability of adenosine to signal through adenosine receptors. In some embodiments, the agent is an extracellular adenosine-generating or adenosine-degrading enzyme, a modified form thereof or a modulator thereof. For example, in some embodiments, the agent is an enzyme (e.g. adenosine deaminase) or another catalytic molecule that selectively binds and destroys the adenosine, thereby abolishing or significantly decreasing the ability of endogenously formed adenosine to signal through adenosine receptors and terminate inflammation.

In some embodiments, the agent is an adenosine deaminase (ADA) or a modified form thereof, e.g., recombinant ADA and/or polyethylene glycol-modified ADA (ADA-PEG), which can inhibit local tissue accumulation of extracellular adenosine. ADA-PEG has been used in treatment of patients with ADA SCID (Hershfield (1995) Hum Mutat.

5:107). In some embodiments, an agent that inhibits extracellular adenosine includes agents that prevent or decrease formation of extracellular adenosine, and/or prevent or decrease the accumulation of extracellular adenosine, thereby abolishing, or substantially decreasing, the immunosuppressive effects of adenosine. In some embodiments, the agent specifically inhibits enzymes and proteins that are involved in regulation of synthesis and/or secretion of pro-inflammatory molecules, including modulators of nuclear transcription factors. Suppression of adenosine receptor expression or expression of the Gs protein- or Gi protein-dependent intracellular pathway, or the cAMP dependent intracellular pathway, can result in an increase/enhancement of immune response.

In some embodiments, the agent can target ectoenzymes that generate or produce extracellular adenosine. In some embodiments, the agent targets CD39 and CD73 ectoenzymes, which function in tandem to generate extracellular adenosine. CD39 (also called ectonucleoside triphosphate diphosphohydrolase) converts extracellular ATP (or ADP) to 5'AMP. Subsequently, CD73 (also called 5'nucleotidase) converts 5'AMP to adenosine. The activity of CD39 is reversible by the actions of NDP kinase and adenylate kinase, whereas the activity of CD73 is irreversible. CD39 and CD73 are expressed on tumor stromal cells, including endothelial cells and Tregs, and also on many cancer cells. For example, the expression of CD39 and CD73 on endothelial cells is increased under the hypoxic conditions of the tumor microenvironment. Tumor hypoxia can result from inadequate blood supply and disorganized tumor vasculature, impairing delivery of oxygen (Carroll and Ashcroft (2005), Expert. Rev. Mol. Med. 7(6):1-16). Hypoxia also inhibits adenylate kinase (AK), which converts adenosine to AMP, leading to very high extracellular adenosine concentration. Thus, adenosine is released at high concentrations in response to hypoxia, which is a condition that frequently occurs the tumor microenvironment (TME), in or around solid tumors. In some embodiments, the agent is one or more of anti-CD39 antibody or antigen binding fragment thereof, anti-CD73 antibody or antigen binding fragment thereof, e.g., MEDI9447 or TY/23, α-β-methylene-adenosine diphosphate (ADP), ARL 67156, POM-3, IPH52 (see, e.g., Allard et al. Clin Cancer Res (2013) 19(20):5626-5635; Hausler et al., Am J Transl Res (2014) 6(2):129-139; Zhang, B., Cancer Res. (2010) 70(16):6407-6411).

In some embodiments, the agent is an inhibitor of hypoxia inducible factor 1 alpha (HIF-1α) signaling. Exemplary inhibitors of HIF-1α include digoxin, acriflavine, sirtuin-7 and ganetespib.

In some embodiments, the agent includes a protein tyrosine phosphatase inhibitor, e.g., a protein tyrosine phosphatase inhibitor described herein. In some embodiments, the protein tyrosine phosphatase inhibitor is an SHP-1 inhibitor, e.g., an SHP-1 inhibitor described herein, such as, e.g., sodium stibogluconate. In some embodiments, the protein tyrosine phosphatase inhibitor is an SHP-2 inhibitor, e.g., an SHP-2 inhibitor described herein.

In some embodiments, the agent is a kinase inhibitor. Kinase inhibitors, such as a CDK4 kinase inhibitor, a BTK kinase inhibitor, a MNK kinase inhibitor, or a DGK kinase inhibitor, can regulate the constitutively active survival pathways that exist in tumor cells and/or modulate the function of immune cells. In some embodiments, the kinase inhibitor is a Bruton's tyrosine kinase (BTK) inhibitor, e.g., ibrutinib. In some embodiments, the kinase inhibitor is a phosphatidylinositol-4,5-bisphosphate 3-kinase (PI3K) inhibitor. In some embodiments, the kinase inhibitor is a CDK4 inhibitor, e.g., a CDK4/6 inhibitor. In some embodiments, the kinase inhibitor is an mTOR inhibitor, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor. In some embodiments, the kinase inhibitor is an MNK inhibitor, or a dual PI3K/mTOR inhibitor. In some embodiments, other exemplary kinase inhibitors include the AKT inhibitor perifosine, the mTOR inhibitor temsirolimus, the Src kinase inhibitors dasatinib and fostamatinib, the JAK2 inhibitors pacritinib and ruxolitinib, the PKCβ inhibitors enzastaurin and bryostatin, and the AAK inhibitor alisertib.

In some embodiments, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In some embodiments, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In some embodiments, the kinase inhibitor is a BTK inhibitor, e.g., ibrutinib (1-[(3R)-3-[4-Amino-3-(4-phenoxyphenyl)-1H-pyrazolo[3,4-d]pyrimidin-1-yl]piperidin-1-yl] prop-2-en-1-one; also known as PCI-32765). In some embodiments, the BTK inhibitor is a BTK inhibitor described in International Application WO 2015/079417.

In some embodiments, the kinase inhibitor is a PI3K inhibitor. PI3K is central to the PI3K/Akt/mTOR pathway involved in cell cycle regulation and lymphoma survival. Exemplary PI3K inhibitor includes idelalisib (PI3Kδ inhibitor). In some embodiments, the agent is idelalisib and rituximab.

In some embodiments, the agent is an inhibitor of mammalian target of rapamycin (mTOR). In some embodiments, the kinase inhibitor is an mTOR inhibitor selected from temsirolimus; ridaforolimus (also known as AP23573 and MK8669); everolimus (RAD001); rapamycin (AY22989); simapimod; AZD8055; PF04691502; SF1126; and XL765. In some embodiments, the agent is an inhibitor of mitogen-activated protein kinase (MAPK), such as vemurafenib, dabrafenib, and trametinib.

In some embodiments, the agent is an agent that regulates pro- or anti-apoptotic proteins. In some embodiments, the agent includes a B-cell lymphoma 2 (BCL-2) inhibitor (e.g., venetoclax, also called ABT-199 or GDC-0199; or ABT-737). Venetoclax is a small molecule (4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl) amino]phenyl}sulfonyl)-2-(1H-pyrrolo[2,3-b]pyridin-5-yloxy)benzamide) that inhibits the anti-apoptotic protein, BCL-2. Other agents that modulate pro- or anti-apoptotic protein include BCL-2 inhibitor ABT-737, navitoclax (ABT-263); Mcl-1 siRNA or Mcl-1 inhibitor retinoid N-(4-hydroxyphenyl) retinamide (4-HPR) for maximal efficacy. In some embodiments, the agent provides a pro-apoptotic stimuli, such as recombinant tumor necrosis factor-related apoptosis-inducing ligand (TRAIL), which can activate the apoptosis pathway by binding to TRAIL death receptors DR-4 and DR-5 on tumor cell surface, or TRAIL-R2 agonistic antibodies.

In some embodiments, the agent includes an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. Plasmacytoid dendritic cells (pDCs), macrophages, and dendritic cells (DCs) can express IDO. In some aspects, a decrease in L-tryptophan (e.g., catalyzed by IDO) results in an immunosuppressive milieu by inducing T-cell anergy and apoptosis. Thus, in some aspects, an IDO inhibitor can enhance the efficacy of the cell therapy, e.g., by decreasing the suppression or death of the administered CAR-expressing cell. Exemplary inhibitors of IDO include but are not limited to 1-methyl-tryptophan, indoximod, and INCB024360.

In some embodiments, the agent includes a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. In some embodiments, the agent includes a hypomethylating agent, e.g., a DNA methyltransferase inhibitor, e.g., azacitidine or decitabine.

In another embodiment, the agent is a transplantation, e.g., allogeneic stem cell transplant.

In some embodiments, the agent is a lymphodepleting therapy. In some embodiments, lymphodepletion is performed on a subject, e.g., prior to administering engineered cells, e.g., CAR-expressing cells. In some embodiments, the lymphodepletion comprises administering one or more of melphalan, Cytoxan, cyclophosphamide, and fludarabine. In some embodiments, a lymphodepleting chemotherapy is administered to the subject prior to, concurrently with, or after administration (e.g., infusion) of engineered cells, e.g., CAR-expressing cells. In an example, the lymphodepleting chemotherapy is administered to the subject prior to administration of engineered cells, e.g., CAR-expressing cells.

In some embodiments, the agent is an oncolytic virus. In some embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

Other exemplary combination therapy, treatment and/or agents include anti-allergenic agents, anti-emetics, analgesics and adjunct therapies. In some embodiments, the agent includes cytoprotective agents, such as neuroprotectants, free-radical scavengers, cardioprotectors, anthracycline extravasation neutralizers and nutrients.

In some embodiments, an antibody used as an agent is conjugated or otherwise bound to a therapeutic agent, e.g., a chemotherapeutic agent (e.g., Cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein. In some embodiments, the agent is an antibody-drug conjugate.

In some embodiments, the agent can modulate, inhibit or stimulate particular factors at the DNA, RNA or protein levels, to enhance or boost the efficacy of the cell therapy. In some embodiments, the agent can modulate the factors at the nucleic acid level, e.g., DNA or RNA, within the administered cells, e.g., cells engineered to express recombinant receptors, e.g., CAR. In some embodiments, an inhibitory nucleic acid, e.g., an inhibitory nucleic acid, e.g., a dsRNA, e.g., an siRNA or shRNA, or a clustered regularly interspaced short palindromic repeats (CRISPR), a transcription-activator like effector nuclease (TALEN), or a zinc finger endonuclease (ZFN), can be used to inhibit expression of an inhibitory molecule in the engineered cell, e.g., CAR-expressing cell. In some embodiments the inhibitor is an shRNA. In some embodiments, the inhibitory molecule is inhibited within the engineered cell, e.g., CAR-expressing cell. In some embodiments, a nucleic acid molecule that encodes a dsRNA molecule that inhibits expression of the molecule that modulates or regulates, e.g., inhibits, T-cell function is operably linked to a promoter, e.g., a HI- or a U6-derived promoter such that the dsRNA molecule that inhibits expression of the inhibitory molecule is expressed within the engineered cell, e.g., CAR-expressing cell. See, e.g., Brummelkamp T R, et al. (2002) Science 296: 550-553; Miyagishi M, et al. (2002) Nat. Biotechnol. 19: 497-500.

In some embodiments, the agent is capable of disrupting the gene encoding an inhibitory molecule, such as any immune checkpoint inhibitors described herein. In some embodiments, disruption is by deletion, e.g., deletion of an entire gene, exon, or region, and/or replacement with an exogenous sequence, and/or by mutation, e.g., frameshift or missense mutation, within the gene, typically within an exon of the gene. In some embodiments, the disruption results in a premature stop codon being incorporated into the gene, such that the inhibitory molecule is not expressed or is not expressed in a form that is capable of being expressed on the cells surface and/or capable of mediating cell signaling. The disruption is generally carried out at the DNA level. The disruption generally is permanent, irreversible, or not transient.

In some aspects, the disruption is carried out by gene editing, such as using a DNA binding protein or DNA-binding nucleic acid, which specifically binds to or hybridizes to the gene at a region targeted for disruption. In some aspects, the protein or nucleic acid is coupled to or complexed with a nuclease, such as in a chimeric or fusion protein. For example, in some embodiments, the disruption is effected using a fusion comprising a DNA-targeting protein and a nuclease, such as a Zinc Finger Nuclease (ZFN) or TAL-effector nuclease (TALEN), or an RNA-guided nuclease such as a clustered regularly interspersed short palindromic nucleic acid (CRISPR)-Cas system, such as CRISPR-Cas9 system, specific for the gene being disrupted. In some embodiments, methods of producing or generating genetically engineered cells, e.g., CAR-expressing cells, include introducing into a population of cells nucleic acid molecules encoding a genetically engineered antigen receptor (e.g. CAR) and nucleic acid molecules encoding an agent targeting an inhibitory molecule that is a gene editing nuclease, such as a fusion of a DNA-targeting protein and a nuclease such as a ZFN or a TALEN, or an RNA-guided nuclease such as of the CRISPR-Cas9 system, specific for an inhibitory molecule.

The dose of the agent can be any therapeutically effective amount, e.g., any dose amount described herein, and the appropriate dosage of the agent may depend on the type of disease to be treated, the type, dose and/or frequency of the engineered cell administered, the severity and course of the disease, whether the engineered cell is administered for preventive or therapeutic purposes, previous therapy, the patient's clinical history and response to the engineered cells, and the discretion of the attending physician. The engineered cell and/or agent can be administered to the patient at one time, repeated or administered over a series of treatments.

V. COMPOSITIONS AND FORMULATIONS

In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, and/or with the provided articles of manufacture or compositions, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject.

Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

VI. KITS AND ARTICLES OF MANUFACTURE

Also provided are articles of manufacture and kits containing engineered cells expressing a recombinant receptor or compositions thereof, and optionally instructions for use, for example, instructions for administering, according to the provided methods. In some embodiments, the instructions provide directions or specify methods for assessing if a subject is likely to response to a cell therapy, e.g. administration of engineered cells expressing a recombinant receptor. In some embodiments, the instructions provide directions or specify methods for assessing if a subject, prior to receiving a cell therapy, is likely or suspected of being likely to respond and/or the degree or level of response following administration of engineered cells expressing a recombinant receptor for treating a disease or disorder. In some aspects, the methods specify assessing a biological sample, e.g. tumor biopsy, from the subject for a frequency of or density of CD4+ immune cells, wherein the biological sample is obtained from a subject that is a candidate for receiving a cell therapy for treatment of a disease or condition.

In some embodiments, provided are articles of manufacture and/or kits that include a composition comprising a therapeutically effective amount of any of the engineered cells described herein, and instructions for administering, to a subject for treating a disease or condition. In some embodiments, the instructions can specify some or all of the elements of the methods provided herein. In some embodiments, the instructions specify particular instructions for administration of the cells for cell therapy, e.g., doses, timing, selection and/or identification of subjects for administration and conditions for administration. In some embodiments, the articles of manufacture and/or kits further comprise an agent for lymphodepleting therapy, and optionally further includes instructions for administering the lymphodepleting therapy. In some embodiments, the instructions can be included as a label or package insert accompanying the compositions for administration.

In some embodiments, provided are kits containing a cell therapy and reagents for detecting the ratio of CD8+ T cells to CD4+ T cells (CD8+:CD4+ ratio) in a sample obtained from a subject having previously received administration of a cell therapy, and instructions for carrying out some or all of the elements of the methods provided herein. In some embodiments, provided are kits containing a cell therapy and reagents for detecting the ratio of CD8+ T cells to CD4+ T cells (CD8+:CD4+ ratio) in a sample obtained from a subject having previously received administration of a cell therapy, and instructions for carrying out some or all of the elements of the methods provided herein. In some embodiments, provided are kits containing a cell therapy and reagents for detecting the frequency of CD8+ T cells, or recombinant receptor-expressing CD8+ (receptor+/CD8+) T cells in one or more sample(s) obtained from a subject having previously received administration of a cell therapy, and instructions for carrying out some or all of the elements of the methods provided herein.

In some embodiments, the instructions specify the criteria for selection or identification of subjects for therapy. In some embodiments, such criteria include subjects having NHL or sub-type thereof and/or a high-risk NHL. In some embodiments, the instructions specify that the subjects to be treated include subjects having a disease or condition characterized or determined to be aggressive NHL, diffuse large B cell lymphoma (DLBCL), primary mediastinal large B cell lymphoma (PMBCL), T cell/histiocyte-rich large B cell lymphoma (TCHRBCL), Burkitt's lymphoma, mantle cell lymphoma (MCL), and/or follicular lymphoma (FL). In particular embodiments, the subject to be treated include subjects with aggressive NHL, in particular, with diffuse large B-cell lymphoma (DLBCL), not otherwise specified (NOS) and in some aspects including de novo and transformed from indolent). In some aspects, the subject or population to be treated may include and/or further include subjects with primary mediastinal B-cell lymphoma (PMBCL) or follicular lymphoma grade 3B (FL3B). In some embodiments, the subject or population to be treated include those subjects having poor performance status. In some aspects, the population to be treated includes, e.g., subjects having an Eastern Cooperative Oncology Group Performance Status (ECOG) that is anywhere from 0-2. In other aspects of any of the embodiments, the subjects to be treated include ECOG 0-1 or do not include ECOG2 subjects. In some embodiments, of any of the embodiments, the subjects to be treated have failed two or more prior therapies. In some embodiments, the subject does not have DLBCL transformed from marginal zone lymphoma (MZL) and chronic lymphocytic leukemia (CLL; Richter's) and/or has a DLBCL characterized as de novo or transformed from an indolent disease. In some embodiments, the subject has mantle cell lymphoma (MCL). In some embodiments, the instructions specify the administration of the cell therapy is for a subject that is or has been identified as having a double/triple hit lymphoma, has been identified as having a chemorefractory lymphoma, (e.g., chemorefractory DLBCL) and/or that has not achieved complete remission (CR) in response to a prior therapy.

In some embodiments, the instructions specify the dose of cells to be administered. For example, in some embodiments, the dose specified in the instructions include a total recombinant receptor (e.g., CAR)-expressing cells between about $1\times10^6$ and $3\times10^8$, e.g., in the range of about $1\times10^7$ to $2\times10^8$ such cells, such as $1\times10^7$, $5\times10^7$, $1\times10^8$ or $1.5\times10^8$ total such cells, or the range between any two of the foregoing values. In some embodiments, the patient is administered multiple doses, and each of the doses or the total dose can be within any of the foregoing values.

In some embodiments, the article of manufacture or kit comprises a container, optionally a vial comprising a plurality of CD4+ T cells expressing a recombinant receptor, and a container, optionally a vial comprising a plurality of CD8+ T cells expressing a recombinant receptor. In some embodiments, the article of manufacture or kit comprises a container, optionally a vial comprising a plurality of CD4+ T cells expressing a recombinant receptor, and further comprises, in the same container, a plurality of CD8+ T cells expressing a recombinant receptor. In some embodiments, a cryoprotectant is included with the cells. In some aspects the container is a bag.

In some embodiments, the container such as the vial comprises greater than or greater than about $10\times10^6$ T cells or recombinant receptor-expressing T cells, greater than or greater than about $15\times10^6$ T cells or recombinant receptor-expressing T cells, greater than or greater than about $25\times10^6$ T cells or recombinant receptor-expressing T cell. In some aspects, the vial comprises between about 10 million cells per ml and about 70 million cells per ml, between about 10 million cells per ml and about 50 million cells per ml, between about 10 million cells per ml and about 25 million cells per ml, between about 10 million cells per ml and about 15 million cells per ml, 15 million cells per ml and about 70 million cells per ml, between about 15 million cells per ml and about 50 million cells per ml, between about 15 million cells per ml and about 25 million cells per ml, between about 25 million cells per ml and about 70 million cells per ml, between about 25 million cells per ml and about 50 million cells per ml, and between about 50 million cells per ml and about 70 million cells per ml.

In some embodiments, the plurality of vials or plurality of cells or unit dose of cells specified for administration, collectively, comprises a dose of cells comprising from or from about $1\times10^5$ to $5\times10^8$ total recombinant receptor-expressing T cells or total T cells, $1\times10^5$ to $1\times10^8$ total recombinant receptor-expressing T cells or total T cells, from or from about $5\times10^5$ to $1\times10^7$ total recombinant receptor-expressing T cells or total T cells, or from or from about $1\times10^6$ to $1\times10^7$ total recombinant receptor-expressing T cells or total T cells, each inclusive. In some aspects, the article comprises one or more unit dose of the CD4+ and CD8+ cells or of the CD4+receptor+ cells and CD8+receptor+ cells, wherein the unit dose comprises between at or about $1\times10^7$ and at or about $2\times10^8$ recombinant receptor-expressing T cells, between at or about $5\times10^7$ and at or about $1.5\times10^8$ recombinant receptor-expressing T cells, at or about $5\times10^7$ recombinant receptor-expressing T cells, at or about $1\times10^8$ recombinant receptor-expressing T cells, or at or about $1.5\times10^8$ recombinant receptor-expressing T cells, optionally wherein the information in the article specifies administration of one or of a plurality of unit doses and/or a volume corresponding to such one or plurality of unit doses. In some cases, the article comprises one or more unit doses of the CD8+ cells, wherein the dose comprises between at or about $5\times10^6$ and at or about $1\times10^8$ recombinant receptor-expressing CD8+ T cells, the dose comprises between at or about $1\times10^7$ and at or about $0.75\times10^8$ recombinant receptor-expressing CD8+ T cells, the dose comprises at or about $2.5\times10^7$ recombinant receptor-expressing CD8+ T cells, or the dose comprises at or about $5\times10^7$ recombinant receptor-expressing CD8+ T cells, or the dose comprises at or about $0.75\times10^8$ recombinant receptor-expressing CD8+ T cells, optionally wherein the information in the article specifies administration of one or of a plurality of unit doses and/or a volume corresponding to such one or plurality of unit doses. In some embodiments, the cells in the article, collectively, comprise a dose of cells comprising no more than $1\times10^8$ total recombinant receptor-expressing T cells or total T cells, no more than $1\times10^7$ total recombinant receptor-expressing T cells or total T cells, no more than $0.5\times10^7$ total recombinant receptor-expressing T cells or total T cells, no more than $1\times10^6$ total recombinant receptor-expressing T cells or total T cells, no more than $0.5\times10^6$ total recombinant receptor-expressing T cells or total T cells.

In some embodiments, the instructions can specify dosage regimen and timing of the administration. For example, in some embodiments, the instructions can specify administering to the subject multiple doses, e.g., two or more doses, of the cells. In some embodiments, the instructions specify the timing of the multiple doses, e.g., the second dose being administered approximately 4, 5, 6, 7, 8, 9, 10, 11, 12, 13, 14, 15, 16, 17, 18, 19, 20 or 21 days after the first dose; and/or the dosage amount in each dose.

In some embodiments, the article of manufacture or kit comprises a plurality of CD4+ T cells expressing a recombinant receptor, and instructions for administering, to a subject having a disease or condition, all or a portion of the plurality of CD4+ T cells and further administering CD8+ T cells expressing a recombinant receptor. In some embodiments, the instructions specify administering the CD4+ T cells prior to administering the CD8+ cells. In some cases, the instructions specify administering the CD8+ T cells prior to administering the CD4+ cells. In some embodiments, the article of manufacture or kit comprises a plurality of CD8+ T cells expressing a recombinant receptor, and instructions for administering, to a subject having a disease or condition, all or a portion of the plurality of CD8+ T cells and CD4+ T cells expressing a recombinant receptor. In some embodiments, the instructions specify dosage regimen and timing of the administration of the cells.

In some aspects, the instructions specify administering all or a portion of the CD4+ T cells and the all or a portion of the CD8+ T cells 0 to 12 hours apart, 0 to 6 hours apart or 0 to 2 hours apart. In some cases, the instructions specify administering the CD4+ T cells and the CD8+ T cells no more than 2 hours, no more than 1 hour, no more than 30 minutes, no more than 15 minutes, no more than 10 minutes or no more than 5 minutes apart.

In some embodiments, the instructions specify the dose or number of cells or cell type(s) and/or a ratio of cell types, e.g., individual populations or sub-types, such as the CD4+ to CD8+ ratio. In some embodiments, the populations or sub-types of cells, such as CD8+ and CD4+ T cells. For example, in some embodiments, the instructions specify that the cells are administered at or within a tolerated range of an output ratio of multiple cell populations or sub-types, such as CD4+ and CD8+ cells or sub-types, of between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, the articles of manufacture and/or kits further include one or more additional agents for therapy, e.g., lymphodepleting therapy and/or combination therapy, as described herein, and optionally instructions for administering the additional agents. In some examples, the articles of manufacture may further contain one or more therapeutic agents. In some embodiments, the therapeutic agent is an immunomodulatory agent, a cytotoxic agent, an anti-cancer agent or a radiotherapeutic.

Provided herein are articles of manufacture and containing a reagent capable of detecting or that is specific for a biomarker in a sample obtained from the subject and methods for using the articles of manufacture. In some embodiments, the sample from the subject is a tumor biopsy sample. In some embodiments, instructions are also provided for using the reagent to assay a biological sample from a subject that is a candidate for treatment, optionally with a cell therapy, said cell therapy optionally including a dose or composition of genetically engineered cells expressing a recombinant receptor. In some embodiments of the method to assess likelihood of a subject responding to a cell therapy, the level or presence of a CAR+ T cell marker, CD4, CD8, CD19, CD20, CD73, FOXP3, CD163, IDO, or PD-L1 is detected and assessed. In some cases, the frequency of cells expressing one or more of a CAR+ T cell marker, CD4, CD8, CD19, CD20, CD73, FOXP3, CD163, IDO, or PD-L1 is detected or assessed. Also provided are methods of detecting and assessing one or more biomarkers in a sample obtained from a subject for assessing likelihood that a subject will achieve a response when treated with the cell therapy.

In some embodiments, using the articles of manufacture include detecting an inflammatory marker indicative of tumor burden. In some cases, the assaying or assessing of an inflammatory marker is using flow cytometry. In some cases, the reagent is a soluble protein that binds the biomarker. In some example, the reagent is a protein that binds a CAR+ T cell marker, CD4, CD8, CD19, CD20, CD73, FOXP3, CD163, IDO, or PD-L1. In some embodiments, the reagent is an antibody or an antigen-binding fragment thereof. In some embodiments, the reagent is an antibody or antigen-binding fragment thereof that specifically binds to a CAR+ T cell marker, CD4, CD8, CD19, CD20, CD73, FOXP3, CD163, IDO, or PD-L1. In some embodiments, the reagent is an antibody or antigen-binding fragment thereof conjugated to a detectable moiety or label and/or an antibody or antigen-binding fragment thereof that can bind a detectable moiety or label.

In some embodiments, the articles of manufacture and/or kits further include one or more reagents for assaying biological samples, e.g., biological samples from subjects who are candidates for administration or who have been administered the therapy, and optionally instructions for use of the reagents or assays. In some aspects, the biological sample is a tumor biopsy sample. In some embodiments, the reagents can be used prior to the administration of the cell therapy or after the administration of cell therapy, for diagnostic purposes, to identify subjects and/or to assess treatment outcomes and response to the therapy. In some embodiments, the reagents can be used prior to the administration of the cell therapy, to identify subjects and/or to assess likelihood of response to the therapy. In some embodiments, the reagents can be used after to the administration of the cell therapy, to monitor the subject and/or to assess treatment outcomes and response to the therapy. For example, in some embodiments, the article of manufacture and/or kits further contain reagents for measuring the level of particular biomarkers, e.g., immune cell biomarkers, that are associated with response, and instructions for measuring. In some embodiments, the reagents include components for performing an in vitro assay to measure the inflammatory markers, such as an immunoassay, an immunofluorescence assay, an aptamer-based assay, a histological or cytological assay, or an mRNA expression level assay. In some embodiments, the in vitro assay is selected from among an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay and avidity assay. In some embodiments, the assay is an immunoassay, in situ hybridization, immunohistochemistry, multiplexed immunohistochemistry, or 5-plex immunofluorescent immunohistochemistry. In some aspects, the reagent is a binding reagent that specifically binds the biomarker, e.g., immune cell biomarker. In some cases, the binding reagent is an antibody or antigen-binding fragment thereof, an aptamer or a nucleic acid probe.

In some embodiments, the articles of manufacture and/or kits comprise one or more reagent capable of detecting one or more biomarkers, e.g., immune cell biomarkers, and instructions for using the reagent to assess a biological sample from a subject that is a candidate for treatment. In some embodiments, the biomarker is a marker of immunosuppression pathway. In some embodiments, the biomarker is a CAR+ T cell marker, CD4, CD8, CD19, CD20, CD73, FOXP3, CD163, IDO, or PD-L1. In some particular embodiments, the biomarker is an immune cell biomarker such as CD4 or CD8. In some embodiments, instructions for assaying presence or absence, level, amount of a biomarker or frequency of cells positive for the biomarker or any parameters associated with one or more biomarkers is included. In some embodiments, the articles of manufacture and/or kits comprise instructions for detecting the biomarker and/or assessing the frequency of cells expressing the biomarker, e.g., immune cell biomarker and/or determining parameters associated with the biomarkers. In some cases, the instructions specify that assessment of the biomarkers or parameters associated the biomarkers is compared to a threshold value. In some embodiments, the instructions are included which specify, if the frequency of the biomarker in the sample prior to administration of the therapy is at or above a threshold value for the biomarker, e.g., immune cell biomarker, the cell therapy is administered at a non-reduced dose, or the cell therapy is not administered with an agent or treatment capable of stimulating, amplifying, potentiating, and/or enhancing an anti-tumor immune response.

In some cases, the instructions specify that if the frequency of biomarker, e.g., immune cell biomarker, in the sample is below a threshold level prior to the administration of the therapy for the biomarker, e.g., immune cell biomarker, the cell therapy is administered with an agent or other treatment capable of stimulating, amplifying, potentiating, and/or enhancing an anti-tumor immune response and the agent or treatment is administered prior to, within one, two, or three days of, or concurrently with the initiation of administration of the cell therapy to the subject. In some cases, the instructions specify that if the frequency of biomarker, e.g., immune cell biomarker, in the sample is below a threshold level for the biomarker, e.g., immune cell biomarker, the cell therapy is administered at an increased dose. In some cases, the instructions specify that if the frequency of biomarker, e.g., immune cell biomarker, in the sample is below a threshold level for the biomarker, e.g., immune cell biomarker, an alternative therapeutic treatment other than the cell therapy is administered.

In some embodiments, the articles of manufacture and/or kits comprise one or more reagents capable of detecting one or more biomarkers, e.g., immune cell biomarkers, and instructions for performing any of the methods provided herein, e.g., any of the assessment steps described herein. In some embodiments, the articles of manufacture and/or kits comprise instructions for selecting subjects for treatment, such as any described herein. In some embodiments, the articles of manufacture and/or kits also include a composition for cell therapy, e.g., containing engineered cells expressing recombinant receptors. In some embodiments, the articles of manufacture and/or kits also include agents, e.g., agents for stimulating, amplifying, potentiating, and/or enhancing an anti-tumor immune response, e.g., of the cell therapy, such as any agents described herein.

The articles of manufacture and/or kits may further include a cell therapy and/or further include instructions for use with, prior to and/or in connection with treatment with the cell therapy.

The articles of manufacture or kits include one or more containers, typically a plurality of containers, packaging material, and a label or package insert on or associated with the container or containers and/or packaging, generally including instructions for administration of the cells to a subject. The articles of manufacture and/or kits may include a container and a label or package insert on or associated with the container.

In some embodiments, the containers contain the cells to be administered, e.g., one or more unit doses thereof. The article of manufacture typically includes a plurality of containers, each containing a single unit dose of the cells. The unit dose may be an amount or number of the cells to be administered to the subject in the first dose or twice the number (or more) the cells to be administered in the first or any one or more consecutive dose(s). It may be the lowest dose or lowest possible dose of the cells that would be administered to the subject in connection with the administration method. In some embodiments, the unit dose is the minimum number of cells or number of cells or the minimum number of reference units or the target reference units or reference units within a target range that would be administered in a single dose to any subject having a particular disease or condition or any subject, according to the methods herein.

Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition. The article of manufacture may include (a) a first container with a composition contained therein, wherein the composition includes engineered cells expressing a recombinant receptor; and (b) a second container with a composition contained therein, wherein the composition includes the second agent. In some embodiments, the article of manufacture may include (a) a first container with a first composition contained therein, wherein the composition includes a subtype of engineered cells expressing a recombinant receptor; and (b) a second container with a composition contained therein, wherein the composition includes a different subtype of engineered cells expressing a recombinant receptor. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

In particular embodiments, the containers are bags, e.g., flexible bags, such as those suitable for infusion of cells to subjects, e.g., flexible plastic or PVC bags, and/or IV solution bags. The bags in some embodiments are sealable and/or able to be sterilized, so as to provide sterile solution and delivery of the cells and compositions. In some embodiments, the containers, e.g., bags, have a capacity of at or about or at least at or about 10, 20, 30, 40, 50, 60, 70, 80, 90, 100, 200, 300, 400, 500, or 1000 mL capacity, such as between at or about 10 and at or about 100 or between at or about 10 and at or about 500 mL capacity, each inclusive. In some embodiments, the containers, e.g., bags, are and/or are made from material which is stable and/or provide stable storage and/or maintenance of cells at one or more of various temperatures, such as in cold temperatures, e.g. below at or about or at or about $-20°$ C., $-80°$ C., $-120°$ C., $135°$ C. and/or temperatures suitable for cryopreservation, and/or other temperatures, such as temperatures suitable for thawing the cells and body temperature such as at or about $37°$ C., for example, to permit thawing, e.g., at the subject's location or location of treatment, e.g., at bedside, immediately prior to treatment.

The containers may be formed from a variety of materials such as glass or plastic. In some embodiments, the container has one or more port, e.g., sterile access ports, for example, for connection of tubing or cannulation to one or more tubes, e.g., for intravenous or other infusion and/or for connection for purposes of transfer to and from other containers, such as cell culture and/or storage bags or other containers. Exemplary containers include infusion bags, intravenous solution bags, vials, including those with stoppers pierceable by a needle for injection.

The article of manufacture may further include a package insert or label with one or more pieces of identifying information and/or instructions for use. In some embodiments, the information or instructions indicates that the contents can or should be used to treat a particular condition or disease, and/or providing instructions therefor. The label or package insert may indicate that the contents of the article of manufacture are to be used for treating the disease or condition. In some embodiments, the label or package insert provides instructions to treat a subject, e.g., the subject from which the cells have been derived, via a method involving the administration of a first and one or more consecutive doses of the cells, e.g., according to any of the embodiments of the provided methods. In some embodiments, the instructions specify administration, in a first dose, of one unit dose, e.g., the contents of a single individual container in the article of manufacture, followed by one or more consecutive doses at a specified time point or within a specified time window and/or after the detection of the presence or absence or amount or degree of one or more factors or outcomes in the subject.

In some embodiments, the instructions specify administering one or more of the unit doses to the subject.

In some embodiments, the label or package insert or packaging comprises an identifier to indicate the specific identity of the subject from which the cells are derived and/or are to be administered. In the case of autologous transfer, the identity of the subject from which the cells are derived is the same as the identity of the subject to which the cells are to be administered. Thus, the identifying information may specify that the cells are to be administered to a particular patient, such as the one from which the cells were originally derived. Such information may be present in the packaging material and/or label in the form of a bar code or other coded identifier, or may indication the name and/or other identifying characteristics of the subject.

The article of manufacture in some embodiments includes one or more, typically a plurality, of containers containing compositions comprising the cells, e.g., individual unit dose forms thereof, and further include one or more additional containers with a composition contained therein which includes a further agent, such as a cytotoxic or otherwise therapeutic agent, for example, which is to be administered in combination, e.g., simultaneously or sequentially in any order, with the cells. Alternatively, or additionally, the article of manufacture may further include another or the same container comprising a pharmaceutically-acceptable buffer. It may further include other materials such as other buffers, diluents, filters, tubing, needles, and/or syringes.

The term "package insert" is used to refer to instructions customarily included in commercial packages of therapeutic products, that contain information about the indications, usage, dosage, administration, combination therapy, contraindications and/or warnings concerning the use of such therapeutic products.

VII. DEFINITIONS

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, a "subject" is a mammal, such as a human or other animal, and typically is human. In some embodiments, the subject, e.g., patient, to whom the agent or agents, cells, cell populations, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. In some embodiments, sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, a composition refers to any mixture of two or more products, substances, or compounds, including cells. It may be a solution, a suspension, liquid, powder, a paste, aqueous, non-aqueous or any combination thereof.

As used herein, "enriching" when referring to one or more particular cell type or cell population, refers to increasing the number or percentage of the cell type or population, e.g., compared to the total number of cells in or volume of the composition, or relative to other cell types, such as by positive selection based on markers expressed by the population or cell, or by negative selection based on a marker not present on the cell population or cell to be depleted. The term does not require complete removal of other cells, cell type, or populations from the composition and does not require that the cells so enriched be present at or even near 100% in the enriched composition.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control or fluorescence minus one (FMO) gating control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control or fluorescence minus one (FMO) gating control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Unless defined otherwise, all terms of art, notations and other technical and scientific terms or terminology used herein are intended to have the same meaning as is commonly understood to which the claimed subject matter pertains. In some cases, terms with commonly understood meanings are defined herein for clarity and/or for ready reference, and the inclusion of such definitions herein should not necessarily be construed to represent a substantial difference over what is generally understood.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

VIII. EXEMPLARY EMBODIMENTS

Among the provided embodiments are:
1. A method of assessing likelihood of a response following administration of a cell therapy, the method comprising:
   (1) assessing a biological sample for a frequency of CD4+ immune cells, wherein the biological sample is obtained from a subject that is a candidate for receiving a cell therapy for treatment of a disease or condition prior to receiving a cell therapy; and
   (2) comparing the frequency to a threshold value, thereby determining a likelihood that a subject will achieve a response when treated with the cell therapy.
2. A method of selecting a subject for treatment, the method comprising:
   (a) assessing a biological sample for a frequency of CD4+ immune cells, wherein:
   the biological sample is from a subject that is a candidate for treatment with a cell therapy, said cell therapy optionally comprising a dose or composition of genetically engineered cells expressing a recombinant receptor; and
   the biological sample is obtained from the subject prior to administering the cell therapy; and (b) selecting a subject in which the frequency of CD4+ immune cells in the sample is at or above a threshold value, thereby identifying a subject that likely to achieve a response when treated with the cell therapy.

3. The method of embodiment 2, wherein the assessing is performed by contacting a biological sample with one or more reagent capable of detecting CD4+ immune cells.

4. The method of any of embodiments 1-3, wherein the biological sample is a tumor sample, optionally a tumor biopsy sample.

5. The method of any of embodiments 1-4, wherein the immune cells are or comprise myeloid cells, T helper cells, monocytes, macrophages, or dendritic cells.

6. The method of any of embodiments 1-5, wherein the immune cells are or comprise T cells.

7. The method of any of embodiments 1-6, wherein the CD4+ immune cells are detected using immunoassay, in situ hybridization, immunohistochemistry, multiplexed immunohistochemistry, or 5-plex immunofluorescent immunohistochemistry.

8. The method of any of embodiments 1-7, wherein the response is a complete response (CR) or partial response (PR).

9. The method of any of embodiments 1-8, wherein the response is durable.

10. The method of any of embodiments 1-9, wherein the response is durable for greater than 3 months, 4 months, 5 months, or 6 months.

11. The method of any of embodiments 1-10, wherein the subject is a human.

12. The method of any of embodiments 1-11, wherein the cell therapy comprises cells engineered to express a recombinant receptor.

13. A method of assessing likelihood of a response following administration of a cell therapy, the method comprising:
(1) assessing a biological sample that is a tumor biopsy sample for a frequency of CD4+ immune cells, wherein the biological sample is obtained from a subject that is a candidate for receiving a cell therapy for treatment of a cancer prior to receiving a cell therapy, and the CD4+ immune cells are detected using immunohistochemistry; and
(2) comparing the frequency to a threshold value, thereby determining a likelihood that a subject will achieve a response that is a complete response (CR) or a partial response (PR), optionally the response that is durable for greater than 3 months, 4 months, 5 months, or 6 months, when treated with the cell therapy.

14. A method of selecting a subject for treatment, the method comprising:
(a) assessing a biological sample that is a tumor biopsy sample for a frequency of CD4+ immune cells, wherein:
the biological sample is from a subject that is a candidate for treatment with a cell therapy, said cell therapy optionally comprising a dose or composition of genetically engineered cells expressing a recombinant receptor;
the biological sample is obtained from the subject prior to administering the cell therapy; and
the CD4+ immune cells are detected using immunohistochemistry; and
(b) selecting a subject in which the frequency of CD4+ immune cells in the sample is at or above a threshold value, thereby identifying a subject that likely to achieve a response that is a complete response (CR) or a partial response (PR), optionally the response is durable for greater than 3 months, 4 months, 5 months, or 6 months, when treated with the cell therapy.

15. The method of any of embodiments 1-14, wherein:
the subject is likely to achieve a response when treated with the cell therapy if the frequency of CD4+ cells is at or above the threshold value; or
the subject is not likely to achieve a response when treated with the cell therapy if the frequency of CD4+ cells is below the threshold value.

16. The method of any of embodiments 1-15, wherein the threshold level is within 25%, within 20%, within 15%, within 10% or within 5% and/or is within one or two standard deviation(s) below the median or mean frequency of CD4+ immune cells in samples obtained from a group of subjects after the initiation of administration of the cell therapy, wherein each of the subjects of the group went on to achieve a response after administration of the cell therapy.

17. The method of any of embodiments 1-16, wherein the threshold value of CD4+ immune cells is determined based on a median frequency of CD4+ immune cells observed from a group of subjects that achieved a response after administration of the cell therapy.

18. The method of embodiment 16 or embodiment 17, wherein the response achieved by the group of subjects is CR or PR.

19. The method of any of embodiments 16-18, wherein the response achieved by the group of subjects is durable at 3 months.

20. The method of any of embodiments 1-19, wherein the threshold level is within 25%, within 20%, within 15%, within 10% or within 5% and/or is within a standard deviation above the median or mean frequency of CD4+ immune cells in samples obtained from a group of subjects after the initiation of administration of the cell therapy, wherein each of the subjects of the group went on to exhibit stable disease (SD) and/or progressive disease (PD).

21. The method of any of embodiments 1-20, wherein the threshold value of CD4+ immune cells is or is greater than about 4%, 5%, 6%, 7%, or 8% CD4+ immune cells of the total cells in the biological sample.

22. The method of any of embodiments 1-21, wherein the frequency is based on or is a density of the CD4+ immune cells.

23. The method of any of embodiments 1-22, wherein the frequency is based on or is a density of the cells measured as CD4+ immune cells/mm$^2$.

24. The method of any of embodiments 1-23, wherein if subject is indicated as likely to achieve a response, selecting the subject for administration of a therapeutic regimen, the therapeutic regimen comprising administering to the subject:
i. the cell therapy, optionally at a non-reduced dose; or
ii. the cell therapy, wherein administration of the cell therapy does not comprise administering, prior to or concurrently with administering the cell therapy, an agent or treatment capable of stimulating, amplifying, potentiating, and/or enhancing an anti-tumor immune response, wherein administration of the agent is to be administered (i) prior to, (ii) within one, two, or three days of, and/or (iii) concurrently with the initiation of administration of the cell therapy to the subject.

25. The method of any of embodiment 1-23, wherein if the subject is indicated as not likely to achieve a response, selecting the subject for administration of a therapeutic regimen, the therapeutic regimen comprising administering to the subject:
i. an agent or other treatment capable of stimulating, amplifying, potentiating, and/or enhancing an anti-tumor immune response and the cell therapy, wherein administration of the agent is to be administered (i) prior to, (ii) within one, two, or three days of, and/or (iii) concurrently with the initiation of administration of the cell therapy to the subject;

ii. the cell therapy at an increased dose and/or administering an additional dose of the cell therapy; or iii. an alternative therapeutic treatment other than the cell therapy.

26. The method of embodiment 24 or embodiment 25, wherein the agent or other treatment is or comprises an immune-inhibitory molecule, is or comprises an immune checkpoint molecule or member of an immune checkpoint pathway and/or is or comprises a modulator of an immune checkpoint molecule or pathway.

27. The method of embodiment 26, wherein the immune checkpoint molecule or pathway is or comprises PD-1, PD-L1, PD-L2, CTLA-4, LAG-3, TIM3, VISTA, an adenosine receptor, CD73, CD39, adenosine 2A Receptor (A2AR), or adenosine or a pathway involving any of the foregoing.

28. The method of any of embodiments 24-26, wherein the agent is BY55, MSB0010718C, ipilimumab, Daclizumab, Bevacizumab, Basiliximab, Ipilimumab, Nivolumab, pembrolizumab, MPDL3280A, Pidilizumab, MK-3475, BMS-936559, Atezolizumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MOXR0916, AMP-224, Avelumab, MEDI4736, PDR001, rHIgM12B7, Ulocuplumab, BKT140, Varlilumab, ARGX-110, MGA271, lirilumab, IPH2201, ARGX-115, Emactuzumab, CC-90002 and MNRP1685A or an antibody-binding fragment thereof.

29. The method of any of embodiments 24-26, wherein the agent is an anti-PD-L1 antibody.

30. The method of embodiment 29, wherein the anti-PD-L1 antibody is MEDI14736, MDPL3280A, BMS-936559, LY3300054, atezolizumab or avelumab or is an antigen-binding fragment thereof.

31. The method of any of embodiments 24-26, wherein the agent is thalidomide or is a derivative or analogue of thalidomide.

32. The method of any of embodiments 24-26 and 31, wherein the agent is lenalidomide or omalidomide, avadomide, a stereoisomer of lenalidomide, pomalidomide, avadomide or a pharmaceutically acceptable salt, solvate, hydrate, co-crystal, clathrate, or polymorph thereof.

33. The method of any of embodiments 24-26, 31 and 32, wherein the agent is lenalidomide, a stereoisomer of lenalidomide or a pharmaceutically acceptable salt, solvate, hydrate, co-crystal, clathrate, or polymorph thereof.

34. The method of any of embodiments 24-26, wherein the agent is a tryptophan metabolism and/or kynurenine pathway modulator.

35. The method of embodiment 34, wherein the tryptophan metabolism and/or kynurenine pathway modulator, is an inhibitor of one or more enzymes selected from the group consisting of indoleamine-pyrrole 2,3-dioxygenase 1 (IDO1), IDO2, tryptophan 2,3-dioxygenase (TDO) and kynureninase.

36. The method of embodiment 34 or embodiment 35, wherein the tryptophan metabolism and/or kynurenine pathway modulator is an inhibitor of indoleamine-pyrrole 2,3-dioxygenase 1 (IDO1).

37. The method of any of embodiments 34-36, wherein the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F00187, PF-06840003 or pharmaceutically acceptable salt or prodrug thereof or a method thereof.

38. The method of any of embodiments 24-37, wherein the agent is delivered directly into the tumor.

39. The method of any of embodiments 24-38, further comprising administering the therapeutic regimen to the selected subject.

40. A method of treatment, the method comprising administering a therapeutic regimen to a subject that is a candidate for receiving a cell therapy for treatment of a disease or condition, wherein the administration is carried out following or based on the results of assessing a biological sample from the subject for frequency of CD4+ immune cells to determine a likelihood that a subject will achieve a response when treated with the cell therapy.

41. The method of embodiment 40, wherein the biological sample is a tumor sample, optionally a tumor biopsy sample.

42. The method of embodiment 40 or embodiment 41, wherein the immune cells are or comprise myeloid cells, T helper cells, monocytes, macrophages, or dendritic cells.

43. The method of any of embodiments 40-42, wherein the immune cells are or comprise T cells.

44. The method of any of embodiments 40-43, wherein the CD4+ immune cells are detected using immunoassay, in situ hybridization, immunohistochemistry, multiplexed immunohistochemistry, or 5-plex immunofluorescent immunohistochemistry.

45. The method of any of embodiments 40-44, wherein the response is a complete response (CR) or partial response (PR).

46. The method of any of embodiments 40-45, wherein the response is durable.

47. The method of any of embodiments 40-46, wherein the response is durable for greater than 3 months, 4 months, 5 months, or 6 months.

48. The method of any of embodiments 40-47, wherein the subject is a human.

49. The method of any of embodiments 40-48, wherein the cell therapy comprises cells engineered to express a recombinant receptor.

50. The method of any of embodiments 40-49, wherein the assessing of the frequency of CD4+ cells comprises a comparison to a threshold value, wherein the comparison indicates the likelihood that a subject will achieve a response when treated with the cell therapy.

51. A method of treatment, the method comprising administering a therapeutic regimen to a subject that is a candidate for receiving a cell therapy for treatment of a cancer, wherein the administration is carried out following or based on the results of assessing a biological sample that is a tumor biopsy sample from the subject for frequency of CD4+ immune cells to determine a likelihood that a subject will achieve a response that is a complete response (CR) or a partial response (PR), optionally the response that is durable for greater than 3 months, 4 months, 5 months, or 6 months, when treated with the cell therapy, wherein the CD4+ immune cells are detected using immunohistochemistry.

52. The method of embodiment 50 or embodiment 51, wherein:

the subject is likely to achieve a response when treated with the cell therapy if the frequency of CD4+ cells is at or above the threshold value; or the subject is not likely to achieve a response when treated with the cell therapy if the frequency of CD4+ cells is below the threshold value.

53. The method of any of embodiments 50-52, wherein the threshold level is within 25%, within 20%, within 15%, within 10% or within 5% and/or is within one or two standard deviation(s) below the median or mean value of CD4+ immune cells in samples obtained from a group of subjects after the initiation of administration of the cell therapy, wherein each of the subjects of the group went on to achieve a response after administration of the cell therapy.

54. The method of any of embodiments 50-53, wherein the threshold value of CD4+ immune cells is determined based on a median frequency of CD4+ immune cells observed from a group of subjects that achieved a response after administration of the cell therapy.

55. The method of any of embodiments 50-54, wherein the response achieved by the group of subjects is CR or PR.

56. The method of any of embodiments 50-55, wherein the response achieved by the group of subjects is durable at 3 months.

57. The method of any of embodiments 50-52, wherein the threshold level is within 25%, within 20%, within 15%, within 10% or within 5% and/or is within a standard deviation above the median or mean frequency of CD4+ immune cells in samples obtained from a group of subjects after the initiation of administration of the cell therapy, wherein each of the subjects of the group went on to exhibit stable disease (SD) and/or progressive disease (PD).

58. The method of any of embodiments 50-57, wherein the threshold value of CD4+ immune cells is or is greater than about 4%, 5%, 6%, 7%, or 8% CD4+ immune cells of the total cells in the biological sample.

59. The method of any of embodiments 40-58, wherein the frequency is based on or is a density of the CD4+ immune cells.

60. The method of any of embodiments 40-59, wherein the frequency is based on or is a density of the cells measured as CD4+ immune cells/mm$^2$.

61. The method of any of embodiments 40-60, wherein if the assessing indicates the subject is likely to achieve a response following administration of the cell therapy, the therapeutic regimen comprises administering to the subject:

i. the cell therapy, optionally at a non-reduced dose; or ii. the cell therapy, wherein administration of the cell therapy does not comprise administering, prior to or concurrently with administering the cell therapy, an agent or treatment capable of stimulating, amplifying, potentiating, and/or enhancing an anti-tumor immune response.

62. The method of any of embodiments 40-60, wherein if the assessing indicates the subject not likely to achieve a response following administration of the cell therapy, the therapeutic regimen comprises administering to the subject:

i. an agent or other treatment capable of stimulating, amplifying, potentiating, and/or enhancing an anti-tumor immune response and the cell therapy, wherein administration of the agent is to be administered (i) prior to, (ii) within one, two, or three days of, (iii) concurrently with the initiation of administration of the cell therapy to the subject;

ii. the cell therapy at an increased dose and/or administering an additional dose of the cell therapy; or iii. an alternative therapeutic treatment other than the cell therapy.

63. The method of embodiment 61 or embodiment 62, wherein the agent or other treatment is or comprises an immune-inhibitory molecule, is or comprises an immune checkpoint molecule or member of an immune checkpoint pathway and/or is or comprises a modulator of an immune checkpoint molecule or pathway.

64. The method of embodiment 63, wherein the immune checkpoint molecule or pathway is or comprises PD-1, PD-L1, PD-L2, CTLA-4, LAG-3, TIM3, VISTA, an adenosine receptor, CD73, CD39, adenosine 2A Receptor (A2AR), or adenosine or a pathway involving any of the foregoing.

65. The method of any of embodiments 61-63, wherein the agent is BY55, MSB0010718C, ipilimumab, Daclizumab, Bevacizumab, Basiliximab, Ipilimumab, Nivolumab, pembrolizumab, MPDL3280A, Pidilizumab, MK-3475, BMS-936559, Atezolizumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MOXR0916, AMP-224, Avelumab, MEDI4736, PDR001, rHIgM12B7, Ulocuplumab, BKT140, Varlilumab, ARGX-110, MGA271, lirilumab, IPH2201, ARGX-115, Emactuzumab, CC-90002 and MNRP1685A or an antibody-binding fragment thereof.

66. The method of any of embodiments 61-63, wherein the agent is an anti-PD-L1 antibody.

67. The method of embodiment 66, wherein the anti-PD-L1 antibody is MEDI4736, MDPL3280A, BMS-936559, LY3300054, atezolizumab or avelumab or is an antigen-binding fragment thereof.

68. The method of any of embodiments 61-63, wherein the agent is thalidomide or is a derivative or analogue of thalidomide.

69. The method of any of embodiments 61-63 and 68, wherein the agent is lenalidomide or omalidomide, avadomide, a stereoisomer of lenalidomide, pomalidomide, avadomide or a pharmaceutically acceptable salt, solvate, hydrate, co-crystal, clathrate, or polymorph thereof.

70. The method of any of embodiments 61-63, 68 and 69, wherein the agent is lenalidomide, a stereoisomer of lenalidomide or a pharmaceutically acceptable salt, solvate, hydrate, co-crystal, clathrate, or polymorph thereof.

71. The method of any of embodiments 61-63, wherein the agent is a tryptophan metabolism and/or kynurenine pathway modulator.

72. The method of embodiment 71, wherein the tryptophan metabolism and/or kynurenine pathway modulator, is an inhibitor of one or more enzymes selected from the group consisting of indoleamine-pyrrole 2,3-dioxygenase 1 (IDO1), IDO2, tryptophan 2,3-dioxygenase (TDO) and kynureninase.

73. The method of embodiment 71 or embodiment 72, wherein the tryptophan metabolism and/or kynurenine pathway modulator is an inhibitor of indoleamine-pyrrole 2,3-dioxygenase 1 (IDO1).

74. The method of any of embodiments 71-73, wherein the tryptophan metabolism and/or kynurenine pathway modulator is selected from 1-methyl-D-tryptophan (1-MT) (indoximod), 4-({2-[(aminosulfonyl)amino]ethyl}amino)-

N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F00187, PF-06840003 or pharmaceutically acceptable salt or prodrug thereof or a method thereof.

75. The method of any of embodiments 61-74, wherein the agent is delivered directly into the tumor.

76. The method of any of embodiments 1-75, wherein the disease or condition is a cancer.

77. The method of embodiment 76, wherein the cancer is a myeloma, lymphoma or leukemia.

78. The method of any of embodiments 1-77, wherein the disease or condition is a B cell malignancy.

79. The method of embodiment 78, wherein the B cell malignancy is selected from acute lymphoblastic leukemia (ALL), chronic lymphoblastic leukemia (CLL), acute myelogenous leukemia (AML), chronic myelogenous leukemia (CML), non-Hodgkin lymphoma (NHL), or Diffuse Large B-Cell Lymphoma (DLBCL), or a subtype of any of the foregoing.

80. The method of any of embodiments 1-79, wherein the disease or condition is NHL and the NHL is selected from the group consisting of aggressive NHL, diffuse large B cell lymphoma (DLBCL), NOS (not otherwise specified) (de novo and transformed from indolent), primary mediastinal large B cell lymphoma (PMBCL), T cell/histiocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

81. The method of any of embodiments 1-80, wherein the cell therapy is a T cell therapy comprising genetically engineered cells expressing a recombinant receptor.

82. The method of embodiment 81, wherein the recombinant receptor is a T cell receptor or a functional non-T cell receptor.

83. The method of embodiment 81 or embodiment 82, wherein the recombinant receptor is a chimeric antigen receptor (CAR).

84. The method of any of embodiments 81-83, wherein the recombinant receptor specifically binds to an antigen associated with a disease or condition and/or expressed in cells associated with the disease or condition.

85. The method of embodiment 84, wherein the antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

86. The method of embodiment 84 or embodiment 85, wherein the antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Rα2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen.

87. The method of any of embodiments 83-86, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3ζ) chain; and/or wherein the CAR further comprises a costimulatory signaling region, which optionally comprises a signaling domain of CD28 or 4-1BB.

88. The method of any of embodiments 1-87, wherein the genetically engineered cells comprise T cells or NK cells.

89. The method of any of embodiments 1-88, wherein the genetically engineered cells comprise T cells, and the T cells comprise CD4+ and/or CD8+ T cells.

90. The method of embodiment 89, wherein the T cells are primary T cells obtained from a subject.

91. The method of any of embodiments 1-90, wherein the cells of the cell therapy are autologous to the subject.

92. The method of any of embodiments 1-90, wherein the cells are allogeneic to the subject.

93. The method of any of embodiments 1-76, wherein the cell therapy comprises the administration of from or from about $1\times10^5$ to about $1\times10^9$, from or from about $5\times10^5$ to about $5\times10^8$, from or from about $1\times10^6$ to about $1\times10^8$ or from or from about $5\times10^7$ to about $1\times10^8$ total recombinant receptor-expressing cells, total T cells, or total peripheral blood mononuclear cells (PBMCs), each inclusive; or (a) at or about $5\times10^7$; (b) at or about $1\times10^8$; (c) no more than at or about $5\times10^7$; (d) no more than at or about $1\times10^8$; and/or (e) between at or about $5\times10^7$ and at or about $1\times10^8$, each inclusive, total recombinant receptor-expressing cells, total T cells, or total peripheral blood mononuclear cells (PBMCs).

94. The method of any of embodiments 1-93, wherein the cell therapy comprises the administration of from or from about $1\times10^5$ to $1\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive.

95. The method of any of embodiments 1-94, wherein the cell therapy comprises the administration of no more than $1\times10^8$ total recombinant receptor-expressing cells, total T cells, or total peripheral blood mononuclear cells (PBMCs), no more than $1\times10^7$ total recombinant receptor-expressing cells, total T cells, or total peripheral blood mononuclear cells (PBMCs), no more than $0.5\times10^7$ total recombinant receptor-expressing cells, total T cells, or total peripheral blood mononuclear cells (PBMCs), no more than $1\times10^6$ total recombinant receptor-expressing cells, total T cells, or total peripheral blood mononuclear cells (PBMCs), no more than $0.5\times10^6$ total recombinant receptor-expressing cells, total T cells, or total peripheral blood mononuclear cells (PBMCs).

96. A kit, comprising a cell therapy and reagents for detecting frequency of CD4+ immune cells in a biological sample obtained from a subject that is a candidate for treatment with the cell therapy, and instructions for comparing the frequency of CD4+ immune cells to a threshold value, thereby identifying a subject that likely to achieve a response when treated with the cell therapy.

97. A kit, comprising a cell therapy and instructions for administering a therapeutic regimen comprising the cell therapy following or based on the results of assessing frequency of CD4+ immune cells in a biological sample obtained from a subject that is a candidate for treatment with the cell therapy.

98. The kit of embodiment 96 or embodiment 97, wherein the biological sample is a tumor biopsy sample.

99. The kit of any of embodiments 96-98, wherein the immune cells are or comprise myeloid cells, T helper cells, monocytes, macrophages, or dendritic cells.

100. The kit of any of embodiments 96-99, wherein the immune cells are or comprise T cells.

101. The kit of any of embodiments 96-100, wherein the CD4+ immune cells are detected using immunoassay, in situ hybridization, immunohistochemistry, multiplexed immunohistochemistry, or 5-plex immunofluorescent immunohistochemistry.

102. The kit of any of embodiments 96-101, wherein the response is a complete response (CR) or partial response (PR).

103. The kit of any of embodiments 96-102, wherein the response is durable.

104. The kit of any of embodiments 96-103, wherein the response is durable for greater than 3 months, 4 months, 5 months, or 6 months.

105. The kit of any of embodiments 96-104, wherein the subject is a human.

106. The kit of any of embodiments 96-105, wherein the cell therapy comprises cells engineered to express a recombinant receptor.

107. A kit, comprising a cell therapy and reagents for immunohistochemistry, for detecting frequency of CD4+ immune cells in a biological sample that is a tumor biopsy sample obtained from a subject that is a candidate for treatment with the cell therapy, and instructions for comparing the frequency of CD4+ immune cells to a threshold value, thereby identifying a subject that likely to achieve a response that is a complete response (CR) or a partial response (PR).

108. A kit, comprising a cell therapy and instructions for administering a therapeutic regimen comprising the cell therapy following or based on the results of assessing frequency of CD4+ immune cells by immunohistochemistry, in a biological sample that is a tumor biopsy sample obtained from a subject that is a candidate for treatment with the cell therapy, wherein the instructions specify comparing the frequency of CD4+ immune cells to a threshold value, thereby identifying a subject that likely to achieve a response that is a complete response (CR) or a partial response (PR), optionally the response that is durable for greater than 3 months, 4 months, 5 months, or 6 months, when treated with the cell therapy.

109. The kit of any of embodiments 96-108, wherein: the instructions specify that the frequency of CD4+ immune cells in the sample indicates the subject is or is likely to achieve a response when treated with the cell therapy if the frequency of CD4+ immune cells is at or above a threshold value; or the instructions specify that the frequency of CD4+ immune cells in the sample indicates the subject is or is likely to achieve a response when treated with the cell therapy if the frequency of CD4+ immune cells is below a threshold value.

110. The kit of any of embodiments 96-109, wherein the threshold level is within 25%, within 20%, within 15%, within 10% or within 5% and/or is within one or two standard deviation(s) below the median or mean value of CD4+ immune cells in samples obtained from a group of subjects after the initiation of administration of the cell therapy, wherein each of the subjects of the group went on to achieve a response after administration of the cell therapy.

111. The kit of any of embodiments 96-110, wherein the threshold value of CD4+ immune cells is determined based on a median frequency of CD4+ immune cells observed from a group of subjects that achieved a response after administration of the cell therapy.

112. The kit of embodiment embodiment 110 or embodiment 111, wherein the response achieved by the group of subjects is CR or PR.

113. The kit of any of embodiments 110-112, wherein the response achieved by the group of subjects is durable at 3 months.

114. The kit of any of embodiments 96-109, wherein the threshold level is within 25%, within 20%, within 15%, within 10% or within 5% and/or is within a standard deviation above the median or mean frequency of CD4+ immune cells in samples obtained from a group of subjects after the initiation of administration of the cell therapy, wherein each of the subjects of the group went on to exhibit stable disease (SD) and/or progressive disease (PD).

115. The kit of any of embodiments 96-114, wherein the threshold value of CD4+ immune cells is or is greater than about 4%, 5%, 6%, 7%, or 8% CD4+ immune cells of the total cells in the biological sample.

116. The kit of any of embodiments 96-115, wherein the frequency is based on or is a density of the CD4+ immune cells.

117. The kit of any of embodiments 96-116, wherein the frequency is based on or is a density of the cells measured as CD4+ immune cells/mm$^2$.

118. The kit of any of embodiments 96-117, wherein the instructions specify if the frequency of CD4+ immune cells in the sample indicates the subject is likely to achieve a response, selecting the subject for administration of a therapeutic regimen, the therapeutic regimen comprising administering to the subject:
  i. the cell therapy, optionally at a non-reduced dose; or
  ii. the cell therapy, wherein administration of the cell therapy does not comprise administering, prior to or concurrently with administering the cell therapy, an agent or treatment capable of stimulating, amplifying, potentiating, and/or enhancing an anti-tumor immune response.

119. The kit of any of embodiments 96-117, wherein the instructions specify if the frequency of CD4+ immune cells in the sample indicates the subject is not likely to achieve a response, selecting the subject for administration of a therapeutic regimen, the therapeutic regimen comprising administering to the subject:
  i. an agent or other treatment capable of stimulating, amplifying, potentiating, and/or enhancing an anti-tumor immune response and the cell therapy, wherein administration of the agent is to be administered (i) prior to, (ii) within one, two, or three days of, (iii) concurrently with and/or (iv) at first fever following, the initiation of administration of the cell therapy to the subject;
  ii. the cell therapy at an increased dose and/or administering an additional dose of the cell therapy; or
  iii. an alternative therapeutic treatment other than the cell therapy.

120. The kit of any of embodiments 96-119, wherein the cell therapy is a cell therapy or is a T cell-engaging therapy, optionally wherein the cell therapy comprises cells engineered to express a recombinant receptor.

121. The kit of any of embodiments 96-120, wherein the cell therapy is an adoptive cell therapy.

122. The kit of any of embodiments 96-121, wherein the cell therapy is or comprises tumor infiltrating lymphocytic (TIL) therapy or comprises genetically engineered cells expressing a recombinant receptor that specifically binds to an antigen associated with a disease or condition and/or expressed in cells associated with the disease or condition.

123. The kit of any of embodiments 96-122, wherein the genetically engineered cells comprise T cells or NK cells.

124. The kit of embodiment 122 or embodiment 123, wherein the genetically engineered cells comprise T cells, and the T cells comprise CD4+ and/or CD8+ T cells.

125. The kit of embodiment 124, wherein the T cells are primary T cells obtained from a subject.

126. The kit of any of embodiments 96-125, wherein the cells of the cell therapy are autologous to the subject.

127. The kit of any of embodiments 96-125, wherein the cells are allogeneic to the subject.

128. The kit of any of embodiments 122-127, wherein the disease or condition is a cancer.

129. The kit of embodiment 127 or embodiment 128, wherein the cancer is a myeloma, leukemia or lymphoma.

130. The kit of any of embodiments 122-129, wherein the disease or condition is a B cell malignancy.

131. The kit of embodiment 130, wherein the B cell malignancy is selected from acute lymphoblastic leukemia (ALL), chronic lymphoblastic leukemia (CLL), acute myelogenous leukemia (AML), chronic myelogenous leukemia (CML), non-Hodgkin lymphoma (NHL), or Diffuse Large B-Cell Lymphoma (DLBCL), or a subtype of any of the foregoing.

132. The kit of any of embodiments 122-131, wherein the disease or condition is NHL and the NHL is selected from the group consisting of aggressive NHL, diffuse large B cell lymphoma (DLBCL), NOS (not otherwise specified) (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

133. The kit of any of embodiments 122-132, wherein the antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR viii), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

134. The kit of any of embodiments 122-133, wherein the antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen.

135. The kit of any of embodiments 122-134, wherein the recombinant receptor is a T cell receptor or a functional non-T cell receptor.

136. The kit of any of embodiments 122-135, wherein the recombinant receptor is a chimeric antigen receptor (CAR).

137. The kit of embodiment 136, wherein the CAR comprises an extracellular antigen-recognition domain that specifically binds to the antigen and an intracellular signaling domain comprising an ITAM, wherein optionally, the intracellular signaling domain comprises an intracellular domain of a CD3-zeta (CD3ζ) chain; and/or wherein the CAR further comprises a costimulatory signaling region, which optionally comprises a signaling domain of CD28 or 4-1BB.

138. The kit of any of embodiments 96-137, further comprising an agent or treatment capable of stimulating, amplifying, potentiating, and/or enhancing an anti-tumor immune response.

139. The kit of embodiment 138, wherein the agent or other treatment is or comprises an immune-inhibitory molecule, is or comprises an immune checkpoint molecule or member of an immune checkpoint pathway and/or is or comprises a modulator of an immune checkpoint molecule or pathway.

140. The kit of embodiment 139, wherein the immune checkpoint molecule or pathway is or comprises PD-1, PD-L1, PD-L2, CTLA-4, LAG-3, TIM3, VISTA, an adenosine receptor, CD73, CD39, adenosine 2A Receptor (A2AR), or adenosine or a pathway involving any of the foregoing.

141. The kit of any of embodiments 138-140, wherein the agent is BY55, MSB0010718C, ipilimumab, Daclizumab, Bevacizumab, Basiliximab, Ipilimumab, Nivolumab, pembrolizumab, MPDL3280A, Pidilizumab, MK-3475, BMS-936559, Atezolizumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MOXR0916, AMP-224, Avelumab, MEDI4736, PDR001, rHIgM12B7, Ulocuplumab, BKT140, Varlilumab, ARGX-110, MGA271, lirilumab, IPH2201, ARGX-115, Emactuzumab, CC-90002 and MNRP1685A or an antibody-binding fragment thereof.

142. The kit of any of embodiment 138 or embodiment 139, wherein the agent is an anti-PD-L1 antibody.

143. The kit of embodiment 142, wherein the anti-PD-L1 antibody is MEDI14736, MDPL3280A, BMS-936559, LY3300054, atezolizumab or avelumab or is an antigen-binding fragment thereof.

144. The kit of embodiment 138 or embodiment 139, wherein the agent is thalidomide or is a derivative or analogue of thalidomide.

145. The kit of any of embodiments 138, 139 and 144, wherein the agent is lenalidomide or omalidomide, avadomide, a stereoisomer of lenalidomide, pomalidomide, avadomide or a pharmaceutically acceptable salt, solvate, hydrate, co-crystal, clathrate, or polymorph thereof.

146. The kit of any of embodiments 138, 139, 144 and 145, wherein the agent is lenalidomide, a stereoisomer of lenalidomide or a pharmaceutically acceptable salt, solvate, hydrate, co-crystal, clathrate, or polymorph thereof.

147. The kit of embodiment 138 or embodiment 139, wherein the agent is a tryptophan metabolism and/or kynurenine pathway modulator.

148. The kit of embodiment 147, wherein the tryptophan metabolism and/or kynurenine pathway modulator, is an inhibitor of one or more enzymes selected from the group consisting of indoleamine-pyrrole 2,3-dioxygenase 1 (IDO1), IDO2, tryptophan 2,3-dioxygenase (TDO) and kynureninase.

149. The kit of embodiment 147 or embodiment 148, wherein the tryptophan metabolism and/or kynurenine pathway modulator is an inhibitor of indoleamine-pyrrole 2,3-dioxygenase 1 (IDO1).

150. The kit of any of embodiments 147-149, wherein the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)

methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F00187, PF-06840003 or pharmaceutically acceptable salt or prodrug thereof or a method thereof.

151. The kit of any of embodiments 138-150, wherein the agent is delivered directly into the tumor.

152. A method of assessing likelihood of a response to a cell therapy, the method comprising:

(a) assessing the ratio of CD8+ cells to CD4+ cells (CD8+:CD4+ ratio) in a sample from a subject having a disease or condition, said subject having previously received administration of a cell therapy comprising a dose or composition of genetically engineered cells expressing a recombinant receptor for treating the disease or condition; and (b) comparing the CD8+:CD4+ ratio to a threshold value, thereby determining a likelihood that a subject will achieve a response when treated with the cell therapy.

153. A method of selecting a subject for treatment with an agent, the method comprising assessing the ratio of CD8+ cells to CD4+ cells (CD8+:CD4+ ratio) in a sample from a subject having a disease or condition, said subject having previously received administration of a cell therapy comprising a dose or composition of genetically engineered cells expressing a recombinant receptor for treating the disease or condition, wherein the subject is selected for administration of the agent if the CD8+:CD4+ ratio is below a threshold level.

154. A method of assessing likelihood of a response to a cell therapy, the method comprising:

(a) assessing the ratio of CD8+ cells to CD4+ cells (CD8+:CD4+ ratio) in a sample that is a tumor biopsy sample from a subject having a cancer, said subject having previously received administration of a cell therapy comprising a dose or composition of genetically engineered cells expressing a recombinant receptor for treating the cancer, and wherein the CD8+:CD4+ ratio is determined based on detection using immunohistochemistry, optionally multiplexed immunohistochemistry; and (b) comparing the CD8+:CD4+ ratio to a threshold value, thereby determining a likelihood that a subject will achieve a response that is a complete response (CR) or a partial response (PR), optionally the response is durable for greater than 3 months, 4 months, 5 months, or 6 months, when treated with the cell therapy.

155. A method of selecting a subject for treatment with an agent, the method comprising assessing the ratio of CD8+ cells to CD4+ cells (CD8+:CD4+ ratio) in a sample that is a tumor biopsy sample from a subject having a cancer, said subject having previously received administration of a cell therapy comprising a dose or composition of genetically engineered cells expressing a recombinant receptor for treating the cancer, wherein the CD8+:CD4+ ratio is determined based on detection using immunohistochemistry, optionally multiplexed immunohistochemistry and the subject is selected for administration of the agent if the CD8+:CD4+ ratio is below a threshold level.

156. The method of any of embodiments 152-155, wherein:

the subject is likely to achieve a response when treated with the cell therapy if the CD8+:CD4+ ratio is at or above the threshold value; or the subject is not likely to achieve a response when treated with the cell therapy if the CD8+:CD4+ ratio is below the threshold value.

157. The method of any of embodiments 152-156, wherein the threshold level is within 25%, within 20%, within 15%, within 10% or within 5% and/or is within one or two standard deviation(s) below the median or mean CD8+:CD4+ ratio in samples obtained from a group of subjects after the initiation of administration of the cell therapy, wherein each of the subjects of the group went on to achieve a response after administration of the cell therapy.

158. The method of any of embodiments 152-157, wherein the threshold value of CD4+ immune cells is determined based on a median CD8+:CD4+ ratio observed from a group of subjects that achieved a response after administration of the cell therapy.

159. The method of embodiment 157 or embodiment 158, wherein the response achieved by the group of subjects is CR or PR.

160. The method of any of embodiments 157-159, wherein the response achieved by the group of subjects is durable at 3 months.

161. The method of any of embodiments 152-160, wherein the threshold level is within 25%, within 20%, within 15%, within 10% or within 5% and/or is within a standard deviation above the median or mean CD8+:CD4+ ratio in samples obtained from a group of subjects after the initiation of administration of the cell therapy, wherein each of the subjects of the group went on to exhibit stable disease (SD) and/or progressive disease (PD).

162. The method of any of embodiments 152-161, wherein the threshold level is a CD8+:CD4+ ratio in a sample from a subject that is at least or at least about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5 or 3.0.

163. A method of assessing likelihood of a response following administration of a cell therapy, the method comprising:

(1) assessing a biological sample for a frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells wherein the biological sample is obtained from a subject having a disease or condition, said subject having previously received administration of a cell therapy comprising a dose or composition of genetically engineered cells expressing a recombinant receptor for treating the disease or condition; and (2) comparing the frequency to a threshold value, thereby determining a likelihood that a subject will achieve a response.

164. A method of selecting a subject for treatment with an agent, the method comprising assessing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in a sample from a subject having a disease or condition, said subject having previously received administration of a cell therapy comprising a dose or composition of genetically engineered cells expressing a recombinant receptor for treating the disease or condition, wherein the subject is selected for administration of the agent if frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is above a threshold level.

165. A method of assessing likelihood of a response following administration of a cell therapy, the method comprising:

(1) assessing a biological sample for a frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells, wherein the biological sample that is a tumor biopsy sample is obtained from a subject having a cancer, said subject having previously received administration of a cell therapy comprising a dose or composition of genetically engineered cells expressing a recombinant receptor for treating the cancer and wherein the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is determined based on detection using immunohistochemistry, optionally multiplexed immunohistochemistry; and (2) comparing the frequency to a threshold value, thereby determining a likelihood that a subject will achieve a response that is a complete response (CR) or a partial response (PR), optionally the response is durable for greater than 3 months, 4 months, 5 months, or 6 months.

166. A method of selecting a subject for treatment with an agent, the method comprising assessing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in a biological sample that is a tumor biopsy sample from a subject having a cancer, said subject having previously received administration of a cell therapy comprising a dose or composition of genetically engineered cells expressing a recombinant receptor for treating the cancer, wherein the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is determined based on detection using immunohistochemistry, optionally multiplexed immunohistochemistry and the subject is selected for administration of the agent if frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is above a threshold level.

167. The method of any of embodiments 163-166, wherein:

the subject is likely to achieve a response when treated with the cell therapy if the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is at or above the threshold value; or the subject is not likely to achieve a response when treated with the cell therapy if the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells is below the threshold value.

168. The method of any of embodiments 163-167, wherein the threshold value is within 25%, within 20%, within 15%, within 10% or within 5% and/or is within a standard deviation above the median or mean frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in samples obtained from a group of subjects after the initiation of administration of the cell therapy, wherein each of the subjects of the group went on to exhibit stable disease (SD) and/or progressive disease (PD).

169. The method of any of embodiments 163-167, wherein the threshold level is within 25%, within 20%, within 15%, within 10% or within 5% and/or is within one or two standard deviation(s) below the median or mean frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in samples obtained from a group of subjects after the initiation of administration of the cell therapy, wherein each of the subjects of the group went on to achieve a response after administration of the cell therapy.

170. The method of any of embodiments 163-167 and 169, wherein the threshold value of CD8+ cells is determined based on a median frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cell observed from a group of subjects that achieved a response after administration of the cell therapy.

171. The method of embodiment 169 or embodiment 170, wherein the response achieved by the group of subjects is CR or PR.

172. The method of any of embodiments 169-171, wherein the response achieved by the group of subjects is durable at 3 months.

173. The method of any of embodiments 163-172, wherein the frequency is based on or is a density of the CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in the sample.

174. The method of any of embodiments 163-173, wherein the frequency is based on or is a density of the cells measured as CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells/mm$^2$ in the sample.

175. A method of assessing likelihood of a response following administration of a cell therapy, the method comprising:

(1) assessing a biological sample for a frequency of CD8+ immune cells, wherein the biological sample is obtained from a subject having a disease or condition, said subject having previously received administration of a cell therapy comprising a dose or composition of genetically engineered cells expressing a recombinant receptor for treating the disease or condition; and (2) comparing the frequency to a threshold value, thereby determining a likelihood that a subject will achieve a response.

176. A method of assessing likelihood of a response to a cell therapy, the method comprising:

(a) assessing a sample from a subject for the frequency of CD8+ immune cells that express a recombinant receptor among total cells expressing the recombinant receptor, said subject having previously received administration of a cell therapy comprising a dose of genetically engineered cells expressing the recombinant receptor for treating a disease or condition; and (b) comparing the frequency of recombinant receptor-expressing CD8+ immune cells to a threshold value, thereby determining a likelihood that a subject will achieve a response when treated with the cell therapy.

177. A method of assessing likelihood of a response following administration of a cell therapy, the method comprising:

(1) assessing a biological sample for a frequency of CD8+ immune cells, wherein the biological sample that is a tumor biopsy sample is obtained from a subject having a cancer, said subject having previously received administration of a cell therapy comprising a dose or composition of genetically engineered cells expressing a recombinant receptor for treating the cancer, wherein the frequency of CD8+ immune cells is determined based on detection using immunohistochemistry; and (2) comparing the frequency to a threshold value, thereby determining a likelihood that a subject will achieve a response that is a complete response (CR) or a partial response (PR), optionally the response is durable for greater than 3 months, 4 months, 5 months, or 6 months.

178. A method of assessing likelihood of a response to a cell therapy, the method comprising:

(a) assessing a sample that is a tumor biopsy sample from a subject for the frequency of CD8+ immune cells that express a recombinant receptor among total cells expressing the recombinant receptor, said subject having previously received administration of a cell therapy comprising a dose of genetically engineered cells expressing the recombinant receptor for treating a cancer, wherein the frequency of CD8+ immune cells is determined based on detection using immunohistochemistry; and (b) comparing the frequency of recombinant receptor-expressing CD8+ immune cells to a threshold value, thereby determining a likelihood that a subject will achieve a response a response that is a complete response (CR) or a partial response (PR), optionally the response is durable for greater than 3 months, 4 months, 5 months, or 6 months when treated with the cell therapy.

179. The method of any of embodiments 175-178, wherein:

the subject is likely to achieve a response when treated with the cell therapy if the frequency of CD8+ immune cells is at or above the threshold value; or the subject is not likely to achieve a response when treated with the cell therapy if the frequency of CD8+ immune cells is below the threshold value.

180. The method of any of embodiments 175-179, wherein the threshold value is within 25%, within 20%, within 15%, within 10% or within 5% and/or is within a standard deviation above the median or mean frequency of CD8+ immune cells in samples obtained from a group of subjects after the initiation of administration of the cell therapy, wherein each of the subjects of the group went on to exhibit stable disease (SD) and/or progressive disease (PD).

181. The method of any of embodiments 175-179, wherein the threshold level is within 25%, within 20%, within 15%, within 10% or within 5% and/or is within one or two standard deviation(s) below the median or mean frequency of CD8+ immune cells in samples obtained from a group of subjects after the initiation of administration of the cell therapy, wherein each of the subjects of the group went on to achieve a response after administration of the cell therapy.

182. The method of any of embodiments 175-179 and 181, wherein the threshold value of CD8+ immune cells is determined based on a median frequency of CD8+ immune cells observed from a group of subjects that achieved a response after administration of the cell therapy.

183. The method of embodiment 181 or embodiment 182, wherein the response achieved by the group of subjects is CR or PR.

184. The method of any of embodiments 181-183, wherein the response achieved by the group of subjects is durable at 3 months.

185. The method of any of embodiments 175-179, wherein the threshold value of CD8+ immune cells is within 25%, within 20%, within 15%, within 10% or within 5% and/or is within one or two standard deviation(s) below the median or mean frequency of CD8+ immune cells in samples obtained from a group of subjects after the initiation of administration of the cell therapy a complete response (CR).

186. The method of any of embodiments 175-179, wherein the threshold value of CD8+ immune cells is within 25%, within 20%, within 15%, within 10% or within 5% and/or is within a standard deviation above the median or mean frequency of CD8+ immune cells in samples obtained from a group of subjects after the initiation of administration of the cell therapy a partial response (PR).

187. The method of any of embodiments 175-186, wherein the frequency is based on or is a density of the CD8+ immune cells.

188. The method of any of embodiments 175-187, wherein the frequency is based on or is a density of the cells measured as CD8+ immune cells/mm$^2$.

189. The method of any of embodiments 152-132h, further comprising selecting a subject for treatment with an agent if the subject is determined not likely to achieve a response.

190. The method of any of embodiments 152-134, wherein the response is a complete response (CR).

191. The method of any of embodiments 152-135, wherein the response is durable.

192. The method of any of embodiments 152-136, wherein the response is durable for greater than 3 months, 4 months, 5 months, or 6 months.

193. The method of any of embodiments 152-137, wherein the sample from the subject is obtained after the initiation of administration of the cell therapy.

194. The method of embodiment 138, wherein the sample from the subject is obtained within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the cell therapy.

195. The method of any of embodiments 152-139, wherein the sample from the subject is obtained at a time before a peak or maximum level of the cells of the cell therapy is detectable in the blood of the subject.

196. A method of assessing likelihood of a response to a cell therapy, the method comprising:

(a) assessing the frequency of CD8+ cells in one or more sample(s) from a subject having a disease or condition, said subject being a candidate for administration of a cell therapy comprising a dose or composition of genetically engineered cells expressing a recombinant receptor for treating the disease or condition, wherein a first sample is obtained prior to administration of the cell therapy and a second sample is obtained after the initiation of administration of the cell therapy; and (b) comparing the increase in the frequency of CD8+ cells in the second sample compared to the first sample to a threshold value, thereby determining a likelihood that a subject will achieve a response when treated with the cell therapy.

197. The method of embodiment 196, wherein:
the subject is likely to achieve a response when treated with the cell therapy if the increase in the frequency of CD8+ cells in the second sample compared to the first sample that is at or above a threshold level; or
the subject is not likely to achieve a response when treated with the cell therapy if the increase in the frequency of CD8+ cells in the second sample compared to the first sample that is below the threshold value.

198. The method of embodiment 196 or embodiment 197, further comprising selecting a subject for treatment with an agent if the subject is determined not likely to achieve a response.

199. The method of any of embodiments 196-198, wherein the response is a complete response (CR) or partial response (PR).

200. The method of any of embodiments 196-199, wherein the response is durable.

201. The method of any of embodiments 196-200, wherein the response is durable for greater than 3 months, 4 months, 5 months, or 6 months.

202. A method of selecting a subject for treatment with an agent, the method comprising assessing the frequency of CD8+ cells in one or more sample(s) from a subject having a disease or condition, said subject being a candidate for administration of a cell therapy comprising a dose or composition of genetically engineered cells expressing a recombinant receptor for treating the disease or condition, wherein a first sample is obtained prior to administration of the cell therapy and a second sample is obtained after the initiation of administration of the cell therapy, wherein the subject is selected for administration of the agent if an increase in the frequency of CD8+ cells in the second sample compared to the first sample is below a threshold level.

203. The method of any of embodiments 196-202, wherein the second sample is obtained within or within about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days after the initiation of administration of the cell therapy.

204. The method of any of embodiments 196-203, wherein the second sample is obtained at a time before a peak or maximum level of the cells of the cell therapy is detectable in the blood of the subject.

205. The method of any of embodiments 196-204, wherein:
the subject is likely to achieve a response when treated with the cell therapy if the increase in the frequency of CD8+ cells is at or above the threshold value; or
the subject is not likely to achieve a response when treated with the cell therapy if the increase in the frequency of CD8+ cells is below the threshold value.

206. The method of any of embodiments 196-205, wherein the threshold level is within 25%, within 20%, within 15%, within 10% or within 5% and/or is within a standard deviation above the median or mean of the increase in the frequency of CD8+ cells in the second sample compared to the first sample obtained from a group of subjects after the initiation of administration of the cell therapy, wherein each of the subjects of the group went on to exhibit stable disease (SD) and/or progressive disease (PD).

207. The method of any of embodiments 196-205, wherein the threshold level is within 25%, within 20%, within 15%, within 10% or within 5% and/or is within one or two standard deviation(s) below the median or mean increase in the frequency of CD8+ cells in samples obtained from a group of subjects after the initiation of administration of the cell therapy, wherein each of the subjects of the group went on to achieve a response after administration of the cell therapy.

208. The method of any of embodiments 196-205 and 207, wherein the threshold value of CD8+ immune cells is determined based on a median increase in the frequency of CD8+ cells observed from a group of subjects that achieved a response after administration of the cell therapy.

209. The method of embodiment 207 or embodiment 208, wherein the response achieved by the group of subjects is CR or PR.

210. The method of any of embodiments 207-209, wherein the response achieved by the group of subjects is durable at 3 months.

211. The method of any of embodiments 196-210, wherein the threshold level is an increase in the frequency of CD8+ cells in the second sample compared to the first sample from a subject that is at least or at least about +0.1%, +0.25%, +0.5%, +0.75%, +1%, +2%, +3%, +4%, +5%, +6%, +7%, +8%, +9%, +10%, +11%, +12%, +13%, +14%, +15% or +20%.

212. The method of any of embodiments 196-211, wherein the frequency is based on or is a density of the CD8+ cells.

213. The method of any of embodiments 196-212, wherein the frequency is based on or is a density of the cells measured as CD8+ cells/mm$^2$.

214. The method of any of embodiments 152-213, wherein the assessing is performed by contacting a biological sample with one or more reagent capable of detecting CD4+ expression and/or CD8+ expression in cells.

215. The method of any of embodiments 152-214, further comprising assessing one or more additional parameters in the samples.

216. The method of any of embodiments 152-215, wherein the additional parameter is the frequency of cells expressing an additional biomarker.

217. The method of any of embodiments 152-216, further comprising comparing the frequency of cells expressing the additional biomarker to a threshold value, thereby determining a likelihood that a subject will achieve a response when treated with the cell therapy.

218. The method of embodiment 217, wherein:
the subject is likely to achieve a response when treated with the cell therapy if the frequency of cells expressing the additional biomarker is at or above the threshold value; or
the subject is not likely to achieve a response when treated with the cell therapy if the frequency of cells expressing the additional biomarker is below the threshold value.

219. The method of embodiment 217 or embodiment 218, wherein the threshold level is within 25%, within 20%, within 15%, within 10% or within 5% and/or is within one or two standard deviation(s) below the median or mean frequency of cells expressing the additional biomarker in samples obtained from a group of subjects after the initiation of administration of the cell therapy, wherein each of the subjects of the group went on to achieve a response after administration of the cell therapy.

220. The method of any of embodiments 217-219, wherein the threshold value of the additional marker is determined based on a median frequency of cells expressing the additional biomarker observed from a group of subjects that achieved a response after administration of the cell therapy.

221. The method of any of embodiments 217-220, wherein the response achieved by the group of subjects is CR or PR.

222. The method of any of embodiments 217-221, wherein the response achieved by the group of subjects is durable at 3 months.

223. The method of embodiment 217 or embodiment 218, wherein the threshold level is within 25%, within 20%, within 15%, within 10% or within 5% and/or is within a standard deviation above the median or mean frequency of frequency of cells expressing the additional biomarker in samples obtained from a group of subjects after the initiation of administration of the cell therapy, wherein each of the subjects of the group went on to exhibit stable disease (SD) and/or progressive disease (PD).

224. The method of any of embodiments 216-223, wherein frequency of cells expressing the additional biomarker is assessed in one or more sample(s) from the subject, wherein a first sample is obtained prior to administration of the cell therapy and a second sample is obtained after the initiation of administration of the cell therapy.

225. The method of embodiment 224, further comprising comparing the increase in the frequency of cells expressing the additional biomarker in the second sample compared to the first sample to a threshold value, thereby determining a likelihood that a subject will achieve a response when treated with the cell therapy.

226. The method of embodiment 225, wherein:
the subject is likely to achieve a response when treated with the cell therapy if the increase in the frequency of cells expressing the additional biomarker is at or above the threshold value; or
the subject is not likely to achieve a response when treated with the cell therapy if the increase in the frequency of cells expressing the additional biomarker is below the threshold value.

227. The method of embodiment 225 or embodiment 226, wherein the threshold level is within 25%, within 20%, within 15%, within 10% or within 5% and/or is within one or two standard deviation(s) below the median or mean increase in frequency of cells expressing the additional biomarker in samples obtained from a group of subjects after the initiation of administration of the cell therapy, wherein each of the subjects of the group went on to achieve a response after administration of the cell therapy.

228. The method of any of embodiments 225-227, wherein the threshold value of CD4+ immune cells is determined based on a median increase in frequency of cells expressing the additional biomarker observed from a group of subjects that achieved a response after administration of the cell therapy.

229. The method of any of embodiments 225-228, wherein the response achieved by the group of subjects is CR or PR.

230. The method of any of embodiments 225-229, wherein the response achieved by the group of subjects is durable at 3 months.

231. The method of embodiment 225 or embodiment 226, wherein the threshold level is within 25%, within 20%, within 15%, within 10% or within 5% and/or is within a standard deviation above the median or mean increase in frequency of frequency of cells expressing the additional biomarker in samples obtained from a group of subjects after the initiation of administration of the cell therapy, wherein each of the subjects of the group went on to exhibit stable disease (SD) and/or progressive disease (PD).

232. The method of any of embodiments 216-231, wherein the frequency is based on or is a density of cells expressing the additional biomarker.

233. The method of any of embodiments 216-232, wherein the frequency is based on or is a density of the cells measured as the number of cells expressing the additional biomarker cells/mm$^2$.

234. The method of any of embodiments 216-233, wherein the additional biomarker is a biomarker associated with immune modulation.

235. The method of any of embodiments 216-234, wherein the additional biomarker is selected from among one or more of CD73, FOXP3, CD163, IDO and PD-L1.

236. The method of any of embodiments 216-235, wherein the additional biomarker is IDO and/or PD-L1.

237. The method of any of embodiments 152-238, wherein the sample is a tumor sample and/or the sample comprises or is likely to comprise tumor cells.

238. The method of any of embodiments 152, 153, 156-164, 167-176 and 179-231, wherein the biological sample is a tumor sample, optionally a tumor biopsy sample.

239. The method of any of embodiments 152-238, wherein the sample is or comprises a lymph node sample, bone marrow sample, blood sample, plasma sample, or serum sample.

240. The method of any of embodiments 152-239, wherein the sample is or comprises a lymph node sample.

241. The method of any of embodiments 152-240, wherein the method is carried out ex vivo.

242. The method of any of embodiments 152-241, wherein the assessment of the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in the sample is determined by immunofluorescence, immunocytochemistry, immunohistochemistry and/or flow cytometry.

243. The method of any of embodiments 152-242, wherein the assessment of the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in the sample is determined multiplexed immunohistochemistry, or 5-plex immunofluorescent immunohistochemistry.

244. The method of any of embodiments 154-243, wherein the assessment of the frequency of the additional biomarker in the sample is determined using immunoassay, in situ hybridization, immunohistochemistry, multiplexed immunohistochemistry, or 5-plex immunofluorescent immunohistochemistry and/or flow cytometry.

245. The method of any of embodiments 152-244, wherein the immune cells are or comprise myeloid cells, T helper cells, monocytes, macrophages, or dendritic cells.

246. The method of any of embodiments 152-245, wherein the immune cells are or comprise T cells.

247. The method of any of embodiments 152-246, wherein the disease or condition is a tumor.

248. The method of embodiment 247, wherein the tumor is associated with a cancer.

249. The method of any of embodiments 152-248, wherein the disease or condition is or comprises a leukemia or a lymphoma.

250. The method of any of embodiments 152-249, wherein the disease or condition is selected from and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL), or a subtype of any of the foregoing.

251. The method of any of embodiments 152-250, wherein the disease or condition is or comprises non-Hodgkin lymphoma (NHL).

252. The method of embodiment 251, wherein the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally follicular lymphoma Grade 3B (FL3B).

253. The method of any of embodiments 152-252, wherein the cell therapy is a T cell therapy comprising genetically engineered cells expressing a recombinant receptor.

254. The method of embodiment 253, wherein the recombinant receptor is a T cell receptor or a functional non-T cell receptor.

255. The method of embodiment 253 or embodiment 254, wherein the recombinant receptor is a chimeric antigen receptor (CAR).

256. The method of any of embodiments 253-255, wherein the recombinant receptor specifically binds to an antigen associated with the disease or condition or expressed in cells of the environment of a lesion associated with the disease or condition.

257. The method of embodiment 256, wherein the antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22Rα), IL-13 receptor alpha 2 (IL-13Rα2), kinase insert domain receptor (kdr), kappa light chain, L1 cell adhesion molecule (L1-CAM), CE7 epitope of L-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

258. The method of embodiment 256 or embodiment 257, wherein the antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vIII, estrogen receptor, Fetal AchR, folate receptor alpha, folate binding protein (FBP), FCRL5, FCRH5, fetal acetylcholine receptor, G250/CAIX, GD2, GD3, gp100, Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, VEGF receptors, VEGF-R2, Wilms Tumor 1 (WT-1), a pathogen-specific antigen.

259. The method of any of embodiments 256-258, wherein the antigen is CD19.

260. The method of any of embodiments 255-259, wherein the CAR comprises an extracellular antigen-recognition domain that specifically binds to the antigen and an intracellular signaling region comprising an ITAM, wherein optionally, the intracellular signaling region comprises an intracellular domain of a CD3-zeta (CD3ζ) chain; and/or wherein the CAR further comprises a costimulatory signaling region, which optionally comprises a signaling domain of CD28 or 4-1BB.

261. The method of any of embodiment 255-260, wherein the CAR further comprises a spacer and/or a hinge region.

262. The method of any of embodiments 152-261, wherein the genetically engineered cells comprise T cells or NK cells.

263. The method of any of embodiments 152-262, wherein the genetically engineered cells comprise T cells, and the T cells comprise CD4+ and/or CD8+ T cells.

264. The method of embodiment 263, wherein the T cells are primary T cells obtained from a subject.

265. The method of any of embodiments 152-264, wherein the cells of the cell therapy are autologous to the subject.

266. The method of any of embodiments 152-264, wherein the cells are allogeneic to the subject.

267. The method of any of embodiments 152-266, wherein the cell therapy comprises the administration of from or from about $1\times10^5$ to about $1\times10^9$, from or from about $5\times10^5$ to about $5\times10^8$, or from or from about $1\times10^6$ to about $1\times10^8$ total recombinant receptor-expressing cells, total T cells, or total peripheral blood mononuclear cells (PBMCs), each inclusive; or (a) at or about $1\times10^7$; (b) at or about $1.5 \times 10^8$; (c) no more than at or about $1 \times 10^7$; (d) no more than at or about $1.5 \times 10^8$; and/or (e) between at or about $1 \times 10^7$ and at or about $1.5 \times 10^8$ total recombinant receptor-expressing cells, total T cells, or total peripheral blood mononuclear cells (PBMCs).

268. The method of any of embodiments 152-267, wherein the cell therapy comprises the administration of from or from about $1 \times 10^5$ to about $1 \times 10^9$, from or from about $5 \times 10^5$ to about $5 \times 10^8$, from or from about $1 \times 10^6$ to about $1 \times 10^8$ or from or from about $5 \times 10^7$ to about $1 \times 10^8$ total recombinant receptor-expressing cells, total T cells, or total peripheral blood mononuclear cells (PBMCs), each inclusive; or (a) at or about $5 \times 10^7$; (b) at or about $1 \times 10^8$; (c) no more than at or about $5 \times 10^7$; (d) no more than at or about $1 \times 10^8$; and/or (e) between at or about $5 \times 10^7$ and at or about $1 \times 10^8$, each inclusive, total recombinant receptor-expressing cells, total T cells, or total peripheral blood mononuclear cells (PBMCs).

269. The method of any of embodiments 1-268, wherein the cell therapy comprises the administration of from or from about $1 \times 10^5$ to $1 \times 10^8$ total recombinant receptor-expressing cells, total T cells, or total peripheral blood mononuclear cells (PBMCs), from or from about $5 \times 10^5$ to $1 \times 10^7$ total recombinant receptor-expressing cells, total T cells, or total peripheral blood mononuclear cells (PBMCs) or from or from about $1 \times 10^6$ to $1 \times 10^7$ total recombinant receptor-expressing cells, total T cells, or total peripheral blood mononuclear cells (PBMCs), each inclusive.

270. The method of any of embodiments 152-269, wherein the cell therapy comprises the administration of no more than $1 \times 10^8$ total recombinant receptor-expressing cells, total T cells, or total peripheral blood mononuclear cells (PBMCs), no more than $1 \times 10^7$ total recombinant receptor-expressing cells, total T cells, or total peripheral blood mononuclear cells (PBMCs), no more than $0.5 \times 10^7$ total recombinant receptor-expressing cells, total T cells, or total peripheral blood mononuclear cells (PBMCs), no more than $1 \times 10^6$ total recombinant receptor-expressing cells, total T cells, or total peripheral blood mononuclear cells (PBMCs), no more than $0.5 \times 10^6$ total recombinant receptor-expressing cells, total T cells, or total peripheral blood mononuclear cells (PBMCs).

271. The method of any of embodiments 152-270, wherein the dose of genetically engineered cells are administered in a single pharmaceutical composition comprising the cells or as a plurality of compositions together comprising the cells.

272. The method of any of embodiments 152-271, wherein the engineered cells administered is a split dose, wherein the cells of the dose are administered in a plurality of compositions, collectively comprising the cells of the dose, over a period of no more than three days.

273. The method of any of embodiments 153, 155, 156-162, 164, 166-195 and 198-272, wherein the agent is an agent capable of stimulating, amplifying, potentiating, and/or enhancing the anti-tumor response of the cell therapy.

274. The method of any of embodiments 153, 155, 156-162, 164, 166-195 and 198-273, wherein the agent is or comprises a dose or composition comprising genetically engineered CD4+ and/or CD8+ T cells expressing a recombinant receptor.

275. The method of any of embodiments 153, 155, 156-162, 164, 166-195 and 198-273, wherein the agent is or comprises a cytokine or a chemokine.

276. The method of any of embodiments 153, 155, 156-162, 164, 166-195 and 198-273, wherein the agent is or comprises an immune-inhibitory molecule, is or comprises an immune checkpoint molecule or member of an immune checkpoint pathway and/or is or comprises a modulator of an immune checkpoint molecule or pathway.

277. The method of embodiment 276, wherein the immune checkpoint molecule or pathway is or comprises PD-1, PD-L1, PD-L2, CTLA-4, LAG-3, TIM3, VISTA, an adenosine receptor, CD73, CD39, adenosine 2A Receptor (A2AR), or adenosine or a pathway involving any of the foregoing.

278. The method of any of embodiments 153, 155, 156-162, 164, 166-195 and 198-273, wherein the agent is BY55, MSB0010718C, ipilimumab, Daclizumab, Bevacizumab, Basiliximab, Ipilimumab, Nivolumab, pembrolizumab, MPDL3280A, Pidilizumab, MK-3475, BMS-936559, Atezolizumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MOXR0916, AMP-224, Avelumab, MEDI4736, PDR001, rHIgM12B7, Ulocuplumab, BKT140, Varlilumab, ARGX-110, MGA271, lirilumab, IPH2201, ARGX-115, Emactuzumab, CC-90002 and MNRP1685A or an antibody-binding fragment thereof.

279. The method of any of embodiments 153, 155, 156-162, 164, 166-195 and 198-273, wherein the agent is an anti-PD-L1 antibody.

280. The method of embodiment 279, wherein the anti-PD-L1 antibody is MEDI14736, MDPL3280A, BMS-936559, LY3300054, atezolizumab or avelumab or is an antigen-binding fragment thereof.

281. The method of any of embodiments any of embodiments 153, 155, 156-162, 164, 166-195 and 198-273, wherein the agent is thalidomide or is a derivative or analogue of thalidomide.

282. The method of embodiment any of embodiments any of embodiments 153, 155, 156-162, 164, 166-195, 198-273 and 281, wherein the agent is lenalidomide or omalidomide, avadomide, a stereoisomer of lenalidomide, pomalidomide, avadomide or a pharmaceutically acceptable salt, solvate, hydrate, co-crystal, clathrate, or polymorph thereof.

283. The method of any of embodiments any of embodiments 153, 155, 156-162, 164, 166-195, 198-273, 281 and 282, wherein the agent is lenalidomide, a stereoisomer of lenalidomide or a pharmaceutically acceptable salt, solvate, hydrate, co-crystal, clathrate, or polymorph thereof.

284. The method of any of embodiments any of embodiments 153, 155, 156-162, 164, 166-195 and 198-273, wherein the agent is a tryptophan metabolism and/or kynurenine pathway modulator.

285. The method of embodiment 284, wherein the tryptophan metabolism and/or kynurenine pathway modulator, is an inhibitor of one or more enzymes selected from the group consisting of indoleamine-pyrrole 2,3-dioxygenase 1 (IDO1), IDO2, tryptophan 2,3-dioxygenase (TDO) and kynureninase.

286. The method of embodiment 284 or embodiment 285, wherein the tryptophan metabolism and/or kynurenine pathway modulator is an inhibitor of indoleamine-pyrrole 2,3-dioxygenase 1 (IDO1).

287. The method of any of embodiments 284-286, wherein the tryptophan metabolism and/or kynurenine pathway modulator is selected from 1-methyl-D-tryptophan (1-MT) (indoximod), 4-({2-[(aminosulfonyl)amino]ethyl}amino)-N-(3-bromo-4-fluorophenyl)-N'-hydroxy-1,2,5-oxadiazole-3-carboximidamide (INCB024360, epacadostat), 4-({2-[(aminosulfonyl)amino]ethyl}amino)-N-(3-chloro-4-fluorophenyl)-N'-hydroxy-1,2,5-oxadiazole-3-carboximidamide, 4-({2-[(aminosulfonyl)amino]

ethyl}amino)-N-[4-fluoro-3-(trifluoromethyl)phenyl]-N'-hydroxy-1,2,5-oxadiazole-3-carboximidamide, 4-({2-[(aminosulfonyl)amino]ethyl}amino)-N'-hydroxy-N-[3-(trifluoromethyl)phenyl]-1,2,5-oxadiazole-3-carboximidamide, 4-({2-[(aminosulfonyl)amino]ethyl}amino)-N-(3-cyano-4-fluorophenyl)-N'-hydroxy-1,2,5-oxadiazole-3-carboximidamide, 4-({2-[(aminosulfonyl)amino]ethyl}amino)-N-[(4-bromo-2-furyl)methyl]-N'-hydroxy-1,2,5-oxadiazole-3-carboximidamide, 4-({2-[(aminosulfonyl)amino]ethyl}amino)-N-[(4-chloro-2-furyl)methyl]-N'-hydroxy-1,2,5-oxadiazole-3-carboximidamide, 1-cyclohexyl-2-(5H-imidazo[5,1-a]isoindol-5-yl)ethanol (NLG919), GDC-0919, F00187, PF-06840003 or pharmaceutically acceptable salt or prodrug thereof or a method thereof.

288. The method of any of embodiments any of embodiments 153, 155, 156-162, 164, 166-195 and 198-287, wherein the agent is delivered directly into the tumor.

289. A kit, comprising a cell therapy and reagents for detecting the ratio of CD8+ cells to CD4+ cells (CD8+:CD4+ ratio) in a sample obtained from a subject having previously received administration of a cell therapy, and instructions for comparing the CD8+:CD4+ ratio to a threshold value, thereby identifying a subject that likely to achieve a response when treated with the cell therapy.

290. A kit, comprising a cell therapy and instructions for administering an additional agent following or based on the results of assessing the CD8+:CD4+ ratio in a sample obtained from a sample obtained from a subject having previously received administration of a cell therapy.

291. A kit, comprising a cell therapy and reagents for detecting the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in one or more sample(s) obtained from a subject having previously received administration of a cell therapy, and instructions for comparing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells to a threshold value, thereby identifying a subject that likely to achieve a response when treated with the cell therapy.

292. A kit, comprising a cell therapy and instructions for administering an additional agent following or based on the results of assessing the frequency of CD8+ cells, CD4+ cells, recombinant receptor-expressing cells, recombinant receptor-expressing CD8+ (receptor+/CD8+) cells and/or recombinant receptor-expressing CD4+ (receptor+/CD4+) cells in one or more sample(s) obtained from a sample obtained from a subject having previously received administration of a cell therapy.

293. The kit of embodiment 292, wherein a first sample is obtained prior to administration of the cell therapy and a second sample is obtained after the initiation of administration of the cell therapy.

294. The kit of any of embodiments 289-293, further comprising reagents for detecting the frequency of cells expressing an additional biomarker.

295. The kit of embodiment 294, wherein the additional biomarker is selected from among one or more of CD73, FOXP3, CD163, IDO and PD-L1.

296. The kit of embodiment 294 or embodiment 295, wherein the additional biomarker is IDO and/or PD-L1.

297. The method of any of embodiments 1-95 or the kit of any of embodiments 96-151 and 289-296, wherein the disease or condition is or comprises non-Hodgkin lymphoma (NHL).

IX. EXAMPLES

The following examples are included for illustrative purposes only and are not intended to limit the scope of the invention.

Example 1 Biomarker Assessment in Pre- and Post-Administration Tumor Biopsies from Subjects with Relapsed and Refractory Non-Hodgkin's Lymphoma (NHL) for Administration of Anti-CD19 CAR-Expressing Cells Expression of several biomarkers was assessed in tumor biopsies collected from subjects before and/or after administration of CAR-expressing cells.

A. Subjects and Treatment

Therapeutic CAR+ T cell compositions containing autologous T cells expressing a chimeric antigen-receptor (CAR) specific for CD19 were administered to subjects with B cell malignancies. Adult human subjects with relapsed or refractory (R/R) aggressive non-Hodgkin's lymphoma (NHL), including diffuse large B-cell lymphoma (DLBCL), de novo or transformed from indolent lymphoma (NOS), primary mediastinal large b-cell lymphoma (PMBCL), follicular lymphoma grade 3b (FL3B), or mantle cell lymphoma (MCL), received lymphodepletion with fludarabine and cyclophosphamide, followed by a single dose of autologous anti-CD19 CAR-expressing T cells at one of two dose levels (DL1, $5\times10^7$ total CAR-expressing T cells; DL2, $1\times10^8$ total CAR-expressing T cells). The therapeutic T cell compositions administered had been generated by a process including immunoaffinity-based enrichment of CD4+ and CD8+ cells from leukapheresis samples from the individual subjects to be treated. Isolated CD4+ and CD8+ T cells were activated and transduced with a viral vector encoding an anti-CD19 CAR, followed by expansion and cryopreservation of the engineered cell populations. The CAR contained an anti-CD19 scFv derived from a murine antibody, an immunoglobulin-derived spacer, a transmembrane domain derived from CD28, a costimulatory region derived from 4-1BB, and a CD3-zeta intracellular signaling domain. The cryopreserved cell compositions were thawed prior to intravenous administration. The therapeutic T cell dose was administered as a defined cell composition by administering a formulated $CD4^+CAR^+$ cell population and a formulated $CD8^+CAR^+$ population administered at a target ratio of approximately 1:1.

Tumor biopsies were collected prior to administration of the CAR+ T cells (pre-treatment) and at 7 to 20 days after administration (post-treatment). Results are described in this example for evaluation through a particular time-point in an ongoing study. Results from 43 biopsies (26 pre-treatment; 17 post-treatment and 15 matched pairs) from 28 total subjects (25 DLBCL and 3 MCL) were examined.

B. Assessment of Biomarkers, Response and Safety Outcomes

Infiltration of CAR+ T cell in the tumor biopsy was quantified using in situ hybridization (ISH) probes specific to the mRNA encoding the anti-CD19 CAR. CAR+ T cells, non-CAR T cells and B cells were enumerated using multiplex immunohistochemistry (IHC)/immunofluorescence (IF) assays detecting for a cell surface surrogate marker for CAR-expressing cells, CD4, CD8, CD19, CD20, CD73, FOXP3, CD163, IDO and PD-L1. Specifically, multiplex IF assays were performed on separate tumor biopsy sections from the same subject, to detect one panel of biomarkers associated with T cells or indicative of tumor burden including a cell surface surrogate marker for CAR-expressing cells, CD4, CD8, CD19, and CD20 on one tissue section, and a separate panel of biomarkers indicative of immunosuppressive pathways including CD73, FOXP3, CD163, IDO and PD-L1 on a separate tissue section. Tumor biopsy sections were stained with hematoxylin and eosin (H&E) and assessed for tissue quality and tumor identification. Immunofluorescence images were analyzed using image analysis software. Potential correlations to response outcomes were assessed using statistical analysis based on univariate t-tests, and the p-values were 2-sided without multiplicity adjustment.

Subjects were assessed for response and safety outcomes, including by assessing the tumor burden at various time points after administration of the CAR+ T cells, including at 3 months after administration, and determining whether the subject had progressive disease (PD), stable disease (SD), partial response (PR), or complete response (CR). Safety outcomes evaluated included neurotoxicity (neurological complications including symptoms of confusion, aphasia, encephalopathy, myoclonus seizures, convulsions, lethargy, and/or altered mental status), graded on a 1-5 scale, according to the National Cancer Institute-Common Toxicity Criteria (CTCAE) scale, version 4.03 (NCI-CTCAE v4.03).

C. Results

The observed objective response rate (ORR; including CR and PR) was 71% (20/28) in the subjects for which biopsies were assessed. Grade 1, 2 CRS was observed in 36% (10/28; grade 1, 2) of the subjects for which biopsies were assessed, and Grades 2-4 NT was observed in 18% (5/28) of the subjects for which biopsies were assessed.

Pre-treatment tumor biopsies were observed to contain varying cellular compositions: tumor cells (median: 77%; range 5-96%), CD4+ cells (0.90%; 0.02-15%), and CD8+ cells (1.5%; 0-23%). The results showed that subjects with a CR or PR at 3 months after CAR+ T cell administration had a higher percentage of endogenous CD4+ cells in pre-treatment tumors compared those with a PD (CR, PR median: 7.9%; PD median: 0.38%; p<0.0001). Percentages of CD8+ cells in pre-treatment tumors did not differ between the 3 month response groups (CR, PR median: 1.9%; PD median: 0.47%; p=0.6496).

In the post-treatment biopsies, CAR+ T cell were observed to have infiltrated the tumor, and constituted up to 22% of cells in the biopsy sample. The level of tumor infiltration in post-treatment samples (7 to 20 days after administration) was observed to be higher in subjects that went on to achieve a CR (median: 3.9%) or PR (median: 1.1%) compared to subjects that went on to achieve a best overall response (BOR) of SD or PD (median: 0.51%). Although both $CD4^+$ and $CD8^+$ CAR T cells were observed to have infiltrated the tumor area at the post-treatment time point (7 to 20 days after administration), subjects that went on to achieve a CR were observed to have higher ratio of $CD8^+CAR^+$ T cells to $CD4^+CAR^+$ T cells, at this post-treatment timepoint, as compared to subjects that went on to achieve a BOR of SD or PD (CR median: 0.83; SD, PD median: 0.14; p=0.0097).

Comparing matched pre- and post-treatment biopsies from individual subjects, results showed a trend towards subjects ultimately achieving a BOR of CR or PR having a larger post-treatment increase in CD8+ cells (CAR+ T and non-CAR T) in tumors, as compared to subjects ultimately achieving a BOR of SD or PD (CR, PR median change: +5.3%; SD, PD median change: +0.06%; p=0.1225).

Expression of immunosuppressive factors, including CD73, FOXP3, CD163, IDO and PD-L1, varied among subjects at pre-treatment (CD73 (median: 1.5%; range 0-42%), FOXP3 (0.10%; 0-1.5%), IDO (0.06%; 0-11%), CD163 (1.2%; 0-24%) and PD-L1 (0.16%; 0-56%)) and post-treatment (CD73 (1.6%; 0-53%), FOXP3 (0.09%; 0-4.3%), IDO (0.28%; 0-15%), CD163 (3.6%; 0-22%) and PD-L1 (3.3%; 0-65%)). Post-treatment increases in CD8+ cells in matched biopsies were observed to be associated with post-treatment increases in IDO ($R^2=0.64$) and PD-L1 ($R^2=0.61$) expression. This result is consistent with a conclusion that infiltration of CD8+CAR+ cells at the time assessed may indicate potential likelihood of achieving a degree of response or duration of response, and that the presence and/or activity of such cells may result in upregulation of TME factors.

D. Conclusion

Durable response at month 3 after CAR+ T cell administration was observed to be associated with higher levels of CD4+ cells in pre-treatment tumors. In post-treatment tumor cells, CAR+ T cells, both CD4+ and CD8+, were observed to infiltrate the tumor and adjacent tissue. ORR was associated with an increase in CAR+ T cells in the tumor biopsy. An increase of $CD8^+$ levels in the post-treatment tumor biopsy compared to $CD8^+$ levels in the pre-treatment tumor biopsy was associated with increased IDO and PD-L1 expression. In some embodiments, therapies targeting these pathways, such as those administered at the time of or following administration of the CAR-T cells, may enhance one or more therapeutic outcomes or duration thereof following CAR+ T cell administration.

Example 2 Analysis of Response and Assessment of T Cells in Pre- and Post-Administration Tumor Biopsies from Subjects with Relapsed and Refractory Non-Hodgkin's Lymphoma (NHL) for Administration of Anti-CD19 CAR-Expressing Cells In the same study as described in Example 1, tumor biopsies collected from subjects before and/or after administration of CAR-expressing cells were analyzed. Therapeutic CAR+ T cell compositions were administered as described above in Example 1. Tumor biopsies were collected prior to administration of the CAR+ T cells (pre-treatment) and at 7 to 14 days after administration (post-treatment). Results from 58 biopsies (32 pre-treatment; 17 post-treatment and 10 matched pairs) from 40 total subjects were examined. Results from the biopsy assessment were analyzed for potential correlations with response outcomes.

Subjects were assessed for response outcomes, including by assessing the tumor burden at various time points after administration of the CAR+ T cells and determining whether the subject had progressive disease (PD), stable disease (SD), partial response (PR), or complete response (CR). The observed objective response rate (ORR; including CR and PR) was 75%, of which 56% of subjects achieved CR.

At a subsequent point in time in the clinical study described in Example 1 above, results were analyzed. The analysis at this time point is based on assessment of a total of 91 subjects (88 assessed for response) that had been administered the anti-CD19 CAR-expressing cells. At this subsequent analysis time point, the objective response rate (ORR) was 74%, including 52% subjects who showed a complete response (CR).

A. Pre-Treatment Biopsies

Figure 1A:
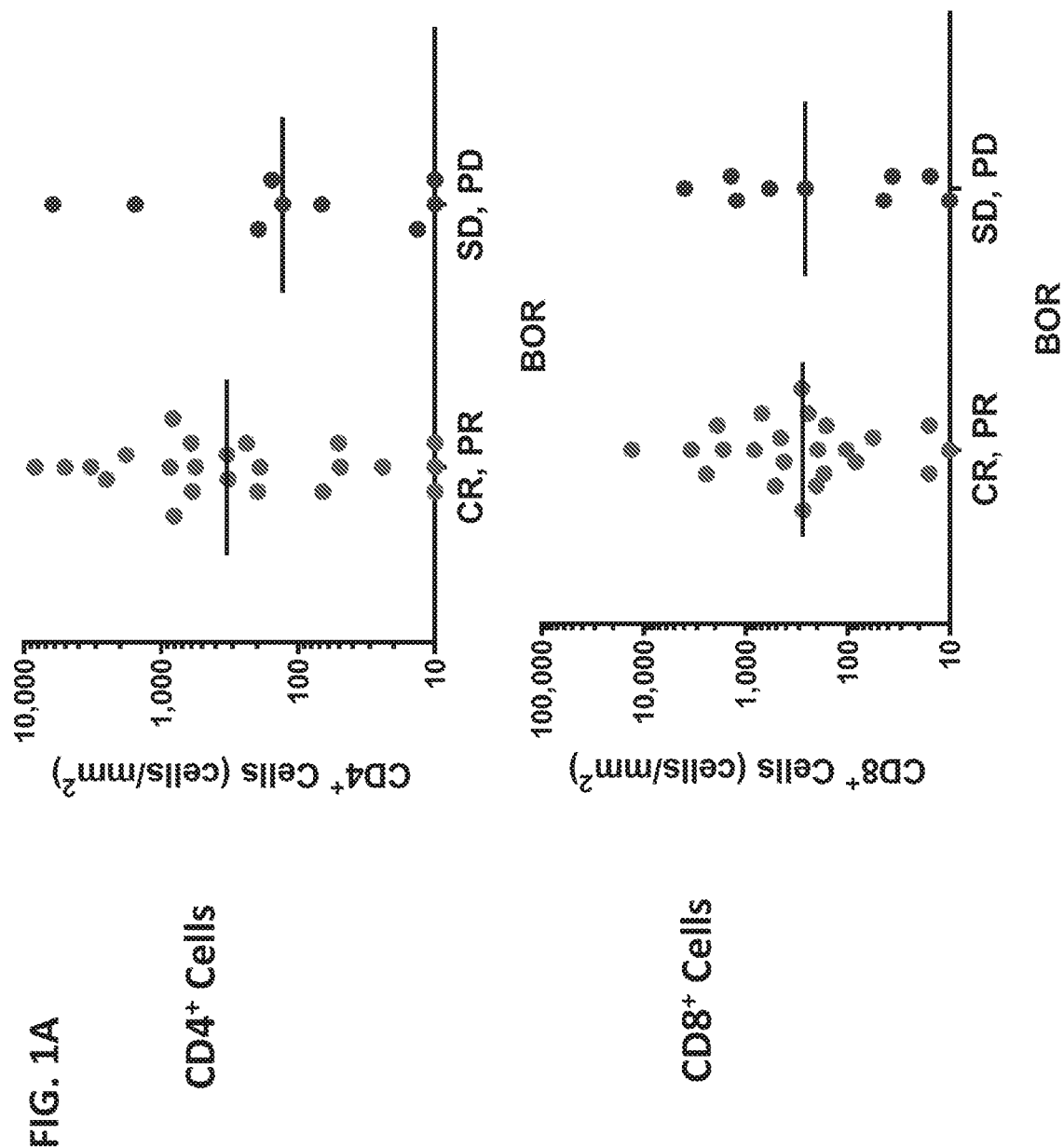
FIG. 1A shows the pre-treatment CD4+ T cell density and CD8+ T cell density in tumor biopsies of subjects that went on to develop a best overall response of complete response (CR)/partial response (PR) or stable disease (SD)/progressive disease (PD).

T cells were enumerated using multiplex immunohistochemistry (IHC)/immunofluorescence (IF) assays detecting for CD4 or CD8. Pre-treatment CD4+ T cell density and CD8+ T cells density in tumor biopsies of subjects that went on to develop a best overall response of CR/PR or SD/PD are shown in FIG. 1A and that went on to develop CR/PR or SD/PD at three months is shown in FIG. 1B.

B. Post-Treatment Biopsies

Infiltration of CAR+ T cell in the tumor biopsy was quantified using in situ hybridization (ISH) probes specific to the mRNA encoding the anti-CD19 CAR. CAR+ T cells, non-CAR T cells and B cells were enumerated using multiplex immunohistochemistry (IHC)/immunofluorescence (IF) assays detecting for a cell surface surrogate marker for CAR-expressing cells, CD4, CD8, CD19, and CD20. CD4+ and CD8+ T cell density was also assessed in post-treatment tumor biopsies. Immunofluorescence images of assays detecting for CAR expression (as determined by the surrogate marker), CD4, CD8, and CD20, were analyzed. CD4+ and CD8+ CAR T cells were observed to infiltrate post-treatment tumor tissue as shown by the presence of CD4+, and CD8+ cells that also were positive for a cell surface surrogate marker for CAR-expressing cells in the biopsy sample.

Figure 2A:
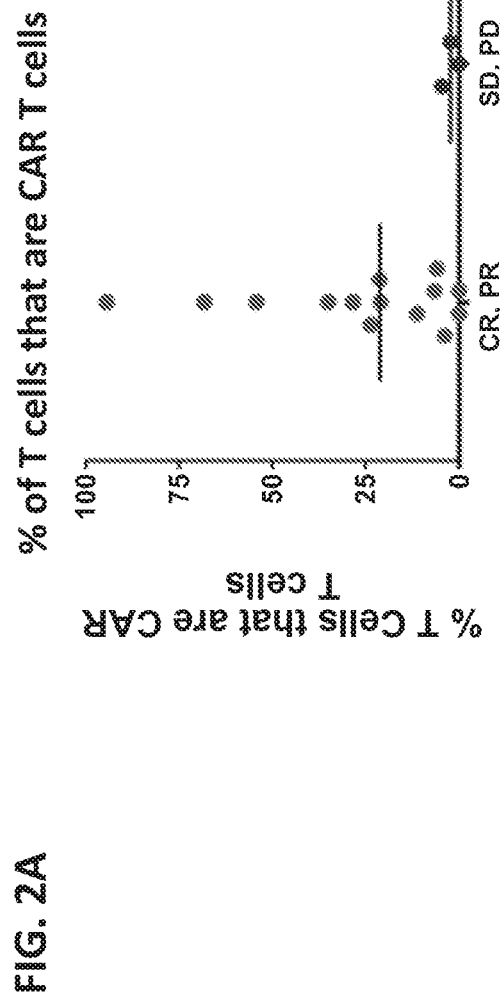
FIG. 2A shows the percentage of T cells positive for the CAR in post-treatment tumor biopsies of subjects who went on to develop a best overall response of CR/PR as compared to SD/PD. $^a$CD8$^+$ proportion analysis includes only tumors with more than 10 CAR T cells counted.
Figure 2B:
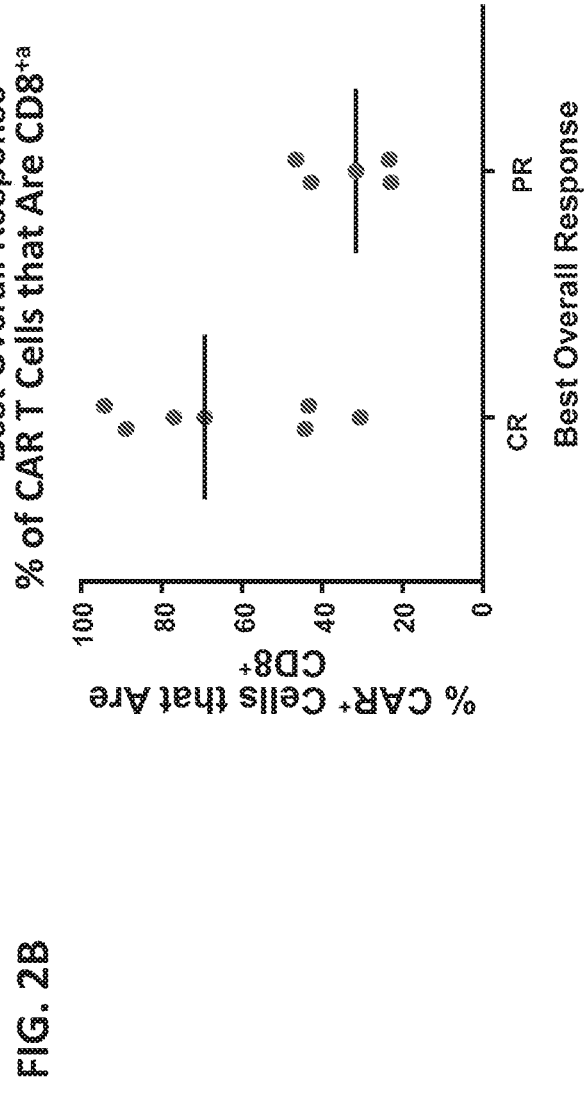
FIG. 2B shows the percentage of CAR T cells positive for CD8 in post-treatment tumor biopsies of subjects who went on to develop a best overall response of CR as compared to PR.
Figure 2C:
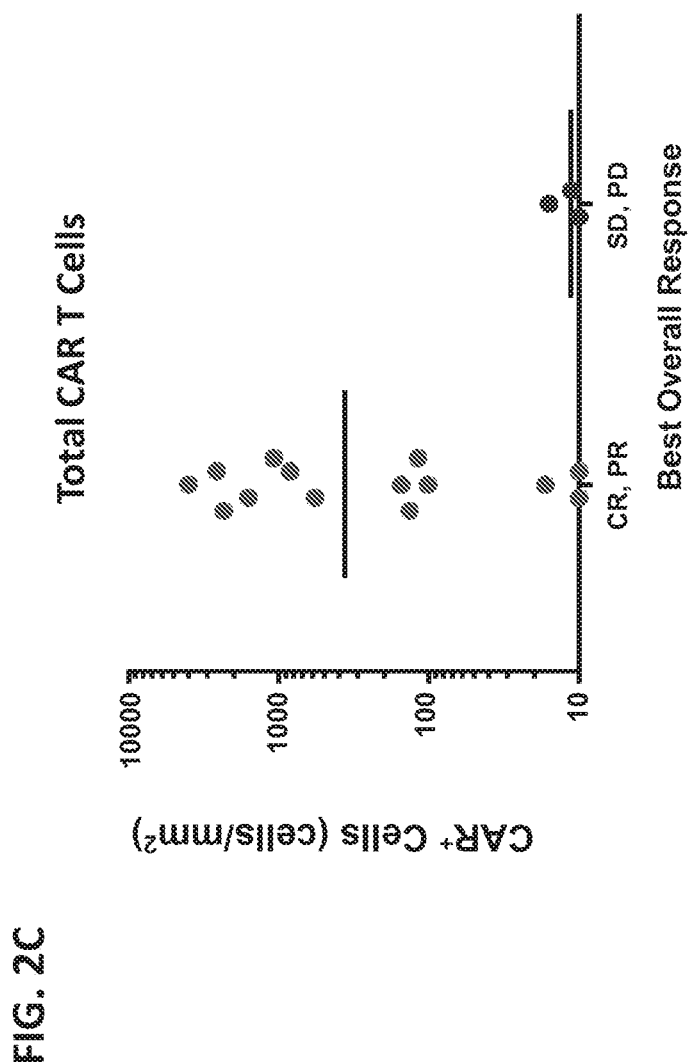
FIG. 2C shows the density (cells/mm$^2$) of total CAR+ T cells in post-treatment tumor biopsies of subjects that went on to develop a best overall response of CR/PR as compared to SD/PD.
Figure 3A:
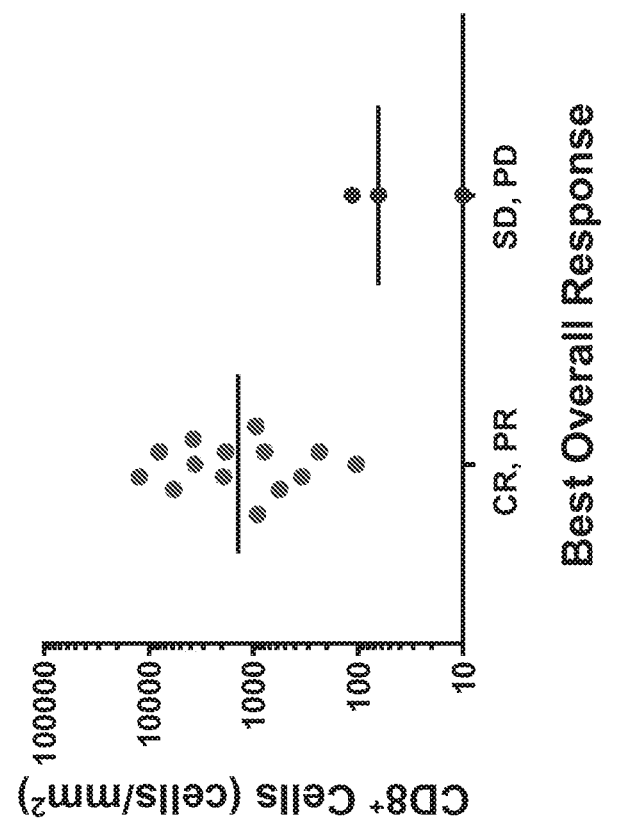
FIGS. 3A and 3B show the total CD4+ and CD8+ T cell density in post-treatment tumors observed in subjects who achieved a best overall response of CR/PR as compared to SD/PD.
Figure 3B:
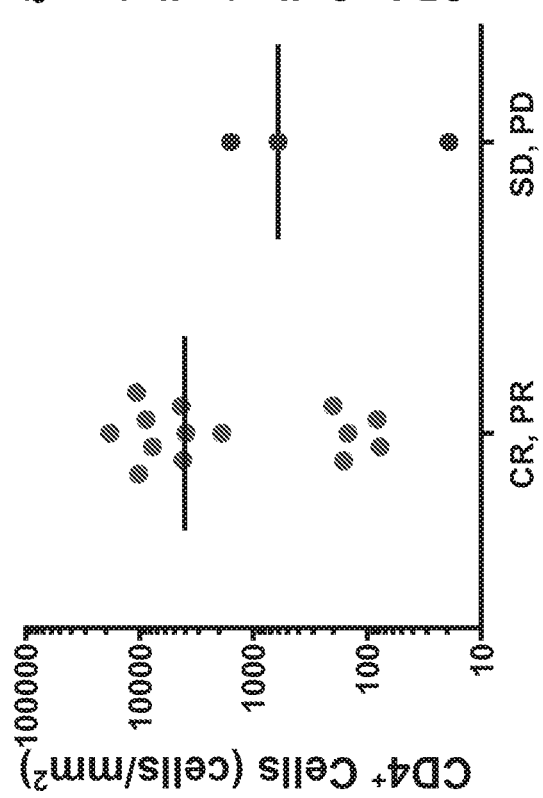

A trend in higher percentage of T cells positive for the CAR (based on detection of the surrogate marker) (FIG. 2A) was observed in subjects who went on to develop a best overall response of CR/PR as compared to a SD/PD. A trend in higher percentage of CAR+ T cells positive for CD8 (FIG. 2B) in post-treatment tumor biopsies was observed in subjects who went on to develop a best overall response of CR as compared to a PR. The density (cells/mm²) of total CAR+ T cells (FIG. 2C), CD4+CAR+ T cells (FIG. 2D) and CD8+CAR+ T cells (FIG. 2E) also trended higher in subjects that went on to develop a best overall response of CR/PR as compared to SD/PD. As shown in FIGS. 3A and 3B, a higher trend in total CD4+ and CD8+ T cell density in post-treatment tumor biopsies was also observed in subjects who achieved a best overall response of CR/PR as compared to SD/PD. As shown by these studies, higher CAR+ T cell and total T cell density, particularly CD8+, in post-treatment tumors was associated with response.

Tumor biopsies from additional subjects treated in the same clinical trial were collected at 7 to 14 days after administration (post-treatment) and analyzed for potential correlations with response outcomes. Post-treatment CAR+ and total CD4+ T cell density and CD8+ T cells density in tumor biopsies of subjects that went on to develop a best overall response of CR/PR or SD/PD, including subjects described in the initial study above, are shown in FIGS. 3C and 3D. A higher trend in CAR+ and total CD4+ and CD8+ T cell density in post-treatment tumor biopsies was observed in subjects who achieved a best overall response of CR/PR as compared to SD/PD.

C. Assessment of Tumors at Disease Progression

Tumor biopsies at disease progression, e.g. following relapse in some subjects, were assessed for CD19 expression and for infiltration of CAR+ T cells. As shown in Table E1A, most tumors at disease progression were observed to be CD19+ and lacked CAR+ T cell infiltration. Such a result was observed in subjects despite the presence of CAR T cells in the peripheral blood as determined from the pharmacokinetic (PK) number of cells/mL in the blood at disease progression. This result is consistent with an observation that, at disease progression, in many patients CAR T cells were rare or absent in tumor tissue despite the presence of CD19 and persistence of peripheral blood CAR T cells.

TABLE E1A

Assessment of Biopsies Obtained at Disease Progression

| Prog. Biopsy | BOR | Tumor CD19 | Blood CAR T Cells (cells/μL) | Tumor CAR T cells |
|---|---|---|---|---|
| 1 | CR | + | 1.2 | – |
| 2 | CR | <LOD | 3.0 | – |
| 3 | CR | + | 138 | – |
| 4 | CR | + | <LOD | – |
| 5 | PR | + | <LOD | Rare |
| 6 | SD | <LOD | <1 | – |
| 7 | SD | + | 13 | – |
| 8 | SD | + | <1 | Rare |
| 9 | PD | + | 23 | – |

BOR, Best overall response; LOD, level of detection; Prog, Progression

Biopsy samples from additional subjects treated in the clinical study described in Example 1 above were obtained at disease progression and analyzed as described above. Results are shown in Table E1B.

TABLE E1B

Assessment of Biopsies Obtained at Disease Progression

| Prog. Biopsy | BOR | Tumor CD19 | Blood CAR T Cells (cells/μL) | Tumor CAR T cells |
|---|---|---|---|---|
| 10 | CR | + | 0.4 | – |
| 11 | PD | + | 23.1 | – |

Example 3 Analysis of Response and Assessment of Immunosuppressive Biomarkers in Pre- and Post-Administration Tumor Biopsies from Subjects with Relapsed and Refractory Non-Hodgkin's Lymphoma (NHL) for Administration of Anti-CD19 CAR-Expressing Cells In the same study as described in Example 2, tumor biopsies were collected before and/or after administration of CAR-expressing cells from additional subjects and assessed to evaluate immunosuppressive pathways by detecting expression of PD-L1, IDO, CD73, CD163, and FOXP3. Results from the biopsy assessment for immunosuppressive pathway biomarkers were analyzed for potential correlations with response outcomes.

A. Pre-Treatment Biopsies

Biomarkers of immunosuppressive pathways were detected by using multiplex immunohistochemistry (IHC)/immunofluorescence (IF) assays detecting for PD-L1, IDO, CD73, CD163, and FOXP3. Immunofluorescence images were analyzed and quantified using image analysis software and potential correlations to response outcomes (complete response (CR), partial response (PR), stable disease (SD)/progressive disease (PD)) were assessed. Variable expression of the immunosuppressive pathway biomarkers in pre-treatment tumor biopsies was observed among subjects. As shown in FIG. 4, expression of immunosuppressive factors in pre-treatment tumors was heterogeneous.

B. Post-Treatment Biopsies

Immunosuppressive factor expression of PD-L1, IDO, CD73, CD163, and FOXP3 was also assessed in tumor biopsies obtained post-treatment. As shown in FIG. 5A, in subjects in which CAR-T cells were present post-treatment, density of cells expressing immunosuppressive factors PD-L1 and IDO trended higher in post-treatment compared to pre-treatment in matched biopsy pairs. As shown in FIG. 5B, density of cells expressing certain immunosuppressive factors trended higher in subjects that achieved CR or PR compared to SD or PD, which may be due to a CAR T cell-mediated immune response.

C. Assessment of Tumors at Disease Progression

Tumor biopsies at disease progression, e.g. following a relapse in some subjects, were assessed for expression of immunosuppressive factors PD-L1, IDO, CD73, CD163, and FOXP3. As shown in FIG. 6A-6B, no significant associations between response outcome and density of cells expressing the immunosuppressive factors PD-L1 and IDO at disease progression was observed in matched biopsy pairs obtained at pre-treatment (PRE) and disease progression (PROG). Biopsy samples from additional subjects treated in the clinical study described in Example 1 above were obtained at disease progression and analyzed for expression of immunosuppressive factors expression of immunosuppressive factors PD-L1, IDO, CD73, CD163, and FOXP3. The results are shown in FIG. 6C. Most tumors at disease progression were observed to have heterogeneous expression of immunosuppressive factors.

D. Safety

Tumor biopsies were collected before and/or after administration of CAR-expressing cells and assessed for expression of immunosuppressive factors by ISH and IF as described above. Results from the biopsy assessment were analyzed for potential correlations with safety outcomes. Safety outcomes were evaluated including cytokine release syndrome (graded 0, 1, or 2) and neurotoxicity (neurological complications including symptoms of confusion, aphasia, encephalophathy, myoclonus seizures, convulsions, lethargy, and/or altered mental status), graded on a 1-5 scale, according to the National Cancer Institute-Common Toxicity Criteria (CTCAE) scale, version 4.03 (NCI-CTCAE v4.03).

Grade 3, 4 CRS was observed in 1% of the subjects for which biopsies were assessed (any grade CRS was observed in 30% of subjects), and grades 3-4 neurotoxicity was observed in 14% of the subjects for which biopsies were assessed (any grade neurotoxicity was observed in 20% of subjects). At a subsequent point in time in the clinical study described in Example 2 above, results were analyzed. The analysis at this time point is based on assessment of a total of 91 subjects for safety that had been administered the anti-CD19 CAR-expressing cells. At this subsequent analysis time point, the incidence of any grade of cytokine release syndrome (CRS) was 35%, with 1% severe CRS; and the incidence of any grade of neurotoxicity (NT) was 19%, with 1% severe NT.

As shown in FIG. 7A, no significant associations between density of pre-treatment T cells (CD4+ or CD8+) or T cells positive for certain immunosuppressive factor expression and safety outcome was observed. In post-treatment tumor biopsies, no significant associations were observed between total CAR T cells density (FIG. 7B) in tumor biopsies and in the density of CD4+ or CD8+ T cells or T cells positive for immunosuppressive factor expression (FIG. 7C) in post-treatment biopsy and safety outcomes such as CRS or neurotoxicity.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) homo sapiens |
| 3 | ESKYGPPCPPCPGQPREPQVYTLPPSQEEMTKNQVSLTCLVKGFYP SDIAVEWESNGQPENNYKTTPPVLDSDGSFFLYSRLTVDKSRWQEG NVFSCSVMHEALHNHYTQKSLSLSLGK | Hinge-CH3 spacer Homo sapiens |
| 4 | ESKYGPPCPPCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQE EMTKNQVSLTCLVKGFYPSDIAVEWESNGQPENNYKTTPPVLDSDG SFFLYSRLTVDKSRWQEGNVFSCSVMHEALHNHYTQKSLSLSLGK | Hinge-CH2-CH3 spacer Homo sapiens |
| 5 | RWPESPKAQASSVPTAQPQAEGSLAKATTAPATTRNTGRGGEEKKK EKEKEEQEERETKTPECPSHTQPLGVYLLTPAVQDLWLRDKATFTC FVVGSDLKDAHLTWEVAGKVPTGGVEEGLLERHSNGSQSQHSRLTL PRSLWNAGTSVTCTLNHPSLPPQRLMALREPAAQAPVKLSLNLLAS SDPPEAASWLLCEVSGFSPPNILLMWLEDQREVNTSGFAPARPPPQ PGSTTFWAWSVLRVPAPPSPQPATYTCVVSHEDSRTLLNASRSLEV SYVTDH | IgD-hinge-Fc Homo sapiens |

-continued

SEQUENCES

| SEQ ID NO. | SEQUENCE | DESCRIPTION |
|---|---|---|
| 6 | LEGGGEGRGSLLTCGDVEENPGPR | T2A artificial |
| 7 | MLLLVTSLLLCELPHPAFLLIPRKVCNGIGIGEFKDSLSINATNIK HFKNCTSISGDLHILPVAFRGDSFTHTPPLDPQELDILKTVKEITG FLLIQAWPENRTDLHAFENLEIIRGRTKQHGQFSLAVVSLNITSLG LRSLKEISDGDVIISGNKNLCYANTINWKKLFGTSGQKTKIISNRG ENSCKATGQVCHALCSPEGCWGPEPRDCVSCRNVSRGRECVDKCNL LEGEPREFVENSECIQCHPECLPQAMNITCTGRGPDNCIQCAHYID GPHCVKTCPAGVMGENNTLVWKYADAGHVCHLCHPNCTYGCTGPGL EGCPTNGPKIPSIATGMVGALLLLLVVALGIGLFM | tEGFR artificial |
| 8 | FWVLVVVGGVLACYSLLVTVAFIIFWV | CD28 (amino acids 153-179 of Accession No. P10747) *Homo sapiens* |
| 9 | IEVMYPPPYLDNEKSNGTIIHVKGKHLCPSPLFPGPSKPFWVLVVV GGVLACYSLLVTVAFIIFWV | CD28 (amino acids 114-179 of Accession No. P10747) *Homo sapiens* |
| 10 | RSKRSRLLHSDYMNMTPRRPGPTRKHYQPYAPPRDFAAYRS | CD28 (amino acids 180-220 of P10747) *Homo sapiens* |
| 11 | RSKRSRGGHSDYMNMTPRRPGPTRKHYQPYAPPRDFAAYRS | CD28 (LL to GG) *Homo sapiens* |
| 12 | KRGRKKLLYIFKQPFMRPVQTTQEEDGCSCRFPEEEEGGCEL | 4-1BB (amino acids 214-255 of Q07011.1) *Homo sapiens* |
| 13 | RVKFSRSADAPAYQQGQNQLYNELNLGRREEYDVLDKRRGRDPEMG GKPRRKNPQEGLYNELQKDKMAEAYSEIGMKGERRRGKGHDGLYQG LSTATKDTYDALHMQALPPR | CD3 zeta *Homo sapiens* |
| 14 | RVKFSRSAEPPAYQQGQNQLYNELNLGRREEYDVLDKRRGRDPEMG GKPRRKNPQEGLYNELQKDKMAEAYSEIGMKGERRRGKGHDGLYQG LSTATKDTYDALHMQALPPR | CD3 zeta *Homo sapiens* |
| 15 | RVKFSRSADAPAYKQGQNQLYNELNLGRREEYDVLDKRRGRDPEMG GKPRRKNPQEGLYNELQKDKMAEAYSEIGMKGERRRGKGHDGLYQG LSTATKDTYDALHMQALPPR | CD3 zeta *Homo sapiens* |
| 16 | RKVCNGIGIGEFKDSLSINATNIKHFKNCTSISGDLHILPVAFRGD SFTHTPPLDPQELDILKTVKEITGFLLIQAWPENRTDLHAFENLEI IRGRTKQHGQFSLAVVSLNITSLGLRSLKEISDGDVIISGNKNLCY ANTINWKKLFGTSGQKTKIISNRGENSCKATGQVCHALCSPEGCWG PEPRDCVSCRNVSRGRECVDKCNLLEGEPREFVENSECIQCHPECL PQAMNITCTGRGPDNCIQCAHYIDGPHCVKTCPAGVMGENNTLVWK YADAGHVCHLCHPNCTYGCTGPGLEGCPTNGPKIPSIATGMVGALL LLLVVALGIGLFM | tEGFR artificial |
| 17 | EGRGSLLTCGDVEENPGP | T2A artificial |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | PGGG-(SGGGG)5-P- wherein P is proline, G is glycine and S is serine | Linker |

| SEQ ID NO. | SEQUENCE | DESCRIPTION |
|---|---|---|
| 23 | GSADDAKKDAAKKDGKS | Linker |
| 24 | ACACGGCCTCGTGTATTACTGT | IGH primer |
| 25 | ACCTGAGGAGACGGTGACC | IGH Primer |
| 26 | MALPVTALLLPLALLLHA | CD8 alpha signal peptide |
| 27 | Glu Arg Lys Cys Cys Val Glu Cys Pro Pro Cys Pro | Hinge |
| 28 | ELKTPLGDTHTCPRCPEPKSCDTPPPCPRCPEPKSCDTPPPCPRCP EPKSCDTPPPCPRCP | Hinge |
| 29 | Glu Ser Lys Tyr Gly Pro Pro Cys Pro Ser Cys Pro | Hinge |
| 30 | Glu Ser Lys Tyr Gly Pro Pro Cys Pro Pro Cys Pro | Hinge |
| 31 | Tyr Gly Pro Pro Cys Pro Pro Cys Pro | Hinge |
| 32 | Lys Tyr Gly Pro Pro Cys Pro Pro Cys Pro | Hinge |
| 33 | Glu Val Val Val Lys Tyr Gly Pro Pro Cys Pro Pro Cys Pro | Hinge |
| 34 | QQGNTLPYT | FMC63 LC-CDR3 |
| 35 | RASQDISKYLN | FMC63 CDR L1 |
| 36 | SRLHSGV | FMC63 CDR L2 |
| 37 | GNTLPYTFG | FMC63 CDR L3 |
| 38 | DYGVS | FMC63 CDR H1 |
| 39 | VIWGSETTYYNSALKS | FMC63 CDR H2 |
| 40 | YAMDYWG | FMC63 CDR H3 |
| 41 | EVKLQESGPGLVAPSQSLSVTCTVSGVSLPDYGVSWIRQPPRKGLE WLGVIWGSETTYYNSALKSRLTIIKDNSKSQVFLKMNSLQTDDTAI YYCAKHYYYGGSYAMDYWGQGTSVTVSS | FMC63 VH |
| 42 | DIQMTQTTSSLSASLGDRVTISCRASQDISKYLNWYQQKPDGTVKL LIYHTSRLHSGVPSRFSGSGSGTDYSLTISNLEQEDIATYFCQQGN TLPYTFGGGTKLEIT | FMC63 VL |
| 43 | DIQMTQTTSSLSASLGDRVTISCRASQDISKYLNWYQQKPDGTVKL LIYHTSRLHSGVPSRFSGSGSGTDYSLTISNLEQEDIATYFCQQGN TLPYTFGGGTKLEITGSTSGSGKPGSGEGSTKGEVKLQESGPGLVA PSQSLSVTCTVSGVSLPDYGVSWIRQPPRKGLEWLGVIWGSETTYY NSALKSRLTIIKDNSKSQVFLKMNSLQTDDTAIYYCAKHYYYGGSY AMDYWGQGTSVTVSS | FMC63 scFv |
| 44 | KASQNVGTNVA | SJ25C1 CDR Li |
| 45 | SATYRNS | SJ25C1 CDR L2 |
| 46 | QQYNRYPYT | SJ25C1 CDR L3 |
| 47 | SYWMN | SJ25C1 CDR H1 |
| 48 | QIYPGDGDTNYNGKFKG | SJ25C1 CDR H2 |
| 49 | KTISSVVDFYFDY | SJ25C1 CDR H3 |
| 50 | EVKLQQSGAELVRPGSSVKISCKASGYAFSSYWMNWVKQRPGQGLE WIGQIYPGDGDTNYNGKFKGQATLTADKSSSTAYMQLSGLTSEDSA VYFCARKTISSVVDFYFDYWGQGTTVTVSS | SJ25C1 VH |
| 51 | DIELTQSPKFMSTSVGDRVSVTCKASQNVGTNVAWYQQKPGQSPKP LIYSATYRNSGVPDRFTGSGSGTDFTLTITNVQSKDLADYFCQQYN RYPYTSGGGTKLEIKR | SJ25C1 VL |

| SEQ ID NO. | SEQUENCE | DESCRIPTION |
|---|---|---|
| 52 | GGGGSGGGGSGGGGS | Linker |
| 53 | EVKLQQSGAELVRPGSSVKISCKASGYAFSSYWMNWVKQRPGQGLEWIGQIYPGDGDTNYNGKFKGQATLTADKSSSTAYMQLSGLTSEDSAVYFCARKTISSVVDFYFDYWGQGTTVTVSSGGGGSGGGGSGGGGSDIELTQSPKFMSTSVGDRVSVTCKASQNVGTNVAWYQQKPGQSPKPLIYSATYRNSGVPDRFTGSGSGTDFTLTITNVQSKDLADYFCQQYNRYPYTSGGGTKLEIKR | SJ25C1 scFv |
| 54 | HYYYGGSYAMDY | FMC63 HC-CDR3 |
| 55 | HTSRLHS | FMC63 LC-CDR2 |
| 56 | GSTSGSGKPGSGEGSTKG | Linker |
| 57 | gacatccagatgacccagaccacctccagcctgagcgccagcctggcgacccgggtgaccatcagctgccgggccagccaggacatcagcaagtacctgaactggtatcagcagaagcccgacggcaccgtcaagctgctgatctaccacaccagccggctgcacagcggcgtgcccagccggttagcggcagcggctccggcaccgactacagcctgaccatctccaacctggaacaggaagatatcgccacctactttgccagcagggcaacacactgccctacacctttggcggcggaacaaagctggaaatcaccggcagcacctccggcagcggcaagcctggcagcggcgagggcagcaccaagggcgaggtgaagctgcaggaaagcggccctggcctggtggcccccagccagagcctgagcgtgacctgcaccgtgagcggcgtgagcctgcccgactacggcgtgagctggatccggcagccccccaggaagggcctggaatggctgggcgtgatctggggcagcgagaccacctactacaacagcgccctgaagagccggctgaccatcatcaaggacaacagcagagcccaggtgttcctgaagatgaacagcctgcagaccgacgacacggccatctactactgcgccaagcactactactacggcggcagctacgccatggactactggggccagggcaccagcgtgaccgtgagcagc | Sequence encoding scFv |
| 58 | X1PPX2P<br>X1 is glycine, cysteine or arginine<br>X2 is cysteine or threonine | Hinge |
| 59 | Glu Pro Lys Ser Cys Asp Lys Thr His Thr Cys Pro Pro Cys Pro | Hinge |
| 60 | atgcttctcctggtgacaagccttctgctctgtgagttaccacaccagcattcctcctgatccca | GMCSFR alpha chain signal sequence |
| 61 | MLLLVTSLLLCELPHPAFLLIP | GMCSFR alpha chain signal sequence |
| 62 | MPLLLLLPLLWAGALA | CD33 signal peptide |

The invention claimed is:

1. A method of treatment, the method comprising administering a therapeutic regimen to a subject, that is a candidate for receiving a cell therapy for treatment of non-Hodgkin lymphoma (NHL) but that has not yet been administered the cell therapy, following assessment of a tumor sample from the subject for frequency of CD4+T cells compared to a threshold value, wherein frequency of CD4+T cells above the threshold value indicates the subject is likely to achieve a response when administered the cell therapy and a frequency of CD4+T cells below the threshold value indicates the subject is not likely to achieve a response when administered the cell therapy, wherein:

if the frequency of CD4+T cells is above the threshold level, administering the cell therapy to the subject; and if the frequency of CD4+T cells is below the threshold level, administering (i) an agent or other treatment capable of stimulating, amplifying, potentiating, and/or enhancing an anti-tumor immune response and the cell therapy; (ii) the cell therapy at an increased dose and/or administering an additional dose of the cell therapy; or (iii) an alternative therapeutic treatment other than the cell therapy.

2. The method of claim 1, wherein the tumor sample is a tumor biopsy sample.

3. The method of claim 1, wherein the CD4+T cells are detected using immunoassay, in situ hybridization, or immunohistochemistry.

4. The method of claim 3, wherein the CD4+T cells are detected using immunohistochemistry and the immunohistochemistry is multiplexed immunohistochemistry or 5-plex immunofluorescent immunohistochemistry.

5. The method of claim 1, wherein the response is a complete response (CR) or a partial response (PR).

6. The method of claim 1, wherein the cell therapy comprises T cells engineered to express a recombinant receptor.

7. The method of claim 6, wherein the recombinant receptor is a T cell receptor (TCR) or a chimeric antigen receptor (CAR).

8. The method of claim 1, wherein the frequency of CD4+T cells is the density of the CD4+T cells in the tumor sample.

9. The method of claim 1, wherein:
the threshold value of CD4+T cells is or is greater than about 4% CD4+T cells of the total cells in the tumor sample.

10. The method of claim 9, wherein the cell therapy comprises T cells engineered to express a recombinant receptor.

11. The method of claim 10, wherein the recombinant receptor is a TCR or a CAR.

12. The method of claim 1, wherein
(A) if the frequency of CD4+T cells is above the threshold value:
the administration of the cell therapy does not comprise administering, prior to or concurrently with administering the cell therapy, an agent or other treatment capable of stimulating, amplifying, potentiating, and/or enhancing an anti-tumor immune response; or
(B) if the frequency of CD4+T cells is below the threshold value, the agent or other treatment is to be administered (i) prior to, (ii) within one, two, or three days of, or (iii) concurrently with the initiation of administration of the cell therapy to the subject.

13. The method of claim 1, wherein the agent or other treatment is or comprises an immune-inhibitory molecule, is or comprises an immune checkpoint molecule or member of an immune checkpoint pathway, or is or comprises a modulator of an immune checkpoint molecule or pathway.

14. The method of claim 1, wherein the NHL is aggressive NHL, diffuse large B cell lymphoma (DLBCL), DLBCL not otherwise specified (DLBCL-NOS), primary mediastinal large B cell lymphoma (PMBCL), T cell/histocyte-rich large B cell lymphoma (TCHRBCL), Burkitt's lymphoma, mantle cell lymphoma (MCL), or follicular lymphoma (FL).

15. The method of claim 1, wherein the cell therapy comprises genetically engineered cells expressing a recombinant receptor, wherein the genetically engineered cells comprise T cells or NK cells.

16. The method of claim 1, wherein the threshold value of CD4+T cells is or is greater than about 300 cells/mm$^2$ in the tumor sample.

17. The method of claim 16, wherein the cell therapy comprises T cells engineered to express a recombinant receptor.

18. The method of claim 17, wherein the recombinant receptor is a TCR or a CAR.

19. The method of claim 1, wherein the threshold value of CD4+T cells is or is greater than:
about 7% CD4+T cells of the total cells in the tumor sample; or
about 800 cells/mm² in the tumor sample.

20. A method of treatment, the method comprising administering a cell therapy to a subject for treatment of non-Hodgkin lymphoma (NHL), wherein, prior to receiving the cell therapy, the subject had been selected for treatment based on assessment of the frequency of CD4+T cells in a tumor sample from the subject, and the frequency of CD4+T cells was above a threshold level.

21. The method of claim 20, wherein the tumor sample is a tumor biopsy sample.

22. The method of claim 20, wherein the CD4+T cells are detected using immunoassay, in situ hybridization, immunohistochemistry, multiplexed immunohistochemistry, or 5-plex immunofluorescent immunohistochemistry.

23. The method of claim 20, wherein the cell therapy comprises T cells engineered to express a recombinant receptor.

24. The method of claim 23, wherein the recombinant receptor is a T cell receptor (TCR) or a chimeric antigen receptor (CAR).

25. The method of claim 24, wherein the NHL is aggressive NHL, diffuse large B cell lymphoma (DLBCL), DLBCL not otherwise specified (DLBCL-NOS), primary mediastinal large B cell lymphoma (PMBCL), T cell/histocyte-rich large B cell lymphoma (TCHRBCL), Burkitt's lymphoma, mantle cell lymphoma (MCL), or follicular lymphoma (FL).

26. The method of claim 23, wherein:
the threshold value of CD4+T cells is or is greater than:
about 4% CD4+T cells of the total cells in the tumor sample; or
about 300 cells/mm² in the tumor sample.

27. The method of claim 26, the recombinant receptor is a TCR or a CAR.

28. The method of claim 20, wherein the frequency of CD4+T cells is the density of the CD4+T cells in the tumor sample.

29. The method of claim 20, wherein the threshold value of CD4+T cells is or is greater than about 4% CD4+T cells of the total cells in the tumor sample.

30. The method of claim 20, wherein the threshold value of CD4+T cells is or is greater than about 300 cells/mm² in the tumor sample.

31. The method of claim 20, wherein the administration of the cell therapy does not comprise administering, prior to or concurrently with administering the cell therapy, an agent or other treatment capable of stimulating, amplifying, potentiating, and/or enhancing an anti-tumor immune response.

32. The method of claim 20, wherein the NHL is aggressive NHL, diffuse large B cell lymphoma (DLBCL), DLBCL not otherwise specified (DLBCL-NOS), primary mediastinal large B cell lymphoma (PMBCL), T cell/histocyte-rich large B cell lymphoma (TCHRBCL), Burkitt's lymphoma, mantle cell lymphoma (MCL), or follicular lymphoma (FL).

33. The method of claim 20, wherein the cell therapy comprises genetically engineered cells expressing a recombinant receptor, wherein the genetically engineered cells comprise T cells or NK cells.

* * * * *

SEQUENCE LISTING

<160> NUMBER OF SEQ ID NOS: 62

<210> SEQ ID NO 1
<211> LENGTH: 12
<212> TYPE: PRT
<213> ORGANISM: Homo sapiens
<220> FEATURE:
<223> OTHER INFORMATION: Spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA

```
<213> ORGANISM: Homo sapiens
<220> FEATURE:
<223> OTHER INFORMATION: Spacer (IgG4hinge)

<400> SEQUENCE: 2
gaatctaagt acggaccgcc ctgccccct tgccct                              36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3
```

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

```
<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4
```

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
            35                  40                  45

Glu Lys Glu Glu Gln Glu Glu Arg Glu Thr Lys Thr Pro Glu Cys Pro
50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
            85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
            115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
            165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
            195                 200                 205

Met Trp Leu Glu Asp Gln Arg Glu Val Asn Thr Ser Gly Phe Ala Pro
            210                 215                 220

Ala Arg Pro Pro Gln Pro Gly Ser Thr Thr Phe Trp Ala Trp Ser
225                 230                 235                 240

Val Leu Arg Val Pro Ala Pro Ser Pro Gln Pro Ala Thr Tyr Thr
                    245                 250                 255

Cys Val Val Ser His Glu Asp Ser Arg Thr Leu Leu Asn Ala Ser Arg
            260                 265                 270

```
Ser Leu Glu Val Ser Tyr Val Thr Asp His
        275                 280
```

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

```
Leu Glu Gly Gly Gly Gly Arg Gly Ser Leu Leu Thr Cys Gly Asp
1               5                   10                  15

Val Glu Glu Asn Pro Gly Pro Arg
            20
```

<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270
```

```
His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
        355

<210> SEQ ID NO 8
<211> LENGTH: 27
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 10
<211> LENGTH: 41
<212> TYPE: PRT
<213> ORGANISM: Homo sapiens
<220> FEATURE:
<223> OTHER INFORMATION: CD28
<300> PUBLICATION INFORMATION:
<308> DATABASE ACCESSION NUMBER: UniProt P10747
<309> DATABASE ENTRY DATE: 1989-07-01

<400> SEQUENCE: 10
```

-continued

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40
```

<210> SEQ ID NO 11
<211> LENGTH: 41
<212> TYPE: PRT
<213> ORGANISM: Homo sapiens
<220> FEATURE:
<223> OTHER INFORMATION: CD28

<400> SEQUENCE: 11

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40
```

<210> SEQ ID NO 12
<211> LENGTH: 42
<212> TYPE: PRT
<213> ORGANISM: Homo sapiens
<220> FEATURE:
<223> OTHER INFORMATION: 4-1BB
<300> PUBLICATION INFORMATION:
<308> DATABASE ACCESSION NUMBER: UniProt Q07011.1
<309> DATABASE ENTRY DATE: 1995-02-01

<400> SEQUENCE: 12

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40
```

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
```

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

```
Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
 50                  55                  60

Val Lys Glu Ile Thr Gly Phe Leu Leu Ile Gln Ala Trp Pro Glu Asn
 65                  70                  75                  80

Arg Thr Asp Leu His Ala Phe Glu Asn Leu Glu Ile Ile Arg Gly Arg
                 85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 17
<211> LENGTH: 18
<212> TYPE: PRT
<213> ORGANISM: Artificial Sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1               5                   10                  15

Gly Pro

<210> SEQ ID NO 18
<211> LENGTH: 22
<212> TYPE: PRT
<213> ORGANISM: Artificial Sequence
<220> FEATURE:
```

<223> OTHER INFORMATION: P2A

<400> SEQUENCE: 18

Gly Ser Gly Ala Thr Asn Phe Ser Leu Leu Lys Gln Ala Gly Asp Val
1               5                   10                  15
Glu Glu Asn Pro Gly Pro
            20

<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15
Pro Gly Pro

<210> SEQ ID NO 20
<211> LENGTH: 20
<212> TYPE: PRT
<213> ORGANISM: Artificial Sequence
<220> FEATURE:
<223> OTHER INFORMATION: E2A

<400> SEQUENCE: 20

Gln Cys Thr Asn Tyr Ala Leu Leu Lys Leu Ala Gly Asp Val Glu Ser
1               5                   10                  15
Asn Pro Gly Pro
            20

<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1               5                   10                  15
Glu Ser Asn Pro Gly Pro
            20

<210> SEQ ID NO 22
<211> LENGTH: 10
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 22

Pro Gly Gly Gly Ser Gly Gly Gly Gly Pro
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Linker

<400> SEQUENCE: 23

Gly Ser Ala Asp Asp Ala Lys Lys Asp Ala Ala Lys Lys Asp Gly Lys
1               5                   10                  15

Ser

<210> SEQ ID NO 24
<211> LENGTH: 22
<212> TYPE: DNA
<213> ORGANISM: Artificial Sequence
<220> FEATURE:
<223> OTHER INFORMATION: IGH primer

<400> SEQUENCE: 24
acacggcctc gtgtattact gt                                                   22

<210> SEQ ID NO 25
<211> LENGTH: 19
<212> TYPE: DNA
<213> ORGANISM: Artificial Sequence
<220> FEATURE:
<223> OTHER INFORMATION: IGH primer

<400> SEQUENCE: 25
acctgaggag acggtgacc                                                       19

<210> SEQ ID NO 26
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 26

Met Ala Leu Pro Val Thr Ala Leu Leu Leu Pro Leu Ala Leu Leu Leu
1               5                   10                  15

His Ala

<210> SEQ ID NO 27
<211> LENGTH: 12
<212> TYPE: PRT
<213> ORGANISM: Artificial Sequence
<220> FEATURE:
<223> OTHER INFORMATION: Hinge

<400> SEQUENCE: 27

Glu Arg Lys Cys Cys Val Glu Cys Pro Pro Cys Pro
1               5                   10

<210> SEQ ID NO 28
<211> LENGTH: 61
<212> TYPE: PRT
<213> ORGANISM: Artificial Sequence
<220> FEATURE:
<223> OTHER INFORMATION: Hinge

<400> SEQUENCE: 28

Glu Leu Lys Thr Pro Leu Gly Asp Thr His Thr Cys Pro Arg Cys Pro
1               5                   10                  15

Glu Pro Lys Ser Cys Asp Thr Pro Pro Cys Pro Arg Cys Pro Glu
                20                  25                  30

Pro Lys Ser Cys Asp Thr Pro Pro Cys Pro Arg Cys Pro Glu Pro

Lys Ser Cys Asp Thr Pro Pro Cys Pro Arg Cys Pro
    50                  55                  60

<210> SEQ ID NO 29
<211> LENGTH: 12
<212> TYPE: PRT
<213> ORGANISM: Artificial Sequence
<220> FEATURE:
<223> OTHER INFORMATION: Hinge

<400> SEQUENCE: 29

Glu Ser Lys Tyr Gly Pro Pro Cys Pro Ser Cys Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Hinge

<400> SEQUENCE: 30

Glu Ser Lys Tyr Gly Pro Pro Cys Pro Pro Cys Pro
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Hinge

<400> SEQUENCE: 31

Tyr Gly Pro Pro Cys Pro Pro Cys Pro
1               5

<210> SEQ ID NO 32
<211> LENGTH: 10
<212> TYPE: PRT
<213> ORGANISM: Artificial Sequence
<220> FEATURE:
<223> OTHER INFORMATION: Hinge

<400> SEQUENCE: 32

Lys Tyr Gly Pro Pro Cys Pro Pro Cys Pro
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Hinge

<400> SEQUENCE: 33

Glu Val Val Val Lys Tyr Gly Pro Pro Cys Pro Pro Cys Pro
1               5                   10

<210> SEQ ID NO 34
<211> LENGTH: 9
<212> TYPE: PRT
<213> ORGANISM: Artificial Sequence
<220> FEATURE:
<223> OTHER INFORMATION: LC-CDR3

<400> SEQUENCE: 34

Gln Gln Gly Asn Thr Leu Pro Tyr Thr
1               5

<210> SEQ ID NO 35
<211> LENGTH: 11
<212> TYPE: PRT
<213> ORGANISM: Artificial Sequence
<220> FEATURE:
<223> OTHER INFORMATION: CDR L1

<400> SEQUENCE: 35

Arg Ala Ser Gln Asp Ile Ser Lys Tyr Leu Asn
1               5                   10

<210> SEQ ID NO 36
<211> LENGTH: 7
<212> TYPE: PRT
<213> ORGANISM: Artificial Sequence
<220> FEATURE:
<223> OTHER INFORMATION: CDR L2

<400> SEQUENCE: 36

Ser Arg Leu His Ser Gly Val
1               5

<210> SEQ ID NO 37
<211> LENGTH: 9
<212> TYPE: PRT
<213> ORGANISM: Artificial Sequence
<220> FEATURE:
<223> OTHER INFORMATION: CDR L3

<400> SEQUENCE: 37

Gly Asn Thr Leu Pro Tyr Thr Phe Gly
1               5

<210> SEQ ID NO 38
<211> LENGTH: 5
<212> TYPE: PRT
<213> ORGANISM: Artificial Sequence
<220> FEATURE:
<223> OTHER INFORMATION: CDR H1

<400> SEQUENCE: 38

Asp Tyr Gly Val Ser
1               5

<210> SEQ ID NO 39
<211> LENGTH: 16
<212> TYPE: PRT
<213> ORGANISM: Artificial Sequence
<220> FEATURE:
<223> OTHER INFORMATION: CDR H2

<400> SEQUENCE: 39

Val Ile Trp Gly Ser Glu Thr Thr Tyr Tyr Asn Ser Ala Leu Lys Ser
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: CDR H3

<400> SEQUENCE: 40

Tyr Ala Met Asp Tyr Trp Gly
1               5

<210> SEQ ID NO 41
<211> LENGTH: 120
<212> TYPE: PRT
<213> ORGANISM: Artificial Sequence
<220> FEATURE:
<223> OTHER INFORMATION: VH

<400> SEQUENCE: 41

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: VL

<400> SEQUENCE: 42

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 43
<211> LENGTH: 245
<212> TYPE: PRT
<213> ORGANISM: Artificial Sequence
<220> FEATURE:
<223> OTHER INFORMATION: scFv

<400> SEQUENCE: 43

Asp Ile Gln Met Thr Gln Thr Thr Ser Ser Leu Ser Ala Ser Leu Gly

```
              1               5                  10                 15
            Asp Arg Val Thr Ile Ser Cys Arg Ala Ser Gln Asp Ile Ser Lys Tyr
                           20                  25                 30

Leu Asn Trp Tyr Gln Gln Lys Pro Asp Gly Thr Val Lys Leu Leu Ile
                           35                  40                 45

Tyr His Thr Ser Arg Leu His Ser Gly Val Pro Ser Arg Phe Ser Gly
                           50                  55                 60

Ser Gly Ser Gly Thr Asp Tyr Ser Leu Thr Ile Ser Asn Leu Glu Gln
             65                 70                  75                 80

Glu Asp Ile Ala Thr Tyr Phe Cys Gln Gln Gly Asn Thr Leu Pro Tyr
                           85                  90                 95

Thr Phe Gly Gly Gly Thr Lys Leu Glu Ile Thr Gly Ser Thr Ser Gly
                          100                 105                110

Ser Gly Lys Pro Gly Ser Gly Glu Gly Ser Thr Lys Gly Glu Val Lys
                          115                 120                125

Leu Gln Glu Ser Gly Pro Gly Leu Val Ala Pro Ser Gln Ser Leu Ser
            130                 135                 140

Val Thr Cys Thr Val Ser Gly Val Ser Leu Pro Asp Tyr Gly Val Ser
            145                 150                 155                160

Trp Ile Arg Gln Pro Pro Arg Lys Gly Leu Glu Trp Leu Gly Val Ile
                          165                 170                175

Trp Gly Ser Glu Thr Thr Tyr Tyr Asn Ser Ala Leu Lys Ser Arg Leu
                          180                 185                190

Thr Ile Ile Lys Asp Asn Ser Lys Ser Gln Val Phe Leu Lys Met Asn
                          195                 200                205

Ser Leu Gln Thr Asp Asp Thr Ala Ile Tyr Tyr Cys Ala Lys His Tyr
            210                 215                 220

Tyr Tyr Gly Gly Ser Tyr Ala Met Asp Tyr Trp Gly Gln Gly Thr Ser
            225                 230                 235                240

Val Thr Val Ser Ser
                          245

<210> SEQ ID NO 44
<211> LENGTH: 11
<212> TYPE: PRT
<213> ORGANISM: Artificial Sequence
<220> FEATURE:
<223> OTHER INFORMATION: CDR L1

<400> SEQUENCE: 44

Lys Ala Ser Gln Asn Val Gly Thr Asn Val Ala
1               5                  10

<210> SEQ ID NO 45
<211> LENGTH: 7
<212> TYPE: PRT
<213> ORGANISM: Artificial Sequence
<220> FEATURE:
<223> OTHER INFORMATION: CDR L2

<400> SEQUENCE: 45

Ser Ala Thr Tyr Arg Asn Ser
1               5

<210> SEQ ID NO 46
<211> LENGTH: 9
<212> TYPE: PRT
<213> ORGANISM: Artificial Sequence
<220> FEATURE:
```

```
<223> OTHER INFORMATION: CDR L3

<400> SEQUENCE: 46

Gln Gln Tyr Asn Arg Tyr Pro Tyr Thr
1               5

<210> SEQ ID NO 47
<211> LENGTH: 5
<212> TYPE: PRT
<213> ORGANISM: Artificial Sequence
<220> FEATURE:
<223> OTHER INFORMATION: CDR H1

<400> SEQUENCE: 47

Ser Tyr Trp Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: CDR H2

<400> SEQUENCE: 48

Gln Ile Tyr Pro Gly Asp Gly Asp Thr Asn Tyr Asn Gly Lys Phe Lys
1               5                   10                  15

Gly

<210> SEQ ID NO 49
<211> LENGTH: 13
<212> TYPE: PRT
<213> ORGANISM: Artificial Sequence
<220> FEATURE:
<223> OTHER INFORMATION: CDR H3

<400> SEQUENCE: 49

Lys Thr Ile Ser Ser Val Val Asp Phe Tyr Phe Asp Tyr
1               5                   10

<210> SEQ ID NO 50
<211> LENGTH: 122
<212> TYPE: PRT
<213> ORGANISM: Artificial Sequence
<220> FEATURE:
<223> OTHER INFORMATION: VH

<400> SEQUENCE: 50

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
                100                 105                 110
```

Gly Gln Gly Thr Thr Val Thr Val Ser Ser
            115                 120

<210> SEQ ID NO 51
<211> LENGTH: 108
<212> TYPE: PRT
<213> ORGANISM: Artificial Sequence
<220> FEATURE:
<223> OTHER INFORMATION: VL

<400> SEQUENCE: 51

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105

<210> SEQ ID NO 52
<211> LENGTH: 15
<212> TYPE: PRT
<213> ORGANISM: Artificial Sequence
<220> FEATURE:
<223> OTHER INFORMATION: Linker

<400> SEQUENCE: 52

Gly Gly Gly Gly Ser Gly Gly Gly Gly Ser Gly Gly Gly Gly Ser
1               5                   10                  15

<210> SEQ ID NO 53
<211> LENGTH: 245
<212> TYPE: PRT
<213> ORGANISM: Artificial Sequence
<220> FEATURE:
<223> OTHER INFORMATION: scFv

<400> SEQUENCE: 53

Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly

```
            115                 120                 125
Gly Gly Gly Ser Gly Gly Gly Ser Asp Ile Glu Leu Thr Gln Ser
            130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
            195                 200                 205

Thr Leu Thr Ile Thr Asn Val Gln Ser Lys Asp Leu Ala Asp Tyr Phe
            210                 215                 220

Cys Gln Gln Tyr Asn Arg Tyr Pro Tyr Thr Ser Gly Gly Thr Lys
225                 230                 235                 240

Leu Glu Ile Lys Arg
                245
```

<210> SEQ ID NO 54
<211> LENGTH: 12
<212> TYPE: PRT
<213> ORGANISM: Artificial Sequence
<220> FEATURE:
<223> OTHER INFORMATION: HC-CDR3

<400> SEQUENCE: 54

```
His Tyr Tyr Tyr Gly Gly Ser Tyr Ala Met Asp Tyr
1               5                   10
```

<210> SEQ ID NO 55
<211> LENGTH: 7
<212> TYPE: PRT
<213> ORGANISM: Artificial Sequence
<220> FEATURE:
<223> OTHER INFORMATION: LC-CDR2

<400> SEQUENCE: 55

```
His Thr Ser Arg Leu His Ser
1               5
```

<210> SEQ ID NO 56
<211> LENGTH: 18
<212> TYPE: PRT
<213> ORGANISM: Artificial Sequence
<220> FEATURE:
<223> OTHER INFORMATION: Linker

<400> SEQUENCE: 56

```
Gly Ser Thr Ser Gly Ser Gly Lys Pro Gly Ser Gly Glu Gly Ser Thr
1               5                   10                  15

Lys Gly
```

<210> SEQ ID NO 57
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 57
gacatccaga tgacccagac cacctccagc ctgagcgcca gcctgggcga ccgggtgacc    60

| | |
|---|---|
| atcagctgcc gggccagcca ggacatcagc aagtacctga actggtatca gcagaagccc | 120 |
| gacggcaccg tcaagctgct gatctaccac accagccggc tgcacagcgg cgtgcccagc | 180 |
| cggtttagcg gcagcggctc cggcaccgac tacagcctga ccatctccaa cctggaacag | 240 |
| gaagatatcg ccacctactt ttgccagcag ggcaacacac tgccctacac ctttggcggc | 300 |
| ggaacaaagc tggaaatcac cggcagcacc tccggcagcg gcaagcctgg cagcggcgag | 360 |
| ggcagcacca agggcgaggt gaagctgcag gaaagcggcc ctggcctggt ggcccccagc | 420 |
| cagagcctga gcgtgacctg caccgtgagc ggcgtgagcc tgcccgacta cggcgtgagc | 480 |
| tggatccggc agccccccag gaagggcctg gaatggctgg gcgtgatctg ggcagcgag | 540 |
| accacctact acaacagcgc cctgaagagc cggctgacca tcatcaagga caacagcaag | 600 |
| agccaggtgt tcctgaagat gaacagcctg cagaccgacg acaccgccat ctactactgc | 660 |
| gccaagcact actactacgg cggcagctac gccatggact actggggcca gggcaccagc | 720 |
| gtgaccgtga gcagc | 735 |

<210> SEQ ID NO 58
<211> LENGTH: 5
<212> TYPE: PRT
<213> ORGANISM: Artificial Sequence
<220> FEATURE:
<223> OTHER INFORMATION: Hinge
<220> FEATURE:
<221> NAME/KEY: VARIANT
<222> LOCATION: (1)...(1)
<223> OTHER INFORMATION: Xaa1 is glycine, cysteine or arginine
<220> FEATURE:
<221> NAME/KEY: VARIANT
<222> LOCATION: (4)...(4)
<223> OTHER INFORMATION: Xaa4 is cysteine or threonine

<400> SEQUENCE: 58

Xaa Pro Pro Xaa Pro
1               5

<210> SEQ ID NO 59
<211> LENGTH: 15
<212> TYPE: PRT
<213> ORGANISM: Artificial Sequence
<220> FEATURE:
<223> OTHER INFORMATION: Hinge

<400> SEQUENCE: 59

Glu Pro Lys Ser Cys Asp Lys Thr His Thr Cys Pro Pro Cys Pro
1               5                   10                  15

<210> SEQ ID NO 60
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 60

| | |
|---|---|
| atgcttctcc tggtgacaag ccttctgctc tgtgagttac cacacccagc attcctcctg | 60 |
| atccca | 66 |

<210> SEQ ID NO 61
<211> LENGTH: 22
<212> TYPE: PRT
<213> ORGANISM: Artificial Sequence
<220> FEATURE:
<223> OTHER INFORMATION: GMCSFR alpha chain signal sequence

```
<400> SEQUENCE: 61

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 62
<211> LENGTH: 16
<212> TYPE: PRT
<213> ORGANISM: Homo sapiens
<220> FEATURE:
<223> OTHER INFORMATION: CD33 signal peptide

<400> SEQUENCE: 62

Met Pro Leu Leu Leu Leu Leu Pro Leu Leu Trp Ala Gly Ala Leu Ala
1               5                   10                  15
```